US009303268B2

(12) United States Patent
Kwok et al.

(10) Patent No.: US 9,303,268 B2
(45) Date of Patent: Apr. 5, 2016

(54) INCREASING LOW LIGHT TOLERANCE IN PLANTS

(75) Inventors: Shing Kwok, Chai Wan (HK); Sam Harris, Malibu, CA (US); James Burns, Valley Village, CA (US)

(73) Assignee: Ceres, Inc., Thousand Oaks, CA (US)

( * ) Notice: Subject to any disclaimer, the term of this patent is extended or adjusted under 35 U.S.C. 154(b) by 558 days.

(21) Appl. No.: 13/620,421

(22) Filed: Sep. 14, 2012

(65) Prior Publication Data

US 2013/0024999 A1 Jan. 24, 2013

Related U.S. Application Data

(62) Division of application No. 12/307,561, filed as application No. PCT/US2007/072877 on Jul. 5, 2007, now Pat. No. 8,344,210.

(60) Provisional application No. 60/818,569, filed on Jul. 5, 2006.

(51) Int. Cl.
*C12N 15/87* (2006.01)
*C12N 15/82* (2006.01)
*C07K 14/415* (2006.01)

(52) U.S. Cl.
CPC .......... *C12N 15/8271* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 5,204,253 | A | 4/1993 | Sanford et al. |
| 5,538,880 | A | 7/1996 | Lundquist et al. |
| 6,013,863 | A | 1/2000 | Lundquist et al. |
| 6,329,571 | B1 | 12/2001 | Hiei |
| 7,173,121 | B2 | 2/2007 | Fang |
| 7,214,789 | B2 | 5/2007 | Pennell |
| 7,378,571 | B2 | 5/2008 | Apuya |
| 7,402,667 | B2 | 7/2008 | Cook et al. |
| 7,429,692 | B2 | 9/2008 | Dang |
| 7,598,367 | B2 | 10/2009 | Cook et al. |
| 2002/0023281 | A1 | 2/2002 | Gorlach et al. |
| 2006/0021083 | A1 | 1/2006 | Cook |
| 2006/0041952 | A1 | 2/2006 | Cook |
| 2006/0260004 | A1 | 11/2006 | Fang et al. |
| 2007/0006335 | A1 | 1/2007 | Cook |

FOREIGN PATENT DOCUMENTS

| | | |
|---|---|---|
| WO | 2005/098007 | 10/2005 |
| WO | 2006/005023 | 1/2006 |
| WO | 2006/034479 | 3/2006 |

OTHER PUBLICATIONS

Bowie et al, Science 247:1306-1310, 1990.*
McConnell et al, Nature 411 (6838):709-713, 2001.*
U.S. Appl. No. 60/505,689, filed Sep. 23, 2003, Cook.
U.S. Appl. No. 60/518,075, filed Nov. 6, 2003, Pennell.
U.S. Appl. No. 60/544,771, filed Feb. 13, 2004, Cook.
U.S. Appl. No. 60/558,869, filed Apr. 1, 2004, Cook.
U.S. Appl. No. 60/583,691, filed Jun. 30, 2004, Alexandrov.
U.S. Appl. No. 60/637,140, filed Dec. 16, 2004, Feldman.
U.S. Appl. No. 60/757,544, filed Jan. 9, 2006, Dang.
U.S. Appl. No. 60/776,307, filed Feb. 24, 2006, Kwok.
Bateman et al., "Pfam 3.1: 1313 multiple alignments and profile HMMs match the majority of proteins" *Nucl. Acids Res.*, 27(1):260-262 (1999).
Bechtold and Pelletier, "In Planta *Agrobacterium*-mediated transformation of adult *Arabidopsis thaliana* plants by vacuum infiltration," *Methods Mol. Biol.*, 1998, 82: 259-266.
Bowie et al, (1990, Science 247:1306-1310).
Boylan et al., "Phytochrome a overexpression inhibits hypocotyl elongation in transgenic Arabidopsis," *Proc. Natl. Acad. Sci.*, 1991, 88(23): 10806-10810.
Bustos et al., "Regulation of b-glucuronidase expression in transgenic tobacco plants by an A/T-rich, cis-acting sequence found upstream of a French bean b-phaseolin gene" *Plant Cell*, 1(9):839-854(1989).
Cerdan and Chory, "Regulation of flowering time by light quality," *Nature*, 2003, 423: 881-885.
Cerdan et al., "A 146 bp fragment of the tobacco Lhcb 1 2 promoter confers very-low-fluence, low-fluence and high-irradiance responses of phytochrom to a minimal CaMV 35S promoter" *Plant Mol. Biol.*, 33:245-255 (1997).
Chen et al., "RF12, a RING-domain zinc finger protein, negatively regulates Constans expression and photoperiodic flowering," *Plant J.*, 2006, 46(5): 823-833.
Chenna et al., "Multiple sequence alignment with the Clustal series of programs" *Nucleic Acids Res.*, 31(13):3497-3500 (2003).
Dai et al., "RF2b, a rice bZIP transcription activator, interacts with RF2a and is involved in symptom development of rice tungro disease" *Proc. Natl. Acad. Sci. USA*, 101(2):687-692 (2004).
Dieffenbach and Dveksler, "PCR Primer: A Laboratory Manual," Cold Spring Harbor Laboratory Press, 1995.
Do et al., "ProbCons: Probabilistic consistency-based multiple sequence alignment," *Genome Res.*, 2005, 15(2): 330-340.
Durbin et al., "3-Markov chains and hidden Markov models; 4-Pairwise alignment using HMMS; 5-Profile HMMs for sequence families" In Biological Sequence Analysis: Probabilistic Models of Proteins and Nucleic Acids, (Cambridge University Press, Cambridge, UK, 1998), pp. 47-134.
Fejes et al., "A 268 bp upstream sequence mediates the circadian clock-regulated transcription of the wheat Cab-1 gene in transgenic plants" *Plant Mol. Biol.*, 15:921-932 (1990).

(Continued)

*Primary Examiner* — Stuart F Baum
(74) *Attorney, Agent, or Firm* — Fish & Richardson P.C.

(57) ABSTRACT

Methods and materials for modulating (e.g., increasing or decreasing) low light tolerance in plants are disclosed. For example, nucleic acids encoding polypeptides that confer plants with tolerance to low light are disclosed as well as methods for using such nucleic acids to transform plant cells. Also disclosed are plants having increased low light tolerance and plant products produced from plants having increased low light tolerance.

17 Claims, 5 Drawing Sheets

(56) References Cited

OTHER PUBLICATIONS

Fromm et al., "An octopine synthase enhancer element directs tissue-specific expression and binds ASF-1, a factor from tobacco nuclear extracts" *The Plant Cell*, 1:977-984 (1989).
Green et al., "Binding site requirements for pea nuclear protein factor GT-1 correlate with sequences required for light-dependent transcriptional activation of the rbcS-3A gene" *EMBO J.*, 7:4035-4044 (1988).
Hu et al., "Characterization of a novel putative zinc finger gene MIF1: involvement in multiple hormonal regulation of Arabidopsis development", *Plant J.*, 2006, 45: 399-422.
Jordano et al., "A sunflower helianthinin gene upstream sequence ensemble contains an enhancer and sites of nuclear protein interaction" *Plant Cell*, 1:855-866 (1989).
Keller and Baumgartner, "Vascular-specific expression of the bean GRP 1.8 gene is negatively regulated" *Plant Cell*, 3(10):1051-1061 (1991).
Kim et al. (2003, NCBI Accession No. BT010401).
Luan et al., "A rice cab gene promoter contains separate cis-acting elements that regulate expression in dicot and monocot plants" *The Plant Cell*, 4:971-981 (1992).
Lubberstedt et al., "Promoters from genes for plastid proteins possess regions with different sensitivities toward red and blue light" *Plant Physiol.*, 104:997-1006 (1994).
Matsuoka et al., "Tissue-specific light-regulated expression directed by the promoter of a C4 gene, maize pyruvate, orthophosphate dikinase, in a C3 plant, rice," Proc. Natl. Acad. Sci. USA, Oct. 1993, 90:9586-9590.
McConnell et al. (2001, Nature 411 (6838): 709-713).
Medberry et al., "The Commelina yellow mottle virus promoter is a strong promoter in vascular and reproductive tissues" *Plant Cell*, 4(2):185-192 (1992).
Meier et al., "Elicitor-inducible and constitutive in vivo DNA footprints indicate novel cis-acting elements in the promoter of a parsley gene encoding pathogenesis-related protein 1" *Plant Cell*, 3:309-316 (1991).
Pfam web cite (describing concensus sequences for a variety of protein motifs and domains at sanger.ac.uk/Pham and genome.wustl.edu.Pfan, 2006.
Rivera et al, "Genomic evidence for two functionally distinct gene classes" *Proc. Natl. Acad. Sci. USA* ,95:6239-6244 (1998).
Sonnhammer et al., "Pfam: A comprehensive database of protein domain families based on seed alignments" *Proteins*, 28:405-420 (1997).
Sonnhammer et al., "Pfam: multiple sequence alignments and HMM-profiles of protein domains" *Nucl. Acids Res.*, 26:320-322 (1998).
Takeda et al. (2011, The Plant Journal 66:1066-1077).
Truernit et al., "The promoter of the *Arabidopsis thaliana* SUC2 sucrose-$H^+$ symporter gene directs expression of β-glucuronidase to the phloem: Evidence for phloem loading and unloading by SUC2" *Planta*, 1995, 196:564-570.
Tseng et al., "Spindly and Gigantea interact and act in Arabidopsis thaliana pathways involved in light responses, flowering, and rhythms in cotyledon movement," *Plant Cell*, 2004, 16(6): 1550-1563.
Yamamoto et al., "The promoter of a pine photosynthetic gene allows expression of a β-glucuronidase reporter gene in transgenic rice plants in a light-independent but tissue-specific manner" *Plant Cell Physiol.*, 1994, 35:773-778.
Zhang et al., "DNA sequences that activate isocitrate lyase gene expression during late embryogenesis and during postgerminative growth," *Plant Physiology*, 110:1069-1079 (1996).
Zhao et al., "Overexpression of LSH1, a member of an uncharacterised gene family, causes enhanced light regulation of seedling development," *Plant J.*, 2004, 37(5): 694-706.

* cited by examiner

```
SEQ-ID-NO-118-CLONE-870022    ----------M ASHSNKGKGI AEGSSQPQSQ P------QPQP HQPQSPPNPP  36
SEQ-ID-NO-112-CLONE-832857    ----------M TSTNTRNKGK CIVE------ ---------- -------GPPP  19
SEQ-ID-NO-100-CLONE-1285138   ----------- MSSDRHTPTK DPPDHPSSSS N-------HHKQ P---LPPQPQQ  33
SEQ-ID-NO-114-CLONE-847799    ----------- MSSDRHTPTK DPPDHPSSSS N-------HHKQ P---LPPQPQQ  33
SEQ-ID-NO-108-CLONE-1505805   MNSIQEME--- -SSNSENTSF NSIGNSNTTN T------AMSV S-NLPPPSST  41
SEQ-ID-NO-110-CLONE-828846    MDMIPQLMEG SSAYGGVINL NIISNNSSSV TGATGGEATQ PLSSSSSPSA  50
SEQ-ID-NO-120-CLONE-1025179   MDHIIGFM-G TTNMSHNTNL MIAAAATTTT T-------SSSS SSSSGGSGTN  44
SEQ-ID-NO-128-CLONE-964932    MDPIHGFM-S TSNISHNTNL MIAAAAATTT T-------TSSS SSSSGGSATN  44
SEQ-ID-NO-104-CLONE-1373087   ----------M DPSGPGPSSA AAGGAPAVAA A---------- ------PQPPA  27
SEQ-ID-NO-106-CLONE-1440417   MDSTSGGATA PGPNSGEPCP SAATAGSSSA S-------QPQQ Q-PEGSSPPA  44
SEQ-ID-NO-126-CLONE-604111    MASASGEAPP PQPTSTEAAP ASGSSAPAIS A-------APPQ P----GGSSPA  42
SEQ-ID-NO-146-CLONE-604111    MASASGGAPP PQPTSTEAAP ASGSSAPAIS A-------APPQ P----GGSSPA  42
SEQ-ID-NO-88-CLONE-28780      ----------M ESADSGRSDP VKGDDPGPSF V---------- -------SSPPA  27
SEQ-ID-NO-122-CLONE-1084747   ----------- MDSGSQRPGP VSEGDPGPSI V-------TP-- ------SSPPA  28
SEQ-ID-NO-116-CLONE-856813    ----------- ---------- MEGETAAKAA A---------- -------SSSS  15
SEQ-ID-NO-124-CLONE-1464359   ----------- ---------- MEGETAVKAA A---------- -------SSSS  15

SEQ-ID-NO-118-CLONE-870022    ALSRYESQKR RDWNTFCQYL RNQQPPVHIS QCGSNHILDF LQYLDQFGKT  86
SEQ-ID-NO-112-CLONE-832857    TLSRYESQKS RDWNTFCQYL MTKMPPVHVW ECESNHILDF LQSRDQFGKT  69
SEQ-ID-NO-100-CLONE-1285138   PLSRYESQKR RDWNTFVQYL KSQNPPLMMS QFDYTHVLSF LRYLDQFGKT  83
SEQ-ID-NO-114-CLONE-847799    PLSRYESQKR RDWNTFVQYL KSQNPPLMMS QFDYTHVLSF LRYLDQFGKT  83
SEQ-ID-NO-108-CLONE-1505805   TPSRYENQKR RDWNTFGQYL KNHRPPLSLS RCSGAHVLEF LRYLDQFGKT  91
SEQ-ID-NO-110-CLONE-828846    NSSRYENQKR RDWNTFGQYL RNHRPPLSLS RCSGAHVLEF LRYLDQFGKT 100
SEQ-ID-NO-120-CLONE-1025179   QLSRYENQKR RDWNTFGQYL RNHRPPLSLS RCSGAHVLEF LRYLDQFGKT  94
SEQ-ID-NO-128-CLONE-964932    QLSRYENQKR RDWNTFGQYL RNHRPPLSLS RCSGAHVLEF LRYLDQFGKT  94
SEQ-ID-NO-104-CLONE-1373087   QLSRYESQKR RDWNTFLQYL RNHRPPLTLA RCSGAHVIEF LRYLDQFGKT  77
SEQ-ID-NO-106-CLONE-1440417   PPSRYESQKR RDWNTFLQYI KNHKPPLTLA RCSGAHVIEF LKYLDQFGKT  94
SEQ-ID-NO-126-CLONE-604111    PPSRYESQKR RDWNTFLQYL QNHKPPLTLA RCSGAHVIEF LKYLDQFGKT  92
SEQ-ID-NO-146-CLONE-604111    PPSRYESQKR RDWNTFLQYL QNHKPPLTLA RCSGAHVIEF LKYLDQFGKT  92
SEQ-ID-NO-88-CLONE-28780      TPSRYESQKR RDWNTFLQYL KNHKPPLALS RCSGAHVIEF LKYLDQFGKT  77
SEQ-ID-NO-122-CLONE-1084747   APSRYESQKR RDWTTFLQYL KNHKPPLSLS RCSGAHAIEF LKYLDQFGKT  78
SEQ-ID-NO-116-CLONE-856813    SPSRYESQKR RDWNTFLQYL RNHKPPLNLS RCSGAHVLEF LKYLDQFGKT  65
SEQ-ID-NO-124-CLONE-1464359   SPSRYESQKR RDWNTFLQYL KNHKPPLTLS RCSGAHVIEF LKYLDQFGKT  65
```

Figure 1

```
SEQ-ID-NO-118-CLONE-870022    KVHI HGCVFF GQVEPAGQCN CPLKQAWGSL DALI GRLRAA FEE-NGGLPE   135
SEQ-ID-NO-112-CLONE-832857    KVHI QGCVFF GQKEPPGECN CPLKQAWGSL DALI GRLRAA YEE-NGGLTE   118
SEQ-ID-NO-100-CLONE-1285138   KVHHQACVFF GQPDPPGPCT CPLKQAWGSL DALI GRLRAA YEEHGGGSPD   133
SEQ-ID-NO-114-CLONE-847799    KVHHQACVFF GQPDPPGPCT CPLKQAWGSL DALI GRLRAA YEEHGGGSPD   133
SEQ-ID-NO-108-CLONE-1505805   KVHTPI CPFY GHPNPPAPCP CPLRQAWGSL DALI GRLRAA FEE-NGGKPE   140
SEQ-ID-NO-110-CLONE-828846    KVHTNI CHFY GHPNPPAPCP CPLRQAWGSL DALI GRLRAA FEE-NGGKPE   149
SEQ-ID-NO-120-CLONE-1025179   KVHTHLCPFF GHPNPPAPCA CPLRQAWGSL DALI GRLRAA FEE-NGGSPE   143
SEQ-ID-NO-128-CLONE-964932    KVHMQI CPFF GHPNPPAPCT CPLRQAWGSL DALI GRLRAA FEE-NGGSPE   143
SEQ-ID-NO-104-CLONE-1373087   KVHASGCAFY GQPSPPGPCP CPLRQAWGSL DALI GRLRAA YEE-SGGTPE   126
SEQ-ID-NO-106-CLONE-1440417   KVHI TGCPYF GHPNPPAPCS CPLKQAWGSL DALI GRLRAA YEE-NGGLPE   143
SEQ-ID-NO-126-CLONE-604111    KVHI TGCPYY GYPNPPAPCA CPLKQAWGSL DALI GRLRAA YEE-NGGRPE   141
SEQ-ID-NO-146-CLONE-604111    KVHI TGCPYY GYPNPPAPCA CPLKQAWGSL DALI GRLRAA YEE-NGGRPE   141
SEQ-ID-NO-88-CLONE-28780      KVHVAACPYF GHQQPPSPCS CPLKQAWGSL DALI GRLRAA YEE-NGGRPD   126
SEQ-ID-NO-122-CLONE-1084747   KVHVAACPYF GHQQPPSPCA CPLKQAWGSL DALI GRLRAA YEE-NGGRPE   127
SEQ-ID-NO-116-CLONE-856813    KVHATACPFF GQPNPPSQCT CPLKQAWGSL DALI GRLRAA FEE- GGGLPE   115
SEQ-ID-NO-124-CLONE-1464359   KVHVAACPFF GVPYPPAQCT CPLRQAWGSL DSLI GRLRAA FEE- GGGLPE   115

SEQ-ID-NO-118-CLONE-870022    RNPFAGGGI R VFLREVRDSQ AKARGVPYKK RKKRKK---- ----------   171
SEQ-ID-NO-112-CLONE-832857    KNPFARGGI R I FLREVRGSQ AKARGVLYKK KKRLVV---- ----------   154
SEQ-ID-NO-100-CLONE-1285138   TNPFANGSI R VHLREVRESQ AKARGI PYRK KKRRKT---- ----------   169
SEQ-ID-NO-114-CLONE-847799    TNPFANGSI R VHLREVRESQ AKARGI PYRK KKRRKT---- ----------   169
SEQ-ID-NO-108-CLONE-1505805   ANPFGARAVR LYLREVRDLQ SKARGI SYEK KKRKRP-PQQ QI QALPLPLP   189
SEQ-ID-NO-110-CLONE-828846    TNPFGARAVR LYLREVRDMQ SKARGVSYEK KKRKRP---- ----LPSSST   191
SEQ-ID-NO-120-CLONE-1025179   TNPFCARAVR LYLREVRDSQ AKARGI SYEK KKRKRP---- ----------   179
SEQ-ID-NO-128-CLONE-964932    TNPFGARAVR LYLREVRDSQ AKARGI SYEK KKRKRP---- ---------P   180
SEQ-ID-NO-104-CLONE-1373087   SNPFAARAVR I YLREVRDSQ AKARGI PYEK KKRKRSQAAQ PAGVEPSGSS   176
SEQ-ID-NO-106-CLONE-1440417   SNPFGARAVR I YLREVREGQ AKARGI PYEK KKKRKR-PNV AVSVASVSVK   192
SEQ-ID-NO-126-CLONE-604111    SNPFGARAVR I YLREVREGQ AKARGI PYEK KKRKRT-TVV TVSSGGGGSS   190
SEQ-ID-NO-146-CLONE-604111    SNPFGARAVR I YLREVREGQ AKARGI PYEK KKRKRT-TVV TVSSGGGGSS   190
SEQ-ID-NO-88-CLONE-28780      SNPFAARAVR I YLREVRESQ AKARGI PYEK KKRKRP---- -----PTVTT   167
SEQ-ID-NO-122-CLONE-1084747   SNPFAARAVR I YLREVRESQ AKARGRPYEK KKRKRP---- -----TTVTT   168
SEQ-ID-NO-116-CLONE-856813    SNPFAAKAVR I YLKEVROTQ AKARGI PYDK KKRKRP---- --------HT   153
SEQ-ID-NO-124-CLONE-1464359   SNPLAAKAI R I YLKEVRETQ AKARGI PYDK KKRKRP---- --------RT   153
```

Figure 1 (continued)

```
SEQ-ID-NO-118-CLONE-870022     -RNPMKSHDG EDGTTGTSSS SNLAS----- ---------- ---------- 195
SEQ-ID-NO-112-CLONE-832857     ---------- -----VGTGT STTWT----- ---------- ---------- 164
SEQ-ID-NO-100-CLONE-1285138    -KNEVVVVKK DVANSSTPNQ ---------- ---------- ---------- 188
SEQ-ID-NO-114-CLONE-847799     -KNEVVVVKK DVANSSTPNQ SFT------- ---------- ---------- 191
SEQ-ID-NO-108-CLONE-1505805    LPMPPPPARS ADTMNLLLMQ TVVVILLVMG LAVVLWSVLG LRASIIALTF 239
SEQ-ID-NO-110-CLONE-828846     SSSSAVASHQ QFQMLPGTSS TTQLKFEK-- ---------- ---------- 219
SEQ-ID-NO-120-CLONE-1025179    -PPPLPPAQP AISSSPN--- ---------- ---------- ---------- 195
SEQ-ID-NO-128-CLONE-964932     QAPLPPPHQP VISNSPNLQ- ---------- ---------- ---------- 199
SEQ-ID-NO-104-CLONE-1373087    SAAAAAAGGG DAGSCGGAAA TTTAQPCGSC TAPSAS---- ---------- 212
SEQ-ID-NO-106-CLONE-1440417    AAAGGSNSGG CEESGGGGDS SAAATSAAAA AA----TTTV ---------- 228
SEQ-ID-NO-126-CLONE-604111     GAVASPSGGG DTAIGGGAGS SASLTSSATA TANDTTTTV- ---------- 229
SEQ-ID-NO-146-CLONE-604111     CAVASPSCCC DTALCGCACS SASLTSSATA TANDTTTTV- ---------- 229
SEQ-ID-NO-88-CLONE-28780       VRVDVASSRQ SDCDPCNVCA PSVAEAVPP- ---------- ---------- 196
SEQ-ID-NO-122-CLONE-1084747    VRVDVAPSRQ SEGDGCNIGD PSSLAEAVPP ---------- ---------- 198
SEQ-ID-NO-116-CLONE-856813     DTATPIACDC DDAEGSG-GA ALVVTAATTV ---------- ---------- 182
SEQ-ID-NO-124-CLONE-1464359    AKETQKPDDG ECAGCSGSGD SALVISATVV ---------- ---------- 183

SEQ-ID-NO-118-CLONE-870022     -  195
SEQ-ID-NO-112-CLONE-832857     -  164
SEQ-ID-NO-100-CLONE-1285138    -  188
SEQ-ID-NO-114-CLONE-847799     -  191
SEQ-ID-NO-108-CLONE-1505805    V  240
SEQ-ID-NO-110-CLONE-828846     -  219
SEQ-ID-NO-120-CLONE-1025179    -  195
SEQ-ID-NO-128-CLONE-964932     -  199
SEQ-ID-NO-104-CLONE-1373087    -  212
SEQ-ID-NO-106-CLONE-1440417    -  228
SEQ-ID-NO-126-CLONE-604111     -  229
SEQ-ID-NO-146-CLONE-604111     -  229
SEQ-ID-NO-88-CLONE-28780       -  196
SEQ-ID-NO-122-CLONE-1084747    -  198
SEQ-ID-NO-116-CLONE-856813     -  182
SEQ-ID-NO-124-CLONE-1464359    -  183
```

Figure 3:
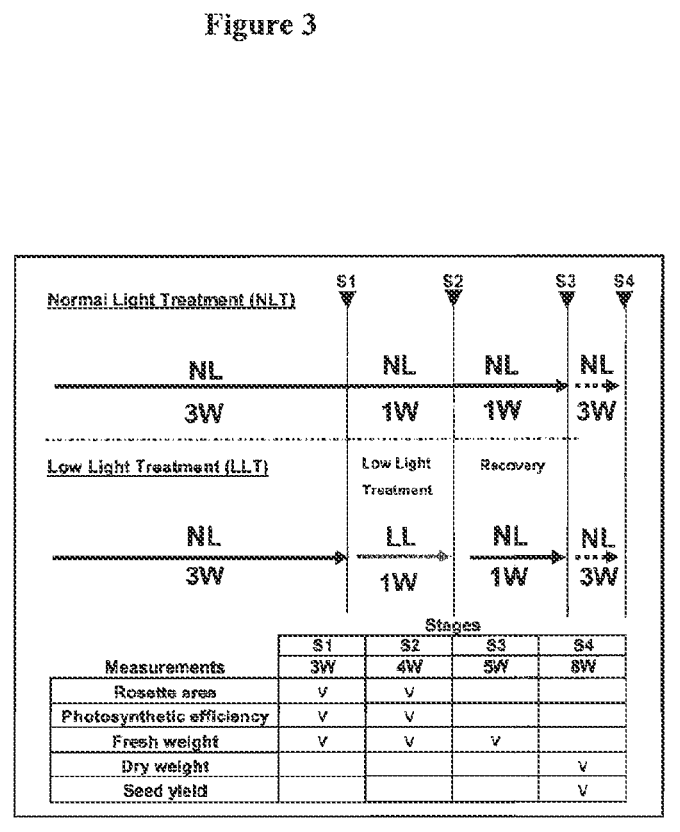

Normal Light Treatment (NLT)

S1 S2 S3 S4

NL 3W → NL 1W → NL 1W → NL 3W

Low Light Treatment (LLT)

NL 3W → LL 1W (Low Light Treatment) → NL 1W (Recovery) → NL 3W

| Measurements | Stages S1 3W | S2 4W | S3 5W | S4 8W |
|---|---|---|---|---|
| Rosette area | V | V | | |
| Photosynthetic efficiency | V | V | | |
| Fresh weight | V | V | V | |
| Dry weight | | | | V |
| Seed yield | | | | V |

SEQUENCE LISTING

```
<160> NUMBER OF SEQ ID NOS: 146

<210> SEQ ID NO 1
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 21876

<400> SEQUENCE: 1

gtctcttaaa aaggatgaac aaacacgaaa ctggtggatt atacaaatgt cgccttatac     60

atatatcggt tattggccaa aagagctatt ttaccttatg gataatggtg ctactatggt    120

tggagttgga ggtgtagttc aggcttcacc ttctggttta agccctccaa tgggtaatgg    180

taaatttccg gcaaaaggtc ctttgagatc agccatgttt tccaatgttg aggtcttata    240

ttccaagtat gagaaaggta aaataaatgc gtttcctata gtggagttgc tagatagtag    300

tagatgttat gggctacgaa ttggtaagag agttcgattt tggactagtc cactcggata    360

ctttttcaat tatggtggtc ctggaggaat ctcttgtgga gtttgatatt tgcgagtata    420

atctttgaac ttgtgtagat tgtacccaaa accgaaaaca tatcctatat aaatttcatt    480

atgagagtaa aattgtttgt tttatgtatc atttctcaac tgtgattgag ttgactattg    540

aaaacatatc ttagataagt ttcgttatga gagttaatga tgattgatga catacacact    600

cctttatgat ggtgattcaa cgttttggag aaaatttatt tataatctct cataaattct    660

ccgttattag ttgaataaaa tcttaaatgt ctcctttaac catagcaaac caacttaaaa    720

atttagattt taaagttaag atggatattg tgattcaacg attaattatc gtaatgcata    780

ttgattatgt aaaataaaat ctaactaccg gaatttattc aataactcca ttgtgtgact    840

gcatttaaat atatgtttta tgtcccatta attaggctgt aatttcgatt tatcaattta    900

tatactagta ttaatttaat tccatagatt tatcaaagcc aactcatgac ggctagggtt    960

ttccgtcacc ttttcgatca tcaagagagt ttttttataa aaaaatttat acaattatac   1020

aatttcttaa ccaaacaaca cataattata agctatttaa catttcaaat tgaaaaaaaa   1080

aatgtatgag aattttgtgg atccattttt gtaattcttt gttgggtaaa ttcacaacca   1140

aaaaaataga aaggcccaaa acgcgtaagg gcaaattagt aaaagtagaa ccacaaagag   1200

aaagcgaaaa ccctagacac ctcgtagcta taagtaccct cgagtcgacc aggattaggg   1260
```

```
tgcgctctca tatttctcac attttcgtag ccgcaagact cctttcagat tcttacttgc   1320

aggttagata ttttctctct ttagtgtctc cgatcttcat cttcttatga ttattgtagc   1380

tgtttagggt ttagattctt agttttagct ctatattgac tgtgattatc gcttattctt   1440

tgctgttgtt atactgcttt tgattctcta gctttagatc cgtttactcg tcgatcaata   1500

ttgttcctat tgagtctgat gtataatcct ctgattaatt gatagcgttt agttttgata   1560

tcgtcttcgc atgtttttta tcatgtcgat ctgtatctgc tctggttata gttgattctg   1620

atgtatttgg ttggtgatgt tccttagatt tgatatacct gttgtctcgt ggtttgatat   1680

gatagctcaa ctggtgatat gtggttttgt ttcagtggat ctgtgtttga ttatattgtt   1740

gacgttttgg ttgttgtatg gttgatggtt gatgtatttt tgttgattct gatgtttcga   1800

tttttgtttt tgttttgaca gct                                            1823


<210> SEQ ID NO 2
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 2

atagagtttt actatgcttt tggaatcttt cttctaatgt gccaactaca gagaaataca     60

tgtattacca ctaggaatcg gaccatatca tagatatcag gattagataa ctagttctcg    120

tcgctatcac ttcgcattaa gttctagtaa ttgttaaaga ttctaatttt ttactaaaca    180

aaaactaaat caacatcaaa tatgcaaagt gtgtgttgtc cacacaagtg actcaaagta    240

tacgcaggtg ggattggacc atattattgc aaatcgtttc cgaaccactc atatttcttt    300

ttttctctcc tttttttatc cggagaatta tggaaccact tcatttcaac ttcaaaacta    360

attttttggt tcagtgatca aatacaaaaa aaaaaaaaaa gttatagata ttaaatagaa    420

aactattcca atcttaaaaa tacaaatgaa accataattt taatttatac aaaactattt    480

aattagctaa gggttgtctt aacgtttaga aaataaaaaa ttatgattgt ctgtttaaaa    540

ttacaatgaa tgaataaaaa aaatatgcaa tgaatgaaag aataaatttt gtacatccga    600

tagaatgaga aaatgaattt tgtacaaacc actcaagaat tcaaaacaat tgtcaaagtt    660

ttcttctcag ccgtgtgtcc tcctctccta gccgccacat ctcacacact aatgctaacc    720

acgcgatgta accgtaagcg ctgagttttt gcatttcaga tttcacttcc accaaacaaa    780

actcgccacg tcatcaatac gaatcattcc gtataaacgt ctagattctt tacagcctac    840

aatgttctct tctttggtcg gccattattt aacgctttga acctaaatct agcccagcca    900

acgaagaaga cgaagcaaat ccaaaccaaa gttctccatt ttcgtagctt ctttaagctt    960

tttcagtatc atagagacac tttttttttt ttgattagaa                        1000


<210> SEQ ID NO 3
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 3

ttagtgaaat tatgacatta agtaaggttt tcttagttag ctaatgtatg gctattcaat     60

tgttatgtta ggctatttta gttagtatat gaatttaggc agtctatgca aatgatttcg    120
```

```
ttttcatttt ttcatatgta aacatcaaga tcaagtaacg ccattcgagt tgatattttt    180

tttttaaatt agtgtgtgta aattttggac cgcttatttg agtttgctaa tgaagttgca    240

tatatattac gttaaaccat aggcaaacta atttgaaaca tccgattcga tttcctgtaa    300

tttttcttgg ttaattgacc aaaatcaaga tcttcagaaa taaaataaaa gacgaaagaa    360

agctgtcgca aagcagattg tgttaaaaaa aagtggattg ggctcaaacg caacttgtcc    420

agcccgtgac aattacccta tacgcaagta agagtaacgt atcactggca aaagttggta    480

ttagttacga tatctttgtc atgggggcat gcatgggcat ggcttaagag ttaagcctta    540

agaagagtcc cacactcgtg actctcatga tcacttgttg tttcttacgg gcaaatacat    600

ttaactttat tcttcattta ttcacctata ttcttttgga taataacttt tctctatata    660

aaataacaaa catcgtacgt ttcatttatt tacaacaagc gatgagaatt aaaaggagac    720

cttaattgat gatactcttc ttttctctcg gttacaacgg gattattaca gataatgata    780

atctatatgg atgctgacgt ggaaaaacaa aatttggtga aacacgtcaa ttaagcacga    840

cttttccatg gctagtggct aagatcgttt catcacatgg ctatatcata taatacttgg    900

atgaattcaa aataaacgac tgagaaaatg tccacgtcac ggcgcaccgc tttggactta    960

agtctcctat aataaataca acaccaaaca ttgcattcca                         1000
```

<210> SEQ ID NO 4
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 4

```
tgaagtcatt taatatgagt ttgacattag gtaaacctaa tctatgagat tatagaatgt     60

agcaaaacta tcaatgtttc ttttccaaaa tattttgtgg tttttctttt tggttcatta    120

tgttttgtta tttgtgaatt attttaatat gaagtaatta tattgatttt atatgatata    180

catattattt tgatataaaa tttaacactt atccattaaa atagcatggg cataatcaaa    240

atcgggacta ttacgatgaa aaagatagtt aaattgtatg ataaaataaa atgtgtaaga    300

ttaaaatttt gggttttaga aaattactaa acaaaatata gacaaagtat gttgactatt    360

atttaaaatt taaatatcat caataagata tagttaaagt cattaagtgt atagcaaaat    420

gaaaattcta agattaaaat tcgattaaaa tttttttttac taaattaaat atttaaaaat    480

agggattatc atttactatt tacaattcta atatcatggg taaaaattga taactttttt    540

taaacccgcc tatctaggtg ggcctaacct agtttactaa ttactatatg attaacttat    600

taccactttt acttcttctt ttttggtcaa attactttat tgttttttat aaagtcaaat    660

tactctttgc attgtaaata atagtagtaa ctaaaatctt aaaacaaaat attcaacctt    720

tcccattatt ggaatggtaa tgtcttcaac accattgacc aacgttaagg aatgtctttt    780

aatatttttg gaacctaaat gctaatactg tataccacaa tcacttatga gtattgaagt    840

tgagatagag gaggtacaag gagaccttat ctgcagaaga caaaaagcca tttttagcaa    900

aactaaagaa agaaaaaaga ttgaaacaca aatatgcgcc actcgtagtc cacccctatc    960

tctttggcaa aagccacttc actctttttc cctttttat                           999
```

<210> SEQ ID NO 5
<211> LENGTH: 1000

<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 5

```
ttaatactaa cattgtagaa agccacaaaa aagaaattga aatgtgagta gatgctgagt     60

cagaggtttg gtcaatacac aacagctaat tgagataata ttatacacgt cacgatgact    120

tgtttttct cctcccaact tgttaatttc tttattctta aaattaaacc atcgcaaaaa    180

cagaagaaca cagctgtttt tctcgactcc caatttctat tttgctgcta aggacatttc    240

atttcattat ttcccaattc aggactcctt agattttcct aaatttgttt tcctaacttg    300

ctctctctca ttctaacatt ttctcatttt tttagattat cttgtacttt ttagtagatt    360

attttatcag gttttacaaa catacattga cattctaaaa agggcttcta aaaattcagt    420

gtggaatgct gatatactaa aaaaaggtca tgcaaaatta tctacgattt atctaaaatt    480

agataatttg ccatatataa ctattaacta ataatcgatc ctttgatttt ttgtttagat    540

aaaacgaaac agctatatct tttttttttg ttatcggatt ttaatcgaat aaaagctgaa    600

aaataacagt tatatcttct tcttttttaa ctaatgaaac agttatatct taaacaaaca    660

acagaaacag taaaatatta atgcaaatcc gcgtcaagag ataaatttta acaaactaat    720

aacaattgag ataagattag cgcaaaagaa actctaattt tagagcgtgt aaacacaaac    780

acgtcttgaa agtaaacgtg aattacacgc ttctaaaacg agcgtgagtt ttggttataa    840

cgaagatacg gtgaagtgtg acacctttct acgttaattt cagtttgagg acacaactca    900

agttatgttt gatatctaag gacttgcact gtctccaaat ctgcaggaag gactttttga    960

ttggatcaat ataaatacca tctccattct cgtctccttc                          1000
```

<210> SEQ ID NO 6
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 6

```
gatcatgatc agtttcaact cgctgtgccc acgtgtcgag agatcggcac gtgcctgagc     60

tctcagccgc tcataaatac acttgtttag tagcaacagt atactatagt agtcctctcc    120

tgtttggctt ttagcttgca tcgatggatg gatggatgga tcgcatgaga gggcttcgcg    180

aaggtacgga accttacaca acgcgtgtcc tttctacgtg gccatcgtgt aggcgtctcg    240

ccatgctacg tgtcccggag gatgtctcga tgccaaccct tataaatact gttccattcc    300

aatcccatcg ccacagccag tgcaaatctg atcgatcaag ataatcgagc a             351
```

<210> SEQ ID NO 7
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 7

```
cccgatcggc cttaatctga gtcctaaaaa ctgttatact taacagttaa cgcatgattt     60

gatggaggag ccatagatgc aattcaatca aactgaaatt tctgcaagaa tctcaaacac    120
```

```
ggagatctca aagtttgaaa gaaaatttat ttcttcgact caaaacaaac ttacgaaatt    180
taggtagaac ttatatacat tatattgtaa ttttttgtaa caaaatgttt ttattattat    240
tatagaattt tactggttaa attaaaaatg aatagaaaag gtgaattaag aggagagagg    300
aggtaaacat tttcttctat tttttcatat tttcaggata aattattgta aaagtttaca    360
agatttccat ttgactagtg taaatgagga atattctcta gtaagatcat tatttcatct    420
acttctttta tcttctacca gtagaggaat aaacaatatt tagctccttt gtaaatacaa    480
attaattttc gttcttgaca tcattcaatt ttaattttac gtataaaata aaagatcata    540
cctattagaa cgattaagga gaaatacaat tcgaatgaga aggatgtgcc gtttgttata    600
ataaacagcc acacgacgta aacgtaaaat gaccacatga tgggccaata gacatggacc    660
gactactaat aatagtaagt tacattttag gatggaataa atatcatacc gacatcagtt    720
tgaaagaaaa gggaaaaaaa gaaaaaataa ataaaagata tactaccgac atgagttcca    780
aaaagcaaaa aaaaagatca agccgacaca gacacgcgta gagagcaaaa tgactttgac    840
gtcacaccac gaaaacagac gcttcatacg tgtcccttta tctctctcag tctctctata    900
aacttagtga gaccctcctc tgttttactc acaaatatgc aaactagaaa acaatcatca    960
ggaataaagg gtttgattac ttctattgga aagaaaaaaa tctttggaaa aggcctgcag   1020
gg                                                                  1022
```

<210> SEQ ID NO 8
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 8

```
catacttaat tctaaaaaaa caacacttat agtttataag cagctcttat gataaaaatc     60
tttctgagtt atagctctgt taaacttgta ttcaccccaa aaacggatgt ttcatttctt    120
attttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgatttttg ttttatcaac cacgtgtttc acttgatgag tagtttatat    300
agttaacatg attcggccac ttcagatttg ggtttgccca catatgacat accgacatag    360
aaggttaaat ccacgtggga aatgccaata ttcaatgttt ggttttcaaa agagaatcat    420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540
aaccctttca ttaaaaaata aaggtaacaa acaaaatttt gtattggaaa aaacattttt    600
tggaatatat aatttggtaa tagaattatg agcaaaaaag aaaaagaaaa gaaagaataa    660
tgagcataat aaagccttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
aaatccttaa gttatacgaa atcacgcttt tccttcgatt tctccgctct tctccactct    900
tcttctctgt tctatcgcag acatttttgt ttatatgcat acataataat aatacactct    960
tgtcaggatt tttgattctc tctttggttt tctcggaaaa                         1000
```

```
<210> SEQ ID NO 9
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 9

caagtcaagt tccaatattc taaggagaaa taatagtata ctaaacatac attagagagg     60

ttaaacttct ttttggattt aagtgtgtat gcataggcta tttattctta agtataacta    120

ttaactgtag ctagatttat acaagaaata cataaaactt tatgcatgtg aggtagccat    180

gaatatacgt acatgttgca atcgattata catgttgtat ttggatttct ctatacatgt    240

tttaacttgt cattctctaa gtatatacat accattaata ctgtgggcat gagtttatga    300

taagactttt cttttggaga ccagttttgt tttcctttcc acctatattt gtctataggc    360

ttcacggtac actagtttac aagtgttttt atatgttcta aataaaattg agattttccg    420

gaacggtatg atctgtttgc aaataaggac gtatatataa cagtatcaaa tatatttgtt    480

gttataaggc aataatatat tttctgagat attgcgtgtt acaaaaaaga aatatttgtt    540

aagaaaaaaa aagatggtcg aaaaagggga gtaggtgggg gcggtcggct tttgattagt    600

aataaaagaa accacacgag tgacctaccg attcgactca acgagtctac cgagctaaca    660

cagattcaac tcgctcgagc ttcgttttat gacaagttgg tttttttttt ttttttaat     720

tttttcatct tcttgggttt ggttgggtca ctcttcaggt caggtgtgta aaaaagaaag    780

aaagaaaaga gagattgttg tgttgtaacc cctttgacta aaatctaatg aacttttta     840

acacaacaaa actccttcag atctgaaagg gttcttcttc tctcttagtc tcttcgtcct    900

tttattctcc gtcgtcgttt catgatctga ctctctggtc ttctcttctt cttcttcttc    960

ttctattttt tcttacttcg tcactgttgt gtctgaac                            998


<210> SEQ ID NO 10
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 10

aaaaaggatg ggtaatggga cctattttcc ccaacatccc acatgcacac ttccctctcc     60

attctctcac atttatttct ttcattctaa tttatccatt ccgtgtgtaa catattcact    120

aataatctca tctcactaac tcattcattg attgtgatat gtttatctag aattagtgtt    180

ttaacactgt gtctacatat gatttccttt tcattgtatg tgaacatgtt aactcactaa    240

tcattttgta ttttcgagtt aacatgagtc tccacttcgg tagactaaag taaagatagg    300

tttgagtata ataaagttta aaatttgctt taaaatcaat atttataaat aagtttttat    360

cataagtgat ttttgtatgt tatattggac cttgtataaa cagactacag aagaaaatta    420

tttatgagaa cttgtaatgt tagagtggac ctcgtataaa ctaattatgt gggcttttac    480

cataaactat ttatgaaaat tattatggcc cacaccacta taactaaagc ccacatattt    540

agcagcccag tttcattgta agagacatgt tcgctctgga actagaattt tctggttttt    600

gggtatttgt tttcttatgt gtagagaaat gatggtaacg attaaatgtt gtgtattaca    660

atttacaatg gtaagacgat taatatattt acacacaatt ttgttgttgc tgtaacacgt    720
```

```
tagtgtgtgt gatgatagaa tttcataaag ctttaactac gaggggcaaa atgttaattc    780

taaatagttg acagcagaaa aagatatgta tacataatat aaggattaaa acgtaaataa    840

taataaataa ggcgagttaa attaaaaccc tgttaaaacc ctagcttgaa acacatgtat    900

aaaaacactt gcgagcgcag cttcatcgcc atcgccattc tctctctcat caaaagcttt    960

tctccttgat tttcgcattc tttagagtct taacgcaaag                         1000


<210> SEQ ID NO 11
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 11

cagccgtaaa tcctccataa atttattttg caagttttgc tcattatata atgagcggaa     60

tttatgatat aatcgtttgt aataatgtta tgttttgatc aaaatttgaa attaaaagta    120

ggtgagaact tgttatacag tgtagataag gtggatcttg aatataaaaa taaaatttat    180

aagatgtatt taaagcagaa aagcataaaa ctttagataa aataatgtaa aaatgtgtta    240

gcatcaatgt tgggatattg gccgacccga acttaatcaa tgtcggaagc cattacttct    300

ctcccaaaag accttttttcc ttcggagaac taggaacttc ctcactacct ttcgcttaac    360

gtgaaagcca taaatttcat atattcataa aaatcagaaa atctaaaact gtttagtatc    420

acctgttttt ggtatagact attggttttg tgttacttcc taaactatat gatttcgtac    480

ttcattggat cttatagaga tgaatattcg taaaaagata agttatctgg tgaaacgtta    540

cttcagtcat gttgggtcta gatttacata ctactatgaa acattttaag ataataatta    600

tcctagccaa ctatatgttc tatattatgg gccaagaaga tatagaacta aaagttcaga    660

atttaacgat ataaattact agtatattct aatacttgaa tgattactgt tttagttgtt    720

tagaataaat agtagcgtgt tggttaagat accatctatc cacatctata tttgtgtggg    780

ttacataaaa tgtacataat attatataca tatatatgta tatttttgat aaagccatat    840

attactcctt gacctctgcc cccatttcct tttactataa ataggaatac tcatgatcct    900

ctaattcagc aatcaacacc aacgaacaca accttttcca aagccaataa taaaagaaca    960

aaagctttta gtttcatcaa agacgaagct gccttagaa                           999


<210> SEQ ID NO 12
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 12

aagatagtac agtttcagtg ttttgagaaa aaaagctgaa ctaaaactaa aatgtttaag     60

gacacaatat ttagtttcaa ttagataatt caacagtttg aacaattttt tttttttttt    120

tttgaagtca tttatttata caatgtttta aaacgcatta agcatttagg cagccgacaa    180

acgcctattg tctaactgta aataggcgct tccacttagg ttcatattgc atatttacta    240

tatgtgtata gtgacaaaaa ccaatatttc tcttattttg gatgaaggta tagtagttgt    300

taaatgttca atataattaa gcattaatga caaataaaat aaaattaatt tagttgataa    360

aaagataatc ttataaaaag atcgatgaat agatataatg gtttactgaa ttctatagct    420
```

```
cttaccttgc acgactatgt cccaaggaga ggaagtacct taactataat tctgaacata    480

attttgtcta tcttggtgag tattatatga cctaaaccct ttaataagaa aaagtataat    540

actggcgtaa cgtaataaat taacacaatc ataagttgtt gacaagcaaa aaaacataca    600

taatttgttt aatgagatat attagttata gttcttatgt caaagtacaa ttatgcctac    660

caaaattaat taatgatttc aacaggaagt ctgagatgat gggccgacgt gtagttacgt    720

ttcttgaatt gtgagagatg gtatttatta tactgaagaa aacattattt actaaataaa    780

ttttcatttc acatcttctg taatcaatgc gggtagatga agaagttgtt aatacgatgg    840

ccaaccatat ggatctcttt tttggcgttt ctatatatag taacctcgac tccaaaggca    900

ttacgtgact caataaaatc aagtcttttg tttcctttta tccaaaaaaa aaaaaaagtc    960

ttgtgtttct cttaggttgg ttgagaatca tttcatttca                         1000


<210> SEQ ID NO 13
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 13

aattaaatga aaccgcccct aaattaggag ggatttgggt aagtggtaac acattcactg     60

gaaacatgtg aagaaaggag gatgtcaagt agctgaaaac tcagtatagt aaccaacggc    120

ttctcaccaa cctttcatta ataatttggt catccctata tttttattca acattttgtt    180

tttcaatagc ttagagcacc ttaatacctt tcagtgtttt tttataaaaa aaacaaaaat    240

tgggattaat catcaatccc caaatgtaac gtttacttag attatgttca tttttctata    300

cacacaaatc atattctttt gttttaatct tcgaaaaacg agaggacatt aaatacccct    360

aaaaaaggag gggacattac taccaacgta cattaacatg tttgatagca aacgatttat    420

tttgttcgtt ttgaaaaggg gaaagtaatg tgtaaattat gtaaagatta ataaactttt    480

atggtatagt aacattttcg aataataaga gagggaaaac actcgccatt gtcggcaatt    540

tagaaccaat attagaaggg ttttttaga gaaaaaggac ttaaaagttt agagacctta    600

acaacaactt atttagaaat agacatgctt aagttgacaa cagcgagttt attttctata    660

tcgaagaaaa atacgaactt tttcttaatt agatttcgaa tgcatgcact atcgagaatc    720

gaccgtcaca agaaaaaact aatatacata ctgtacatat ctatattcaa tattggtggg    780

gatgggttta atgtgtattt ataattcatg gataaattca cacaataagg tccatgaaac    840

tagaaggtac caaaaataag cattaatgac tctttgccac ttatatatat gattctctca    900

tagtaccatt ttattctccc aaacctatct tcttcttcct ctcttgtctc tctcgctctc    960

tctcttctac attgtttctt gaggtcaatc tattaaaa                           998


<210> SEQ ID NO 14
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 14

gattgaatga tgagtgtgca cccttgtatt actaataaaa aatttagcaa cagttataag     60
```

ctaacgtcat ccatgagtca ttcattagat tcactatttg cgttctcaaa aatcgaattg 120
ttaaaatttg agaagctcta atatacgagt caatgagatg tggcaaaagc atgtccttga 180
ccataaaatt tcgaggggtc aactcattag ataaggacaa gaatcaacca attgaaggcg 240
tcttctataa caagtttctt tattactaat attaaagtcc aatggggtga gggggagaag 300
aacttaaata aaaggaaata attggtaagt gaataaaatc taaatacgat actagatgat 360
tgatttgtgc tagtgcatgg tattagatca gatatgtgtt actattcgaa ttcaaattgg 420
catattccat gttgttgata agaaaattgt agaagtgtaa aagctgagtt actatattca 480
aactagtggt ttacataaag tgagacaaca actgtttcac aaaaatgact ataaaatagt 540
aagtagtatt aggtcaattg attttaaaat tttaatcaaa ttcaaatttg tgatataatc 600
aaatttgttt atagaaaatg ttaagaaatc aattttggca gaactaattc agtgagaaac 660
aatcatttac aaaaacaatt ttaacattat ttaacagtaa gatttgacat ttaacccgtt 720
cgtgtgaacc catcatatct aacatggctc tacccatgac gcctccatgc catggacaat 780
tttgacagat cagaagttct gaacgtggac gaggtaagaa caccatgatg atacgattgg 840
agttagttat gtcgccaccg acatcactgc caatctcatt aataaaagtg gtactaaatc 900
tctaatctct attaactata aatataacaa agaaccaaaa gaaagtttct tatctctctt 960
atctttcata atttccaaga aacacaaacc ttttctacta 1000

<210> SEQ ID NO 15
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 15
acgttcagag gcatcgcttt tgtacaaatt gaagcgggtt tgttcaatat ttaaaataac 60
acaggaaaca ttcaaatgta ttattgatgt tgcttaggtt tgtgaaatga tatgaaccat 120
atcgtatata ttactagatt tttcttatat gttttaaggg tagtggggct gacctatcat 180
tctgtttggc attaccaatc agactatcag agtattcacc attcaggatt ccataactag 240
aaaaagaagg ggtttacatt ttctcatact gtataatttt ctactatcag agattttatc 300
gattacatta atctcatagt gattattctg atttataaaa aagttgacaa aataattaaa 360
accagtattt tataacaaga ttgtctctct cccatggcca ttattttgac ctctgactta 420
tttaaatctt aattaacagc ataatactgt attaagcgta tttaaatgaa acaaaataaa 480
agaaaaaaag aacaaaacga aagagtggac cacatgcgtg tcaagaaagg ccggtcgtta 540
ccgttaaggt gtgtcgaact gtgattgggc cacgttaacg gcgtatccaa aagaaagaaa 600
gggcacgtgt atagatctag gaaaaaagaa agaatggacg gtttagattg tatctaggta 660
ccaggaaatg gaacgtcaca ccaaacggta cgtgtcggat cctgcccgtt gatgctgacg 720
gtcagcaact tccccttatt catgcccccc tgcccgttaa ttacgtgtaa cccttccatg 780
cgaaaatcaa accctttttt ttttttgcgt tcttcttcaa cttttctttt taaatcaaac 840
cttttctttt taaaatcaca ttgcatttcc taacgctcaa caaaatctct ctctactaat 900
atctctctct ctctctctct attgttgaag aagactcata atcggagatt gtttgttttt 960
ggtttgctct gtaaattgga gaagttttgt tagagatcaa 1000

<210> SEQ ID NO 16

<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 16

```
aacattttct ttaacttact cttaaatttt aatagtaagt tgatgcatgt tatgttgatc     60

cgtcttgatc acaaatattg ttttatggac gaattctttg acagtaaatg gctatagtga    120

ctcagcttgg agcatcccga tatgaaaaca aagtgcagta ttgtgtcgtg gtcatcacta    180

acgcactttc ctagaactat cgcgcgtgtt tgacctatgc aacacaccag atgtcatgaa    240

cgtatactta aatagaaaca atgatataga caattggcta tattctgtca tggaacgcaa    300

accggataac atgtctatta gattcatcgg acttgatcat ggttatgtct taatagacga    360

attctttgtt aacgattggt taaaacggct cacgttagag catcctacta tgacttcaaa    420

attgataaat attacatgga aatcacttta attttagtta gaaggtagtt aatttagata    480

ttcttattta ataaattaaa aaatagaaga aaaaaagatg agaagagttt ttgtttataa    540

aataagaaat atcttttatt gtaattttaa aattaaacaa atttaattta tattaaaatt    600

atctttgttt tattgttaag gcaataatta tttttttggt gggaattgtt aaaacaataa    660

ttagtatact gttaagtggt cctttaataa taagataacg tgatttaaaa aagaacgaga    720

caggctaata tagtagagag gaaaaaatac aatttaggcc caataaagcc caatatagag    780

ttgtgctcaa acacaggtct tcgccagatt tcctatgacg ccgtgtgtca atcatgacgc    840

caagtgtcat tcaagaccgt cacgtggcgt tgtttctaca cataggcgat ccatacaaat    900

cagtaacaaa cacgaaaaga gcattcatat gtacgaaagt agaaaagaag agactctttg    960

tgataaaact aagtaagaaa tagcataaaa gtaaaaggga                         1000
```

<210> SEQ ID NO 17
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 17

```
gtttccaaaa ctagtattct ttatttgctc tattcattat atttttatat ttgtaacgtc     60

ccgaccgtct ttattaggtt tcgacaatca cttctcggaa ggtcgtccat cctgaaatta    120

ctctatccta aacatgttta actataaaat tctctcgaaa cttttgtaac gtatataacc    180

acataaattc tcttaaactt atttgcatac accattatat ttctgaaatc gatatgttac    240

aatattattt aatatttaga ttacttttac tgaatcgaat taaatatcaa atcgaaacaa    300

atctaatcta ccaaaaataa ttttgttata aacatttctt gcctagttct acctcatata    360

cattttagtt aaagaaagaa atcacaacaa ttcccataat tcaataatta aatccacaaa    420

atcttggagt aagtaagaga aataaaaaga tagtatctta acataaacaa ttcaaagatg    480

ctctctcaca caattcacac acacttacaa aacaaaagac agaaacaatg ttttcattca    540

aatcaaaaga agttataaca ctagtacaaa aaaagctcaa attctaatag taactctttt    600

tatttcccaa ttacccaaag attctctctc acttcacaaa actagctttg agagtcgtgt    660

tccacaaaat ccattaaagc tgaaacggtt ttgctcacca ttcaaacaaa tacaaaattg    720

caaaacccca aattataaca aaataatata aaaattaaac cgctaaaaag agtgaaccaa    780
```

```
caaaaatcgc cgaatgtgtg tgtaatgaga aaaccgaccc atcatcccaa tcatctcttc    840

ccgtgtcact ctcttcctct cccacgtttc ttctctcttc cctttatggg ttttaacttc    900

tccttcttct tcttcttcaa tcttcagttt tcaaattcaa caacaattca cattttgatt    960

tcttcatcat ctctctctct ctcgcttctc tctcaaatcg                         1000
```

<210> SEQ ID NO 18
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 18

```
tagtgcgcgt ggggagaggg aatggtgaaa ccttagtggt taagttatga ggaaaatgat     60

aaaaggataa aacaatcaaa tgcagcttga aacggccata acataaagta ccttatggtg    120

gtgcgaatat ttttgtgttt ctttcactct tttattgctg aaagctacga cacttgtctt    180

aatatattgt ttccgcaagt cacatgatct actttttatt taacgtctag aaacgccgag    240

atatatgatg attagtatat cacgtctatg caaattgtta gttcgtgttt ggccaaaaga    300

tatcgagaca tgtctgaaga accgagtctg gttttgagat atttcttcaa gcattactat    360

acaatagaaa aaggagacac gcgaatatga taatagcaaa aggcataaaa aggcgaaaat    420

taaagaaaaa cgtaaagtga tttggcctca atcaacggga acgtatctta attttagagg    480

ttcttctttt acttttgaga cgagagagtt tgcgtctttg cgagctgctt tggttgacta    540

aacattatca tattgaaaac caaaatacaa cggaggaata tttgtcacag tttcactttc    600

acattgtttc cttaacgttt aatcaacctt gttcaaaatt tctatagttg taatcatcat    660

tgtttacaaa attttcgttc aaagatgatt ttaaataaaa ttgtgaaaga aaaccttttc    720

tgaaataagg attggatgat agtgttaaaa gaaaaatatg aactgaggca aaaagaggag    780

tggtccccgg aagattgtga aatgtgtcat ctaaaccagc cagacgtagt cacgtgttct    840

ctctagcttt atgaacttcc ttagccagca ccatcattgt gattgtagta tatatgtaac    900

cctaccttca tctctcccat tttccattct ccatatagac tcctttacaa tatacaaaac    960

ctatccaaaa gcgaagaagc caagcaaaca tattataaaa                         1000
```

<210> SEQ ID NO 19
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 19

```
gtcatatctt atcaacacgt caacgatcaa aacctttagc ctattaaatt caacggctta     60

gatcaaaacg aaactaggtg ggtcccactt ttaatatcgt ggctgcataa catttcctcg    120

ataactgaag ccgttgtggt ctttctcaga atctggtgct taaacactct ggtgagttct    180

agtacttctg ctatgatcga tctcattacc atttcttaaa tttctctccc taaatattcc    240

gagttcttga tttttgataa cttcaggttt tctctttttg ataaatctgg tctttccatt    300

ttttttttt tgtggttaat ttagtttcct atgttcttcg attgtattat gcatgatctg    360

tgtttggatt ctgttagatt atgttattgg tgaatatgta tgtgtttttg catgtctggt    420
```

```
tttggtctta aaaatgttca aatctgatga tttgattgaa gctttttag tgttggtttg    480

attcttctca aaactactgt taatttacta tcatgttttc caactttgat tcatgatgac   540

acttttgttc tgctttgtta taaaattttg gttggtttga ttttgtaatt atagtgtaat   600

tttgttagga atgaacatgt tttaatactc tgttttrcga tttgtcacac attcgaatta   660

ttaatcgata atttaactga aaattcatgg ttctagatct tgttgtcatc agattatttg   720

tttcgataat tcatcaaata tgtagtcctt ttgctgattt gcgactgttt catttttttct   780

caaaattgtt ttttgttaag tttatctaac agttatcgtt gtcaaaagtc tctttcattt   840

tgcaaaatct tcttttttttt tttgtttgta actttgtttt ttaagctaca catttagtct   900

gtaaaatagc atcgaggaac agttgtctta gtagacttgc atgttcttgt aacttctatt   960

tgtttcagtt tgttgatgac tgctttgatt ttgtaggtca aa                      1002
```

<210> SEQ ID NO 20
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 20

```
tgtggccact aaagatttac ccttaaccgg gcccatataa gcccacgtca agtggcgctt    60

atacgctctc cgtaagagag ccaacatttg gtatgtaatg ttgcaaatta ttcttcaaga   120

caataaattc aaatataatt caatattgtc caaatatagt gatgtacttc agttgtgcac   180

atagaaactc cactaaacca acttttagat agatgcattc acaaattttc aacaatgtcg   240

cgaaagtcta atccatcacc agattctaac attttaatta ttatatttaa ctatacatac   300

tctaatcagc atgagtcaaa cgtgtacaat agcccaagca tataataaga ccaaagtcaa   360

actcaaataa atgtctccaa actcaaaact tgaaaaagac ctaattatta catggtagat   420

atgactttgt cgacaagtaa accaactaat cctcgaagct accttctctt cccagttatt   480

atgtgtgatc gatttataaa tctcttcttc taataacacc tatatttttc ttatgatgtg   540

aataaatata aaacttttaa ctttaaaaca tatttatccg aaatattgca cttagatttc   600

aaatagataa ataatagtac tatctaactg atattgaaaa gacctaacac ggaaaacagt   660

tttataaaaa atcccaaatg tgggtaatta tcttgatttc ttgggggaaa cagaaaatgg   720

attaagatta atcggagtcg tgtcaagcag ctcgttaata actgtagcaa gttgactgag   780

taagcatcaa cgtgtcatct ccgtaaagcc cattatttct agtctcgccg cgtcttctct   840

tccacgtagc acttcacttt ttctctcctt ttgtttcctt tggaacacaa acgtttctat   900

ttataggaat aattacgtcg tccgtatctg tgtcggaaca tagatccaaa ttaaaagcga   960

cttacttaat tacatatcgt tcgtgttttt ttcttcaaaa a                       1001
```

<210> SEQ ID NO 21
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 21

```
tcgattggcc cgatcggccc caaaatcaag ctgagccgct tcaaacttca gcttttgaaa    60

tcacccccaa actcatgtcc tcttatcatt ataactaaag gatctttcat tttatttaac   120
```

```
tcatcgtctt gcactaccca acccaaaggt tccaactata cccgaagctt tctaaaggtc    180
caaagacttt ttttttcgag ccagactatt caagccaaga aaagccaaac cccacaagcc    240
agtacttttc aattccatat tataaactta tctgtcttgt tttagtccca ctaaaaacaa    300
cagaatttaa tttaggttga gctaaaaccc ttgacaaaag tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttggg tttgaaattg ccttttctcc    600
catataagca cgtcggttcc taaataactc tttctagcgg agagtgtctt tccaataatt    660
taataaaaat ggtgtttgta tatcaaaaaa aaaagaaaaa agaaactgat cgagatagaa    720
cgtttgcagt tttataaaca atttaaaaaa caaaaaaaat taaactcaat gtattttta     780
ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

<210> SEQ ID NO 22
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 22

```
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taaagtgata    600
ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900
ctttccctta ctttattgtt gcttttaaac cttcaatttg ctcataaacc aaatatataa    960
tatcaaaaca aacaaacaaa aaatcagaat tcccctaata                         1000
```

```
<210> SEQ ID NO 23
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 23

aaagttttga attattggga atcaatttcg aagttttgta attctttggg ggctaatagg      60

atattttatt ttcttggttt cgtctattgt tgtttttcta tttatggttg ggcttttaga     120

actctggaca ggcccatgtc atatgttttc ccttctcctt atatttttca tttttcattt     180

tgttaaatta atgcataata tccaaaaaca atttaaattt ttgaaggaac cctttagtta     240

cggctccgaa gctttcacaa gtgagaatgt gagatcaaag aaggcaaatg gaggatttta     300

aaagttaaaa tcatctttta tctgcaaaag ttgacaattt ttttgtatca aatctaaatc     360

atcaaactct cttaaactac aagagcataa caacctctat gtaatccatg aaataatctg     420

cttgaaggac ataacataaa tcattatggc tagagtgact aacttcaatc aaatcctctt     480

aactctagct cccttacaat ggtatcgtaa aacattatgc attagggatt gttgtcctag     540

gaaaataaaa taaaaatccc cacagaccaa ctaccatttt aacttaaaaa taagcttcgt     600

ccgcgacgaa ttgttttcca tcctaaaaat agaatggtgt aatctgctaa tggtttagtt     660

ccattaactt gcaagttcta ttgaaagcct aaatgtcaat aaagatatta aaattcggag     720

tcaaaagaca aatgaatcaa aagcaacaag acaagtcagc tccattcttc actacccatc     780

ttttacaata aatcatctct cttttcacaa atttcaaact actctcattg ccctttagct     840

ttgttataga gccaacacta cagagagact cacacacttg tttcaataat taaatctgaa     900

tttggctctt cttataaact a                                               921


<210> SEQ ID NO 24
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 24

aactacaagg gagacataat atcaccatct ggttcctgtt atcatctgaa gatttcttgt      60

tttaccttcc agtgataaaa tgatccttat aatacatata gatatattaa attgctgtat     120

tttaagatta tagatatata aggtacatga gagtgtttat ttaaaaaaat tcacttggaa     180

ttcatgtttt gtgatacgtt agattggaat ccatttggga aaagaagaat catctgttct     240

tatgtctcaa attttgactt cattcacttt tcttcttgtc ttttaagaaa gcttccacaa     300

tctaactgtt cgatgtgaaa actgagattc gagtaagaaa atgtgaactg tgttatactg     360

ttttttaatt agataattta gattgcactc agataaatta ataacattcc tcgaatactt     420

ttatgtgatt ggatatatta ggtatatctg ccaaccaacc aataaactgc tatgtttaaa     480

caaattaaat aaattagtat atgtttactc aagaataaag aagatagaaa agaaaattct     540

atatgagcta aatttgctgg aggaggcatc ggacgtgggt accagacctt tccaagcaca     600

cgagtagtgc ttagccatgt catgctaaca tacaccattt ggttcataca aaatccaaat     660

caaaatctat ttttaaaatc ttttgcacac gtctttgaaa aacacctctc atactatagc     720

tacggaagct tcaatttcaa ggtttgtcta aaagctaacg att                       763
```

<210> SEQ ID NO 25
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 25

```
atactggtat gcttaaggtt gaagccaaga tctctgtctt acccaagtaa ccactttcta     60

ttagaaggga tcaacactaa gaatatggag atttaagcct aagggctaag gcggttctca    120

acaatacatg atgtgaatac aatcacagac gatttactga ggtttgttga taagatcttg    180

atcagtctct gcatcatctg ttcaacaatc tcaatctttg actgtttgct ttcggagcca    240

taaacagagg aatcccttat tccctgttat aggagcaata caccaagtat tatttccatg    300

gctgaaattc tcttatggaa acctaattgt tccattgaag ctgtaaaatc gaatctggtg    360

aatattctcg agcaaagccg catgctaatt atgtcaattc agaagagttt gattaggaga    420

ctcgaagcga gtttgatgat ctttcttgat gttcaactcc gattgtaagg gtataattga    480

cttttcatgt attacggctc caccacctga cactaaggca ctctttgtcc atctcgttgg    540

tatcatcgga ttcggatggt aaaaataaaa agagcagagg aaacttgtta ctcatgcaag    600

cttctcaggt gccacgtcac tccattacgt gtcatcttca cacaccatct cgctcaaaac    660

cgatctcatt tttcaaacct taaaggcaga agcaactgat taagttaaca ctcttgagaa    720

gctctcgatt aagcttgaac ttggaggatc a                                  751
```

<210> SEQ ID NO 26
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 26

```
tctctttaaa tcagttaact aaccgtttat atatttacga taaggtttga agagattatt     60

gataaaataa tacatttcat aatcccgcgt tcaaccgttt aaagtaacat ttaagttgac    120

tatatctaat tttttttcca ttaaatatgg agctggtaaa ctttatcaac ttctaaaaag    180

tgtaacaaca aaaattaggt caatcacaat tctgtttttt ttattatttt ggattgactt    240

ccaattgcaa atagtcttag tgatcaccat tatcatacat atatacatca agtaggtttc    300

atcatgatat accacaaagt atttgacaag ccatatggtt ttggatcaaa aagtcggtcc    360

aaaattaatg ttttatgtgc aagaaccgac ccattgtaca cacgtgttaa catcttcaag    420

actttcatct ctatttttct tttggtcatt aagataccca ttgatccgaa tctgttacat    480

tcccacctac ttttttaatt tttactatcc actccaaatt aaacacaacc gatgatttta    540

ataattggaa gcttttaaaa atatttcaaa acaagcctct ttgtgtttgt ctatatatat    600

acacgtaata agaaggtgaa tgaatctcac agcttacttg ttctaaggct tccaataacg    660

aaaacagta                                                           669
```

<210> SEQ ID NO 27
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 27

```
cgggaaacga caatctgatc tctagtccag tcgattggcc cgatcggccg attataaact     60

tacatgagac aagtataaat aattattata aacttattaa gtttaagatc aaggcttttg    120

tgcaatgtat caatgaatgt tagatgtgat atgatgaaag caatgtttta aacacataca    180

tagtcattga tcggaatgtg tgttattaga aatgcatgcc taagccgata gggttatcta    240

tgtttggtct tggacattat agccaaattt cgaatctaat tcttccaata tatatttttt    300

tttttttgct tagggccact actagtattg cttatcaatt ttaagagctc atgaaaatgc    360

aacaatatag tagttgcaaa tccttgtttc aagagaaatc aaagggccac ttgtgaattg    420

aataataata atatttgcaa ataacctttc actaaaccat accaacaaaa ccacacagat    480

ttggcaaaga cataaccttt gggagacgtg aaaaggctca aaatttgaca attgtcctta    540

caaattcgct cattagtgca attgtgagat ttgtttgcat ccaaatccaa ttcataactc    600

acactcgtct caaattcgaa aaggcctgca gggccagtgc actgggatcc aacaatgtcc    660

tccgactcgt ccaagatcaa gaggaagcgg aaccgcaccg cg                       702
```

<210> SEQ ID NO 28
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 28

```
ttctaggaag actggtcaag ctaagctgtt tctgtttttt gtttttgtac tttacttttt     60

gtttgctagt gggaactggg tttattgggc cttgaagttg ataaaagatg aataaaagac    120

atatcgccta aagcccatat gagaagcaga agacaaaaac ctccaacttt gggcataaat    180

tttgattata gttaaaagtc cagacccaat ttggcacctg gcttagttac gattctaagg    240

catgacacct gcctaatatg tttattacag aaaataaaga gaatcagcta ggtgtccctt    300

attgaacaca ttaacaaact ccaacgacac tacgtgtctt cgtgactctt actatatcca    360

aaaacctata gctaaagctg aattttccat gattagtata gtcccaacca aaaaaatact    420

gaagaaggca taagc                                                     435
```

<210> SEQ ID NO 29
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 29

```
agtgtatttg aaaacgacat tgaagaatta atatattttt ttttaatttt agttttttat     60

agtacaaata ttaaaacaaa caatcctacc atatcataac atttgtaaat aacattttaa    120

gttttgtttt gagttttaat taattttcta tgacaaaaaa atgaagtcaa tagactaagt    180

gaatcatata gtataaataa acacaattta aatagtttca aataaattta gaaagaataa    240

aacaaataga aatcagaagg tgtctgtttc ctcctcgcaa catacgatca aagagaaaca    300

acttgaccct ttacattgct caagagctca tctcttccct ctacaaaaat ggccgcacgt    360

ctccaacctt ctcccaactc cttcttccgc catcatc                             397
```

<210> SEQ ID NO 30
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 30
agcagaacaa ctatatttat tgtgtcacat aaatctgaga tcatttataa ccaccaaaga 60
acctatacac agtaaatgac aaatgtatct ccctctatct ctattgccca tatgtagatg 120
ctaaagtaag atttctcttt tttttaatgt actttttttt gtataaagta tattccataa 180
gaaaaaggaa aagcttgttt atggatcaat tgaccccaaa aaaagttttt agatcaaagc 240
ccaatataaa aaaaaaacac agtagtgaca caaaggaact taaataaacc atgaattgat 300
ctataaacag tagagatcga taaggcgaac attttccatg tgaagtgtct tctttcatct 360
ataatatttt tgacatccaa taatttcctc tataatatca ttcacataat tgatagaaac 420
attatgttag aattgtccac atcatttgag ctgtaatata ttctgtttta acaaattata 480
tggtagttgc ttaatcttat gtccatcttc ttctatgcat cgttttcgcg cctagttgtc 540
cagtccattt caactaccta cctctaattc ttatcttaaa acaacatttt ttaatttaag 600
tattatgctc aaagactaac tagatagaaa accgttatta aacattaaac gaattaaaag 660
tcttacatgg aaaatgtagg tttataaacc acgagttatg attgacaata aaaaaaatgc 720
aaatcatcaa tcaaaagaga cttgagtgcg actctatatc aaccattgca attaaaatta 780
tctatcacaa aaattttaga cagattaagt taatttagtc taaattcact aatttatttt 840
ctataattag taattaacta tatttattta tttacacatt ttctgataat ttagaaattt 900
gcatgaataa caaatataag attttggaaa ttagtagcaa atttaattaa taattatttt 960
tgcctaaatg aaccaaacta taaaacctcc acatacacca gtcatcaaat ttacagagac 1020
aaca 1024

<210> SEQ ID NO 31
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 31
ctcgagagat gaagtcttag taatgtttga acaaacaata atcacgtttt ccatcaaatt 60
cgagcattta aagtttatat tactacatgc cccaagatga taccgtccat ctcatccgaa 120
aatatttctg aaattgcgct aagacaacaa tgtttgctca aattcgatca tttaaagttt 180
acaaatctct catcaatctt acaaacttct cacactaaac agaggtacat attttcttat 240
aaagacaaaa ggttcgaaca gctggcttct caactcgagt tgtttgtcag ggcctctctt 300
cactaactac aagttggtac ttcaaatatt ggtggctagc ttcacgtgat attgtctaca 360
aattaaaccc atgaaaaagc tgcattaatt gttccaagtg aaccctgagg agtgtcaata 420
gtctttgctt tagtgtgatc attaaaccaa atctctaaat tcctaatttg tactaacatt 480
tggaacgtat ttcctactct tctccctgct ccaactccca aaaataagat tagttagatt 540
tctataacta atatacatgt atactcccaa aaacagtaaa accatattaa taaagctaat 600

```
tttgcataga tttatttcgg taaaccggcg gttcaagttg ggaaaaaaa agacaaacgg     660

tctaaagtca tccaaagaca aaaaaccaaa gacaagttga gagagacgag accaatcaca    720

acattgcttc gtagattgcg tgacatcatc cttgacggct actttcattt gtgtcttatt    780

tggataaaac gcacgtgttt aattcacgaa ccttcatagc aataagaaat ttccattact    840

ttcatatttt caactttttt tattacccat tacatgctta aaatattaat tcacaagtct    900

ttgtcaaaat tcaatatttt ccaggttcat gaaccctttt tatctcaatc tactctataa    960

tatctcccta taaattacaa caaaacctct ttatttttca                          1000
```

<210> SEQ ID NO 32
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 32

```
gtcagtgaag tcgattggta gtacttgaaa cacttggttg gtttcatgta tttggcctat      60

atataaacaa acatcgtaat tatatacgga tttttttcgg aattttacgc catatctgta    120

agtatatata acatgcatgt cgttttcaaa ttcatatgat gaacgatcca cgtaagtgct    180

actactccta caatattgca tgagagagat atgtatttat aaattttatt ttgaagaaga    240

aataagaggg aaggttactt gggtggatcg atgtgaaaac aaaagaagaa aaagcgaaac    300

ccactaagcc attacatgat atcgaccttc ttatcttttt cctctttatt ttatttttct    360

catcttcttt ttgtcaggac ttttttctac ttaatgaaac ctccaaacta tctaactaat    420

acactcccat gtagaataaa gaaaattata taagatattg ttgatatttt gtaactagaa    480

aatatatttg ctctgtaatt tttcgtaagt taaatcaaca ttttaaagta gaaacaaata    540

ttactgcaaa aagtaggatc attatttttg tccaaaatct cagttagcta tagggttgta    600

gtaaaaacaa aacacattct tgatttgccc caaaaaataa agagagagaa gaatattgtt    660

caaaagtggt ctcttctctc tctaattatg ttttcactaa acccaattag attcaaacag    720

tctacaaagt ccaaaagata aacatgggac aacaattcga tgcaaaaaat cctcttttca    780

tgctcttttt ttattctcta gtcttttaaa ttactaataa aaactcacaa atccaccaaa    840

cccattctct acaactcacc ttcatctaga tttacccact cccaccgaga aacacaagaa    900

aaaaaatata catatataaa tatacaagac aacacatgat gctgatgcaa tatacacaac    960

aaagtattaa atcttagata ttgtgggtct ccctttcttc tattcatttt cttattcatt   1020

aaaa                                                                 1024
```

<210> SEQ ID NO 33
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 33

```
ccgttcgagt atttgaaaat ttcgggtaca cccgcctaaa taggcggacc ttatctagta      60

tatatataca tttgaactat attgtttact ttttagttga tttaggctat gtcatgacat    120

tgacataaat ctacctgtta tttatcacgt gtaattcgtg taaagtgtaa actagaaagt    180

tcaaatacgt atttgttttt gttctgttat ataggattgt catagttgta aatctacaat    240
```

```
ttattacaac atgaataagt acacaagcaa tgtaattgga tttaattgct aaactcttta    300
catggtcaat ctaaatttga taagaaatac gtcacatatt actaagactg atagtttttt    360
tgttgtcacc aattattttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaaacgc cttagttata aatcgttagt    540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
aagttcatca ctggtggaaa atgttaaacc ggtttttttct catttttttcc gccatgttaa    840
ccaccggttt aaaaagaccg taacacattg aaagattaat aagggtatat ttgtaattac    900
ggtttgctgg caatttttaa ttattatttt aattagagaa aatagagaag ccctatcaat    960
gtacatggta tatatataaa aggcaaaacc ctagaaaacg atactattcg actcagccgt   1020
cctt                                                                1024
```

<210> SEQ ID NO 34
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 34

```
aatctgatct ctagtccagt cgattggtac ttgagggaaa catcatattt ttaaaccttg     60
tctcagtaag ctaacacaca ccccttgtga ttacttatcc atgtttatcc acaagaatgc    120
agttggattg agatattttc ttctttgttg aaatcaggcc tcaaggtgtt catgtggtct    180
gcaaaaaaat tcccaaaaat aaagatagtg acatctgaaa tcgataatgg attagacgaa    240
gagtttcgtg ttattccttg gtatgggcgg gtttggggac agatattttg gcacagacga    300
ggactaggcc actgtggtcc tgcagcatta ggtgtccctt ccatgtcctg cattacattt    360
tattgatgga ttcatcaccc tatctactac aacggctaca caaactatga agagttttgt    420
ttactaataa atgcccaagt gaggggtcga tcgaacccgg gacacgtttt tcagtttacc    480
atatagaatt atccttggaa cccttgatac tccatagaac atcaccacct ctgttgtcat    540
ctcaggaatc caggttcaaa cctagtctct ctctccctag tgggaggtat atggccactg    600
ggccaatgat gacaaaatgc aaaaaaaata aaatacattt gggttcatta tctaaaatat    660
ctcttgtgtt tgtaagtttt ggttgcacac tcgtgtggtt gaagtgtgtg tgagaggtac    720
tatacaatac actctgcttt tgttttgtac ctatctcttt ctcttctcca catatccaag    780
actttgggga taaagctgag atcattggtt gccatttggt tgtgtagaag caatcaccca    840
tttgctttat ccgaggttga taaatttcct cgggttctcc ttctgacacg tatgacaaat    900
tctaatagta tattcctcgt agatattacc tatatattct caatagttgc aggtacttaa    960
ggctttgtct tggcatcctc gtcctcttca gcaaaactcg tctctcttgc actccaaaaa   1020
gcaa                                                                1024
```

<210> SEQ ID NO 35
<211> LENGTH: 999

<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 35

```
cttatccttt aacaatgaac aggtttttag aggtagcttg atgattcctg cacatgtgat     60
cttggcttca ggcttaattt tccaggtaaa gcattatgag atactcttat atctcttaca    120
tacttttgag ataatgcaca agaacttcat aactatatgc tttagtttct gcatttgaca    180
ctgccaaatt cattaatctc taatatcttt gttgttgatc tttggtagac atgggtacta    240
gaaaaagcaa actacaccaa ggtaaaatac ttttgtacaa acataaactc gttatcacgg    300
aacatcaatg gagtgtatat ctaacggagt gtagaaacat ttgattattg caggaagcta    360
tctcaggata ttatcggttt atatggaatc tcttctacgc agagtatctg ttattcccct    420
tcctctagct ttcaatttca tggtgaggat atgcagtttt ctttgtatat cattcttctt    480
cttctttgta gcttggagtc aaaatcggtt ccttcatgta catacatcaa ggatatgtcc    540
ttctgaattt ttatatcttg caataaaaat gcttgtacca attgaaacac cagctttttg    600
agttctatga tcactgactt ggttctaacc aaaaaaaaaa aaatgtttaa tttacatatc    660
taaaagtagg tttagggaaa cctaaacagt aaaatatttg tatattattc gaatttcact    720
catcataaaa acttaaattg caccataaaa ttttgtttta ctattaatga tgtaatttgt    780
gtaacttaag ataaaaataa tattccgtaa gttaaccggc taaaaccacg tataaaccag    840
ggaacctgtt aaaccggttc tttactggat aaagaaatga aagcccatgt agacagctcc    900
attagagccc aaaccctaaa tttctcatct atataaaagg agtgacatta gggtttttgt    960
tcgtcctctt aaagcttctc gttttctctg ccgtctctc                           999
```

<210> SEQ ID NO 36
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 36

```
tcgattggga ttactacttc atctagtaag gttctgaaaa cgtttgttgt tgataaggaa     60
gattcgtctc aggttattac tgttgatctt caaggtttgt gattgtgacg cttatacatg    120
tgctgaaact gtggtgttta tttattgaaa acaaaaaaaa agtctctctt gtagtttcat    180
tgtactaaat agaaaacaag aaacgttttt ttctttaatc ttctacattg ataatattgg    240
atcaaaggat tgtttctgca agacacaaca caaacatact tatactagtt tacttctact    300
aagtactaac tacataccca tacacacact tgcacctaga ctttacttct agacatcatt    360
accctaaggt agaaccaagc ttacaagcaa gttttaccga caactcttac attacaactc    420
tagtctgtag tctttaacgt agacttacta actagtcatt agtggtttaa ttttttaaat    480
tttcatccat atgtttttgt tgtagatata aactaaagtc ggtcacattt aataattgtc    540
attatgtccg cgtaaaagtc aattcagcta ttggacattt atgaaatgta agattttctc    600
tctcatttcc ccgtgcgtga agacatgcat tggtttttct gtaataatca acaaatccaa    660
accccttttc gatctttatt tggacattgt tagagacaaa atttctctat agtctttttc    720
ctaatttgat accatgtttt tgtttctgca caaatttact cactggttta actaactatc    780
```

```
cacttattta tgattttacc attaggcgtc agctagccct agtcaaattt gtaaacaagc    840

caagctatct acataaatcg agatgtcatt aacgttaatc gtcgttaatt cgaatttgaa    900

aacatagata gctttagcag tacaatgggc aatggtaaga agaatagcaa aaggcccaat    960

atttggtttg cagaaattaa agccttaaaa aaaagcccac agatatttgt caaagaaccc   1020

taat                                                                1024
```

<210> SEQ ID NO 37
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 37

```
aaagattgag ttgagagaga tggtggagac gcagaacaga caaagggagt ttaccatata     60

gtgctctaaa gggcaatgag attgcagtga tgtggctatc cggggaatca tcgcaggtta    120

ttccttccca tgagcaacaa tcaatggatg ggttccaatt cagaggagaa acagaagaag    180

aaacgtttcc agagaaccac agtagggatt ctcgatcttg cgagttgcag agagcctctg    240

aaactgcaat agaaaggaca ctgatgaaaa gaacacactg aaggagtatg ccaatcatgt    300

gaaaactcag agcttgtatt ggtcttgtgg ttgatgaagt tctcacaaaa cctttggctt    360

tgaatctccc ctcattagtc atggtgagaa caagaacaag acgagaaaca gacaaagaag    420

atgaaaaaac ttgttggcca gtgttgacta agggggaata gccccagaca taacaaaatt    480

agacttgtcg tacatcttta atattttttt atctgtttct ttgtcctgac gctttcatta    540

ttcctgtgat caattttctc ataccattgg tccatcgtta atcctttctt aatttcattt    600

tctacgtaac atgagaggag accaagtcct atgagaacag ttgacgtaac agtggttgtt    660

aagttaagtt aaaaagagga agctagtgag agtgaccgtt aggtagagaa gtgagatctt    720

taaccactct tctttctctc tctctctgct tttttcgtcg tctttcacat ctactgttcg    780

caaactctct tatgcttcca ataatggtga taccaattga gacttgcagg agaatctcct    840

cttctccaca ctctatcaac tggtcagcca tggaatggtc gtttcagttt caatattcct    900

ggattctttt taaggattcc tgtttctctt ctgttcctgg tatattctta acgacgaaat    960

tagtatcgga tcctggtaat acattttgaa gcttttaagt accattgcac tgggatccaa   1020

caat                                                                1024
```

<210> SEQ ID NO 38
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 38

```
gaggtcagtg agtcgattgg tgcaaaattg aaaaattgaa gggtgaaaca aatttaaaga     60

taatatctat taaatcctct aattttaaaa atttagcaaa aattgtattt tcttatggat    120

ctgttagttc acacgtatct taattagtac caaatcatat ctaatgatta gtgataaaac    180

tagttagata tctatatgtg tctttaccat ttaacttgaa tccttcttct ttttttacg    240

taaacaactt gaatccttcg ttaatacata aatttaaagc attttttctt taattctatt    300

gatcggtata tatttactat aagttttagc tcatatgcaa tttcaaatga tatgctttta    360
```

```
aattttgtct aggtgtgata gttgtatctt taacataaat cttatagcaa aattatactt    420
gatattctaa atttatctat ttgctcttgt gaacctcata ttagtctaga gaaactttga    480
aatcctttca attagttgta tgtccaatac atttttacta acatttatta gtctttttaa    540
ttaagattat tgttagaaaa aaaaagattt tttaaaaata aataatatgt tttagataca    600
atgtgagtta ggcttcttat attttaaaaa ataaatttat ttcatactta aaaatagttt    660
ggaatttcaa tttatttggc tgaataccat aaaatatgtc aatttgaacc ttatacccat    720
tgactatttg gtgttagaaa ccctttaaca aaaaaaaact atttggtgtt agatatcaaa    780
ataaaaaaag tttaaccatt ggtttcttat attgaattgg atattgttac atgtattaaa    840
gttttttgg tttaatttg aaacgttgat agaaactatt aagtttaagt ttggtagtat     900
atttatttgt ggaaaattta attgccatta aatataacgt caactttttt tggtttttt    960
tgagaagtta cgttgtgatt ttgatttcct atataaaagt tagattacgt catttttaa   1020
```

<210> SEQ ID NO 39
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 39

```
ttcatcttta tatttaagag tttaaaaact gcaacttttg tttttctttc actaagtctt     60
atggccacag ttaattaaaa gcagatgaaa ggtggtccaa tggaaaagga gaatgtgatt    120
gggctagttg ggagagttct gatgtctagt gttgggtaca cgtgtccgtc agttacacat    180
agcattaaat cagacggcat gtcattattc aaatctagtt cacatagtac gactaatagc    240
tgataaatta atgattatac agcatatgaa ttatgaattc aaaaaaaaaa aaaaattgaa    300
aatgttaagg agatgctata ttttacaaaa ttcatcgcaa tgctttctac taatttgcta    360
agtggtcttc tccagttagt cttgtcgatt ccaagcgata ttattaaatc ttgaagcatc    420
gctcaaagca ttatagctta agataaccaa attgttatta aaaacaccta gtgaaatttt    480
taaattaaaa caattttgat atctttgtaa tatctaatac tactctttct gtgtctaaaa    540
ggattaattt tcaaaaattt cacacatatt aaaaaaaaaa aaaaattact agctaaacaa    600
ttttcaataa tcataaaaca atagtaactt aataattttt ttttattttc aaaatagtcc    660
ttcaagttta caattcattt tagtattata atcaacaaaa tttgtattaa aaagttggaa    720
aattaatctt tgtggaacaa aaaaatctag aaatcatttt ttagaattag agagaggttt    780
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat attttcccat atgaaatccc    960
tatataaacc catcatcatc tcccactttt ttcatatcca                        1000
```

<210> SEQ ID NO 40
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 40

```
ttctcgttct ctagaatatt gctggaccgg attaggtcaa tattattggg ccagattaga     60

tattgaattg tcgacgttgc ttacgttacg ttatatcttg tttaagaatt aaacctatcg    120

acttagtctt aattaagaaa acattgcctt aaattctctg gtctgcgacc gttttttga     180

ccgttaaccc ctaattaaag aaacaaaata attatagaaa gagcactgaa atgtgattat    240

tttaacagta ctcttatgag aaaattcgta ctttttagtt ttttttttgt acaaatctct    300

aagaaaaaca ctactactaa ttaagaaacg tttcaaacaa ttttattttc gttggctcat    360

aatctttctt tctcggtccg ggactaaccg ttggcaaaaa aaaaaaaaaa gttgacaata    420

attattaaag cgtaaatcat acctctcaaa taaaaacttg aatttggaaa caaagacaac    480

taaaaaactc gaatttaaga gaattcctaa aatcaagtga agtatcatca cttggtaaaa    540

tttcataacc gttggcttct atttctatgt gtgccttggt ttgcaggaga taatatttca    600

tttccaacca atgatattcg tacacatagt caaacaaatg tttgtctttg ttattatatt    660

gagaaagaaa caagaaagag agagagagat agataagacg aaggaagtga agcttccaag    720

cgcccaccgt taaaaatctc gtgtgcaagt ttcaaataca agtggccggt ggtctccata    780

atttgatcgt catccaatta aaaaggaaga aaaagcgtgt tttatacaag aaaactcatt    840

aaaatagcaa gtctagaaat atctcaacac taatctacca cgtctattac acacacacac    900

acacacactt gatcttaatt tattttcaag attcaagaaa atacccattc cattaccaca    960

acttgaccac acgcctatat ataaaacata aaagcccttt cccc                    1004
```

```
<210> SEQ ID NO 41
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 41

atttggttga taacgttttc actcgactaa ttatatactt cagaaggata gtaatagaat     60

accaaaataa ttaaatgatt ggttagtgcc ttagtggaga ctttttaacc gattctaata    120

gactaatgat gtagctaagc atttatttgg gatcatcact gtttgaaaac gtgaaatgtg    180

ataaaagtta tgaaacgatt aaaatataaa ataaccgtac aaaacattat gtaccgtttt    240

tttctctgtt cttttggcga tttggtttag ttcgttacac tctaaatgtt attgcagata    300

tatatataat gatgcatttg catctgagga acatataatt ccggttaaca cttccaaatc    360

ttatatccgt ctaggtaggg attttataaa tcatttgtgt catcatgcgt tatgcttgtc    420

ggctttgacc ataacgcaga gatatagaac tagcttttac ttaactttta gatttattat    480

ttgatctaga gttaagtgga gatatatagt gtttttgtta gattattggt ggatgtgaga    540

gtttgtcttt agtttcaagt tgagaatata aggcaagagg agactctgag gcaatcagag    600

gttttgattg gcaaaatatc caaaaggccc aaaccaagtc gaagcccatc tcgtacaaaa    660

aaagaaagag atctgtaaga aaaaatattc tttgatattc ttacaaaaat aagtgtaaaa    720

cttttattag tcaaaatctt caatctttaa aaactctcat cactcctacg aaagcgcgtg    780

agagttatga gacattcctt aatagcatta ctcacaagtc acaagttcaa aacgtctgac    840

tgaaacagaa acaagccttt gttgaagtct tgaagaagag acattagtac tcgtcgtata    900

gccataaaag gtaatatacg aaatttcttc gctaatctct tcaccttcct ctacgcgttt    960

cactttcact ttataaatcc aaatctccct tcgaaaacat                         1000
```

<210> SEQ ID NO 42
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 42
gttttgaaga acaatctgga tcgaaatcta acataaggtc atcgtattca agttacgcag 60
tcaaggactt gacatcatcc tactctggtc tgaggttacc acttccaaag atgggatttt 120
tcgactcggt atgcttccta agaaattcgt tttattgaac ctagcaaata tcttgtaatg 180
taagattcct gagatgatga agaaaaaaca aacttttgtt acagcaggag aacggagaga 240
aagaaaacag agaaccaaat gctcttgaag caaacagaag aagaagacac aaatccaaac 300
ttgagacttc ttctacacca gaaaaccgca gcattctggg acaacgcaaa acacgaaagt 360
gaaacgggca atgatatata tgtcttgggt gcgttacaag gcatcgtttg caactgttga 420
gttggataag tcaactgtct tcttttcctt tggttgtagt agctgccttt tttttccttt 480
gttgctttaa gaaatagccc gaaaaaaaga atgttctaca tttcggagca gaaaactaac 540
cgaatgagtt tttggtcgga tcatcggatc gatcagatat attttgagtt acgaactgtt 600
ataaaaaaag ccataatttt gtgttgagtt tgcaaaatac cttataactt gttatttgag 660
attgcacctc catatatatt aattcgtaag agtatttatt aagtaagctt tagtataaat 720 cctttttttcc tttaaagtaa gttaatgttc tactaaataa tagtaaagtt gaagaaccgc 780 tccgtttttta caccatgcac gtgttatcta acaaagaaaa tatggtacac ctaatggcta 840
atgcaaagga caacacaatg aaactaactt gactctgtgt tatagaaacc catagacatc 900
tgcatacatc ctagtatttg tataaattgg actcaaattc ctgaggacaa tcatagcaaa 960
caatcacatc atcgcaatat acataaacaa aagaggaaga aaaa 1004

<210> SEQ ID NO 43
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 43
taacaatcct tgggaacatt gcatccatag atatccggtt aagatcgatc tttgaactca 60
taaaaactag tagattggtt ggttggtttc catgtaccag aaggcttacc ctattagttg 120
aaagttgaaa ctttgttccc tactcaattc ctagttgtgt aaatgtatgt atatgtaatg 180
tgtataaaac gtagtactta aatgactagg agtggttctt gagaccgatg agagatggga 240
gcagaactaa agatgatgac ataattaaga acgaatttga aaggctctta ggtttgaatc 300
ctattcgaga atgtttttgt caaagatagt ggcgattttg aaccaaagaa aacatttaaa 360
aaatcagtat ccggttacgt tcatgcaaat agaaagtggt ctaggatctg attgtaattt 420
tagacttaaa gagtctctta agattcaatc ctggctgtgt acaaaactac aaataatcta 480
ttttagacta tttgggcctt aactaaactt ccactccatt atttactgag gttagagaat 540
agacttgcga ataaacacat tccccgagaa atactcatga tcccataatt agtcggaggg 600
tatgccaatc agatctaaga acacacattc cctcaaattt taatgcacat gtaatcatag 660
tttagcacaa ttcaaaaata atgtagtatt aaagacagaa atttgtagac tttttttttgg 720

```
cgttaaaaga agactaagtt tatacgtaca ttttatttta agtggaaaac cgaaattttc    780

catcgaaata tatgaattta gtatatatat ttctgcaatg tactattttg ctattttggc    840

aactttcagt ggactactac tttattacaa tgtgtatgga tgcatgagtt tgagtataca    900

catgtctaaa tgcatgcttt gtaaaacgta acggaccaca aaagaggatc catacaaata    960

catctcatag cttcctccat tattttccga cacaaacaga gca                     1003
```

<210> SEQ ID NO 44
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 44

```
gggatgcggt tccgcttcct cttgatcttg gacgagtcgg aggacattgt tggatcccag     60

tgcaatggta atataaaaca agaaaacaag agattttata ggacaatcac taaatgacat    120

ttaattgatt aaacatttat tcattaataa ttgtatgtta ctaacttcaa catttaataa    180

ttttgtttaa gatacgttta catcagagac tattaatatt tttacaggtt gtaactttaa    240

actttgtctt gaatcgaaca tgactataga ttttgggcaa acttaaagat aacaacattt    300

ccgttttttt tcaaattatt acaaatcaaa ctgatatatt agacacaaca cgattacacg    360

taatgaaaaa agaaaaagat aaaaagataa aagaagggat cgattctgtt tggtctggtt    420

tagtgagatt caaagttaag ctcttccttt caagacatgc cttcttaaac cgggaatgtg    480

aacgtttgta atgtagtccg tccagttaat gcttccaaca tcaaatccaa attctctctt    540

ctcgtcctct gacatattct ccattaatct ctggggtatt gctgttatca aatctgtaaa    600

agaaaccaaa aaaaaaagat gaaaactttg cgggtaccgg ttttgtctgc tctaagaatt    660

agaatgttaa tgagttctgt cttaccttcc accatagaaa gtgtatggct cataaatagt    720

agcaaggtgt ttggcttgtt caacagattt cttgcatata aactttagct tctgcatcat    780

cttactatcc actgaactca taccactcat caacccactc cgttcttgag catctctcca    840

caaatgatcc gagaaatcat caacggaatt gaaaagtttc atcaaacgca ccataatagg    900

atcaccttta gagtccatgc atggagatgt tttgtagtgg ttataaagaa gctccgctaa    960

gtcttcgaaa accagcgggt ttatcgccga agaagcgatc tgatacacgt ttatttcagg   1020

ttcc                                                                1024
```

<210> SEQ ID NO 45
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 45

```
cgattggatt tagtctatac attatagggc gcaagtttgt ggatttaaga attatataaa     60

aacttgaaat atatagtttt tatgcattct cctcttgtgt aatacataaa ccaaatatga    120

gataggttaa tctgtatttc agataatatt aaattccaaa caatattttt acttgttata    180

agaaggcaat taatatctct ctgttaatgg caagtggtac caagtagtat taaactatta    240

atgcaatgga agagtactgt tggaaattat aatcctctat cacacattca aacagatctc    300
```

ctgaaatctt ctcttccaaa cttgtacttc tctgatccaa atgtaggctc caaaatatag 360
acatttacca tttactaagt ccacaactcc tttcttgtct ccttcaaaaa tgactcttgt 420
gtaaccacca tatgactccg acagttcggc attgccatga tgagagctta aaaattcacc 480
ttcctgagca tttcaagtct tcactccctt agcttgacct gaaccaagat aaaatgcctt 540
tgtcgtcccg taatatccat cctgctttgg acggcatcat agttacattc gatccatcct 600
atttacaatg ttattttagt attaaaaaca tgacaataaa tttgttgtta aacatattca 660
aatacaatat gattggattt ataagtaatt gtaatatgaa atgtccttag taatatgtta 720
aaaaatacat agatacacac acgtactaaa agaggcaacg cgggagatgt cattagagga 780
agaactagga agcagagcgt tcatgcaaaa tgctaccaaa aacgttaatg caatatctca 840
actaatcagc acagtccatt tcatactgag aatgtaaaaa ccaatcagca tcgtccattt 900
tttcatctaa ttatttgtta actcttaatt ggccacaact tccaaccaca tgacgctctt 960
tctattccct ttatatattc ccatctcaaa tgttcttgga gacacaaaat atcataaaca 1020
tata 1024

<210> SEQ ID NO 46
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 46
gtcgattgga tgatgaacat tctacatata taattattat gtttaagcac ttagacagca 60
taaattcttt ctaattatat aaatctaacc ttgttacatt gtacatctat aaattacttg 120
aagaaataac gagttctatt tctttttaaa aattaaaaat actataccat atctcagtga 180
ttaagttgaa ccaaaaggta cggaggagaa acaagcattt gattcttcct tattttattt 240
tattcatctc tcactaatga tggtggagaa aaaaagaaaa tacctaacaa acaaatatat 300
attgtcatac aaaaatattt ctatattttt agttaattag tttatattcc tcacttttca 360
gggcttatat aagaaagtga gcaaacacaa atcaaaatgc agcagcaaat actatcatca 420
cccatctcct tagttctatt ttataattcc tcttcttttt gttcatagct ttgtaattat 480
agtcttattt ctctttaagg ctcaataaga ggaggtacta ttactacact tctctctact 540
tttacttgta ttttagcatt aaaatcctaa aatccgtttt aaattcaaaa ataaacttag 600
agatgtttaa tctcgattcg gtttttcggc tttaggagaa taattatatg aaattagtat 660
ggatatcttt actagtttcc attcaaatga ttctgatttc aatctaatac tctcactctt 720
taattaaact atatgtagtg taatttcaca ctgttaaatt tctaccatgt catgtatatt 780
agagttgcat agaaaattgt aaaacatcca tttgaattcg aatgaaacaa aatgttttaa 840
aataaaattt tggtttttaa aagaaaaatc taaaactgaa ttatatcgtt taaccaagtt 900
gtaaaagtca taaaacgtag tatcttgtaa atcgctcttc cacggtccaa atagacttct 960
agtaataaac aagtaaaact aattttggtt tcttac 996

<210> SEQ ID NO 47
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 47
gtcagtgagt cgattggatc acagtccttt atgataaaac aaactcataa ttattccacc 60
gacaacatgc gttttaaatt attttttctt aaattatatt atattatatt gatatcaacc 120
tagctaaaat aattcggatg gcgaaatcgg acaattttta atagaaaaaa tgggtatgaa 180
gatagtctat gattccgttc ttagcgacta gagggacctg ctcaaatctc ccgggtgata 240
cgcgatgtca agctcaatag aaccccacaa ccgacgagac cgagaaatcc ttgatttggg 300
ctagaagatt ttgaaataaa tttaatatat tctaagtaac ttgcttaaat tttttttcaa 360
actctaaaga cataactaac ataaagtaaa aaaaaaaaag ttaatacatg ggaagaaaaa 420
aattaaacta atgattagct ctctaacgtg tttaatctcg tatcaagttt ttttttaaaa 480
attatattgc tattaaaaca ttgtactatt gtttctattt tgtttagcta ttattcttgt 540
gaaatgaaaa gttgtgttta ttcaattact aaatggcaat atttatcttg gaaaactata 600
cctctaattg gattaggccc tagacatcct ctttagctta ttgacgttaa aattattccc 660
aaaactatta aagtttagta gtttgaaaga tgcatcaaga cctactcaga taggtaaaag 720
tagaaaacta cagttagtgt gattatattt taaaatatat aaaacaatct tattaaacta 780
aatattcaag atatatactc aaatggaaga taaaaacatt tagtctgtta ccactaccag 840
cctagctagt cactaatagt cactttggaa ctgagtagat atttgcatct tgagttacca 900
tggactcaaa agtccaaaaa gagaccccga gtgaaaatgc taccaactta ataacaaaga 960
agcatttaca gcggtcaaaa agtatctata aatgtttaca caacagtagt cataagcacc 1020
attg 1024

<210> SEQ ID NO 48
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 48
taccaaaaat aaggagtttc caaaagatgg ttctgatgag aaacagagcc catccctctc 60
cttttcccct tcccatgaaa gaaatcggat ggtcctcctt caatgtcctc cacctactct 120
tctcttcttt cttttttct ttcttattat taaccattta attaatttcc ccttcaattt 180
cagtttctag ttctgtaaaa agaaaataca catctcactt atagatatcc atatctattt 240
atatgcatgt atagagaata aaaaagtgtg agtttctagg tatgttgagt atgtgctgtt 300
tggacaattg ttagatgatc tgtccatttt tttcttttt cttctgtgta taaatatatt 360
tgagcacaaa gaaaaactaa taaccttctg ttttcagcaa gtagggtctt ataaccttca 420
aagaaatatt ccttcaattg aaaacccata aaccaaaata gatattacaa aaggaaagag 480
agatattttc aagaacaaca taattagaaa agcagaagca gcagttaagt ggtactgaga 540
taaatgatat agtttctctt caagaacagt ttctcattac ccaccttctc ctttttgctg 600
atctatcgta atcttgagaa ctcaggtaag gttgtgaata ttatgcacca ttcattaacc 660
ctaaaaataa gagatttaaa ataaatgttt cttctttctc tgattcttgt gtaaccaatt 720
catgggtttg atatgtttct tggttattgc ttatcaacaa agagatttga tcattataaa 780
gtagattaat aactcttaaa cacacaaagt ttctttattt tttagttaca tccctaattc 840
tagaccagaa catggatttg atctatttct tggttatgta ttcttgatca ggaaaaggga 900

```
tttgatcatc aagattagcc ttctctctct ctctctagat atctttcttg aatttagaaa    960

tctttattta attatttggt gatgtcatat ataggatcaa                         1000
```

<210> SEQ ID NO 49
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 49

```
tagtttttga tttaatctac gtttttctta atcataaatg ggtaattatt agtttttgca     60

aaatcaaaat ccaaaaattg ttctaaacac tgcaaccatt taaggcctat atcactcaga    120

aaatttctgg tgggagaact aatcgtttgt cctttctaaa tctcacatat tagaatttag    180

aattagtgtg ctacataaga atattagttc agctcggaac aactattttt tggtaaaaca    240

gagaacttaa acaaatgcat tattttatca acatgcattt tgaattgaat ataaaatttc    300

ataattgtaa agacataaat tacataaaat tttacatgaa aaaatagata tagaaagaaa    360

atgaaactaa ctgatgatat gctctctaaa ttttttaatc tcataacaag aattcaaatt    420

aattagttca tatttttggt taatataaca tttacctgtc taagttggaa ctttcatttt    480

tttctgtttt gtttagtcag tattcttaat gtgaaacgga aagttgaatt tattcaaact    540

taaattcaat agcattaatt aaaggcgaaa gctattatct ctacatgtgg ttcaaactag    600

acatccaatt taattagctt attgacgttg aaatgttttc caaaactact atagtttggc    660

aatttgaaag atgcatcaga actactcaga caggtaaaag tagaacctct agctgtgtga    720

attgtatgtt agtccataaa gaacatcttg taaacttcat acttaagata tatattacaa    780

tatatacttg aatggtagat aaaaacgatt agtctgattg ctagcatact cacaactatt    840

tggaaatgag taagatattg gcattctaga gttactacta tggagacaaa agtcgaataa    900

aagagacctc acgtgaaaat gttacgagct agtaaaaaaa gcatttacac taacggtaaa    960

aaaagtatct ataaatgttt acacaaggta gtagtcatt                           999
```

<210> SEQ ID NO 50
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 50

```
ttggattttt tttttgttga gtcagcagac catctaatct ctctttttcc accacagcct     60

gctttctatg aagcatttgg gcttacggtt gtggaatcaa tgacttgtgc actcccaacg    120

tttgctacct gtcatggtgg acccgcagag attatcgaaa acggagtttc tgggttccac    180

attgacccat atcatccaga ccaggttgca gctaccttgg tcagcttctt tgagacctgt    240

aacaccaatc caaatcattg ggttaaaatc tctgaaggag ggctcaagcg aatctatgaa    300

aggttggccc attctccttg acaggcttaa caatacaact tgtatcgctt caacaagatg    360

atggcttaat aaggattttt gcatgtatag gtacacatgg aagaagtact cagagagact    420

gcttaccctg gctggagtct atgcattctg gaaacatgtg tctaagctcg aaaggagaga    480

aacacgacgt tacctagaga tgttttactc attgaaattt cgtgatttgg ttagtgtaac    540
```

```
ccactgttat tcttttgatg tctacatcta ctttacttac attattcttt tcttcggttt    600

gcaggccaat tcaatcccgc tggcaacaga tgagaactga tcatgacagg gtaggatttt    660

atttcctgca ctttctttag atcttttgtt tgtgttatct tgaataaaaa ttgttgggtt    720

ttgtttcctt cagtggtttg attttggact tatttgtgtt aatgttgttt tggctgttct    780

cttaatatca ataacaaata aatttactgg ttggtatcta agatctaaca atagttacta    840

tttttagagg taaagacacc aaccttgtta tattggtcag agagctaaaa ccttgacttg    900

ttgggaaaac aaaactctaa tgacagaaaa tctgacatga tgccttataa ttcacagcct    960

catgttctac ataaatccta acaatagcac tttgtttct                           999


<210> SEQ ID NO 51
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 51

gataaactga taatggaaaa gaacaaagaa accagttttt aactatttgc atatgtaatt     60

tatttgttgc aaattatatt tagttaaaat gtttcctcta tttatatata tatatatcag    120

tcaagcacta tgtataagaa atgtcaattt ataaattttt acatgtcctt taacagaaag    180

aaaatgaatt tttacatgtc attcatagag agtcactcgt ttatttctta tatagagaat    240

aacacactca catgcatatg catgcaatat gatacatttt atgacaaaga taatcaacgg    300

aaacggtcaa gacataattt gataaacaac ttgcacgatg cacagatctg atcaaatata    360

taactcttta acatatccaa aatattcaaa aagaaaaact cgatccaaac tagcaacatc    420

acgctcacgc ggtaggctaa aaatttatta atctccaaaa gtctttctta tgaacactgc    480

aaacacaaca acttgaaaag tcatataggt ttagatgatg acgcgtattg gctatcgctt    540

accggagtgg ctcataaata caataaacaa tacgtaaaag tcaaagtcaa atatatttag    600

tcaactataa ccattaatcg ggcaaaacct ttagctgtca aaacaacgtg aaaacgatat    660

ttgtatatat catcaagaat cagtagataa gagaatgatt taatcccctg actattacaa    720

ttttggtgta ataaacagtc tctattggtt tttattcttt gttttaattt ctcatgacct    780

atagagagaa ttaggtagtt tcgaaaattg gctaatcaac ttttgaaaac tactgtctac    840

tttgcttaaa ttctctacac ttagtttcgg ataagataat tgtcggacta atagttaatc    900

ccttgacaat ctttgatatt ataaaaggtt tagttaatct cttctctata taaatattca    960

tacaccagct ttcaaaaata tataatccaa acaccaaaaa caaa                    1004


<210> SEQ ID NO 52
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 52

gtggcacatg ctgaaacccc gagcatctct ccggaagaca cgcgtcgttc gctccaaaga     60

aaacagtcac agctgccgga gaatctccgc cgtcttcttc tgccaccgga aaaactctct    120

ccaccacttt cagtgcccac ctcgtgttat atccactgta tcctcgtagc accatatcag    180

cctaataaaa ttttatgtat caaattttaa gacatagccg aaactacact atactagaca    240
```

```
ataataatat gatttgtttc ctgaaaaatt atggtttcat gagaaacatt aatcatctat    300

aaaacaaatt agctatggca tcgaagagtt atcaatcaaa actgatgaat ctttacttaa    360

tatatacaac atatctttac cttgcggcgg agaagatcgg cgagagaagc accccagcca    420

ccgtcactaa aggattcttc agtgatggaa tcaccaaaga gaaaaacctt ccgtctcatc    480

atcttccaca caatcttctt gagaaaatct gagagataag aaaggtgtag tggttttgct    540

gaagtgatcg tgtttgattt agtaaagaaa tgctttattt attgttgggg gaaacataaa    600

taaataaagt aaaagtggat gcactaaatg ctttcaccca ctaatcaccg acctttcatg    660

gtttattgtg aaatacactc atagatagac atacaatacc ttatgtacgt aaataacatt    720

ttatttgtcg acacttatgt aagtaacgca tagattattt tctatgtgat tgccactctc    780

agactctcag tttcaaccaa taataacaat aactacaaca acattaatca taaacatatg    840

ctctggttta caattaaagc ttagattaag aaactgtaac aacgttacag aaaaaaaatg    900

ttatttacgt tttgtaagat tagtctctag aatcatcacc gttttttata tattaatgat    960

tctttcttat atataaaacc tttctcgaaa tacccatgaa a                       1001
```

<210> SEQ ID NO 53
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 53

```
atacaacaga tggcagatat cgagttaaat acgtgaatca gccgttacga tattttaaaa     60

ctagaaaatt atttaaaaat attgcaaaat accatttaat ttcattgttc ataaaaaaaa    120

gaaattcaaa aacttaaaaa ctgattcaaa aatttggatt aattctcatt aacagtcttc    180

aacactacaa caacatgttt ctaatttatt ttatatttta ataattaaac aatatatacg    240

tctgcacatt gttgctccga cataatctag tataaaaata gttgcagcat atgtgaaaag    300

caagcagcat ttatcactca atacttttaa ttttatctgt tgtatgtatt aaggttttgt    360

agctttaaga aaacgcttat aatataaaat aacttctaaa agatatttca tgcgtataca    420

ataaatattt gtgaaaaaac atttcgaaaa cgtgtacaat atataaacta ttgtgttatc    480

ttttgacatt caaacaaatg ttgacaatgt aattttatcc atgatatgat tggccaatta    540

gctgcgaggt aaaaatccgt atacgagtaa aagtaagata aaatttcgca agaagatttt    600

tagcaggaaa tctaagacaa gtgtcatgaa cgtgtcaatc aacaaacgaa aaggagaatt    660

atagaatcca gattcgacgt accacattaa taaatatcaa aacattttat gttattttat    720

ttttgctctg gcagttacac tctttttcat tgctccaata aaaaaatcac tcgcatgcat    780

gcatatatat acaccatagt aaactccgcc tcttcttcat tttaaaagta tcagtttaca    840

ctgacacaat ccttaactat tttcctttgt tcttcttcat ctttattaca catttttttc    900

aaggtaacaa ataatctttt taagtcactt tttatactctt taaatcttag attgatatat    960

gaatgcatgt taatatttca agatttatag gtctaccaaa c                       1001
```

<210> SEQ ID NO 54
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 54

```
aaacgttgca agattattga ttgtgagaaa gagtgctcaa ggtagtactg atttctgtaa      60
agctcacggt ggtgggaaac gatgttcttg gggagatggg aaatgtgaga aaatttgcta     120
gaggaaagaa gcggtttatg cgctgcgcat aacactatta tgtctcggga gaacaaagat     180
ggaagcaaga gcggtttgat tggaccggga ctctttagtg gccttgtttt tggctctact     240
tctgatcatt ctcagtctgg agctagcgct gtctctgatt gtactgattc tgttgaacga     300
atacagtttg agaataggca gaagaacaag aagatgatga taccgatgca ggttctagta     360
ccttcatcaa tgaaatctcc aagtaattca catgaaggag aaacaaacat ctatgacttc     420
atggttccgg aggagagagt tcacggcggt gggctagtaa tgtctttact tggtggctcc     480
attgatcgaa actgaaagcc atttatggta aaagtgtcac attctcagca aaaacctgtg     540
taaagctgta aaatgtgtgg gaatctccga atctgtttgt agccggttac gttatgctgg     600
atcaaaaact caagatttgt tggatattgt tatgctggat cggtggtgaa accacttccc     660
ggttgctaaa taaataaacg tttttgtttt ataatctttt tcactaaacg gcagtatggg     720
cctttagtgg gcttccttta agcgaccaat acaatcgtcg caccggaatc tactaccatt     780
tataggttta ttcatgtaaa acctcggaaa atttgagagc cacaacggtc aagagacaaa     840
aacaacttga agataaaggg ataaggaagg cttcctacat gatggacaac atttctttcc     900
acacaaattc tcataataaa aatcttataa tacaaatact tacgtcataa tcattcaatc     960
tagtccccat gttttaaggt cctgtttctt gtctgataca aat                      1003
```

<210> SEQ ID NO 55
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 55

```
ttggtttgca ttgtgaagat ttgtattaac tatagaacat tgaattgatg gtgttaagtt      60
cttacacaag cgtgcttctc ggtttgaact gtttcttttg tatgttgaat cagagcttag     120
tttataggaa ccagagtatc tacttagtca ttctctgatg ctaagtgcta aggttctacc     180
tagttgccct ctaggccctt atgttattga taacttatga agctatttga acacttgatt     240
cttaggagac ctaagttggt acagccagat agagtgtatg ttcttgttct ctatgtgaca     300
ggatcaagct gccacacata gttcaagggt atgctctgtg tgggtttgct cagattgagg     360
acaaatctat acaaggaagt agagtctttg acattttgat gttgtatgat aagaagaaga     420
aaggagagta ataaagaaag agaaaaggga aacagaaaca cgtgggagaa catcccaaag     480
aggaagcaca cgcggatctt catgcaaagc tccccgattc tcccatgtgg tccctttctc     540
cctttgtccc cctcctcttt cttcttttct catttactc ctttttttac cattatacaa      600
cgaatctttt ttatcataat tttttggttt tggtttattt tccaataaca ctttcttggt     660
tacttcccat tctcactttt tcatataaga aactcacttt gggaaactta tgtttgagaa     720
tgacaagtct ttttagagaa agtgatgtaa caaatctaaa gtgattatat aataaccttg     780
cacaatgttt ttgatttttt gtaagattcg aatattaggt ttattattcg tagggaataa     840
acttactttc aaaagcgttc ataagttaat actttcatat atgatcataa gtacggacac     900
```

tattgttttt tgtttgtttg tgtttattct aaaagaaagt agcttttaat tgaaatgtcc 960
tcggaggcac agtttaaagt tcgagtgtaa cagtttctaa ggca 1004

<210> SEQ ID NO 56
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 56
ttattagatt aatagattgc attgcattgc ttgtgctttc aatttacaaa ttgtctccca 60
actccatcga cacatctctt tttgtgtata taagattcag acttgttata ttttttttat 120
aaatatgtta ttagcatctt aagttaaatt gatttttttat atctgcatta aggattacac 180
gactatattt gcgattgtgt gttggttaaa atataattta ggattgtctt taactacatt 240
taggattata tgactatatt tggttaaata taaaatctag ctgtgattat tagtattcaa 300
aaataagtag cctaaccaat taaaacaacg gctattgggg caaattagaa catttagtg 360 tgtccaaaat ataatggtca ttaggtcata ttcctcctag cttcatcgca gcataattga 420
atgattgcct tatttagaag agcttttcca ctttcccaaa atctaggtgg gatcttttg 480 ttttgacctt catttttctt gtttaccatt tttagctaaa ttatttacga ttacaaaaga 540
tatcaaaagt tggatcataa tacaatttat agacttactg tagaaaattc gtatgtacaa 600
gtacaacaaa ttcttcataa taaattttga aaattctatt acaaatgttg taagaaatag 660
aatttgaaat atatataaac taaggagaaa aaaaaagaga acatgcattg ctctagtcag 720
agtggaccaa catcaacgag ataagataac ataaaaacca actcaccata actaaaaaca 780
tcccaagaga tccaacgatt catatcaaac acaaaaacat cgaacgatca gatttaaacc 840
atctctggta tctccaaaac acaaacactt ttttttttct tttgtctgaa tggaacaaaa 900
gcatgcgaca tctctgtgtc tttatcttct ctctcctctt cttgaaaaac tgaaccttta 960
attctttctt cacatctcct ttagctttct gaagctgcta 1000

<210> SEQ ID NO 57
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 57
gattggtatg aaatttcgga gaccaacaaa aaaaacttta ttgagcttgg agtgaagcta 60
tatatatggg gcaagatcat aatatgttta tatcggcctt ttcgttaact gaaaataata 120
gttttgagaa atatatcaaa tggtaaacag acatcatctt tgaaaaatac catcaatgaa 180
gttaatattg ttattggcat atggtttacc catcttaatt ttaatgcaac caaacaaaca 240
agaaacaaaa actgtataag atacaaggtg ttttacgatt ttccgtctta aaaccgaaat 300
atttttgttc ctacgacttt aaacggactt tgcttaagtt gtgtgcatgt aagctcgtcg 360
tccctcgatt gtcatcaaca ttcaccaata tcagcctcta tcacacgagt gaaggtggtg 420
attcggctta atgaaaacag agaaatattt caatatgatt cctattaaat tttaaatctt 480
ttttctcaat ctctagattt tcattaaaag catcatgatt tttttccact atgttcatat 540
atctctatca cagttttagg tacattgtag aaattggata agatacgtca tacgtctaac 600

```
atgaatttgg tctagcaagg aaggtttgag ataataagtg aaaagaaaac acaagataat     660

aaattataat ttataaatgc tttatagtat tgaaaaataa gatgattttt ttttttttta     720

ataccggatt ggctgatcca cttatgatga ctcaaatgtt attaagtttc aagacaattt     780

atgatgacac aaatcacaat gagtcaatag tagccacgaa gccagaaaaa aaaaatgtac     840

tacaaaaaga taatgatagt acaaaatgat acgtcgtact gccacatgta cgacacaact     900

cgattaccaa aaagcagagc catccaacca taaaactcaa aacacacaga ttccactggc     960

gtgtgctctc ctcacttcac tcgtccttga aacttgaggt actga                    1005
```

<210> SEQ ID NO 58
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 58

```
taaatagtga cattggtaag aagaaaaaaa acactattaa atagtgaaaa aatggtttat       60

aactctctta attaacatta cttattattg ctagcaccta aaatctccca caaaatattt      120

gttgtaaaac acaaatttac aaaatgattt tgtttttaaa ttagtaacac atgttcatat      180

atacgttaat aagaacatac cctatatgat tttatataaa aaaatttctt tgagacgtct      240

tattcttttt tctttaataa tatgcaattg tgagagtttg gatttgaatg gtagcattag      300

aagcaaactt gaaccaaaca tatttcatga agtcaaactt gaaccaatgt gatcactaat      360

cacagtgttc gcagtgtaag gcatcagaaa atagaagaag ggacatagct atgaatcata      420

taatcttgac acatgtttta taggttttag gtgtgtatgc taacaaaaaa tgagacagct      480

ttcttctaat agacttaata tttgggctaa atgtaccaca gttgtgaatt tcttacaaaa      540

atgggccgag ctacaaaaaa ctacaggccc actctcaact cttatcaaac gacagcgttt      600

tacttttttta aaagcacaca ctttttgttt ggtgtcggtg acggtgagtt tcgtccgctc      660

ttcctttaaa ttgaagcaac ggttttgatc cgatcaaatc caacggtgct gattacacaa      720

agcccgagac gaaaacgttg actattaagt taggttttaa tctcagccgt taatctacaa      780

atcaacggtt ccctgtaaaa cgaatcttcc ttccttcttc acttccgcgt cttctctctc      840

aatcacctca aaaaaatcga tttcatcaaa atattcaccc gcccgaattt gactctccga      900

tcatcgtctc cgaatctaga tcgacgagat caaaacccta gaaatctaaa tcggaatgag      960

aaattgattt tgatacgaat tagggatctg tgtgttgagg ac                        1002
```

<210> SEQ ID NO 59
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 59

```
agtcgattgg tacactctta atttaattag agtaagagat caacaaaaat atagaatttt       60

ctttatatcg aagtgctacg accttatata tatagaaaaa aaagcatagg tgaatctcta      120

aattgagatt gtgctgtagt aaacatatta agtttttagt ttttttaaga aatgaatctt      180

tttgttgatt aattcaaact agtagtcatt aagattccgg agattccaat ttagaaaagt      240
```

```
caaagattca aagaacaagt ccaggtccac atgttgaatc cgattcatca tccactcatc    300

cttcatatct tcctccaccg tctccgccca aaaaatcaat aacaataaaa aatcctaaaa    360

aaacatattt gattttgaaa aaactttatc atatattata ttaattaaat agttatccga    420

tgactcatcc tatggtcagg gccttgctgt ctctgacgtc cttaattatc attattttta    480

aatttgtctc tctcagaaaa ttacgccaca atcttcctct ttccctttc cgaaaacagc     540

taatatttgt ggacctaaac taaataacgt agcctctaga ttttatataa ttactaatac    600

tatatgctac tacttgttat tatttactcc aatcatatat gataccaatc aagaatcact    660

acataagtag aaaactttgc aatgagtcca ttaattaaaa ttaagaataa acttaaaatt    720

ttatggtatt ttaagattcc ctttggattg taatgacaag aaatcagcaa attagtcgta    780

actcgtaaga ataaacaaga tcaattttta ctttctttac aaagattccg ttgtaatttt    840

agaaattttt ttttgtcact gttttttat agattaattt atctgcatca atccgattaa     900

gaagtgtaca catgggcatc tatatatatc taacaggtaa aacgtgtatg tacatgcata    960

aggttttacg tgcttctata aatatatgtg gcagt                               995
```

<210> SEQ ID NO 60
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 60

```
ccagtcgatt ggcgcctcgc atgcctatca tatttaaccg tcaataatgg atttggcggt     60

tttggtaggc cgggtcaacc ggattaaaag aaaacggttt ggagtccttc cttgcaattg    120

aattttcaca cattcgggtt ttgtgatttc tctgtcataa tgggcccggc acatatggtt    180

cataacccat gtgggcctat ggtataattt ttccaattaa aactattgtt aggtcgataa    240

aacaaaaaac aataaaaacg agtggaatac acataccaaa aagaatgtga tgaacattag    300

taattttatt ttgatggtta atgaaaaaca aaataaatgc atcttggcat cttccgttgg    360

aaagcgcaaa tagggcagat tttcagacag atatcactat gatgggggt gagagaaaga     420

aaacgaggcg tacctaatgt aacactactt aattagtcgt tagttatagg acttttttt     480

tgtttgggcc tagttatagg atcataaggt aaaaatgaag aatgaatatt agattagtag    540

gagctaatga tggagttaag tatgcacgtg taagaactgg gaagtgaaac ctcctgtatg    600

gtgaagaaac tatacaacaa agccctttgt tggtgtatac gtattaattt ttattctttt    660

atcacaagcg atacgtatct taagacataa taaatatata tcttactcat aataaatatc    720

ttaagatata tatacagtat acacctgtat atatataata aataggcata tagtagaaat    780

taatatgagt tgttgttgtt gcaaatatat aaatcaatca aaagatttaa aacccaccat    840

tcaatcttgg taagtaacga aaaaaaaggg aagcaagaag aaccacagaa aagggggcta    900

acaactagac acgtagatct tcatctgccc gtccatctaa cctaccacac tctcatcttc    960

tttttcccgt gtcagtttgt tatataagct ctcactctcc ggtatatttc cccattgcac   1020

tgga                                                                1024
```

<210> SEQ ID NO 61
<211> LENGTH: 911
<212> TYPE: DNA
<213> ORGANISM: Arabidopsis thaliana
<220> FEATURE:

<221> NAME/KEY: misc_feature
<223> OTHER INFORMATION: Ceres Promoter YP0263

<400> SEQUENCE: 61

```
atctagctgt ggattccacc aaaattctgg cagggccatg atctaaaaac tgagactgcg     60
cgtgttgttt tgcagtgatt tgtatttcat atttgcacca tcctacacag tccacttggt    120
atcgtaacca aacataagga gaacctaatt acattattgt tttaatttcg tcaaactggt    180
ttttaccttt tagttacata gttgattctt catttgtttt agtagttatg gagcacaata    240
atgtgcaaca aagaaagatc atagtggatt aatatgttga gaggtcagaa attcttggtt    300
aacaaaaaaa agttacaagg actgagattt tgggtgggag aaagccatag cttttaaaac    360
atgattgaac ttaaaagtga tgttatggtt tgaggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc    600
ttaaacattt atttcaaact taaacactaa agaacatata tgaatagaag tttatataaa    660
ttactatata tctaccataa atctcttata attatgatgt cacgatgagg aagtgttgaa    720
acgttaaaat gccaaaatat aagcatgcga cggaattttg gcagaagatt gtagagttgt    780
aatctgtcgc aatcattact cgtgctagca tttttcattt tcccttcatt tgtggataac    840
gcacgatata acattctaca caccaacaag attctataaa aacgcaaagg ttgtctccat    900
agaatatcgt c                                                         911
```

<210> SEQ ID NO 62
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 62

```
aaacattaat atgtagtaac tatgggcgta tgctttactt tttaaaatgg gcctatgcta     60
taattgaatg acaaggatta aacaactaat aaaattgtag atgggttaag atgacttatt    120
tttttactta ccaatttata aatgggcttc gatgtactga aatatatcgc gcctattaac    180
gaggccattc aacgaatgtt ttaagggccc tatttcgaca ttttaaagaa cacctaggtc    240
atcattccag aaatggatat tataggattt agataatttc ccacgtttgg tttatttatc    300
tattttttga cgttgaccaa cataatcgtg cccaaccgtt tcacgcaacg aatttatata    360
cgaaatatat atatttttca aattaagata ccacaatcaa aacagctgtt gattaacaaa    420
gagatttttt tttttggtt ttgagttaca ataacgttag aggataaggt ttcttgcaac    480
gattaggaaa tcgtataaaa taaaatatgt tataattaag tgttttattt tataatgagt    540
attaatataa ataaaacctg caaaaggata gggatattga ataataaaga gaaacgaaag    600
agcaatttta cttctttata attgaaatta tgtgaatgtt atgtttacaa tgaatgattc    660
atcgttctat atattgaagt aaagaatgag tttattgtgc ttgcataatg acgttaactt    720
cacatataca cttattacat aacatttatc acatgtgcgt cttttttttt ttttactttg    780
taaaatttcc tcacttttaa gacttttata acaattacta gtaaaataaa gttgcttggg    840
gctacaccct ttctccctcc aacaactcta tttatagata acattatatc aaaatcaaaa    900
catagtccct ttcttctata aaggtttttt cacaaccaaa tttccattat aaatcaaaaa    960
```

ataaaaactt aattagtttt tacagaagaa aagaaaaca 999

<210> SEQ ID NO 63
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 63
gggattatat atgatagacg attgtatttg cgggacattg agatgtttcc gaaaatagtc 60
atcaaatatc aaaccagaat ttgatgtgaa aacactaatt aaaacatata attgacaact 120
agactatatc atttgttaag ttgagcgttg aaagaaaatg aaagagtgta gactgtagta 180
cgtatgagtt tcccaaaaga tggtgcttga atattattgg gaagagactt tggttggttc 240
ggttgaatga agatttttac ctgccatgtt gatagagaaa ggcaaataaa tgtaggggtc 300
gatgtctaac gtaaagactg gatcaaccaa gagtcctcct cctcgtcttc accaaaaaaa 360
aagagtcctc ctcgtggaaa cttatttctt ctccagccaa gatctcatct catctcttca 420
ctctatgaaa tataaaggaa tcttatggtt tttctaaaaa ctatagtacg tctatatacc 480
aaaggaaaca atataaaatc agttaatctg ataaattttg agtaaataat aaagttaact 540
ttgtacttac ctatatcaaa ctaattcaca aaataaagta ataataacaa agaattttta 600
gtagatccac aatatacaca cacactatga gaaatcataa tagagaattt taatgatttt 660
gtctaactca tagcaacaag tcgctttggc cgagtggtta aggcgtgtgc ctgctaagta 720
catgggctct gcccgcgaga gttcgaatct ctcaggcgac gtttcttttg ttttcggcca 780
taaaggaaaa agcccaatta acacgtctcg cttataagcc cataaagcaa acaatgggct 840
gtctctgtct cactcacaca cgcgttttcc tactttttga ctatttttat aaccggcggg 900
tctgacttaa ttagggtttt ctttaataat cagacactct ctcactcgtt tcgtcaacat 960
tgaacacaga caaaaccgcg t 981

<210> SEQ ID NO 64
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 64
gaaaacaatc ataggttacg ctattatcat cgaaaggtat gtgatgcata ttcccattga 60
accagatttc catatatttt atttgtaaag tgataatgaa tcacaagatg attcaatatt 120
aaaaatgggt aactcacttt gacgtgtagt acgtggaaga atagttagct atcacgcata 180
catatatcta tgaataagtg tgtatgacat aagaaactaa aatatttacc taaagtccag 240
ttactcatac tgatttcatg catatatgta ttatttattt atttttaata aagaagcgat 300
tggtgttttc atagaaatca tgatagattg ataggtattt cagttccaca aatctagatc 360
tgtgtgctat acatgcatgt attaattttt tccccttaaa tcatttcagt tgataatatt 420
gctctttgtt ccaactttag aaaaggtatg aaccaacctg acgattaaca agtaaacatt 480
aattaatctt tatatgagat aaaaccgagg atatatatga ttgtgttgct gtctattgat 540
gatgtgtcga tattatgctt gttgtaccaa tgctcgagcc gagcgtgatc gatgccttga 600

```
caaactatat atgtttcccg aattaattaa gttttgtatc ttaattagaa taacattttt    660

atacaatgta atttctcaag cagacaagat atgtatccta tattaattac tatatatgaa    720

ttgccgggca cctaccagga tgtttcaaat acgagagccc attagtttcc acgtaaatca    780

caatgacgcg acaaaatcta gaatcgtgtc aaaactctat caatacaata atatatattt    840

caagggcaat ttcgacttct cctcaactca atgattcaac gccatgaatc tctatataaa    900

ggctacaaca ccacaaagga tcatcagtca tcacaaccac attaactctt caccactatc    960

tctcaatctc tcgtttcatt tcttgacgcg tgaaaa                              996
```

<210> SEQ ID NO 65
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 65

```
taattttttt atttttggaa ctaacactta ttagtttagg tttccatcac ctatttaatt     60

cgtaattctt atacatgcat ataatagaga tacatatata caaatttatg atcatttttg    120

cacaacatgt gatctcattc attagtatgc attatgcgaa aacctcgacg cgcaaaagac    180

acgtaatagc taataatgtt actcatttat aatgattgaa gcaagacgaa aacaacaaca    240

tatatatcaa attgtaaact agatatttct taaaagtgaa aaaaaacaaa gaaatataaa    300

ggacaatttt gagtcagtct cttaatatta aaacatatat acataaataa gcacaaacgt    360

ggttacctgt cttcatgcaa tgtggacttt agtttatcta atcaaaatca aaataaaagg    420

tgtaatagtt ctcgtcattt ttcaaatttt aaaaatcaga accaagtgat ttttgtttga    480

gtattgatcc attgtttaaa caatttaaca cagtatatac gtctcttgag atgttgacat    540

gatgataaaa tacgagatcg tctcttggtt ttcgaatttt gaactttaat agtttctttt    600

tttagggaaa ctttaatagt tgtttatcat aagattagtc acctaatggt tacgttgcag    660

taccgaacca attttttacc cttttttcta aatgtggtcg tggcataatt tccaaaagag    720

atccaaaacc cggtttgctc aactgataag ccggtcggtt ctggtttgaa aaacaagaaa    780

taatctgaaa gtgtgaaaca gcaacgtgtc tcggtgtttc atgagccacc tgccacctca    840

ttcacgtcgg tcattttgtc gtttcacggt tcacgctcta gacacgtgct ctgtccccac    900

catgactttc gctgccgact cgcttcgctt tgcaaactca aacatgtgtg tatatgtaag    960

tttcatccta ataagcatct cttaccacat taattaaaaa                         1000
```

<210> SEQ ID NO 66
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 66

```
ttagttcatt gaaacgtcaa ctttttactt gcaaccactt tgtaggacca ttaactgcaa     60

aataagaatt ctctaagctt cacaaggggt tcgtttggtg ctataaaaac attgttttaa    120

gaactggttt actggttcta taaatctata aatccaaata tgaagtatgg caataataat    180

aacatgttag cacaaaaaat actcattaaa ttcctaccca aaaaaaatct ttatatgaaa    240

ctaaaactta tatacacaat aatagtgata caaagtaggt cttgatattc aactattcgg    300
```

```
gattttctgg tttcgagtaa ttcgtataaa aggtttaaga tctattatgt tcactgaaat    360

cttaactttg ttttgtttcc agttttaact agtagaaatt gaaattttta aaaattgtta    420

cttacaataa aatttgaatc aatatcctta atcaaaggat cttaagacta gcacaattaa    480

aacatataac gtagaatatc tgaaataact cgaaaatatc tgaactaagt tagtagtttt    540

aaaatataat cccggtttgg accgggcagt atgtacttca atacttgtgg gttttgacga    600

ttttggatcg gattgggcgg gccagccaga ttgatctatt acaaatttca cctgtcaacg    660

ctaactccga acttaatcaa agattttgag ctaaggaaaa ctaatcagtg atcacccaaa    720

gaaaacattc gtgaataatt gtttgctttc catggcagca aaacaaatag gacccaaata    780

ggaatgtcaa aaaaaagaaa gacacgaaac gaagtagtat aacgtaacac acaaaaataa    840

actagagata ttaaaaacac atgtccacac atggatacaa gagcatttaa ggagcagaag    900

gcacgtagtg gttagaaggt atgtgatata attaatcggc ccaaatagat tggtaagtag    960

tagccgtcta tatcatccat actcatcata acttcaacct                        1000
```

<210> SEQ ID NO 67
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 67

```
aagacacccg taaatgttgt catgtagaag aaactagaaa cgttaaacgc atcaaatcaa     60

gaaattaaat tgaaggtaat ttttaacgcc gcctttcaaa tattcttcct aggagaggct    120

acaagacgcg tatttctttc gaattctcca aaccattacc attttgatat ataataccga    180

catgccgttg ataaagtttg tatgcaaatc gttcattggg tatgagcaaa tgccatccat    240

tggttcttgt aattaaatgg tccaaaaata gtttgttccc actactagtt actaatttgt    300

atcactctgc aaaataatca tgatataaac gtatgtgcta tttctaatta aaactcaaaa    360

gtaatcaatg tacaatgcag agatgaccat aaaagaacat taaaacacta cttccactaa    420

atctatgggg tgccttggca aggcaattga ataaggagaa tgcatcaaga tgatatagaa    480

aatgctattc agtttataac attaatgttt tggcggaaaa ttttctatat attagacctt    540

tctgtaaaaa aaaaaaaatg atgtagaaaa tgctattatg tttcaaaaat ttcgcactag    600

tataatacgg aacattgtag tttacactgc tcattaccat gaaaaccaag gcagtatata    660

ccaacattaa taaactaaat cgcgatttct agcaccccca ttaattaatt ttactattat    720

acattctctt tgcttctcga aataataaac ttctctatat cattctacat aataaataag    780

aaagaaatcg acaagatcta aatttagatc tattcagctt tttcgcctga gaagccaaaa    840

ttgtgaatag aagaaagcag tcgtcatctt cccacgtttg gacgaaataa aacataacaa    900

taataaaata ataaatcaaa tatataaatc cctaatttgt ctttattact ccacaatttt    960

ctatgtgtat atatataccc acctctctct tgtgtatttg                        1000
```

<210> SEQ ID NO 68
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 68

```
tataaaccat tcctataaca ccatatttaa acataacaat gaattgcttg gatttcaaac     60
tttattaaat ttggatttta aattttaatt tgattgaatt ataccccctt aattggataa    120
attcaaatat gtcaactttt tttttgtaag attttttttat ggaaaaaaaa attgattatt    180
cactaaaaag atgacaggtt acttataatt taatatatgt aaaccctaaa aagaagaaaa    240
tagtttctgt tttcacttta ggtcttatta tctaaacttc tttaagaaaa tcgcaataaa    300
ttggtttgag ttctaacttt aaacacatta atatttgtgt gctatttaaa aaataattta    360
caaaaaaaaa aacaaattga cagaaaatat caggttttgt aataagatat ttcctgataa    420
atatttaggg aatataacat atcaaaagat tcaaattctg aaaatcaaga atggtagaca    480
tgtgaaagtt gtcatcaata tggtccactt ttctttgctc tataacccaa aattgaccct    540
gacagtcaac ttgtacacgc ggccaaacct ttttataatc atgctattta tttccttcat    600
ttttattcta tttgctatct aactgatttt tcattaacat gataccagaa atgaatttag    660
atggattaat tcttttccat ccacgacatc tggaaacact tatctcctaa ttaaccttac    720
ttttttttta gtttgtgtgc tccttcataa aatctatatt gtttaaaaca aaggtcaata    780
aatataaata tggataagta taataaatct ttattggata tttctttttt taaaaaagaa    840
ataaatcttt tttggatatt ttcgtggcag catcataatg agagactacg tcgaaaccgc    900
tggcaaccac ttttgccgcg tttaatttct ttctgaggct tatataaata gatcaaaggg    960
gaaagtgaga tataatacag acaaaacaag agaaaaga                            998
```

<210> SEQ ID NO 69
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 69

```
acaagtacca ttcacttttt tacttttcaa tgtatacaat catcatgtga taaaaaaaaa     60
aatgtaacca atcaacacac tgagatacgg ccaaaaaatg gtaatacata aatgtttgta    120
ggttttgtaa tttaaatact ttagttaagt tatgatttta ttatttttgc ttatcactta    180
tacgaaatca tcaatctatt ggtatctctt aatcccgctt tttaatttcc accgcacacg    240
caaatcagca aatggttcca gccacgtgca tgtgaccaca tattgtggtc acagtactcg    300
tccttttttt ttcttttgta atcaataaat ttcaatccta aaacttcaca cattgagcac    360
gtcggcaacg ttagctccta aatcataacg agcaaaaaag ttcaaattag ggtatatgat    420
caattgatca tcactacatg tctacataat taatatgtat tcaaccggtc ggtttgttga    480
tactcatagt taagtatata tgtgctaatt agaattagga tgaatcagtt cttgcaaaca    540
actacggttt catataatat gggagtgtta tgtacaaaat gaaagaggat ggatcattct    600
gagatgttat gggctcccag tcaatcatgt tttgctcgca tatgctatct tttgagtctc    660
ttcctaaact catagaataa gcacgttggt tttttccacc gtcctcctcg tgaacaaaag    720
tacaattaca ttttagcaaa ttgaaaataa ccacgtggat ggaccatatt atatgtgatc    780
atattgcttg tcgtcttcgt tttcttttaa atgtttacac cactacttcc tgacacgtgt    840
ccctattcac atcatccttg ttatatcgtt ttacttataa aggatcacga acaccaaaac    900
atcaatgtgt acgtcttttg cataagaaga aacagagagc attatcaatt attaacaatt    960
```

```
acacaagaca gcgagattgt aaaagagtaa gagagagag                        999


<210> SEQ ID NO 70
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 70

cacggtcaaa gtattgctaa catggtcatt acattgaaaa agaaaattaa ttgtctttac     60

tcatgtttat tctatacaaa taaaaatatt aaccaaccat cgcactaaca aaatagaaat    120

cttattctaa tcacttaatt gttgacaatt aaatcattga aaaatacact taaatgtcaa    180

atattcgttt tgcatacttt tcaatttaaa tacatttaaa gttcgacaag ttgcgtttac    240

tatcatagaa aactaaatct cctaccaaag cgaaatgaaa ctactaaagc gacaggcagg    300

ttacataacc taacaaatct ccacgtgtca attaccaaga gaaaaaaaga gaagataagc    360

ggaacacgtg gtagcacaaa aaagataatg tgatttaaat taaaaaacaa aaacaaagac    420

acgtgacgac ctgacgctgc aacatcccac cttacaacgt aataaccact gaacataaga    480

cacgtgtacg atcttgtctt tgttttctcg atgaaaacca cgtgggtgct caaagtcctt    540

gggtcagagt cttccatgat tccacgtgtc gttaatgcac caaacaaggg tactttcggt    600

attttggctt ccgcaaatta gacaaaacag ctttttgttt gattgatttt tctcttctct    660

ttttccatct aaattctctt tgggctctta atttcttttt gagtgttcgt tcgagatttg    720

tcggagattt tttcggtaaa tgttgaaatt ttgtgggatt ttttttattt tctttattaa    780

actttttttt attgaattta taaaaaggga aggtcgtcat taatcgaaga aatggaatct    840

tccaaaattt gatattttgc tgttttcttg ggatttgaat tgctctttat catcaagaat    900

ctgttaaaat ttctaatcta aaatctaagt tgagaaaaag agagatctct aatttaaccg    960

gaattaatat tctccgaccg aagttattat gttgcaggct                        1000


<210> SEQ ID NO 71
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 71

tttaaaaaat tggataaaac accgataaaa attcacattt gcaaatttta ttcagtcgga     60

atatatattt gaaacaagtt ttgaaatcca ttggacgatt aaaattcatt gttgagagga    120

taaatatgga tttgttcatc tgaaccatgt cgttgattag tgattgacta ccatgaaaaa    180

tatgttatga aaagtataac aacttttgat aaatcacatt tattaacaat aaatcaagac    240

aaaatatgtc aacaataata gtagtagaag atattaattc aaattcatcc gtaacaacaa    300

aaaatcatac cacaattaag tgtacagaaa aaccttttgg atatatttat tgtcgctttt    360

caatgatttt cgtgaaaagg atatatttgt gtaaaataag aaggatcttg acgggtgtaa    420

aaacatgcac aattcttaat ttagaccaat cagaagacaa cacgaacact tctttattat    480

aagctattaa acaaaatctt gcctattttg cttagaataa tatgaagagt gactcatcag    540

ggagtggaaa atatctcagg atttgctttt agctctaaca tgtcaaacta tctagatgcc    600

aacaacacaa agtgcaaatt cttttaatat gaaaacaaca ataatatttc taatagaaaa    660
```

```
ttaaaaaggg aaataaaata tttttttaaa atatacaaaa gaagaaggaa tccatcatca    720

aagttttata aaattgtaat ataatacaaa cttgtttgct tccttgtctc tccctctgtc    780

tctctcatct ctcctatctt ctccatatat acttcatctt cacacccaaa actccacaca    840

aaatatctct ccctctatct gcaaattttc caaagttgca tcctttcaat ttccactcct    900

ctctaatata attcacattt tcccactatt gctgattcat tttttttgt gaattatttc     960

aaacccacat aaaaaaatct ttgtttaaat ttaaaacca                           999
```

<210> SEQ ID NO 72
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 72

```
actcaacaat aggacaagcc aaaaaaattc caattattgt gttactctat tcttctaaat     60

ttgaacacta atagactatg acatatgagt atataatgtg aagtcttaag atattttcat    120

gtgggagatg aataggccaa gttggagtct gcaaacaaga agctcttgag ccacgacata    180

agccaagttg atgaccgtaa ttaatgaaac taaatgtgtg tggttatata ttagggaccc    240

atggccatat acacaatttt tgtttctgtc gatagcatgc gtttatatat atttctaaaa    300

aaactaacat atttactgga tttgagttcg aatattgaca ctaatataaa ctacgtacca    360

aactacatat gtttatctat atttgattga tcgaagaatt ctgaactgtt ttagaaaatt    420

tcaatacact taacttcatc ttacaacggt aaaagaaatc accactagac aaacaatgcc    480

tcataatgtc tcgaaccctc aaactcaaga gtatacattt tactagatta gagaatttga    540

tatcctcaag ttgccaaaga attggaagct tttgttacca aacttagaaa cagaagaagc    600

cacaaaaaaa gacaaaggga gttaaagatt gaagtgatgc atttgtctaa gtgtgaaagg    660

tctcaagtct caactttgaa ccataataac attactcaca ctccctttt ttttcttttt     720

ttttcccaaa gtaccctttt taattccctc tataacccac tcactccatt ccctctttct    780

gtcactgatt caacacgtgg ccacactgat gggatccacc tttcctctta cccacctccc    840

ggtttatata aacccttcac aacacttcat cgctctcaaa ccaactctct cttctctctt    900

ctctcctctc ttctacaaga agaaaaaaaa cagagccttt acacatctca aaatcgaact    960

tactttaacc accaaatact gattgaacac acttgaaa                            998
```

<210> SEQ ID NO 73
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 73

```
catagtaaaa gtgaatttaa tcatactaag taaaataaga taaaacatgt tatttgaatt     60

tgaatatcgt gggatgcgta tttcggtatt tgattaaagg tctggaaacc ggagctccta    120

taacccgaat aaaaatgcat aacatgttct tccccaacga ggcgagcggg tcagggcact    180

agggtcattg caggcagctc ataaagtcat gatcatctag gagatcaaat tgtatgtcgg    240

ccttctcaaa attacctcta agaatctcaa acccaatcat agaacctcta aaaagacaaa    300
```

```
gtcgtcgctt tagaatgggt tcggtttttg gaaccatatt tcacgtcaat ttaatgttta    360

gtataatttc tgaacaacag aattttggat ttatttgcac gtatacaaat atctaattaa    420

taaggacgac tcgtgactat ccttacatta agtttcactg tcgaaataac atagtacaat    480

acttgtcgtt aatttccacg tctcaagtct ataccgtcat ttacggagaa agaacatctc    540

tgtttttcat ccaaactact attctcactt tgtctatata tttaaaatta agtaaaaaag    600

actcaatagt ccaataaaat gatgaccaaa tgagaagatg gttttgtgcc agattttagg    660

aaaagtgagt caaggtttca catctcaaat ttgactgcat aatcttcgcc attaacaacg    720

gcattatata tgtcaagcca attttccatg ttgcgtactt ttctattgag gtgaaaatat    780

gggtttgttg attaatcaaa gagtttgcct aactaatata actacgactt tttcagtgac    840

cattccatgt aaactctgct tagtgtttca tttgtcaaca atattgtcgt tactcattaa    900

atcaaggaaa aatatacaat tgtataattt tcttatattt taaaattaat tttgatgtat    960

taccccttta taaataggct atcgctacaa caccaataac                          1000
```

```
<210> SEQ ID NO 74
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 74
```

```
tttcgatcct cttcttttt aggtttcttg atttgatgat cgccgccagt agagccgtcg      60

tcggaagttt cagagattaa aaccatcacc gtgtgagttg gtagcgaatt aacggaaagt    120

ctaagtcaag attttttaaa aagaaattta tgtgtgaaaa gaagccgttg tgtatattta    180

tataatttag aaaatgtttc atcattttaa ttaaaaaatt aataatttgt agaagaaaga    240

agcatttttt atacataaat catttacctt ctttactgtg tttttcttca cttacttcat    300

ttttactttt ttacaaaaaa gtgaaaagta aattacgtaa ttggtaacat aaattcactt    360

taaatttgca tatgttttgt tttcttcgga aactatatcg aaaagcaaac ggaaagaact    420

tcacaaaaaa ccctagctaa ctaaagacgc atgtgttctt cttattcttc atatatcctc    480

tgtttcttgt gttctgtttt gagtcttaca ttttcaatat ctgactctga ttactatatc    540

taaaagggaa catgaagaac ttgagaccat gttaaactgt acaatgcctt caaacatggc    600

taactaaaga tacattagat ggctttacag tgtgtaatgc ttattatctt taggtttttt    660

aaatcccttg tattaagtta tttaccaaat tatgttcttg tactgcttat tggcttggtt    720

gttgtgtgct ttgtaaacaa cacctttggc tttatttcat cctttgtaaa cctactggtc    780

tttgttcagc tcctcttgga agtgagtttg tatgcctgga acgggtttta atggagtgtt    840

tatcgacaaa aaaaaaatgt agcttttgaa atcacagaga gtagttttat attcaaatta    900

catgcatgca actaagtagc aacaaagttg atatggccga gttggtctaa ggcgccagat    960

taaggttctg gtccgaaagg gcgtgggttc aaatcccact gtcaacattc tctttttctc   1020

aaattaatat ttttctgcct caatggttca ggcccaatta tactagacta ctatcgcgac   1080

taaaataggg actagccgaa ttgatccggc ccagtatcag ttgtgtatca ccacgttatt   1140

tcaaatttca aactaaggga taaagatgtc atttgacata tgagatattt ttttgctcca   1200

ctgagatatt tttctttgtc ccaagataaa atatcttttc tcgcatcgtc gtctttccat   1260

ttgcgcatta aaccaaaaag tgtcacgtga tatgtcccca accactacga attttaacta   1320
```

```
cagatttaac catggttaaa ccagaattca cgtaaaccga ctctaaacct agaaaatatc   1380

taaaccttgg ttaatatctc agccccctta taaataacga gacttcgtct acatcgttct   1440

acacatctca ctgctcacta ctctcactgt aatcccttag atcttctttt caaatttcac   1500

cattgcactg gatg                                                     1514
```

<210> SEQ ID NO 75
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 75

```
gtgggtaaaa gtatccttct ttgtgcattt ggtattttta agcatgtaat aagaaaaacc     60

aaaatagacg gctggtattt aataaaagga gactaatgta tgtatagtat atgatttgtg    120

tggaatataa taaagttgta aaatatagat gtgaagcgag tatctatctt ttgactttca    180

aaggtgatcg atcgtgttct ttgtgatagt tttggtcgtc ggtctacaag tcaacaacca    240

ccttgaagtt ttcgcgtctc ggtttcctct tcgcatctgg tatccaatag catacatata    300

ccagtgcgga aaatggcgaa gactagtggg cttgaaccat aaggtttggc cccaatacgg    360

attccaaaca acaagcctag cgcagtcttt tgggatgcat aagactaaac tgtcgcagtg    420

atagacgtaa gatatatcga cttgattgga atcgtctaag ctaataagtt taccttgacc    480

gtttatagtt gcgtcaacgt ccttatggag attgatgccc atcaaataaa cctgaaaatc    540

catcaccatg accaccataa actcccttgc tgccgctgct ttggcttgag caaggtgttt    600

ccttgtaaag ctccgatctt tggataaagt gttccacttt ttgcaagtag ctctgacccc    660

tctcagagat gtcaccggaa tcttagacag aacctcctct gccaaatcac ttggaagatc    720

ggacaatgtc atcattttg caggtaattt ctccttcgtt gctgctttgg cttgagcacg    780

gtgcttcttt gtaaagctcc gatctttgga taagagcgga tcggaatcct ctaggaggtg    840

ccagtccctt gacctattaa tttatagaag gttttagtgt attttgttcc aatttcttct    900

ctaacttaac aaataacaac tgcctcatag tcatgggctt caaattttat cgcttggtgt    960

atttcgttat ttgcaaggcc ttggcccatt ttgagcccaa taactaaatc tagccttttc   1020

agaccggaca tgaacttcgc atattggcgt aactgtgcag ttttaccttt ttcggatcag   1080

acaagatcag atttagacca cccaacaata gtcagtcata tttgacaacc taagctagcc   1140

gacactacta aaaagcaaac aaaagaagaa ttctatgttg tcattttacc ggtggcaagt   1200

ggacccttct ataaaagagt aaagagacag cctgtgtgtg tataatctct aattatgttc   1260

accgacacaa tcacacaaac ccttctctaa tcacacaact tcttcatgat ttacgacatt   1320

aattatcatt aactctttaa attcacttta catgctcaaa aatatctaat ttgcagcatt   1380

aatttgagta ccgataacta ttattataat cgtcgtgatt cgcaatcttc ttcattagat   1440

gctgtcaagt tgtactcgca cgcggtggtc cagtgaagca aatccaacgg tttaaaacct   1500

tcttacattt ctagatctaa tctgaaccgt cagatatcta gatctcattg tctgaacaca   1560

gttagatgaa actgggaatg aatctggacg aaattacgat cttacaccaa ccccctcgac   1620

gagctcgtat atataaagct tatacgctcc tccttcacct tcgtactact actaccacca   1680

catttcttta gctcaacctt cattactaat ctccttttaa ggtatgttca cttttcttcg   1740

attcatactt tctcaagatt cctgcatttc tgtagaattt gaaccaagtg tcgatttttg   1800
```

```
tttgagagaa gtgttgattt atagatctgg ttattgaatc tagattccaa tttttaattg   1860

attcgagttt gttatgtgtg tttatactac ttctcattga tcttgtttga tttctctgct   1920

ctgtattagg tttctttcgt gaatcagatc ggaa                               1954
```

<210> SEQ ID NO 76
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 76

```
gatcggcctt cttcaggtct tctctgtagc tctgttactt ctatcacagt tatcgggtat     60

ttgagaaaaa agagttagct aaaatgaatt tctccatata atcatggttt actacaggtt    120

tacttgattc gcgttagctt tatctgcatc caaagttttt tccatgatgt tatgtcatat    180

gtgataccgt tactatgttt ataactttat acagtctggt tcactggagt ttctgtgatt    240

atgttgagta catactcatt catcctttgg taactctcaa gtttaggttg tttgaattgc    300

ctctgttgtg atacttattg tctattgcat caatcttcta atgcaccacc ctagactatt    360

tgaacaaaga gctgtttcat tcttaaacct ctgtgtctcc ttgctaaatg gtcatgcttt    420

aatgtcttca cctgtctttc tcttctatag atatgtagtc ttgctagata gttagttcta    480

cagctctctt ttgtagtctt gttagagagt tagttgagat attacctctt aaaagtatcc    540

ttgaacgctt tccggttatg accaatttgt tgtagctcct tgtaagtaga acttactggg    600

accagcgaga cagtttatgt gaatgttcat gcttaagtgt cgaacgtatc tatctctact    660

atagctctgt agtcttgtta gacagttagt tttatatctc catttttttg tagtcttgct    720

agttgagata ttacctcttc tcttcaaagt atccttgaac gctcaccggt tatgaaatct    780

ctacactata gctctgtagt cttgctagat agttagttct ttagctctct ttttgtagcc    840

tagttcttta gctctccttt tgtagccttg ctacagagta agatgggata ttacctcctt    900

gaacgctctc cggttatgac caatttgttg tagctccttg taagtagaac ttaggataga    960

gtgagtcaac tttaagaaag aacctagtat gtggcataac cagattgcag gctctgtctc   1020

ggctacagta acgtaactct atagctcttt gttttgttca gaaagaacca gtgattggat   1080

gattcgtcct tagaaactgg acctaacaac agtcattggc tttgaaatca agccacaaca   1140

atgcctatat gaaccgtcca tttcatttat ccgtttcaaa ccagcccatt acatttcgtc   1200

ccattgataa ccaaaagcgg ttcaatcaga ttatgtttta attttaccaa attctttatg   1260

aagtttaaat tatactcaca ttaaaaggat tattggataa tgtaaaaatt ctgaacaatt   1320

actgattttg gaaaattaac aaatattctt tgaaatagaa gaaaaagcct ttttcctttt   1380

gacaacaaca tataaaatca tactcccatt aaaaagattt taatgtaaaa ttctgaatat   1440

aagatatttt ttacaacaac aaccaaaaat atttattttt ttcctttttt acagcaacaa   1500

gaaggaaaaa cttttttttt tgtcaagaaa aggggagatt atgtaaacag ataaaacagg   1560

gaaaataact aaccgaactc tcttaattaa catcttcaaa taaggaaaat tatgatccgc   1620

atatttagga agatcaatgc attaaaacaa cttgcacgtg gaaagagaga ctatacgctc   1680

cacacaagtt gcactaatgg tacctctcac aaaccaatca aaatactgaa taatgccaac   1740

gtgtacaaat tagggtttta cctcacaacc atcgaacatt ctcgaaacat tttaaacagc   1800

ctggcgccat agatctaaac tctcatcgac caatttttga ccgtccgatg gaaactctag   1860
```

```
cctcaaccca aaactctata taaagaaatc ttttccttcg ttattgctta ccaaatacaa   1920

accctagccg ccttattcgt cttcttcgtt ctctagtttt ttcctcagtc tctgttctta   1980

gatcccttgt agtttccaaa tcttccgata aggcct                              2016
```

<210> SEQ ID NO 77
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 77

```
acagttttct tttctcatct tacaacaagt ttccaggagg atagagacat aaacgaagct     60

cggattgtat cgttcttttt agcttttatt cacatccgaa agtcctgtag tttagattct    120

gttatcttgc ggttttgagt taatcagaaa cagagtaatc aatgtaatgt tgcaggctag    180

atctttcatc tttggaaatt tgtttttttc tcatgcaatt tctttagctt gaccatgagt    240

gactaaaaga tcaatcagta gcaatgattt gatttggcta agagacattt gtccacttgg    300

catcttgatt tggatggtta caacttgcaa gacccaattg gatacttgct atgacaactc    360

caactcaaga gtgtcgtgta actaagaacc ttgactaatt tgtaatttca atcccaagtc    420

atgttactat atgttttttt gtttgtatta ttttctctcc tacaattaag ctctttgacg    480

tacgtaatct ccggaaccaa ctcctatatc caccatttac tccacgttgt ctccaattat    540

tggacgttga aacttgacac aacgtaaacg tatctacgtg gttgattgta tgtacatatg    600

tacaaacgta cacctttctc ctctttcact tcatcacttg gcttgtgaat tcattaattc    660

ctgcgaa                                                              667
```

<210> SEQ ID NO 78
<211> LENGTH: 252
<212> TYPE: DNA
<213> ORGANISM: Arabidopsis thaliana
<220> FEATURE:
<221> NAME/KEY: misc_feature
<223> OTHER INFORMATION: Ceres Promoter PD0898

<400> SEQUENCE: 78

```
cgcaggcccg atcggcctaa ataattatag tcataagagg acccaaataa ataaataatg     60

ggattctctg aggtgtattt ttttatgcac acgtaaaagc gtgaaagatt tgtaaaccta    120

ctttatatat atacttccat ctctttgtct ttgttacaat ttgaatcaga gagaaattaa    180

gaagcgaaaa acaaagaacg agaggaggcg agaggtatag aagaatattc cttgtggccg    240

gcaaggccaa tc                                                        252
```

<210> SEQ ID NO 79
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 79

```
caaagtattt gacaagccat atggttttgg atcaaaaagt cggtccaaaa ttaatgtttt     60

atgtgcaaga accgacccat tgtacacacg tgttaacatc ttcaagactt tcatctctat    120

ttttcttttg gtcattaaga tacccattga tccgaatctg ttacattccc acctactttt    180
```

ttaattttta ctatccactc caaattaaac acaaccgatg attttaataa ttggaagctt 240
tttaaaatat ttctccacgt gcctctttgt gtttgtctat ata 283

<210> SEQ ID NO 80
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 80
tagttccatt acaatttcca aatgatttgt tacaaagcta caagattatt cgaaatagga 60
tttcatccat aagagagaat ggtgtggtcg acgctacaat gttgatttat tggttgtggt 120
ttgcatcttg ggatgtcaa atcctaagtt tcaagttctt gtaaaaacgt tttcaggttt 180
ctttaatata ttttaatatt aatgtaaaaa gaaaagatat agcttttgta caaaaaaatt 240
tgtttaatca ctatgtagga ggatgcgatc aaattcatgg aatgatgtat tattagcttt 300
tctatcctca ctctaaaaac aatactatag tgagttaaat aatttgatca tttcaatgta 360
gattaaaatt ttattaaaag aagaaaaatt taaaagccta taacaaaata aaaaaggagg 420
ctcgaggtat gatgggtgta gcagaagagc tggcaacagc tatcgactga gtgattacga 480
actcagtact cagtgttctc agctcacaca ctcttttttt gttctctttc ttttggacag 540
ctttcatttt ctcttttctt ttttctattt tgtttcaaaa ttccatccat attaaaatag 600
gcctgatcat gagaataaag gaaatactaa tgatgagttt ctcaataatg caataagatg 660
caattattat gagctattta ctattgaaaa tgagcaaata aatgtcaaaa cacaatctgg 720
ttaagttaga gcaactccat tgtataggat tcatgtagtt tctaagaaaa caaaatgtat 780
taatatttta cttttacatc caaaaaacca acttatatga gtaatagaaa cgatcctaat 840
attaggaatt ttagagattt tctctcatct gtttcttaac ttttcaatat ttttattttt 900
taaaattgta tgagtttcta ctaagaaact actgctggag ttggtcttag cttcccaatg 960
cttctccacc tatatatatg catatctcct tcttaaaac 999

<210> SEQ ID NO 81
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 81
aagcggcaat ttagtaagaa gtactcaaag tatcatttac caaaagtata tggttttggg 60
aagagttgtt agggatgtat tctttctaaa cagatgatat gacgatgttc ttgaaaacta 120
atgttaaaga cggaatctct ggcatcttca ctcgggagat atattaaacc gttgattgta 180
gttagccatg tacttagctt agtgcacaaa taatctgctg caagaaatct ttttctatta 240
taatatctct catttaaaca ttagaacata ttgtttaact tgttcttcta gaaataaaac 300
tgctaatttc ttatggtaaa ctattttcct ttagattgca caatcgaact cgaaaatcta 360
gtggagacta tgtgactatg tttatatata tgaaacctaa atcaaattat cccaataatt 420
gggagacaca aaagaaaaat tacgaaagaa aacaggaaat caaatcaaaa gataaagaga 480
aggtaaaaaa aggcaagaag cactaatgtt taatatttat agttttctcc attaaagaaa 540
aagcgatgat gtgtgttctc atcttttgtg aaagtatata tattgctttt gcttttctca 600

```
aaagcaaaag actcatccaa caagaacaaa aaaaaaaact aaagctcaat ccaaaagacg    660

aagaatgcat tggatactac aacttctttt tcacttttct ttcaaattta caattatgat    720

tttcacaata cagtttattc aaaaataaat aaaaaaacga ggcatgaaaa taatgattat    780

cctcttcact tattaagcca ctcactataa gcagagcaac tccagaacat agtgagcccc    840

caaaacatta aagcatgatg atgtctaatg atgatgatct tcttcgttcc atttctctaa    900

atttttggga tttctgcgaa gacccttctt ctctttctct tctctgaact tcaagattcg    960

tgtcggacaa atttttgttt ttatttttct gatgttaca                           999
```

<210> SEQ ID NO 82
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 82

```
tgaattgagt aaaatgtgtt ttcaaacagt taggtggtag aaggtaaagg taataacatc     60

atgatcttac taaaagaatt gttgcatact aactatcaat attctcaaca acataatata    120

atgttttttt aggtaatttt ccattttaat tttttgtgat taaacaatta aacaactcga    180

atgatgatga taaaaaaaaa aaattaacaa ctcgaataag ttaaagtagc aatacacatg    240

tcgttcaatt caaccaataa agtaagactt atatttttaa gaagttgact aatagcttaa    300

taagttggaa aacttgtgta gtttcttaat tcccacgtgc agtaagaaat aaaaatgaaa    360

aaaattatta tatccttccc actctgcgac ttttctttta ttttatcaaa tattaaaaag    420

attcatatca cagtttacac attgaaatca taaacgataa ttatgtattt tgtaataaaa    480

agttagttct gaagctcata ctttggatag tcgctagtcg ctaatatgct ccttgtaata    540

attaaagtca ctacgacgca cgtcaaagcc gatatttagg gcttaattga tgcgtgtttt    600

tcttttcata taatagtaat ataaattagt actaataaag tatgatggat ggttgagaca    660

gaaaagaaaa aagatgactg tatggtcatc attacaaaga agaatgtatt cttcatgttc    720

ttaagaataa taaaatgtca cttgtaaatc aagttggtaa gcattttgag aactttgttc    780

gatgcaacgt atgatgattt atgtagacaa aagataaaac cgtatcttca actattgcca    840

agaaaagata aaacctaatc tagtcagtct ctcaacataa atacaaccca atagccaaac    900

tgtgtccaat tcggagagaa actaaactaa aacaaaacac aaaagcccaa cataagccca    960

ataaaaccca ttttataaac agaacattac taacactca                           999
```

<210> SEQ ID NO 83
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 83

```
atgatgaaca ttctacatat ataattatta tgtttaagca cttagacagc ataaattctt     60

tctaattata taaatctaac cttgttacat tgtacatcta taaattactt gaagaaataa    120

cgagttctat ttctttttaa aaattaaaaa tactatacca tatctcagtg attaagttga    180

accaaaaggt acggaggaga aacaagcatt tgattcttcc ttattttatt ttattcatct    240
```

```
ctcactaatg atggtggaga aaaaaagaaa atacctaaca aacaaatata tattgtcata    300
caaaaatatt tctatatttt tagttaatta gtttatattc ctcacttttc agggcttata    360
taagaaagtg agcaaacaca aatcaaaatg cagcagcaaa tactatcatc acccatctcc    420
ttagttctat tttataattc ctcttctttt tgttcatagc tttgtaatta tagtcttatt    480
tctctttaag gctcaataag aggaggtact attactacac ttctctctac ttttacttgt    540
attttagcat taaaatccta aaatccgttt taaattcaaa aataaactta gagatgttta    600
atctcgattc ggtttttcgg ctttaggaga ataattatat gaaattagta tggatatctt    660
tactagtttc cattcaaatg attctgattt caatctaata ctctcactct ttaattaaac    720
tatatgtagt gtaatttcac actgttaaat ttctaccatg tcatgtatat tagagttgca    780
tagaaaattg taaaacatcc atttgaattc gaatgaaaca aaatgtttta aaataaaatt    840
ttggttttta aaagaaaaat ctaaaactga attatatcgt ttaaccaagt tgtaaaagtc    900
ataaaacgta gtatcttgta aatcgctctt ccacggtcca aatagacttc tagtaataaa    960
caagtaaaac taattttggt ttcttactaa ttttcacaga                         1000
```

<210> SEQ ID NO 84
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 84

```
ttagctgaac caggaaattg atctcttata ccagtttccg ggtttagatt ggtttgatgg     60
cgatttgatt aaacccccga aattttatgt cgtagttgtg catagtatta ttattctttg    120
cggacaatag acgtatcggg accaagttct gtagcaaaat tgtataagct taagtttgat    180
gaaatttaaa ggtaatcact aaaacccaaa tgggacaata aaccggtgaa gatttagagt    240
ttttaatttt gactcatgaa tctggagaaa gagccctcgt taaaaggagt gaatcaatcc    300
atagggggaaa aagttttgtc tttttaaaaa ctaaagaacc aaaccttaat agaagcagct    360
caatgtgtga caactttcca ctggcactaa gataaagtga ctagcgatga gtgcaattat    420
tgaaatagta gatggtaaat attacataca agagtaaaaa tatctttatg tcaatgctta    480
attcagtgtt tctggttaac aagagaaact tctctaactt tcgtaattgg gtcttataaa    540
attttatgca attatgattt taccctttta ctacttttca ttagctttca cgaatctatt    600
ttgacaagag aaatcattag aggtaaacat gctttttggt caagggcctt aacagttcca    660
ccaatcaagc tcaaaagttg tacttaaccg acatcttctg tgaaaacata taattacatg    720
tacaaatcaa aactacctta tgaaataaat agaaatattg cagttcattt ctaatttaac    780
ctcttcaact tttaaaacta tttacatttc tttatgtcat ttctagtcat tttgatgcaa    840
attgtaccat ttatggatta tcttcacaaa tttttaagtt ggtgaaaact ttttggtggg    900
tagttaaaac ttgaaataga aatttacttt accaaaataa actaatgaaa agtaatcact    960
ccactcccta taataagatt tccaacgttc ccactaagc                           999
```

<210> SEQ ID NO 85
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 85

```
agaagtattc acgcaccaag gttatatttg tagtgacata ttctacaatt atcacatttt      60
tctcttatgt ttcgtagtcg cagatggtca attttttcta taataatttg tccttgaaca     120
caccaaactt tagaaacgat gatatatacc gtattgtcac gctcacaatg aaacaaacgc     180
gatgaatcgt catcaccagc taaaagccta aaacaccatc ttagttttca ctcagataaa     240
aagattattt gtttccaacc tttctattga attgattagc agtgatgacg taattagtga     300
tagtttatag taaaacaaat ggaagtggta ataaatttac acaacaaaat atggtaagaa     360
tctataaaat aagaggttaa gagatctcat gttatattaa atgattgaaa gaaaaacaaa     420
ctattggttg atttccatat gtaatagtaa gttgtgatga aagtgatgac gtaattagtt     480
gtatttatag taaaacaaat taaaatggta aggtaaattt ccacaacaaa acttggtaaa     540
aatcttaaaa aaaaaaaaag aggtttagag atcgcatgcg tgtcatcaaa ggttcttttt     600
cactttaggt ctgagtagtg ttagactttg attggtgcac gtaagtgttt cgtatcgcga     660
tttaggagaa gtacgtttta cacgtggaca caatcaacgg tcaagatttc gtcgtccaga     720
tagaggagcg atacgtcacg ccattcaaca atctcctctt cttcattcct tcattttgat     780
tttgagtttt gatctgcccg ttcaaaagtc tcggtcatct gcccgtaaat ataaagatga     840
ttatatttat ttatatcttc tggtgaaaga agctaatata aagcttccat ggctaatctt     900
gtttaagctt ctcttcttct tctctctcct gtgtctcgtt cactagtttt ttttcggggg     960
agagtgatgg agtgtgtttg ttgaatagtt ttgacgatca                         1000
```

<210> SEQ ID NO 86
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 86

```
atctataacg agttaacatg ttgccagttt gaatcaagaa gcttggatga tgaatgaatg      60
gatcggtttg tggtacaatt cttaaaattg tagtagagga gacagagaaa aaacatgata     120
agactttggt atttacaact tgacggagac aagacagtaa gccaaatctg tcacaaaaac     180
actcaaactc ttttctcagt gttttgagtt taaagagaga cttattcact tccccttttcg    240
taacacttat ttgtctccca accaaacagt ttctgtcctt tcccttgtcc tcccacgtgc     300
atctttatat ctcatgactt ttcgtttcta gatcttgaat aatgtcttag tggattaggt     360
ttgttgtcgg taaattaggt gaccgttttt ttcttatatt tggaagatcg cgggatgaag     420
cagatactga gtttcagggc atacacacct aatttgaaaa tcattgttag tccaatttca     480
ctttaatctt gtttacaaaa aaattgatct gaaaatgttg atgggataag taaaaatgta     540
agttttgcta gtagtcatga tataataata gcaaaaccag atcaattttg agcaaaagga     600
agaaacaaaa aacagatcga tcccacgagc aagactaagt gtaaagtggt tcccacaaga     660
gccatatgga tatggtcctt caacttttaa agcccattac ttcagtggtc gacccgacat     720
tacgccacga gtagtcacgc acgcacgact ccgttcacgt gacattcacg ttgatatttc     780
cccctctact ctcttctgct tggttgatct aaaaaacatg aagagaccaa cctaatttca     840
tattaatata tgatatagac ttcatactca acagtcactt tcgtaatcca aatccatatc     900
ttacgaaatt agttcttaat aaaggttgtg gattaagtta taatattgtg ttaagagtta     960
```

```
agacacagca tataaccttg taccaacagt gctttattct taaatggaaa caaaacatat   1020

gtcaatgtca agcatacagc taaaatatca ttatctaata ttaagagtaa aacaagataa   1080

ttaaaaattg aaacaacacc atatttttat agctttactt atcgtatttt tctagtcttc   1140

atggtaattg tgttgcttta ttttgtttat aaatgaattt ggttcgacca gatagtctaa   1200

tatcagtttt taaacactgg ttttaataaa atcatatgtc ggcaattcaa cctgttacgt   1260

tgtatgattg tatcctagtc aaatagggga ggaggtacta gtcgtttcaa ttagtttacg   1320

taatcaatcc aaagaaacta taagctataa agatcctcaa tttgttggtt acaataaaaa   1380

caacagttgt caaaatttat gtttataaaa agtaataact atgttccttc ccatatagag   1440

caaagtacct caggataggc aaaccgtact taatagccct tattcataat ttgatccaac   1500

tcttccccac aaaattgcaa ctgatgaagt caatacttgt atagtgagtc aagctataaa   1560

tgtctagtga tagttttgtc tcttaaaagg ttaacaaaag ttatgacaag ctgaaaaatc   1620

agagtttgct aggagtatta cttacagtta tcagtttaag tatcacattt atagtattgt   1680

atacaatgat tcttaaattc caccttttcc gtgcgaaacc aaattttcta ttggaaacat   1740

agaatgtaaa caaaaatatg ggacgttgtc cgttccaaca ttaaccaaac ttgtctatta   1800

ctaatattcg tgttggtttg atgttggatg tctaaattcg ttgaatcatg tgtctcttga   1860

cgaaatatgc atcttcttat ttcttagtat agatgcactt tatcattctt ttagtacatg   1920

cttaattttt ttttttaaaa tatgttgatt gtcatattgc caaaagtatg aattaaagac   1980

gcacatctaa cacaagttag cagccgtaaa tccttccata aatttatttt gcaagttttg   2040

ctcattatat aatgagcgga atttatgata taatcgtttg taataatgtt atgttttgat   2100

caaaatttga aattaaaagt aggtgagaac ttgttataca gtgtagataa ggtggatctt   2160

gaatataaaa ataaaattta taagatgtat ttaaagcaga aaagcataaa actttagata   2220

aaataatgta aaaatgtgtt agcatcaatg ttgggatatt ggccgacccg aacttaatca   2280

atgtcggaag ccattacttc tctcccaaaa gaccttttc cttcggagaa ctaggaactt   2340

cctcactacc tttcgcttaa cgtgaaagcc ataaatttca tatattcata aaaatcagaa   2400

aatctaaaac tgtttagtat cacctgtttt tggtatagac tattggtttt gtgttacttc   2460

ctaaactata tgatttcgta cttcattgga tcttatagag atgaatattc gtaaaaagat   2520

aagttatctg gtgaaacgtt acttcagtca tgttgggtct agatttacat actactatga   2580

aacattttaa gataataatt atcctagcca actatatgtt ctatattatg ggccaagaag   2640

atatagaact aaaagttcag aatttaacga tataaattac tagtatattc taatacttga   2700

atgattactg ttttagttgt ttagaataaa tagtagcgtg ttggttaaga taccatctat   2760

ccacatctat atttgtgtgg gttacataaa atgtacataa tattatatac atatatatgt   2820

atatttttga taaagccata tattactcct tgacctctgc ccccatttcc ttttactata   2880

aataggaata ctcatgatcc tctaattcag caatcaacac caacgaacac aaccttttcc   2940

aaagccaata ataaaagaac aaaagctttt agtttcatca aagacgaagc tgccttagaa   3000
```

<210> SEQ ID NO 87
<211> LENGTH: 815
<212> TYPE: DNA
<213> ORGANISM: Arabidopsis thaliana
<220> FEATURE:
<221> NAME/KEY: misc_feature
<223> OTHER INFORMATION: Ceres CLONE ID no. 28780
<220> FEATURE:
<221> NAME/KEY: misc_feature
<223> OTHER INFORMATION: Encodes the peptide sequence at SEQ ID NO. 88

<400> SEQUENCE: 87

```
aactactaaa cactaaatta tcaatccgct ctcttctcaa aaaaaaaaaa tcgactctaa      60
aatcaaactc tctcaaagct ccccaaaaaa accctagttc tgaatggaat cggcggattc     120
cggacgatcc gatccggtaa aaggagacga cccgggtcca tctttcgtct cttcaccacc     180
agctacacct agcaggtatg agtcacagaa gcgacgcgac tggaacacgt tcttgcagta     240
cctcaagaac cacaagccgc ctctcgcgtt gtcacggtgt agcggagcgc atgtgatcga     300
gtttctcaag tacctcgacc agttcggtaa gaccaaagtc cacgtggcgg cttgtcctta     360
cttcggccat cagcaacctc cgtctccttg ctcatgccct ctcaagcaag cttggggatc     420
tctcgatgct ttgatcggac ggttgagagc tgcctacgag gagaacggtg gacggccgga     480
ttctaacccg ttcgccgcac gtgcggttcg gatttacttg agggaagtca gagagagtca     540
ggcaaaggct cgtgggattc cttacgagaa aaagaaacgg aaacggccgc caactgtcac     600
caccgttaga gttgacgtcg cttcttcgag acaaagtgac ggagaccctt gtaacgtcgg     660
tgctccatct gttgccgagg ccgtaccgcc ttagatcgaa ttatatataa tattatagtt     720
ttcttgatta atgatatata tatacttatc tctatgtatg tatggaactc acttcatctt     780
ttgttcctta gtacctaatt attaaatttt gttcc                                815
```

<210> SEQ ID NO 88
<211> LENGTH: 196
<212> TYPE: PRT
<213> ORGANISM: Arabidopsis thaliana
<220> FEATURE:
<221> NAME/KEY: MISC_FEATURE
<223> OTHER INFORMATION: Ceres CLONE ID no. 28780
<220> FEATURE:
<221> NAME/KEY: misc_feature
<222> LOCATION: (13)..(145)
<223> OTHER INFORMATION: Pfam Name: DUF640
Pfam Description: Protein of unknown function (DUF640)

<400> SEQUENCE: 88

```
Met Glu Ser Ala Asp Ser Gly Arg Ser Asp Pro Val Lys Gly Asp Asp
1               5                   10                  15

Pro Gly Pro Ser Phe Val Ser Ser Pro Pro Ala Thr Pro Ser Arg Tyr
            20                  25                  30

Glu Ser Gln Lys Arg Arg Asp Trp Asn Thr Phe Leu Gln Tyr Leu Lys
        35                  40                  45

Asn His Lys Pro Pro Leu Ala Leu Ser Arg Cys Ser Gly Ala His Val
    50                  55                  60

Ile Glu Phe Leu Lys Tyr Leu Asp Gln Phe Gly Lys Thr Lys Val His
65                  70                  75                  80

Val Ala Ala Cys Pro Tyr Phe Gly His Gln Gln Pro Pro Ser Pro Cys
                85                  90                  95

Ser Cys Pro Leu Lys Gln Ala Trp Gly Ser Leu Asp Ala Leu Ile Gly
            100                 105                 110

Arg Leu Arg Ala Ala Tyr Glu Glu Asn Gly Gly Arg Pro Asp Ser Asn
        115                 120                 125

Pro Phe Ala Ala Arg Ala Val Arg Ile Tyr Leu Arg Glu Val Arg Glu
    130                 135                 140

Ser Gln Ala Lys Ala Arg Gly Ile Pro Tyr Glu Lys Lys Lys Arg Lys
145                 150                 155                 160

Arg Pro Pro Thr Val Thr Thr Val Arg Val Asp Val Ala Ser Ser Arg
```

```
                165                 170                 175

Gln Ser Asp Gly Asp Pro Cys Asn Val Gly Ala Pro Ser Val Ala Glu
            180                 185                 190

Ala Val Pro Pro
        195


<210> SEQ ID NO 89
<211> LENGTH: 198
<212> TYPE: PRT
<213> ORGANISM: Glycine max
<220> FEATURE:
<221> NAME/KEY: MISC_FEATURE
<223> OTHER INFORMATION: Ceres CLONE 1073674
<220> FEATURE:
<221> NAME/KEY: misc_feature
<222> LOCATION: (14)..(146)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 89

Met Asp Ser Gly Ser Gln Arg Pro Gly Pro Val Ser Glu Gly Asp Pro
1               5                   10                  15

Gly Pro Ser Ile Val Thr Pro Ser Ser Pro Pro Ala Thr Pro Ser Arg
            20                  25                  30

Tyr Glu Ser Gln Lys Arg Arg Asp Trp Thr Thr Phe Leu Gln Tyr Leu
        35                  40                  45

Lys Asn His Lys Pro Pro Leu Ser Leu Ser Arg Cys Ser Gly Ala His
    50                  55                  60

Ala Ile Glu Phe Leu Lys Tyr Leu Asp Gln Phe Gly Lys Thr Lys Val
65                  70                  75                  80

His Val Ala Ala Cys Pro Tyr Phe Gly His Gln Gln Pro Pro Ser Pro
                85                  90                  95

Cys Ala Cys Pro Leu Lys Gln Ala Trp Gly Ser Leu Asp Ala Leu Ile
            100                 105                 110

Gly Arg Leu Arg Ala Ala Tyr Glu Glu Asn Gly Gly Arg Pro Glu Ser
        115                 120                 125

Asn Pro Phe Ala Ala Arg Ala Val Arg Ile Tyr Leu Arg Glu Val Arg
    130                 135                 140

Glu Ser Gln Ala Lys Ala Arg Gly Arg Pro Tyr Glu Lys Lys Lys Arg
145                 150                 155                 160

Lys Arg Pro Thr Thr Val Thr Thr Val Arg Val Asp Val Ala Ser Ser
                165                 170                 175

Arg Gln Ser Glu Gly Asp Gly Cys Asn Ile Gly Asp Pro Ser Tyr Val
            180                 185                 190

Ala Glu Ala Val Pro Pro
        195


<210> SEQ ID NO 90
<211> LENGTH: 198
<212> TYPE: PRT
<213> ORGANISM: Brassica napus
<220> FEATURE:
<221> NAME/KEY: MISC_FEATURE
<223> OTHER INFORMATION: Ceres CLONE 1118987
<220> FEATURE:
<221> NAME/KEY: misc_feature
<222> LOCATION: (13)..(146)
<223> OTHER INFORMATION: Pfam Name: DUF640
```

```
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 90

Met Glu Ser Thr Asp Ser Gly Ser Gln Gln His Gly Gly Asp Pro Gly
1               5                   10                  15

Pro Ser Ser Val Thr Pro Ser Ser Pro Pro Ala Thr Pro Pro Ser Arg
            20                  25                  30

Tyr Glu Ser Gln Lys Arg Arg Asp Trp Asn Thr Phe Leu Gln Tyr Leu
        35                  40                  45

Lys Asn His Lys Pro Pro Leu Ala Leu Ser Arg Cys Ser Gly Ala His
    50                  55                  60

Val Ile Glu Phe Leu Lys Tyr Leu Asp Gln Phe Gly Lys Thr Lys Val
65                  70                  75                  80

His Val Ala Thr Cys Pro Tyr Phe Gly His Gln Gln Pro Pro Ser Pro
                85                  90                  95

Cys Ala Cys Pro Leu Lys Gln Ala Trp Gly Ser Leu Asp Ala Leu Ile
            100                 105                 110

Gly Arg Leu Arg Ala Ala Tyr Glu Glu His Gly Gly Arg Pro Asp Ser
        115                 120                 125

Asn Pro Phe Ala Ala Arg Ala Val Arg Ile Tyr Leu Arg Glu Val Arg
    130                 135                 140

Glu Ser Gln Ala Lys Ala Arg Gly Ile Pro Tyr Glu Lys Lys Lys Arg
145                 150                 155                 160

Lys Arg Ala Pro Thr Val Thr Thr Ala Arg Ile Asp Val Ala Pro Ser
                165                 170                 175

Arg Gln Ser Glu Gly Gly Gly Gly Cys Asn Asp Ser Asp Pro Ser Val
            180                 185                 190

Ala Glu Ala Val Pro Pro
        195


<210> SEQ ID NO 91
<211> LENGTH: 672
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT 1461298
<220> FEATURE:
<221> NAME/KEY: misc_feature
<223> OTHER INFORMATION: Encodes the peptide sequence at SEQ ID NO. 92

<400> SEQUENCE: 91

atggactcaa catctggagt agcttctgcg cccgacccga atagtggaga accgggtcca      60

tcagcgggat catcttcagc atcagcatca ctgccacaac aacagcaacc agagggatca     120

tcaccgccag caccaccaag tagatacgag tcgcagaaga ggagagactg gaacactttc     180

ttacagtact taaagaacca caagccacca ttaactctag ctcgttgcag tggtgcacat     240

gtgatcgagt tcttgaaata cttggatcaa tttggtaaga ccaaagtcca cataacgggc     300

tgtccttatt ttgggcaccc gaacccgcca gcaccttgct cttgtccact taagcaggcc     360

tggggtagtc ttgatgcgct aatcggacgg cttagagctg cttatgaaga aaacggtgga     420

cggccagaat cgaacccttt tggggctaga gctgtcagga tttacttgag ggaagttcga     480

gaaggtcaag ctaaagctag agggattccc tacgagaaga agaagcgaaa aaggtctaat     540
```

```
gttgctgttg ctacggtgaa tgtgtcggtg gaggcagctg gtggtggctc tactagtggt    600

ggcggagggg ggagtggtga tgctgatagt agtgctgctg cagcagctgc tgctgctaca    660

acaaccgtat ag                                                        672


<210> SEQ ID NO 92
<211> LENGTH: 223
<212> TYPE: PRT
<213> ORGANISM: Populus balsamifera subsp. trichocarpa
<220> FEATURE:
<221> NAME/KEY: MISC_FEATURE
<223> OTHER INFORMATION: Ceres ANNOT 1461298
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 92

Met Asp Ser Thr Ser Gly Val Ala Ser Ala Pro Asp Pro Asn Ser Gly
1               5                   10                  15

Glu Pro Gly Pro Ser Ala Gly Ser Ser Ser Ala Ser Ala Ser Leu Pro
            20                  25                  30

Gln Gln Gln Gln Pro Glu Gly Ser Ser Pro Pro Ala Pro Pro Ser Arg
        35                  40                  45

Tyr Glu Ser Gln Lys Arg Arg Asp Trp Asn Thr Phe Leu Gln Tyr Leu
    50                  55                  60

Lys Asn His Lys Pro Pro Leu Thr Leu Ala Arg Cys Ser Gly Ala His
65                  70                  75                  80

Val Ile Glu Phe Leu Lys Tyr Leu Asp Gln Phe Gly Lys Thr Lys Val
                85                  90                  95

His Ile Thr Gly Cys Pro Tyr Phe Gly His Pro Asn Pro Pro Ala Pro
            100                 105                 110

Cys Ser Cys Pro Leu Lys Gln Ala Trp Gly Ser Leu Asp Ala Leu Ile
        115                 120                 125

Gly Arg Leu Arg Ala Ala Tyr Glu Glu Asn Gly Gly Arg Pro Glu Ser
    130                 135                 140

Asn Pro Phe Gly Ala Arg Ala Val Arg Ile Tyr Leu Arg Glu Val Arg
145                 150                 155                 160

Glu Gly Gln Ala Lys Ala Arg Gly Ile Pro Tyr Glu Lys Lys Lys Arg
                165                 170                 175

Lys Arg Ser Asn Val Ala Val Ala Thr Val Asn Val Ser Val Glu Ala
            180                 185                 190

Ala Gly Gly Gly Ser Thr Ser Gly Gly Gly Gly Gly Ser Gly Asp Ala
        195                 200                 205

Asp Ser Ser Ala Ala Ala Ala Ala Ala Ala Ala Thr Thr Thr Val
    210                 215                 220


<210> SEQ ID NO 93
<211> LENGTH: 212
<212> TYPE: PRT
<213> ORGANISM: Oryza sativa subsp. japonica
<220> FEATURE:
<221> NAME/KEY: MISC_FEATURE
<223> OTHER INFORMATION: Public GI 34907938
<220> FEATURE:
<221> NAME/KEY: misc_feature
<222> LOCATION: (13)..(145)
```

```
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 93

Met Asp Pro Ser Gly Pro Gly Pro Ser Ser Ala Ala Ala Gly Gly Ala
1               5                   10                  15

Pro Ala Val Ala Ala Ala Pro Gln Pro Pro Ala Gln Leu Ser Arg Tyr
            20                  25                  30

Glu Ser Gln Lys Arg Arg Asp Trp Asn Thr Phe Leu Gln Tyr Leu Arg
        35                  40                  45

Asn His Arg Pro Pro Leu Thr Leu Ala Arg Cys Ser Gly Ala His Val
    50                  55                  60

Ile Glu Phe Leu Arg Tyr Leu Asp Gln Phe Gly Lys Thr Lys Val His
65                  70                  75                  80

Ala Ser Gly Cys Ala Phe Tyr Gly Gln Pro Ser Pro Pro Gly Pro Cys
                85                  90                  95

Pro Cys Pro Leu Arg Gln Ala Trp Gly Ser Leu Asp Ala Leu Ile Gly
            100                 105                 110

Arg Leu Arg Ala Ala Tyr Glu Glu Ser Gly Gly Thr Pro Glu Ser Asn
        115                 120                 125

Pro Phe Ala Ala Arg Ala Val Arg Ile Tyr Leu Arg Glu Val Arg Asp
    130                 135                 140

Ser Gln Ala Lys Ala Arg Gly Ile Pro Tyr Glu Lys Lys Lys Arg Lys
145                 150                 155                 160

Arg Ser Gln Ala Ala Gln Pro Ala Gly Val Glu Pro Ser Gly Ser Ser
                165                 170                 175

Ser Ala Ala Ala Ala Ala Ala Gly Gly Gly Asp Ala Gly Ser Gly Gly
            180                 185                 190

Gly Ala Ala Ala Thr Thr Thr Ala Gln Pro Gly Gly Ser Gly Thr Ala
        195                 200                 205

Pro Ser Ala Ser
    210


<210> SEQ ID NO 94
<211> LENGTH: 167
<212> TYPE: PRT
<213> ORGANISM: Parthenium argentatum
<220> FEATURE:
<221> NAME/KEY: MISC_FEATURE
<223> OTHER INFORMATION: Ceres CLONE 1603237
<220> FEATURE:
<221> NAME/KEY: misc_feature
<222> LOCATION: (6)..(148)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 94

Met Leu Ser Pro Thr Ser Ser Ser Ser Ser Ile Ala Ser Thr Ala Ser
1               5                   10                  15

Thr Ala Thr Ser Arg Leu Asn Arg Tyr Glu Ser Gln Lys Arg Arg Asp
            20                  25                  30

Trp Asn Thr Phe Gly Gln Phe Leu Arg Asn His Asp Pro Pro Leu Thr
        35                  40                  45
```

```
Leu Ser Asn Cys Thr Ser Thr His Val Ile Glu Phe Leu Arg Tyr Leu
    50                  55                  60

Asp Pro Phe Gly Lys Thr Lys Val His Thr His Leu Cys Pro Ser Phe
65                  70                  75                  80

Gly Gln Pro Asn Pro Pro Thr Leu Cys Pro Cys Pro Leu Arg Gln Ala
                85                  90                  95

Trp Gly Ser Leu Asp Ala Leu Ile Gly Arg Leu Arg Ala Ala Phe Glu
            100                 105                 110

Glu Asn Gly Gly Gln Pro Glu Ser Asn Pro Phe Gly Ala Arg Ala Val
        115                 120                 125

Arg Phe Tyr Leu Arg Glu Val Lys Asp Ala Gln Ala Lys Ala Arg Gly
    130                 135                 140

Ile Ser Cys Glu Lys Lys Arg Thr Lys Lys Arg Pro Pro Pro Pro Thr
145                 150                 155                 160

Pro Asp Ile Cys Leu Asp Arg
                165


<210> SEQ ID NO 95
<211> LENGTH: 20
<212> TYPE: DNA
<213> ORGANISM: Arabidopsis thaliana
<220> FEATURE:
<221> NAME/KEY: misc_feature
<223> OTHER INFORMATION: TUB-F1: Forward primer for tubulin gene
      amplification

<400> SEQUENCE: 95

gttgagccgt acaatgcaac                                                   20


<210> SEQ ID NO 96
<211> LENGTH: 19
<212> TYPE: DNA
<213> ORGANISM: Arabidopsis thaliana
<220> FEATURE:
<221> NAME/KEY: misc_feature
<223> OTHER INFORMATION: TUB-R1: Reverse primer for tubulin gene
      amplification

<400> SEQUENCE: 96

ctgttcgtcc acttccttg                                                    19


<210> SEQ ID NO 97
<211> LENGTH: 24
<212> TYPE: DNA
<213> ORGANISM: Arabidopsis thaliana
<220> FEATURE:
<221> NAME/KEY: misc_feature
<223> OTHER INFORMATION: 05917-F: Forward primer used to detect
      At1g07090

<400> SEQUENCE: 97

agcaggtatg agtcacagaa gcga                                              24


<210> SEQ ID NO 98
<211> LENGTH: 24
<212> TYPE: DNA
<213> ORGANISM: Arabidopsis thaliana
<220> FEATURE:
<221> NAME/KEY: misc_feature
<223> OTHER INFORMATION: 05917-R: Reverse primer used to detect
      At1g07090

<400> SEQUENCE: 98
```

acagatggag caccgacgtt acaa 24

<210> SEQ ID NO 99
<211> LENGTH: 576
<212> TYPE: DNA
<213> ORGANISM: Arabidopsis thaliana
<220> FEATURE:
<221> NAME/KEY: misc_feature
<223> OTHER INFORMATION: Ceres SEED LINE ME16572
<220> FEATURE:
<221> NAME/KEY: misc_feature
<223> OTHER INFORMATION: Ceres ANNOT ID no. 1285138
<220> FEATURE:
<221> NAME/KEY: misc_feature
<223> OTHER INFORMATION: Encodes the peptide sequence at SEQ ID NO. 100

<400> SEQUENCE: 99
atgtcttcgg atcgtcacac accgacgaaa gatccaccgg atcatccgtc ttcttcctcc 60
aaccaccaca agcaaccact tcctcctcaa ccgcagcaac cactcagccg ctatgaatcg 120
cagaaacgcc gcgactggaa cacgttcgtc caatacctaa aatcacaaaa tccaccgttg 180
atgatgtctc aattcgacta cacgcacgtg ctaagtttcc taaggtactt agatcagttt 240
ggtaagacca aagtacatca tcaagcttgt gtcttcttcg gacaaccgga tccaccaggt 300
ccgtgcacgt gtcctctcaa acaagcttgg ggaagcctag atgctttgat cggacggcta 360
agagctgctt acgaggaaca cggtggcggg tcacctgata ctaacccgtt tgcaaacggg 420
tcgatccggg ttcacttgag ggaagtgaga gaatctcaag ccaaggctcg tgggattccg 480
tacaggaaga agaaaaggag gaagactaaa aacgaggtcg ttgttgtcaa gaaggatgtt 540
gcaaactctt cgactcctaa tcagtagttc acttga 576

<210> SEQ ID NO 100
<211> LENGTH: 188
<212> TYPE: PRT
<213> ORGANISM: Arabidopsis thaliana
<220> FEATURE:
<221> NAME/KEY: misc_feature
<223> OTHER INFORMATION: Ceres SEED LINE ME16572
<220> FEATURE:
<221> NAME/KEY: misc_feature
<223> OTHER INFORMATION: Ceres ANNOT ID no. 1285138
<220> FEATURE:
<221> NAME/KEY: misc_feature
<223> OTHER INFORMATION: Functional Homolog of Ceres Clone ID no. 28780
at SEQ ID NO. 88
<220> FEATURE:
<221> NAME/KEY: misc_feature
<222> LOCATION: (19)..(152)
<223> OTHER INFORMATION: Pfam Name: DUF640
Pfam Description: Protein of unknown function (DUF640)

<400> SEQUENCE: 100

Met Ser Ser Asp Arg His Thr Pro Thr Lys Asp Pro Pro Asp His Pro
1 5 10 15

Ser Ser Ser Ser Asn His His Lys Gln Pro Leu Pro Pro Gln Pro Gln
20 25 30

Gln Pro Leu Ser Arg Tyr Glu Ser Gln Lys Arg Arg Asp Trp Asn Thr
35 40 45

Phe Val Gln Tyr Leu Lys Ser Gln Asn Pro Pro Leu Met Met Ser Gln
50 55 60

Phe Asp Tyr Thr His Val Leu Ser Phe Leu Arg Tyr Leu Asp Gln Phe
65 70 75 80

Gly Lys Thr Lys Val His His Gln Ala Cys Val Phe Phe Gly Gln Pro
85 90 95

```
Asp Pro Pro Gly Pro Cys Thr Cys Pro Leu Lys Gln Ala Trp Gly Ser
            100                 105                 110

Leu Asp Ala Leu Ile Gly Arg Leu Arg Ala Ala Tyr Glu Glu His Gly
        115                 120                 125

Gly Gly Ser Pro Asp Thr Asn Pro Phe Ala Asn Gly Ser Ile Arg Val
    130                 135                 140

His Leu Arg Glu Val Arg Glu Ser Gln Ala Lys Ala Arg Gly Ile Pro
145                 150                 155                 160

Tyr Arg Lys Lys Lys Arg Arg Lys Thr Lys Asn Glu Val Val Val Val
                165                 170                 175

Lys Lys Asp Val Ala Asn Ser Ser Thr Pro Asn Gln
            180                 185
```

<210> SEQ ID NO 101
<211> LENGTH: 573
<212> TYPE: DNA
<213> ORGANISM: Arabidopsis thaliana
<220> FEATURE:
<221> NAME/KEY: misc_feature
<223> OTHER INFORMATION: Ceres SEED LINE ME16623
<220> FEATURE:
<221> NAME/KEY: misc_feature
<223> OTHER INFORMATION: Ceres ANNOT ID no.1290753
<220> FEATURE:
<221> NAME/KEY: misc_feature
<223> OTHER INFORMATION: Ceres SEED LINE ME23453
<220> FEATURE:
<221> NAME/KEY: misc_feature
<223> OTHER INFORMATION: Ceres ANNOT ID no. 853637
<220> FEATURE:
<221> NAME/KEY: misc_feature
<223> OTHER INFORMATION: Encodes the peptide sequence at SEQ ID NO. 102

<400> SEQUENCE: 101

```
atggatttga tctctcacca accaaacaag aaccctaatt cctcaacaca actaacacca     60

ccttcctcaa gccggtacga gaaccaaaaa cgccgtgact ggaacacttt ctgtcaatac    120

ctccggaacc accgtcctcc gctctctctc ccctcgtgta gcggcgcaca cgtgctcgag    180

ttcctccgct accttgacca gttcgggaaa acaaaagttc accaccagaa ctgtgccttc    240

tttggcctcc ctaaccctcc tgctccttgt ccttgtcctc tccggcaagc ttggggctca    300

ctcgacgctc ttatcggccg cctccgcgcc gcctacgagg agaacggtgg cccacctgaa    360

gctaacccat ttggctcacg cgccgtcagg ttattcctcc gtgaagtcag agactttcaa    420

gccaaagctc gaggtgttag ctatgagaag aagaggaaga gagtcaacag gcagaaaccg    480

caaacgcagc cgcctctaca gcttcagcaa cagcaacagc agccacaaca aggtcagtct    540

atgatggcta attactcggg tgcaacagta tga                                 573
```

<210> SEQ ID NO 102
<211> LENGTH: 190
<212> TYPE: PRT
<213> ORGANISM: Arabidopsis thaliana
<220> FEATURE:
<221> NAME/KEY: misc_feature
<223> OTHER INFORMATION: Ceres SEED LINE ME16623
<220> FEATURE:
<221> NAME/KEY: misc_feature
<223> OTHER INFORMATION: Ceres ANNOT ID no. 1290753
<220> FEATURE:
<221> NAME/KEY: misc_feature
<223> OTHER INFORMATION: Ceres SEED LINE ME23453
<220> FEATURE:
<221> NAME/KEY: misc_feature
<223> OTHER INFORMATION: Ceres ANNOT ID no. 853637

```
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (7)..(139)
<223> OTHER INFORMATION: Pfam Name: DUF640
      Pfam Description: Protein of unknown function (DUF640)

<400> SEQUENCE: 102

Met Asp Leu Ile Ser His Gln Pro Asn Lys Asn Pro Asn Ser Ser Thr
1               5                   10                  15

Gln Leu Thr Pro Pro Ser Ser Ser Arg Tyr Glu Asn Gln Lys Arg Arg
            20                  25                  30

Asp Trp Asn Thr Phe Cys Gln Tyr Leu Arg Asn His Arg Pro Pro Leu
        35                  40                  45

Ser Leu Pro Ser Cys Ser Gly Ala His Val Leu Glu Phe Leu Arg Tyr
    50                  55                  60

Leu Asp Gln Phe Gly Lys Thr Lys Val His His Gln Asn Cys Ala Phe
65                  70                  75                  80

Phe Gly Leu Pro Asn Pro Pro Ala Pro Cys Pro Cys Pro Leu Arg Gln
                85                  90                  95

Ala Trp Gly Ser Leu Asp Ala Leu Ile Gly Arg Leu Arg Ala Ala Tyr
            100                 105                 110

Glu Glu Asn Gly Gly Pro Pro Glu Ala Asn Pro Phe Gly Ser Arg Ala
        115                 120                 125

Val Arg Leu Phe Leu Arg Glu Val Arg Asp Phe Gln Ala Lys Ala Arg
    130                 135                 140

Gly Val Ser Tyr Glu Lys Lys Arg Lys Arg Val Asn Arg Gln Lys Pro
145                 150                 155                 160

Gln Thr Gln Pro Pro Leu Gln Leu Gln Gln Gln Gln Gln Gln Pro Gln
                165                 170                 175

Gln Gly Gln Ser Met Met Ala Asn Tyr Ser Gly Ala Thr Val
            180                 185                 190


<210> SEQ ID NO 103
<211> LENGTH: 639
<212> TYPE: DNA
<213> ORGANISM: Oryza sativa
<220> FEATURE:
<221> NAME/KEY: misc_feature
<223> OTHER INFORMATION: Ceres SEED LINE ME25698
<220> FEATURE:
<221> NAME/KEY: misc_feature
<223> OTHER INFORMATION: Ceres ANNOT ID no. 1373087
<220> FEATURE:
<221> NAME/KEY: misc_feature
<223> OTHER INFORMATION: Encodes the peptide sequence at SEQ ID NO. 104

<400> SEQUENCE: 103

atggatccgt ctggccccgg tccgtcctct gcggcggctg gcggcgcgcc ggccgtggcg     60

gcggcgccgc agccgccggc gcagctgagc aggtacgagt cgcagaagcg gagggactgg    120

aacacgttcc tgcagtacct gcggaaccac cggccgccgc tgacgctggc gcggtgcagc    180

ggcgcgcacg tgatcgagtt cctgaggtac ctggaccagt tcgggaagac caaggtgcac    240

gcgtcggggt gcgccttcta cggccagccc agcccgccgg ggccgtgccc gtgcccgctg    300

cgtcaggcgt ggggatccct cgacgcgctc atcggccgcc tccgcgccgc gtacgaggag    360

agcggcggca cgcccgagtc caacccgttc gccgcgcgcg ccgtccggat ctacctccgc    420
```

```
gaggtgcggg actcgcaggc caaggcgcgc ggcatcccgt acgagaagaa gaagcgcaag    480

cgctcgcagg cggcgcagcc cgccggcgtc gagccgtccg gctcgtcttc tgctgcagct    540

gcagctgccg gtggtggaga cgcgggcagc ggtggcggtg cagctgctac taccacagct    600

caacctggag ggagtggcac tgcaccaagc gcctcctga                           639
```

```
<210> SEQ ID NO 104
<211> LENGTH: 212
<212> TYPE: PRT
<213> ORGANISM: Oryza sativa
<220> FEATURE:
<221> NAME/KEY: misc_feature
<223> OTHER INFORMATION: Ceres SEED LINE ME25698
<220> FEATURE:
<221> NAME/KEY: misc_feature
<223> OTHER INFORMATION: Ceres ANNOT ID no. 1373087
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (13)..(145)
<223> OTHER INFORMATION: Pfam Name: DUF640
      Pfam Description: Protein of unknown function (DUF640)

<400> SEQUENCE: 104

Met Asp Pro Ser Gly Pro Gly Pro Ser Ser Ala Ala Ala Gly Gly Ala
1               5                   10                  15

Pro Ala Val Ala Ala Ala Pro Gln Pro Pro Ala Gln Leu Ser Arg Tyr
            20                  25                  30

Glu Ser Gln Lys Arg Arg Asp Trp Asn Thr Phe Leu Gln Tyr Leu Arg
        35                  40                  45

Asn His Arg Pro Pro Leu Thr Leu Ala Arg Cys Ser Gly Ala His Val
    50                  55                  60

Ile Glu Phe Leu Arg Tyr Leu Asp Gln Phe Gly Lys Thr Lys Val His
65                  70                  75                  80

Ala Ser Gly Cys Ala Phe Tyr Gly Gln Pro Ser Pro Pro Gly Pro Cys
                85                  90                  95

Pro Cys Pro Leu Arg Gln Ala Trp Gly Ser Leu Asp Ala Leu Ile Gly
            100                 105                 110

Arg Leu Arg Ala Ala Tyr Glu Glu Ser Gly Gly Thr Pro Glu Ser Asn
        115                 120                 125

Pro Phe Ala Ala Arg Ala Val Arg Ile Tyr Leu Arg Glu Val Arg Asp
    130                 135                 140

Ser Gln Ala Lys Ala Arg Gly Ile Pro Tyr Glu Lys Lys Lys Arg Lys
145                 150                 155                 160

Arg Ser Gln Ala Ala Gln Pro Ala Gly Val Glu Pro Ser Gly Ser Ser
                165                 170                 175

Ser Ala Ala Ala Ala Ala Ala Gly Gly Gly Asp Ala Gly Ser Gly Gly
            180                 185                 190

Gly Ala Ala Ala Thr Thr Thr Ala Gln Pro Gly Gly Ser Gly Thr Ala
        195                 200                 205

Pro Ser Ala Ser
    210


<210> SEQ ID NO 105
<211> LENGTH: 687
<212> TYPE: DNA
<213> ORGANISM: Populus balsamifera subsp. trichocarpa
<220> FEATURE:
```

```
<221> NAME/KEY: misc_feature
<223> OTHER INFORMATION: Ceres SEED LINE ME25953
<220> FEATURE:
<221> NAME/KEY: misc_feature
<223> OTHER INFORMATION: Ceres ANNOT ID no. 1440417
<220> FEATURE:
<221> NAME/KEY: misc_feature
<223> OTHER INFORMATION: Encodes the peptide sequence at SEQ ID NO. 106

<400> SEQUENCE: 105

atggactcga catctggagg agccactgca cccggcccga atagtggaga accttgtcca     60

tcagcagcaa cagcaggatc gtcttcagca tcgcagccac aacagcaacc ggagggatca    120

tcaccgccag caccaccaag tagatacgag tcacagaaga ggagagactg gaacactttc    180

ttacagtaca taaagaacca caagccacct ttaaccctag ctcgttgcag tggtgcacat    240

gtgattgagt tcttgaaata cttggatcaa tttggtaaga ctaaagtcca cataacgggt    300

tgtccttatt ttgggcaccc gaacccgcca gcaccttgtt cttgtccact aaagcaggct    360

tggggtagtc ttgatgcgct aatcggacgg cttagagctg cttatgaaga aaacggtgga    420

ctgccagaat caaacccttt tggggctaga gctgttagga tttatttgag ggaagttcga    480

gaaggtcaag ctaaagccag agggattcct tatgagaaga agaagaagcg aaaaaggcct    540

aatgttgctg tttccgtagc gagtgtgtcg gtgaaggcag ctgctggtgg ctctaatagt    600

ggcggtggag aagaaagtgg tggtggtggt gatagtagtg ccgccgctac aagtgctgct    660

gcggctgctg ctacaactac cgtatag                                        687


<210> SEQ ID NO 106
<211> LENGTH: 228
<212> TYPE: PRT
<213> ORGANISM: Populus balsamifera subsp. trichocarpa
<220> FEATURE:
<221> NAME/KEY: misc_feature
<223> OTHER INFORMATION: Ceres SEED LINE ME25953
<220> FEATURE:
<221> NAME/KEY: misc_feature
<223> OTHER INFORMATION: Ceres ANNOT ID no. 1440417
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 106

Met Asp Ser Thr Ser Gly Gly Ala Thr Ala Pro Gly Pro Asn Ser Gly
1               5                   10                  15

Glu Pro Cys Pro Ser Ala Ala Thr Ala Gly Ser Ser Ser Ala Ser Gln
            20                  25                  30

Pro Gln Gln Gln Pro Glu Gly Ser Ser Pro Pro Ala Pro Pro Ser Arg
        35                  40                  45

Tyr Glu Ser Gln Lys Arg Arg Asp Trp Asn Thr Phe Leu Gln Tyr Ile
    50                  55                  60

Lys Asn His Lys Pro Pro Leu Thr Leu Ala Arg Cys Ser Gly Ala His
65                  70                  75                  80

Val Ile Glu Phe Leu Lys Tyr Leu Asp Gln Phe Gly Lys Thr Lys Val
                85                  90                  95

His Ile Thr Gly Cys Pro Tyr Phe Gly His Pro Asn Pro Pro Ala Pro
            100                 105                 110
```

```
Cys Ser Cys Pro Leu Lys Gln Ala Trp Gly Ser Leu Asp Ala Leu Ile
        115                 120                 125

Gly Arg Leu Arg Ala Ala Tyr Glu Glu Asn Gly Gly Leu Pro Glu Ser
    130                 135                 140

Asn Pro Phe Gly Ala Arg Ala Val Arg Ile Tyr Leu Arg Glu Val Arg
145                 150                 155                 160

Glu Gly Gln Ala Lys Ala Arg Gly Ile Pro Tyr Glu Lys Lys Lys Lys
                165                 170                 175

Arg Lys Arg Pro Asn Val Ala Val Ser Val Ala Ser Val Ser Val Lys
            180                 185                 190

Ala Ala Ala Gly Gly Ser Asn Ser Gly Gly Gly Glu Glu Ser Gly Gly
        195                 200                 205

Gly Gly Asp Ser Ser Ala Ala Ala Thr Ser Ala Ala Ala Ala Ala Ala
    210                 215                 220

Thr Thr Thr Val
225


<210> SEQ ID NO 107
<211> LENGTH: 723
<212> TYPE: DNA
<213> ORGANISM: Populus balsamifera subsp. trichocarpa
<220> FEATURE:
<221> NAME/KEY: misc_feature
<223> OTHER INFORMATION: Ceres SEED LINE ME25957
<220> FEATURE:
<221> NAME/KEY: misc_feature
<223> OTHER INFORMATION: Ceres ANNOT ID no. 1505805
<220> FEATURE:
<221> NAME/KEY: misc_feature
<223> OTHER INFORMATION: Encodes the peptide sequence at SEQ ID NO. 108

<400> SEQUENCE: 107

atgaattcaa tccaagaaat ggagagctcc aactctgaaa acacaagttt caacagcata      60

ggcaacagca acaccaccaa cacagccatg tcagtctcaa acttgccacc accatcctcc     120

accactccga gtcgctatga gaatcaaaag cgccgagact ggaacacctt tggccagtac     180

ctcaagaacc acaggcctcc tctttctctg tccaggtgca gtggtgctca tgtccttgaa     240

ttccttcgct accttgacca atttggcaag accaaagtgc acactccaat ctgccccttt     300

tatggccacc caaacccacc cgccccctgc ccatgccctc tccgccaggc ctggggtagc     360

cttgacgcgc tcattggacg cctccgagca gcctttgagg aaaatggagg gaaacctgaa     420

gcaaaccctt ttggagctcg tgctgttagg ctgtatcttc gtgaggttcg tgatttgcag     480

tctaaagcaa gagggattag ctatgagaaa aagaagcgta agcgtccacc acagcaacaa     540

atccaagccc tgccactgcc acttccactg ccaatgccac caccaccagc tagatctgcg     600

gataccatga atctgctttt gatgcaaaca gtggtagtaa tattactagt aatgggacta     660

gcggtagtgt tatggtctgt gttgggactg agagcatcta taattgctct tacatttgtg     720

taa                                                                   723


<210> SEQ ID NO 108
<211> LENGTH: 240
<212> TYPE: PRT
<213> ORGANISM: Populus balsamifera subsp. trichocarpa
<220> FEATURE:
<221> NAME/KEY: misc_feature
<223> OTHER INFORMATION: Ceres SEED LINE ME25957
<220> FEATURE:
<221> NAME/KEY: misc_feature
<223> OTHER INFORMATION: Ceres ANNOT ID no. 1505805
<220> FEATURE:
```

```
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (27)..(159)
<223> OTHER INFORMATION: Pfam Name: DUF640
      Pfam Description: Protein of unknown function (DUF640)

<400> SEQUENCE: 108

Met Asn Ser Ile Gln Glu Met Glu Ser Ser Asn Ser Glu Asn Thr Ser
1               5                   10                  15

Phe Asn Ser Ile Gly Asn Ser Asn Thr Thr Asn Thr Ala Met Ser Val
            20                  25                  30

Ser Asn Leu Pro Pro Pro Ser Ser Thr Thr Pro Ser Arg Tyr Glu Asn
        35                  40                  45

Gln Lys Arg Arg Asp Trp Asn Thr Phe Gly Gln Tyr Leu Lys Asn His
    50                  55                  60

Arg Pro Pro Leu Ser Leu Ser Arg Cys Ser Gly Ala His Val Leu Glu
65                  70                  75                  80

Phe Leu Arg Tyr Leu Asp Gln Phe Gly Lys Thr Lys Val His Thr Pro
                85                  90                  95

Ile Cys Pro Phe Tyr Gly His Pro Asn Pro Pro Ala Pro Cys Pro Cys
            100                 105                 110

Pro Leu Arg Gln Ala Trp Gly Ser Leu Asp Ala Leu Ile Gly Arg Leu
        115                 120                 125

Arg Ala Ala Phe Glu Glu Asn Gly Gly Lys Pro Glu Ala Asn Pro Phe
    130                 135                 140

Gly Ala Arg Ala Val Arg Leu Tyr Leu Arg Glu Val Arg Asp Leu Gln
145                 150                 155                 160

Ser Lys Ala Arg Gly Ile Ser Tyr Glu Lys Lys Lys Arg Lys Arg Pro
                165                 170                 175

Pro Gln Gln Gln Ile Gln Ala Leu Pro Leu Pro Leu Pro Leu Pro Met
            180                 185                 190

Pro Pro Pro Pro Ala Arg Ser Ala Asp Thr Met Asn Leu Leu Leu Met
        195                 200                 205

Gln Thr Val Val Val Ile Leu Leu Val Met Gly Leu Ala Val Val Leu
    210                 215                 220

Trp Ser Val Leu Gly Leu Arg Ala Ser Ile Ile Ala Leu Thr Phe Val
225                 230                 235                 240


<210> SEQ ID NO 109
<211> LENGTH: 660
<212> TYPE: DNA
<213> ORGANISM: Arabidopsis thaliana
<220> FEATURE:
<221> NAME/KEY: misc_feature
<223> OTHER INFORMATION: Ceres SEED LINE ME25288
<220> FEATURE:
<221> NAME/KEY: misc_feature
<223> OTHER INFORMATION: Ceres ANNOT ID no. 828846
<220> FEATURE:
<221> NAME/KEY: misc_feature
<223> OTHER INFORMATION: Encodes the peptide sequence at SEQ ID NO. 110

<400> SEQUENCE: 109

atggatatga ttccccaatt gatggaaggc tcttcagctt acggaggtgt cacaaacctc      60

aacatcatct caaacaactc ctcctccgtc accggagcca ccggaggtga agcaacgcaa     120

ccactgtctt cctcctcctc accatcggcg aactcaagcc gttacgagaa ccagaagagg     180
```

```
agagactgga acacgttcgg acagtactta aggaaccatc ggccaccgct ttcgctttcc    240

cgatgcagtg gagctcacgt gctcgagttc ctccgttact tggaccagtt cggtaagaca    300

aaagtccaca cgaacatttg tcacttctat ggccatccta atcctccggc accgtgtccg    360

tgtcctctcc gacaagcttg gggaagtctt gacgctctta tcggtcgtct tcgagctgcc    420

tttgaggaaa acggaggcaa gcctgagacg aatccttttg gagctcgtgc cgttaggctt    480

tatctaaggg aagttagaga tatgcagagt aaagctagag gtgttagcta cgagaagaag    540

aagcgaaagc gtcctcttcc ttcgtcgtcg acttcttctt cctccgccgt agctagccac    600

cagcaatttc aaatgctacc gggtactagt tctactactc aattaaagtt tgagaagtaa    660


<210> SEQ ID NO 110
<211> LENGTH: 219
<212> TYPE: PRT
<213> ORGANISM: Arabidopsis thaliana
<220> FEATURE:
<221> NAME/KEY: misc_feature
<223> OTHER INFORMATION: Ceres SEED LINE ME25288
<220> FEATURE:
<221> NAME/KEY: misc_feature
<223> OTHER INFORMATION: Ceres ANNOT ID no. 828846
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (36)..(168)
<223> OTHER INFORMATION: Pfam Name: DUF640
      Pfam Description: Protein of unknown function (DUF640)

<400> SEQUENCE: 110

Met Asp Met Ile Pro Gln Leu Met Glu Gly Ser Ser Ala Tyr Gly Gly
1               5                   10                  15

Val Thr Asn Leu Asn Ile Ile Ser Asn Asn Ser Ser Ser Val Thr Gly
            20                  25                  30

Ala Thr Gly Gly Glu Ala Thr Gln Pro Leu Ser Ser Ser Ser Ser Pro
        35                  40                  45

Ser Ala Asn Ser Ser Arg Tyr Glu Asn Gln Lys Arg Arg Asp Trp Asn
    50                  55                  60

Thr Phe Gly Gln Tyr Leu Arg Asn His Arg Pro Pro Leu Ser Leu Ser
65                  70                  75                  80

Arg Cys Ser Gly Ala His Val Leu Glu Phe Leu Arg Tyr Leu Asp Gln
                85                  90                  95

Phe Gly Lys Thr Lys Val His Thr Asn Ile Cys His Phe Tyr Gly His
            100                 105                 110

Pro Asn Pro Pro Ala Pro Cys Pro Cys Pro Leu Arg Gln Ala Trp Gly
        115                 120                 125

Ser Leu Asp Ala Leu Ile Gly Arg Leu Arg Ala Ala Phe Glu Glu Asn
    130                 135                 140

Gly Gly Lys Pro Glu Thr Asn Pro Phe Gly Ala Arg Ala Val Arg Leu
145                 150                 155                 160

Tyr Leu Arg Glu Val Arg Asp Met Gln Ser Lys Ala Arg Gly Val Ser
                165                 170                 175

Tyr Glu Lys Lys Lys Arg Lys Arg Pro Leu Pro Ser Ser Ser Thr Ser
            180                 185                 190

Ser Ser Ser Ala Val Ala Ser His Gln Gln Phe Gln Met Leu Pro Gly
        195                 200                 205

Thr Ser Ser Thr Thr Gln Leu Lys Phe Glu Lys
```

```
    210                 215


<210> SEQ ID NO 111
<211> LENGTH: 495
<212> TYPE: DNA
<213> ORGANISM: Arabidopsis thaliana
<220> FEATURE:
<221> NAME/KEY: misc_feature
<223> OTHER INFORMATION: Ceres SEED LINE ME23423
<220> FEATURE:
<221> NAME/KEY: misc_feature
<223> OTHER INFORMATION: Ceres ANNOT ID no. 832857
<220> FEATURE:
<221> NAME/KEY: misc_feature
<223> OTHER INFORMATION: Encodes the peptide sequence at SEQ ID NO. 112

<400> SEQUENCE: 111

atgacgagta caaacacgag aaacaaaggc aaatgcatag tagaaggacc accaccgact      60

ctaagccgtt atgagtcaca aaaaagccgc gactggaaca cgttttgcca gtatctcatg     120

accaagatgc caccagttca cgtatgggag tgtgaatcaa accacatcct cgatttcctc     180

caaagtcgtg accagtttgg taaaacaaaa gttcatatcc aaggatgcgt tttcttcgga     240

cagaaagagc caccaggaga gtgtaactgc ccgttgaaac aggcgtgggg aagcttagat     300

gctttgatcg gacggctgag agcagcttac gaggagaacg gtggcttaac ggagaaaaac     360

ccgtttgccc ggggagggat taggattttt ctgagggaag tgagaggttc acaggcgaag     420

gcgagaggag ttttgtacaa aaaaaagaag cgtcttgtag ttgttggtac gggaactagt     480

actacttgga cttaa                                                     495


<210> SEQ ID NO 112
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres SEED LINE ME23423
<220> FEATURE:
<221> NAME/KEY: misc_feature
<223> OTHER INFORMATION: Ceres ANNOT ID no. 832857
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (5)..(137)
<223> OTHER INFORMATION: Pfam Name: DUF640
      Pfam Description: Protein of unknown function (DUF640)

<400> SEQUENCE: 112

Met Thr Ser Thr Asn Thr Arg Asn Lys Gly Lys Cys Ile Val Glu Gly
1               5                   10                  15

Pro Pro Pro Thr Leu Ser Arg Tyr Glu Ser Gln Lys Ser Arg Asp Trp
            20                  25                  30

Asn Thr Phe Cys Gln Tyr Leu Met Thr Lys Met Pro Pro Val His Val
        35                  40                  45

Trp Glu Cys Glu Ser Asn His Ile Leu Asp Phe Leu Gln Ser Arg Asp
    50                  55                  60

Gln Phe Gly Lys Thr Lys Val His Ile Gln Gly Cys Val Phe Phe Gly
65                  70                  75                  80

Gln Lys Glu Pro Pro Gly Glu Cys Asn Cys Pro Leu Lys Gln Ala Trp
                85                  90                  95

Gly Ser Leu Asp Ala Leu Ile Gly Arg Leu Arg Ala Ala Tyr Glu Glu
```

```
            100                 105                 110

Asn Gly Gly Leu Thr Glu Lys Asn Pro Phe Ala Arg Gly Gly Ile Arg
        115                 120                 125

Ile Phe Leu Arg Glu Val Arg Gly Ser Gln Ala Lys Ala Arg Gly Val
    130                 135                 140

Leu Tyr Lys Lys Lys Lys Arg Leu Val Val Val Gly Thr Gly Thr Ser
145                 150                 155                 160

Thr Thr Trp Thr


<210> SEQ ID NO 113
<211> LENGTH: 576
<212> TYPE: DNA
<213> ORGANISM: Arabidopsis thaliana
<220> FEATURE:
<221> NAME/KEY: misc_feature
<223> OTHER INFORMATION: Ceres SEED LINE ME23459
<220> FEATURE:
<221> NAME/KEY: misc_feature
<223> OTHER INFORMATION: Ceres ANNOT ID no. 847799
<220> FEATURE:
<221> NAME/KEY: misc_feature
<223> OTHER INFORMATION: Encodes the peptide sequence at SEQ ID NO. 114

<400> SEQUENCE: 113

atgtcttcgg atcgtcacac accgacgaaa gatccaccgg atcatccgtc ttcttcctcc      60

aaccaccaca agcaaccact tcctcctcaa ccgcagcaac cactcagccg ctatgaatcg     120

cagaaacgcc gcgactggaa cacgttcgtc caatacctaa aatcacaaaa tccaccgttg     180

atgatgtctc aattcgacta cacgcacgtg ctaagtttcc taaggtactt agatcagttt     240

ggtaagacca aagtacatca tcaagcttgt gtcttcttcg gacaaccgga tccaccaggt     300

ccgtgcacgt gtcctctcaa acaagcttgg ggaagcctag atgctttgat cggacggcta     360

agagctgctt acgaggaaca cggtggcggg tcacctgata ctaacccgtt tgcaaacggg     420

tcgatccggg ttcacttgag ggaagtgaga gaatctcaag ccaaggctcg tgggattccg     480

tacaggaaga agaaaaggag gaagactaaa aacgaggtcg ttgttgtcaa gaaggatgtt     540

gcaaactctt cgactcctaa tcagtcgttc acttga                               576


<210> SEQ ID NO 114
<211> LENGTH: 191
<212> TYPE: PRT
<213> ORGANISM: Arabidopsis thaliana
<220> FEATURE:
<221> NAME/KEY: misc_feature
<223> OTHER INFORMATION: Ceres SEED LINE ME23459
<220> FEATURE:
<221> NAME/KEY: misc_feature
<223> OTHER INFORMATION: Ceres ANNOT ID no. 847799
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (19)..(152)
<223> OTHER INFORMATION: Pfam Name: DUF640
      Pfam Description: Protein of unknown function (DUF640)

<400> SEQUENCE: 114

Met Ser Ser Asp Arg His Thr Pro Thr Lys Asp Pro Pro Asp His Pro
1               5                   10                  15

Ser Ser Ser Ser Asn His His Lys Gln Pro Leu Pro Pro Gln Pro Gln
            20                  25                  30
```

```
Gln Pro Leu Ser Arg Tyr Glu Ser Gln Lys Arg Arg Asp Trp Asn Thr
        35                  40                  45

Phe Val Gln Tyr Leu Lys Ser Gln Asn Pro Pro Leu Met Met Ser Gln
    50                  55                  60

Phe Asp Tyr Thr His Val Leu Ser Phe Leu Arg Tyr Leu Asp Gln Phe
65                  70                  75                  80

Gly Lys Thr Lys Val His His Gln Ala Cys Val Phe Phe Gly Gln Pro
                85                  90                  95

Asp Pro Pro Gly Pro Cys Thr Cys Pro Leu Lys Gln Ala Trp Gly Ser
            100                 105                 110

Leu Asp Ala Leu Ile Gly Arg Leu Arg Ala Ala Tyr Glu Glu His Gly
        115                 120                 125

Gly Gly Ser Pro Asp Thr Asn Pro Phe Ala Asn Gly Ser Ile Arg Val
    130                 135                 140

His Leu Arg Glu Val Arg Glu Ser Gln Ala Lys Ala Arg Gly Ile Pro
145                 150                 155                 160

Tyr Arg Lys Lys Lys Arg Arg Lys Thr Lys Asn Glu Val Val Val Val
                165                 170                 175

Lys Lys Asp Val Ala Asn Ser Ser Thr Pro Asn Gln Ser Phe Thr
            180                 185                 190
```

<210> SEQ ID NO 115
<211> LENGTH: 549
<212> TYPE: DNA
<213> ORGANISM: Arabidopsis thaliana
<220> FEATURE:
<221> NAME/KEY: misc_feature
<223> OTHER INFORMATION: Ceres SEED LINE ME23517
<220> FEATURE:
<221> NAME/KEY: misc_feature
<223> OTHER INFORMATION: Ceres ANNOT ID no. 856813
<220> FEATURE:
<221> NAME/KEY: misc_feature
<223> OTHER INFORMATION: Encodes the peptide sequence at SEQ ID NO. 116

<400> SEQUENCE: 115

```
atggagggag aaaccgcagc caaagcagcg gcaagttcct cctcatcccc gagccggtac     60

gagtctcaaa agaggcgaga ctggaacact ttccttcagt atctaaggaa ccacaagcca    120

cctctgaatc tgtctcgttg tagtggcgca cacgtccttg agttccttaa gtacctcgac    180

cagtttggta agaccaaagt ccatgccacg gcttgtccct tcttcggaca acctaaccca    240

ccgtctcagt gcacttgccc tctcaagcaa gcttggggaa gtctcgatgc tctcatcggc    300

cgtctaaggg ctgctttcga ggaaatcggc ggtggtcttc ctgagtcaaa ccctttcgct    360

gccaaggctg ttaggatcta tcttaaagaa gtccgtcaaa cacaggctaa ggctcgaggg    420

attccttacg acaagaagaa aagaaaacgt ccgcatacag acacggcaac tccaatcgcc    480

ggtgacggag acgatgccga aggaagtggt ggtgctgctt tggtcgttac ggctgcaact    540

acggtatag                                                            549
```

<210> SEQ ID NO 116
<211> LENGTH: 182
<212> TYPE: PRT
<213> ORGANISM: Arabidopsis thaliana
<220> FEATURE:
<221> NAME/KEY: misc_feature
<223> OTHER INFORMATION: Ceres SEED LINE ME23517
<220> FEATURE:
<221> NAME/KEY: misc_feature
<223> OTHER INFORMATION: Ceres ANNOT ID no. 856813
<220> FEATURE:

<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (1)..(134)
<223> OTHER INFORMATION: Pfam Name: DUF640
      Pfam Description: Protein of unknown function (DUF640)

<400> SEQUENCE: 116

```
Met Glu Gly Glu Thr Ala Ala Lys Ala Ala Ala Ser Ser Ser Ser Ser
1               5                   10                  15

Pro Ser Arg Tyr Glu Ser Gln Lys Arg Arg Asp Trp Asn Thr Phe Leu
            20                  25                  30

Gln Tyr Leu Arg Asn His Lys Pro Pro Leu Asn Leu Ser Arg Cys Ser
        35                  40                  45

Gly Ala His Val Leu Glu Phe Leu Lys Tyr Leu Asp Gln Phe Gly Lys
    50                  55                  60

Thr Lys Val His Ala Thr Ala Cys Pro Phe Phe Gly Gln Pro Asn Pro
65                  70                  75                  80

Pro Ser Gln Cys Thr Cys Pro Leu Lys Gln Ala Trp Gly Ser Leu Asp
                85                  90                  95

Ala Leu Ile Gly Arg Leu Arg Ala Ala Phe Glu Glu Ile Gly Gly Gly
            100                 105                 110

Leu Pro Glu Ser Asn Pro Phe Ala Ala Lys Ala Val Arg Ile Tyr Leu
        115                 120                 125

Lys Glu Val Arg Gln Thr Gln Ala Lys Ala Arg Gly Ile Pro Tyr Asp
    130                 135                 140

Lys Lys Lys Arg Lys Arg Pro His Thr Asp Thr Ala Thr Pro Ile Ala
145                 150                 155                 160

Gly Asp Gly Asp Asp Ala Glu Gly Ser Gly Gly Ala Ala Leu Val Val
                165                 170                 175

Thr Ala Ala Thr Thr Val
            180
```

<210> SEQ ID NO 117
<211> LENGTH: 588
<212> TYPE: DNA
<213> ORGANISM: Arabidopsis thaliana
<220> FEATURE:
<221> NAME/KEY: misc_feature
<223> OTHER INFORMATION: Ceres SEED LINE ME16579
<220> FEATURE:
<221> NAME/KEY: misc_feature
<223> OTHER INFORMATION: Ceres ANNOT ID no. 870022
<220> FEATURE:
<221> NAME/KEY: misc_feature
<223> OTHER INFORMATION: Encodes the peptide sequence at SEQ ID NO. 118

<400> SEQUENCE: 117

```
atggctagtc atagcaacaa aggcaaaggc atagcagaag gatcgtctca accgcaatcg     60

caaccgcaac cacaaccaca ccaaccgcaa tcacctccta acccgccagc gttaagccgg    120

tacgagtcac agaaacgacg agactggaac acgttttgtc aatacctgcg taaccaacag    180

ccaccggttc acatctcgca gtgtggatca aaccacatcc tcgatttcct ccaatatctc    240

gaccagtttg ggaagacaaa ggttcatatc catggatgcg ttttcttcgg acaggttgag    300

ccagcgggac agtgtaactg tcctttaaaa caagcgtggg ggagtttaga tgctttgatc    360

ggacggctaa gagcggcttt cgaggagaac ggaggattgc cggagagaaa ccccttttgcc    420

ggcggcggaa ttagggtttt tctgagggaa gtgagagatt cacaggcgaa ggcaagagga    480
```

```
gttccgtaca agaaaagaaa aaagaggaag aagaggaatc ctatgaagag tcatgatggt    540

gaagatggta ctacgggaac tagtagtagc tccaacttgg cttcttag                 588


<210> SEQ ID NO 118
<211> LENGTH: 195
<212> TYPE: PRT
<213> ORGANISM: Arabidopsis thaliana
<220> FEATURE:
<221> NAME/KEY: misc_feature
<223> OTHER INFORMATION: Ceres SEED LINE ME16579
<220> FEATURE:
<221> NAME/KEY: misc_feature
<223> OTHER INFORMATION: Ceres ANNOT ID no. 870022
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (22)..(154)
<223> OTHER INFORMATION: Pfam Name: DUF640
      Pfam Description: Protein of unknown function (DUF640)

<400> SEQUENCE: 118

Met Ala Ser His Ser Asn Lys Gly Lys Gly Ile Ala Glu Gly Ser Ser
1               5                   10                  15

Gln Pro Gln Ser Gln Pro Gln Pro Gln Pro His Gln Pro Gln Ser Pro
            20                  25                  30

Pro Asn Pro Pro Ala Leu Ser Arg Tyr Glu Ser Gln Lys Arg Arg Asp
        35                  40                  45

Trp Asn Thr Phe Cys Gln Tyr Leu Arg Asn Gln Gln Pro Pro Val His
    50                  55                  60

Ile Ser Gln Cys Gly Ser Asn His Ile Leu Asp Phe Leu Gln Tyr Leu
65                  70                  75                  80

Asp Gln Phe Gly Lys Thr Lys Val His Ile His Gly Cys Val Phe Phe
                85                  90                  95

Gly Gln Val Glu Pro Ala Gly Gln Cys Asn Cys Pro Leu Lys Gln Ala
            100                 105                 110

Trp Gly Ser Leu Asp Ala Leu Ile Gly Arg Leu Arg Ala Ala Phe Glu
        115                 120                 125

Glu Asn Gly Gly Leu Pro Glu Arg Asn Pro Phe Ala Gly Gly Gly Ile
    130                 135                 140

Arg Val Phe Leu Arg Glu Val Arg Asp Ser Gln Ala Lys Ala Arg Gly
145                 150                 155                 160

Val Pro Tyr Lys Lys Arg Lys Lys Arg Lys Lys Arg Asn Pro Met Lys
                165                 170                 175

Ser His Asp Gly Glu Asp Gly Thr Thr Gly Thr Ser Ser Ser Ser Asn
            180                 185                 190

Leu Ala Ser
        195


<210> SEQ ID NO 119
<211> LENGTH: 838
<212> TYPE: DNA
<213> ORGANISM: Arabidopsis thaliana
<220> FEATURE:
<221> NAME/KEY: misc_feature
<223> OTHER INFORMATION: Ceres SEED LINE ME24513
<220> FEATURE:
<221> NAME/KEY: misc_feature
<223> OTHER INFORMATION: Ceres SEED LINE ME24480
<220> FEATURE:
```

```
<221> NAME/KEY: misc_feature
<223> OTHER INFORMATION: Ceres SEED LINE ME24762
<220> FEATURE:
<221> NAME/KEY: misc_feature
<223> OTHER INFORMATION: Ceres CLONE ID no. 1025179
<220> FEATURE:
<221> NAME/KEY: misc_feature
<223> OTHER INFORMATION: Encodes the peptide sequence at SEQ ID NO. 120

<400> SEQUENCE: 119

acgatagcct ctcatcttct tttttcctct ccatcatctt ctcttatcaa ctttagactc     60

acaagcctcc tctcatcttc accataaccg aaaaaccaaa caaaaaatcc ttagataatc    120

agatcttgat attatggatc atatcatcgg ctttatgggc acaacaaaca tgtcacataa    180

cacaaacctt atgatcgctg ccgcagccac taccactacg acctcttcgt cttcctcttc    240

ttcctccgga ggctcgggga ctaaccagct aagcaggtac gagaatcaga agagaagaga    300

ttggaacact ttcggacagt atctacgcaa tcaccgtcca ccactttctc tctcccgttg    360

cagtggtgct catgttcttg aattcctcag gtacctcgac caattcggca agactaaggt    420

tcacacacac ctatgtccgt tcttcggaca cccaaaccca ccagcaccat gtgcctgtcc    480

actccgacaa gcgtggggta gtctggacgc actcattggc cgtcttagag ctgcttttga    540

agagaacggt ggttcaccag agacgaaccc ttttggtgca cgagccgttc gactctacct    600

aagggaagta cgtgactcgc aggctaaagc acgtgggatc agctatgaaa aaaagaagcg    660

caagcgacct cctccgccac taccaccggc tcagccggcg atttcaagta gccctaatta    720

acattaagtc atgagtaaga tgtttcaatg aactacgttt gtttacaaat ttttatcaat    780

gacgaacatg cacgagttct tttaaagtca catgcccttt cctaaacttt tatttgac      838


<210> SEQ ID NO 120
<211> LENGTH: 195
<212> TYPE: PRT
<213> ORGANISM: Arabidopsis thaliana
<220> FEATURE:
<221> NAME/KEY: misc_feature
<223> OTHER INFORMATION: Ceres SEED LINE ME24513
<220> FEATURE:
<221> NAME/KEY: misc_feature
<223> OTHER INFORMATION: Ceres SEED LINE ME24480
<220> FEATURE:
<221> NAME/KEY: misc_feature
<223> OTHER INFORMATION: Ceres SEED LINE ME24762
<220> FEATURE:
<221> NAME/KEY: misc_feature
<223> OTHER INFORMATION: Ceres CLONE ID no. 1025179
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 120

Met Asp His Ile Ile Gly Phe Met Gly Thr Thr Asn Met Ser His Asn
1               5                   10                  15

Thr Asn Leu Met Ile Ala Ala Ala Ala Thr Thr Thr Thr Thr Ser Ser
            20                  25                  30

Ser Ser Ser Ser Ser Ser Gly Gly Ser Gly Thr Asn Gln Leu Ser Arg
        35                  40                  45

Tyr Glu Asn Gln Lys Arg Arg Asp Trp Asn Thr Phe Gly Gln Tyr Leu
    50                  55                  60
```

```
Arg Asn His Arg Pro Pro Leu Ser Leu Ser Arg Cys Ser Gly Ala His
65                  70                  75                  80

Val Leu Glu Phe Leu Arg Tyr Leu Asp Gln Phe Gly Lys Thr Lys Val
                85                  90                  95

His Thr His Leu Cys Pro Phe Phe Gly His Pro Asn Pro Pro Ala Pro
            100                 105                 110

Cys Ala Cys Pro Leu Arg Gln Ala Trp Gly Ser Leu Asp Ala Leu Ile
        115                 120                 125

Gly Arg Leu Arg Ala Ala Phe Glu Glu Asn Gly Gly Ser Pro Glu Thr
    130                 135                 140

Asn Pro Phe Gly Ala Arg Ala Val Arg Leu Tyr Leu Arg Glu Val Arg
145                 150                 155                 160

Asp Ser Gln Ala Lys Ala Arg Gly Ile Ser Tyr Glu Lys Lys Lys Arg
                165                 170                 175

Lys Arg Pro Pro Pro Pro Leu Pro Pro Ala Gln Pro Ala Ile Ser Ser
            180                 185                 190

Ser Pro Asn
        195


<210> SEQ ID NO 121
<211> LENGTH: 939
<212> TYPE: DNA
<213> ORGANISM: Brassica napus
<220> FEATURE:
<221> NAME/KEY: misc_feature
<223> OTHER INFORMATION: Ceres SEED LINE ME25665
<220> FEATURE:
<221> NAME/KEY: misc_feature
<223> OTHER INFORMATION: Ceres CLONE ID no. 1084747
<220> FEATURE:
<221> NAME/KEY: misc_feature
<223> OTHER INFORMATION: Encodes the peptide sequence at SEQ ID NO. 122

<400> SEQUENCE: 121

acactctttc tctcattttc tctctctttt aaaacactaa tcactaaaat cttgattcac      60

tgtatcctca aaaccaactc taaatcaaac tctctcaaag aaaacaagcc aaagccctac     120

tttggatgga ttcagggtca caacgaccgg ggcctgtcag cgaaggcgat ccgggtccgt     180

ccatcgtaac cccctcttca ccgcctgcgg cgcctagcag gtacgagtca cagaaacgac     240

gtgactggac cacgttctta cagtacctca agaaccacaa gccgcctctt tccttgtcac     300

ggtgtagcgg ggcacatgcc atcgagttcc tcaagtactt agatcagttc ggtaagacca     360

aagtccacgt ggcggcgtgt ccttacttcg gccatcagca acctccgtct ccttgcgctt     420

gtcctctcaa gcaagcctgg gggtctctcg atgccctgat cggacggctg agagcagcct     480

atgaggagaa cggtggacgg cccgagtcga acccgttcgc ggcacgtgcg gtcaggattt     540

acttgaggga agtcagagaa agtcaagcca aggcccgtgg gagaccctac gagaaaaaga     600

aacggaaacg gccaacaact gttaccaccg tgagagttga cgttgctccg tcgagacaaa     660

gtgaaggaga tggttgtaac atcggtgatc cgtcgtctct ggccgaggct gtacctcctt     720

aattacgtta ttattattgt catgatatat taaatacatt atacatgtct ggaactcaca     780

tcaccaaaaa aaaactcaca tcaccttctt gagttaacta tcgaaaatat atttttgttc     840

tagttcagtt gatctttgat gaattacgtt cttgaatttt tcttttaatt cttatgaatt     900

ccacacattt ttaaggacta attaacgagg ttttcattc                            939


<210> SEQ ID NO 122
```

```
<211> LENGTH: 198
<212> TYPE: PRT
<213> ORGANISM: Brassica napus
<220> FEATURE:
<221> NAME/KEY: misc_feature
<223> OTHER INFORMATION: Ceres SEED LINE ME25665
<220> FEATURE:
<221> NAME/KEY: misc_feature
<223> OTHER INFORMATION: Ceres CLONE ID no. 1084747
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (14)..(146)
<223> OTHER INFORMATION: Pfam Name: DUF640
      Pfam Description: Protein of unknown function (DUF640)

<400> SEQUENCE: 122

Met Asp Ser Gly Ser Gln Arg Pro Gly Pro Val Ser Glu Gly Asp Pro
1               5                   10                  15

Gly Pro Ser Ile Val Thr Pro Ser Ser Pro Pro Ala Ala Pro Ser Arg
            20                  25                  30

Tyr Glu Ser Gln Lys Arg Arg Asp Trp Thr Thr Phe Leu Gln Tyr Leu
        35                  40                  45

Lys Asn His Lys Pro Pro Leu Ser Leu Ser Arg Cys Ser Gly Ala His
    50                  55                  60

Ala Ile Glu Phe Leu Lys Tyr Leu Asp Gln Phe Gly Lys Thr Lys Val
65                  70                  75                  80

His Val Ala Ala Cys Pro Tyr Phe Gly His Gln Gln Pro Pro Ser Pro
                85                  90                  95

Cys Ala Cys Pro Leu Lys Gln Ala Trp Gly Ser Leu Asp Ala Leu Ile
            100                 105                 110

Gly Arg Leu Arg Ala Ala Tyr Glu Glu Asn Gly Gly Arg Pro Glu Ser
        115                 120                 125

Asn Pro Phe Ala Ala Arg Ala Val Arg Ile Tyr Leu Arg Glu Val Arg
    130                 135                 140

Glu Ser Gln Ala Lys Ala Arg Gly Arg Pro Tyr Glu Lys Lys Lys Arg
145                 150                 155                 160

Lys Arg Pro Thr Thr Val Thr Thr Val Arg Val Asp Val Ala Pro Ser
                165                 170                 175

Arg Gln Ser Glu Gly Asp Gly Cys Asn Ile Gly Asp Pro Ser Ser Leu
            180                 185                 190

Ala Glu Ala Val Pro Pro
        195


<210> SEQ ID NO 123
<211> LENGTH: 802
<212> TYPE: DNA
<213> ORGANISM: Zea mays
<220> FEATURE:
<221> NAME/KEY: misc_feature
<223> OTHER INFORMATION: Ceres SEED LINE ME25661
<220> FEATURE:
<221> NAME/KEY: misc_feature
<223> OTHER INFORMATION: Ceres CLONE ID no. 1464359
<220> FEATURE:
<221> NAME/KEY: misc_feature
<223> OTHER INFORMATION: Encodes the peptide sequence at SEQ ID NO. 124

<400> SEQUENCE: 123

agacacacga cccacacaca cacacacaga gattcacaag caaaatcaag aaccctaaaa     60
```

```
tctaaagaac gtcctgacat aatcacacga tcaaaaatgg agggagaaac cgcagtgaag    120

gcagcggcaa gttcctcatc atcaccaagc cgctatgagt cgcaaaagag acgagactgg    180

aacactttcc tacagtatct aaaaaaccac aagccacctt taaccctgtc tcgttgcagt    240

ggcgcacacg tcatcgagtt ccttaagtac ctcgaccagt ttggtaagac caaagtccac    300

gtcgcggctt gtcccttctt cggagtaccg tacccaccgg ttcagtgcac ttgccctctc    360

aggcaggctt ggggaagcct cgactctctc atcggccgtc taagggctgc gttcgaggaa    420

atcggcggtg gtcttccaga gtcaaaccct ttagctgcca aagcgattag gatctatctt    480

aaagaagtac gtgaaactca ggctaaggct cgagggattc catacgacaa gaagaaacgg    540

aaacgacctc gtacagctaa ggaaactcag aagcccgatg atggagaagg tgccggtgga    600

agtggaagtg gtgattctgc tttggttatt tctgcaactg tggtatagtc caaatataag    660

atgctaaaac taaatataag aaaactttgg catagtaatt ctctccgtgt tctttacttt    720

ataaatttta tatgttgtgt agtcgtttat ttgagttgta gaatgcaatt ataaatggaa    780

aagacggatc atagattatt at                                             802


<210> SEQ ID NO 124
<211> LENGTH: 183
<212> TYPE: PRT
<213> ORGANISM: Zea mays
<220> FEATURE:
<221> NAME/KEY: misc_feature
<223> OTHER INFORMATION: Ceres SEED LINE ME25661
<220> FEATURE:
<221> NAME/KEY: misc_feature
<223> OTHER INFORMATION: Ceres CLONE ID no. 1464359
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (1)..(134)
<223> OTHER INFORMATION: Pfam Name: DUF640
      Pfam Description: Protein of unknown function (DUF640)

<400> SEQUENCE: 124

Met Glu Gly Glu Thr Ala Val Lys Ala Ala Ala Ser Ser Ser Ser Ser
1               5                   10                  15

Pro Ser Arg Tyr Glu Ser Gln Lys Arg Arg Asp Trp Asn Thr Phe Leu
            20                  25                  30

Gln Tyr Leu Lys Asn His Lys Pro Pro Leu Thr Leu Ser Arg Cys Ser
        35                  40                  45

Gly Ala His Val Ile Glu Phe Leu Lys Tyr Leu Asp Gln Phe Gly Lys
    50                  55                  60

Thr Lys Val His Val Ala Ala Cys Pro Phe Phe Gly Val Pro Tyr Pro
65                  70                  75                  80

Pro Ala Gln Cys Thr Cys Pro Leu Arg Gln Ala Trp Gly Ser Leu Asp
                85                  90                  95

Ser Leu Ile Gly Arg Leu Arg Ala Ala Phe Glu Glu Ile Gly Gly Gly
            100                 105                 110

Leu Pro Glu Ser Asn Pro Leu Ala Ala Lys Ala Ile Arg Ile Tyr Leu
        115                 120                 125

Lys Glu Val Arg Glu Thr Gln Ala Lys Ala Arg Gly Ile Pro Tyr Asp
    130                 135                 140

Lys Lys Lys Arg Lys Arg Pro Arg Thr Ala Lys Glu Thr Gln Lys Pro
145                 150                 155                 160
```

```
Asp Asp Gly Glu Gly Ala Gly Gly Ser Gly Ser Gly Asp Ser Ala Leu
                165                 170                 175

Val Ile Ser Ala Thr Val Val
            180


<210> SEQ ID NO 125
<211> LENGTH: 858
<212> TYPE: DNA
<213> ORGANISM: Glycine max
<220> FEATURE:
<221> NAME/KEY: misc_feature
<223> OTHER INFORMATION: Ceres SEED LINE ME24758
<220> FEATURE:
<221> NAME/KEY: misc_feature
<223> OTHER INFORMATION: Ceres SEED LINE ME25680
<220> FEATURE:
<221> NAME/KEY: misc_feature
<223> OTHER INFORMATION: Ceres SEED LINE ME24978
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Encodes the peptide sequence at SEQ ID NO. 126

<400> SEQUENCE: 125

agtcccataa acctcacttc ctcaacctca atccaacaga aacaaaaaaa aacctcactt      60

agatcacata gatcaaacaa caaaacacag agttacctaa attgaaccta ccccagtagg     120

ttctacaagc tcttgatcat ggcctcagca tcaggggagg caccaccacc ccaacccact     180

tcaacagaag ctgctccagc atcaggctct tcagctccag ccatatcagc agcaccacca     240

caacccggag gatcatcgcc ggcgcctccg agccgctacg aatcgcaaaa gcgtcgagac     300

tggaacacgt ttctgcagta cctgcagaac cacaagcccc cattaacgct ggcgcggtgc     360

agtggcgcac acgtcattga gttcttgaag tacttggacc aattcgggaa aaccaaggtt     420

cacatcacgg ggtgcccgta ctacgggtac cccaaccctc ctgcgccctg cgcttgccca     480

ctgaaacaag cgtggggaag ccttgacgcc ctgatcgggc gactcagggc ggcttacgag     540

gaaaacggag gccgccctga gtctaacccg ttcggcgcca gggccgtcag aatttacctc     600

agggaggtaa gagaaggtca ggctaaagca agagggatcc cttatgagaa gaagaagcgg     660

aagaggacca ccgtggtgac ggtgagtagt ggtggtggtg gtagtagcgg tgcagttgcc     720

tctccgagtg gcggtggtga taccgctatt ggtggtggag ctggttctag tgctagttta     780

acttcttcag caactgccac agctaatgat actacaacca cagtataatt ttaatagtta     840

tttaattatt tatttttc                                                   858


<210> SEQ ID NO 126
<211> LENGTH: 229
<212> TYPE: PRT
<213> ORGANISM: Glycine max
<220> FEATURE:
<221> NAME/KEY: misc_feature
<223> OTHER INFORMATION: Ceres SEED LINE ME24758
<220> FEATURE:
<221> NAME/KEY: misc_feature
<223> OTHER INFORMATION: Ceres SEED LINE ME25680
<220> FEATURE:
<221> NAME/KEY: misc_feature
<223> OTHER INFORMATION: Ceres SEED LINE ME24978
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Functional Homolog of Ceres Clone ID no. 28780
```

```
      at SEQ ID NO. 88
<220> FEATURE:
<221> NAME/KEY: misc_feature
<222> LOCATION: (28)..(107)
<223> OTHER INFORMATION: Pfam Name: DUF640
      Pfam Description: Protein of unknown function (DUF640)

<400> SEQUENCE: 126

Met Ala Ser Ala Ser Gly Glu Ala Pro Pro Pro Gln Pro Thr Ser Thr
1               5                   10                  15

Glu Ala Ala Pro Ala Ser Gly Ser Ser Ala Pro Ala Ile Ser Ala Ala
            20                  25                  30

Pro Pro Gln Pro Gly Gly Ser Ser Pro Ala Pro Pro Ser Arg Tyr Glu
        35                  40                  45

Ser Gln Lys Arg Arg Asp Trp Asn Thr Phe Leu Gln Tyr Leu Gln Asn
    50                  55                  60

His Lys Pro Pro Leu Thr Leu Ala Arg Cys Ser Gly Ala His Val Ile
65                  70                  75                  80

Glu Phe Leu Lys Tyr Leu Asp Gln Phe Gly Lys Thr Lys Val His Ile
                85                  90                  95

Thr Gly Cys Pro Tyr Tyr Gly Tyr Pro Asn Pro Pro Ala Pro Cys Ala
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Asn Gly Gly Arg Pro Glu Ser Asn Pro
    130                 135                 140

Phe Gly Ala Arg Ala Val Arg Ile Tyr Leu Arg Glu Val Arg Glu Gly
145                 150                 155                 160

Gln Ala Lys Ala Arg Gly Ile Pro Tyr Glu Lys Lys Lys Arg Lys Arg
                165                 170                 175

Thr Thr Val Val Thr Val Ser Ser Gly Gly Gly Gly Ser Ser Gly Ala
            180                 185                 190

Val Ala Ser Pro Ser Gly Gly Gly Asp Thr Ala Ile Gly Gly Gly Ala
        195                 200                 205

Gly Ser Ser Ala Ser Leu Thr Ser Ser Ala Thr Ala Thr Ala Asn Asp
    210                 215                 220

Thr Thr Thr Thr Val
225


<210> SEQ ID NO 127
<211> LENGTH: 897
<212> TYPE: DNA
<213> ORGANISM: Brassica napus
<220> FEATURE:
<221> NAME/KEY: misc_feature
<223> OTHER INFORMATION: Ceres SEED LINE ME25647
<220> FEATURE:
<221> NAME/KEY: misc_feature
<223> OTHER INFORMATION: Ceres CLONE ID no. 964932
<220> FEATURE:
<221> NAME/KEY: misc_feature
<223> OTHER INFORMATION: Encodes the peptide sequence at SEQ ID NO. 128

<400> SEQUENCE: 127

acgatacccc ctcctctcct cctttttcct ctccaccatc ttcccttatc aactcaagac     60

ccataaagtt caagactcaa gactcataaa gctcctctca tattcatcat aacctaaaac    120

caaaacctca aagagttaat aaaacctaaa ttatacatca gatcttgata tcatggatcc    180

tatccacggc tttatgagca catcaaacat ctcacacaac acaaacctta tgatcgccgc    240
```

```
cgcagcagcc accactacca ctacctcctc ctcctcgtct tcctctggcg gctccgcgac    300

aaaccaactg agtaggtacg agaatcagaa gagaagagac tggaacactt tcggacaata    360

tctacgcaac caccgtccac cactttctct ctcccgttgc agtggtgctc atgttcttga    420

gttcctcagg tacctcgacc aattcggcaa gaccaaggtt cacatgcaaa tatgtccttt    480

ctttggacac ccaaacccac cagcaccatg tacctgccca ctcagacaag cgtggggcag    540

cctcgacgca ctcattggcc ggcttcgagc tgcttttgaa gagaacggtg gttcaccaga    600

gacgaaccct tttggtgcac gagctgttcg actctaccta agggaagttc gtgattcgca    660

ggctaaagcg cgtgggatca gctatgaaaa gaagaagcgg aagcgacctc ctcaggcgcc    720

actaccaccg cctcatcagc cggtgatttc gaatagtcct aatttgcaat aagtcatatc    780

agtaagatat gtttcagtca actacgtttc cttacaactt tatatagtat ttgtcaatga    840

cgaacatgca ggagttgtct aaaaagctgc atgcccttct tctttatttg gccagct       897
```

```
<210> SEQ ID NO 128
<211> LENGTH: 199
<212> TYPE: PRT
<213> ORGANISM: Brassica napus
<220> FEATURE:
<221> NAME/KEY: misc_feature
<223> OTHER INFORMATION: Ceres SEED LINE ME25647
<220> FEATURE:
<221> NAME/KEY: misc_feature
<223> OTHER INFORMATION: Ceres CLONE ID no. 964932
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 128

Met Asp Pro Ile His Gly Phe Met Ser Thr Ser Asn Ile Ser His Asn
1               5                   10                  15

Thr Asn Leu Met Ile Ala Ala Ala Ala Ala Thr Thr Thr Thr Thr Ser
            20                  25                  30

Ser Ser Ser Ser Ser Ser Gly Gly Ser Ala Thr Asn Gln Leu Ser Arg
        35                  40                  45

Tyr Glu Asn Gln Lys Arg Arg Asp Trp Asn Thr Phe Gly Gln Tyr Leu
    50                  55                  60

Arg Asn His Arg Pro Pro Leu Ser Leu Ser Arg Cys Ser Gly Ala His
65                  70                  75                  80

Val Leu Glu Phe Leu Arg Tyr Leu Asp Gln Phe Gly Lys Thr Lys Val
                85                  90                  95

His Met Gln Ile Cys Pro Phe Phe Gly His Pro Asn Pro Pro Ala Pro
            100                 105                 110

Cys Thr Cys Pro Leu Arg Gln Ala Trp Gly Ser Leu Asp Ala Leu Ile
        115                 120                 125

Gly Arg Leu Arg Ala Ala Phe Glu Glu Asn Gly Gly Ser Pro Glu Thr
    130                 135                 140

Asn Pro Phe Gly Ala Arg Ala Val Arg Leu Tyr Leu Arg Glu Val Arg
145                 150                 155                 160

Asp Ser Gln Ala Lys Ala Arg Gly Ile Ser Tyr Glu Lys Lys Lys Arg
                165                 170                 175

Lys Arg Pro Pro Gln Ala Pro Leu Pro Pro Pro His Gln Pro Val Ile
```

```
        180                 185                 190

Ser Asn Ser Pro Asn Leu Gln
        195


<210> SEQ ID NO 129
<211> LENGTH: 874
<212> TYPE: DNA
<213> ORGANISM: Glycine max
<220> FEATURE:
<221> NAME/KEY: misc_feature
<223> OTHER INFORMATION: Ceres SEED LINE ME24507
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Encodes the peptide sequence at SEQ ID NO. 146

<400> SEQUENCE: 129

agtcccataa acctcacttc ctcaacctca atccaacaga aacaaaaaaa aacctcactt      60

agatcacata gatcaaacaa caaaacacag agttacctaa attgaaccta ccccagtagg     120

ttctacaagc tcttgatcat ggcctcagca tcaggggggg caccaccacc ccaacccact     180

tcaacagaag ctgctccagc atcaggctct tcagctccag ccatatcagc agcaccacca     240

caacccggag gatcatcgcc ggcgcctccg agccgctacg aatcgcaaaa gcgtcgagac     300

tggaacacgt ttctgcagta cctgcagaac cacaagcccc cattaacgct ggcgcggtgc     360

agtggcgcac acgtcattga gttcttgaag tacttggacc aattcgggaa aaccaaggtt     420

cacatcacgg ggtgcccgta ctacgggtac cccaaccctc ctgcgccctg cgcttgccca     480

ctgaaacaag cgtggggaag ccttgacgcc ctgatcgggc gactcagggc ggcttacgag     540

gaaaacggag gccgccctga gtctaacccg ttcggcgcca gggccgtcag aatttacctc     600

agggaggtaa gagaaggtca ggctaaagca agagggatcc cttatgagaa gaagaagcgg     660

aagaggacca ccgtggtgac ggtgagtagt ggtggtggtg gtagtagcgg tgcagttgcc     720

tctccgagtg gcggtggtga taccgctatt ggtggtggag ctggttctag tgctagttta     780

acttcttcag caactgccac agctaatgat actacaacca cagtataatt ttaatagtta     840

tttaattatt tatttttcaa aaaaaaaaaa aaaa                                 874


<210> SEQ ID NO 130
<211> LENGTH: 1278
<212> TYPE: DNA
<213> ORGANISM: Gossypium hirsutum
<220> FEATURE:
<221> NAME/KEY: misc_feature
<223> OTHER INFORMATION: Ceres CLONE ID no. 1855399
<220> FEATURE:
<221> NAME/KEY: misc_feature
<223> OTHER INFORMATION: Encodes the peptide sequence at SEQ ID NO. 131

<400> SEQUENCE: 130

aaatctttcc cgtgaaagga tcccatggag cactacttct ttcaatgaac cctaaacacc      60

ctcaattatc atactcttat ttgactgacc taatcaaaca gaagcagcta ataagggttt     120

gtcaattgtg agtgactgat aaatagcttg gattttggaa tctctcccta cacttggatt     180

tcagataaaa acaaaatccc aggtgggaaa aattcatcac tgcccatcaa cagttcatca     240

ccaaaacccc aacagtttcc tcttcttttt ttccaagtca atggattctg cctccggagg     300

gagtgacaat agcatcaaag aggctatacc agcaacagct tcagccctgc tgtccgcggc     360

ttcacaacaa ggaggaggag gtggtagtga gtcgtctcct tccccagctc caccgagtag     420
```

```
gtacgagtca caaaagcgtc gagactggaa cactttcttg cagtacttga ccaaccataa    480

acccccatta acactagctc gttgcagtgg cgcacacgta attgagttct tgaaatacct    540

tgaccagttc ggcaagacta aggttcacat aacggattgt ccctatttcg gacatgtaaa    600

cccacctgct ccctgcgctt gcccactgaa gcaagcgtgg ggtagcctcg acgcgctgat    660

cggacggctc agagctgctt atgaagaaaa cggtggacgt ccagaatcca acccttttgg    720

cgcaagggct gtgaggattt atttgaggga agtgagagaa gggcaggcta aagctagagg    780

gattccttat gagaagaaga agcgaaaaag gcccactgtc acaactacgg ctgtcggggt    840

caatgtgtcc aggacttcca ctcaaccagt tgatggcggt gggggtcgcg gcggcattgg    900

tggtggagat gatagtgttg gtgctaaaac tggggcaaat gttggtagtg ccaccgcagt    960

tgctgctgct accactaata gcgtatagtt ctttttccct attaacaaat tcttttcctc   1020

ttttttgcc tttaacagct gttttaaatg tgattacgag ttatatatat ctggtggttc   1080

tgtcgggaaa ttggattgac atcccatgaa ccaaatttag aatttaggta gaattctagt   1140

tttaatctct ttcaatcaat ctctcctatt ttcccctttc tctactttct tcatcatttc   1200

ttgctatgca tgtacttgaa aaaggaatat aagaagtttt aatctttttt ccctttctaa   1260

aaaaaaaaaa aaaaaaa                                                   1278


<210> SEQ ID NO 131
<211> LENGTH: 235
<212> TYPE: PRT
<213> ORGANISM: Gossypium hirsutum
<220> FEATURE:
<221> NAME/KEY: misc_feature
<223> OTHER INFORMATION: Ceres CLONE ID no. 1855399
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (29)..(161)
<223> OTHER INFORMATION: Pfam Name: DUF640
      Pfam Description: Protein of unknown function (DUF640)

<400> SEQUENCE: 131

Met Asp Ser Ala Ser Gly Gly Ser Asp Asn Ser Ile Lys Glu Ala Ile
1               5                   10                  15

Pro Ala Thr Ala Ser Ala Leu Leu Ser Ala Ala Ser Gln Gln Gly Gly
            20                  25                  30

Gly Gly Gly Ser Glu Ser Ser Pro Ser Pro Ala Pro Pro Ser Arg Tyr
        35                  40                  45

Glu Ser Gln Lys Arg Arg Asp Trp Asn Thr Phe Leu Gln Tyr Leu Thr
    50                  55                  60

Asn His Lys Pro Pro Leu Thr Leu Ala Arg Cys Ser Gly Ala His Val
65                  70                  75                  80

Ile Glu Phe Leu Lys Tyr Leu Asp Gln Phe Gly Lys Thr Lys Val His
                85                  90                  95

Ile Thr Asp Cys Pro Tyr Phe Gly His Val Asn Pro Pro Ala Pro Cys
            100                 105                 110

Ala Cys Pro Leu Lys Gln Ala Trp Gly Ser Leu Asp Ala Leu Ile Gly
        115                 120                 125

Arg Leu Arg Ala Ala Tyr Glu Glu Asn Gly Gly Arg Pro Glu Ser Asn
    130                 135                 140

Pro Phe Gly Ala Arg Ala Val Arg Ile Tyr Leu Arg Glu Val Arg Glu
```

```
145                 150                 155                 160

Gly Gln Ala Lys Ala Arg Gly Ile Pro Tyr Glu Lys Lys Lys Arg Lys
                165                 170                 175

Arg Pro Thr Val Thr Thr Thr Ala Val Gly Val Asn Val Ser Arg Thr
            180                 185                 190

Ser Thr Gln Pro Val Asp Gly Gly Gly Gly Arg Gly Gly Ile Gly Gly
        195                 200                 205

Gly Asp Asp Ser Val Gly Ala Lys Thr Gly Ala Asn Val Gly Ser Ala
    210                 215                 220

Thr Ala Val Ala Ala Ala Thr Thr Asn Ser Val
225                 230                 235


<210> SEQ ID NO 132
<211> LENGTH: 2276
<212> TYPE: DNA
<213> ORGANISM: Panicum virgatum
<220> FEATURE:
<221> NAME/KEY: misc_feature
<223> OTHER INFORMATION: Ceres CLONE ID no. 1858527
<220> FEATURE:
<221> NAME/KEY: misc_feature
<223> OTHER INFORMATION: Encodes the peptide sequence at SEQ ID NO. 133

<400> SEQUENCE: 132

gtccccgcat atctgaccac atcttcttcc cccacctctc cccaagctcg ctcacctcag     60

ctgctggcct cctcctctcc cgtccctttc caccgatcga gcttcttcta actgctggta    120

tgctgccttc gtgttcaact cgagccgtcg ctttgcaatt ctttgcatac tttcttgcaa    180

aaaaaaatct ttgtatgcat gtttcatgtt tctgaagctg tacgattgat cttgctgctc    240

ttattcggct catcatccgc acatctgtcc atgcatgtcg tcagcttgtg ttgtgtagct    300

tctgtttccc tggtgtctgg tcgatcgatc gtgcgcgcac ggattgtcta gtggtaggct    360

cttggccctg cgcctacagt acgcccacac atggatcaag ggccctgtaa accctgttct    420

gcagcgaccc accgtgtcga tcattaaccg ggcggcgaca ctctggctgt tctggatcaa    480

ttcgccttcg ccttcttgga gtaggtaggt agacgcatgt tcgacagttc tctcccctct    540

tttctgatgc acctcgcact catctctggc attcaggcag agccgaccag ccagctcctg    600

aataaactga atgtttgctg acctctagtc ctgcctctgt tcgtcctgct ttgctcaccg    660

atcgccggcg tggcgcaggc gaagccgaaa tttttctgtt atttgctttg cagttttgtt    720

ttactcctcc gttccgtttt gtgcttttcg ccctttcccc tgtgctttgc ttcagacttt    780

ccgtgtaggc gtcagttctt gcatgtctgc taaggatcag cggcctcagt cctcaggtgc    840

tctagacttg aaatcccact accggttgat aggtactact aggtggccgc tagctccgac    900

ctgaaaccct agttcattca gaatatctga tccgtcctag ctctgctggc cggccaagaa    960

cagacgaagc gactgtttct tgtccgatcg gcccttttgc atacgatcag tattattgtt   1020

tcttgtccga ccattggtcg aagcgttgga ctaacaggca tggcacatgg tgccggtgca   1080

ggtgcagatc tgggttggcc ttcgtggaca ggctgcggcg aaggagctat ggagatggcc   1140

ggcgcggcga acagcccggg cccggcagcg gcgcggccga gccggtacga gtcgcagaag   1200

cgccgggact ggcagacgtt cggcagtac ctgcgcaacc accggccgcc gctggagctg   1260

gcccggtgca gcggcgcgca cgtgctcgag ttcctccgct acctggacca gttcggcaag   1320

accaaggtgc acgcgccggg gtgccccttc ttcggccacc cgtcgccgcc ggcgccgtgc   1380

ccgtgcccgc tcaagcaggc gtggggcagc ctcgacgcgc tcgttggccg cctccgcgcc   1440
```

```
gccttcgagg agcacggcgg ccgccccgag gccaatccct tcggggtgcg cgccgtccgg   1500

ctctacctcc gcgaggtccg cgacacccag gccaaggcgc gcggcatcgc ctacgagaag   1560

aagcgccgca agcgccaccc gccggcacac aggcaggcca agcagcagca ggacgccggc   1620

cagcagcagc agcagcagca ctaccacccc caccaccacc accaggcgtc gcccgccgcg   1680

gctgcggtga ccgagagtag gcgcgtgctg gcggacatgg ccgagccgct ggcgccgcac   1740

ttcctgatcc cgcacgcgca gttcctccac ggccacttcc tggtgccggt caccgagccg   1800

accgaccccg ccgcgggcat gggcggcggc ggcaccggcg aggacttggt gctggcaatg   1860

gcggccgccg ccgaggcgca cgccgccgcg gccgggttct tgatgccgct gtccgtgttt   1920

cactagctag cttgctgggt ccactctccg ctgcctctat agctccaggg gcagggatgc   1980

aaggctaggt aattaggcgt aatcaagcat gcaggttttg ctaatggcga tcggcctgat   2040

ctctgcgcgc cgtttggtcg tccatccggc ttttggtgtt tatgcgcttg catcaaccgc   2100

tgctgccttt tggttgtatt ttgggtgcgt ggttttgtgt acgcagtgat agaatggctg   2160

gattagaccg ctgtgtgtgt ttttctccat gacttggatc ttgtgggaat ttcatgtact   2220

acagctgatc tcaatcgact taacattgtt cctggtaaaa aaaaaaaaaa aaaaaa       2276
```

```
<210> SEQ ID NO 133
<211> LENGTH: 288
<212> TYPE: PRT
<213> ORGANISM: Panicum virgatum
<220> FEATURE:
<221> NAME/KEY: misc_feature
<223> OTHER INFORMATION: Ceres CLONE ID no. 1858527
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (24)..(156)
<223> OTHER INFORMATION: Pfam Name: DUF640
      Pfam Description: Protein of unknown function (DUF640)

<400> SEQUENCE: 133

Met Ala His Gly Ala Gly Ala Gly Ala Asp Leu Gly Trp Pro Ser Trp
1               5                   10                  15

Thr Gly Cys Gly Glu Gly Ala Met Glu Met Ala Gly Ala Ala Asn Ser
            20                  25                  30

Pro Gly Pro Ala Ala Ala Arg Pro Ser Arg Tyr Glu Ser Gln Lys Arg
        35                  40                  45

Arg Asp Trp Gln Thr Phe Gly Gln Tyr Leu Arg Asn His Arg Pro Pro
    50                  55                  60

Leu Glu Leu Ala Arg Cys Ser Gly Ala His Val Leu Glu Phe Leu Arg
65                  70                  75                  80

Tyr Leu Asp Gln Phe Gly Lys Thr Lys Val His Ala Pro Gly Cys Pro
                85                  90                  95

Phe Phe Gly His Pro Ser Pro Pro Ala Pro Cys Pro Cys Pro Leu Lys
            100                 105                 110

Gln Ala Trp Gly Ser Leu Asp Ala Leu Val Gly Arg Leu Arg Ala Ala
        115                 120                 125

Phe Glu Glu His Gly Gly Arg Pro Glu Ala Asn Pro Phe Gly Val Arg
    130                 135                 140

Ala Val Arg Leu Tyr Leu Arg Glu Val Arg Asp Thr Gln Ala Lys Ala
145                 150                 155                 160

Arg Gly Ile Ala Tyr Glu Lys Lys Arg Arg Lys Arg His Pro Pro Ala
```

```
                165                 170                 175

His Arg Gln Ala Lys Gln Gln Gln Asp Ala Gly Gln Gln Gln Gln Gln
            180                 185                 190

Gln His Tyr His Pro His His His His Gln Ala Ser Pro Ala Ala Ala
        195                 200                 205

Ala Val Thr Glu Ser Arg Arg Val Leu Ala Asp Met Ala Glu Pro Leu
    210                 215                 220

Ala Pro His Phe Leu Ile Pro His Ala Gln Phe Leu His Gly His Phe
225                 230                 235                 240

Leu Val Pro Val Thr Glu Pro Thr Asp Pro Ala Ala Gly Met Gly Gly
                245                 250                 255

Gly Gly Thr Gly Glu Asp Leu Val Leu Ala Met Ala Ala Ala Ala Glu
            260                 265                 270

Ala His Ala Ala Ala Ala Gly Phe Leu Met Pro Leu Ser Val Phe His
        275                 280                 285
```

<210> SEQ ID NO 134
<211> LENGTH: 797
<212> TYPE: DNA
<213> ORGANISM: Unknown
<220> FEATURE:
<221> NAME/KEY: misc_feature
<223> OTHER INFORMATION: Ceres CLONE ID no. 1896482
<220> FEATURE:
<221> NAME/KEY: misc_feature
<223> OTHER INFORMATION: Encodes the peptide sequence at SEQ ID NO. 135

<400> SEQUENCE: 134

```
atggattctg caacggaccc gaataccatc aaggaggatc cagtatcagt tacagtttca      60

gcaccaccgt ccaagggtat ccagcaagga gttggtgagt cgccgtcgtc ttctacttcc     120

ccagcagcac cgagtcgtta cgagtcacaa aagcgtcgag actggaacac gttcttgcag     180

tacttgaaga accataagcc gccattgact ctggctcgtt gcagcggagc acacgtgatc     240

gagttcttga agtacctcga ccagttcggg aaaaccaagg ttcacatgac gggttgtcct     300

tatttcggac acccgaaccc gcctggtcct tgctcttgtc cactcaagca agcgtggggt     360

agcctcgacg cgctgatcgg acggctgaga gctgcttacg aagagagcgg gggacgaccg     420

gaatcaaacc cgtttgcggc aagggctgtg aggatttatt tgagggaagt gagggaagga     480

caggctagag ctagagggat acctaatgag aaaaagaagc gaaaaaggac ttctgttaca     540

actagcgctg tagggatcaa tgtgtcggcg gtggctgcca ctcaagcggt tgattatggt     600

ggggttagcg gaggaactgc gagtaatctt ggtactgcta ctaccactac tagcttatag     660

attcttcaat gattatttta tatatatatt ttgctttcaa tatttgatat aaatgtgata     720

tgtggcggtt ctttcttaaa actggatcaa tatccccatg aaccaaattt agatggaaat     780

ataattttaa tctttct                                                    797
```

<210> SEQ ID NO 135
<211> LENGTH: 219
<212> TYPE: PRT
<213> ORGANISM: Unknown
<220> FEATURE:
<221> NAME/KEY: misc_feature
<223> OTHER INFORMATION: Ceres CLONE ID no. 1896482
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature

```
<222> LOCATION: (28)..(160)
<223> OTHER INFORMATION: Pfam Name: DUF640
      Pfam Description: Protein of unknown function (DUF640)

<400> SEQUENCE: 135

Met Asp Ser Ala Thr Asp Pro Asn Thr Ile Lys Glu Asp Pro Val Ser
1               5                   10                  15

Val Thr Val Ser Ala Pro Pro Ser Lys Gly Ile Gln Gln Gly Val Gly
            20                  25                  30

Glu Ser Pro Ser Ser Ser Thr Ser Pro Ala Ala Pro Ser Arg Tyr Glu
        35                  40                  45

Ser Gln Lys Arg Arg Asp Trp Asn Thr Phe Leu Gln Tyr Leu Lys Asn
    50                  55                  60

His Lys Pro Pro Leu Thr Leu Ala Arg Cys Ser Gly Ala His Val Ile
65                  70                  75                  80

Glu Phe Leu Lys Tyr Leu Asp Gln Phe Gly Lys Thr Lys Val His Met
                85                  90                  95

Thr Gly Cys Pro Tyr Phe Gly His Pro Asn Pro Pro Gly Pro Cys Ser
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Ser Gly Gly Arg Pro Glu Ser Asn Pro
    130                 135                 140

Phe Ala Ala Arg Ala Val Arg Ile Tyr Leu Arg Glu Val Arg Glu Gly
145                 150                 155                 160

Gln Ala Arg Ala Arg Gly Ile Pro Asn Glu Lys Lys Lys Arg Lys Arg
                165                 170                 175

Thr Ser Val Thr Thr Ser Ala Val Gly Ile Asn Val Ser Ala Val Ala
            180                 185                 190

Ala Thr Gln Ala Val Asp Tyr Gly Gly Val Ser Gly Gly Thr Ala Ser
        195                 200                 205

Asn Leu Gly Thr Ala Thr Thr Thr Thr Ser Leu
    210                 215


<210> SEQ ID NO 136
<211> LENGTH: 1125
<212> TYPE: DNA
<213> ORGANISM: Gossypium hirsutum
<220> FEATURE:
<221> NAME/KEY: misc_feature
<223> OTHER INFORMATION: Ceres CLONE ID no. 1934537
<220> FEATURE:
<221> NAME/KEY: misc_feature
<223> OTHER INFORMATION: Encodes the peptide sequence at SEQ ID NO. 137

<400> SEQUENCE: 136

aagaattatt ttttggacgt ctcatcattt agtttttttt tcctctcttt cacactttat      60

cacttcaaat ttcttcttcg ttttgatttt cattcaaaac catctctgaa ttgtttttta     120

aaagccaatc ttcggatccc agcagttttt tcagtgaacc ctagtcaaaa agagaagcag     180

ctagagcaaa gagtttatga attgttagtg attgattgat tgatagtata tgttagagtt     240

tatatagaaa agaaaacgac gatttgatgg aaatttagtg acagccaatt atcatcaaaa     300

gtgcgaagcc ctaatagttt tttttaagtc aatggattct gcaacgaacc cgaatatcat     360

caagaaggat ccagtaccag ttacagtttc agcaccatcg tccacgggta tccagcaagg     420

agttggtgag tcgccgtcgt cttctacttc cccagcagca ccgagtcggt acgagtcaca     480

aaagcgtcga gactggaaca cgttcttgca gtacttgaag aaccataagc cgccattgac     540
```

```
tctggctcgt tgcagcggcg cacacgtgat cgagttcttg aagtacctcg accagttcgg    600

gaaaaccaag gttcacatga cgggttgtcc ttatttcgga cacccgaacc cgcctggtcc    660

ttgctcttgt ccactcaagc aagcgtgggg tagcctcgac gcgctgatcg gacggctgag    720

agctgcttac gaagagagcg ggggacgacc ggaatcgaac ccgtttgcgg caagggctgt    780

gaggatttat ttgagggaag tgagggaagg acaggctaga gctagaggga taccttatga    840

gaaaaagaag cgaaaaaggc cttctgtcac aactagcgct gtaggggtca atgtgtcggc    900

ggtggctgcc actcaagcgg ttgattatgg tgggggtagc ggaggaactg cgggtaatct    960

tggtactgct actaccacta ctagcttata aattcttcaa tgattattat atatatatat   1020

attgctttca atatttgata taaatgtgat atgtggcggt tctttcttaa aattggatcc   1080

atatccccat gaaccaaatt tagacaaaaa aaaaaaaaaa aaaaa                   1125


<210> SEQ ID NO 137
<211> LENGTH: 219
<212> TYPE: PRT
<213> ORGANISM: Gossypium hirsutum
<220> FEATURE:
<221> NAME/KEY: misc_feature
<223> OTHER INFORMATION: Ceres CLONE ID no. 1934537
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (28)..(160)
<223> OTHER INFORMATION: Pfam Name: DUF640
      Pfam Description: Protein of unknown function (DUF640)

<400> SEQUENCE: 137

Met Asp Ser Ala Thr Asn Pro Asn Ile Ile Lys Lys Asp Pro Val Pro
1               5                   10                  15

Val Thr Val Ser Ala Pro Ser Ser Thr Gly Ile Gln Gln Gly Val Gly
            20                  25                  30

Glu Ser Pro Ser Ser Ser Thr Ser Pro Ala Ala Pro Ser Arg Tyr Glu
        35                  40                  45

Ser Gln Lys Arg Arg Asp Trp Asn Thr Phe Leu Gln Tyr Leu Lys Asn
    50                  55                  60

His Lys Pro Pro Leu Thr Leu Ala Arg Cys Ser Gly Ala His Val Ile
65                  70                  75                  80

Glu Phe Leu Lys Tyr Leu Asp Gln Phe Gly Lys Thr Lys Val His Met
                85                  90                  95

Thr Gly Cys Pro Tyr Phe Gly His Pro Asn Pro Pro Gly Pro Cys Ser
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Ser Gly Gly Arg Pro Glu Ser Asn Pro
    130                 135                 140

Phe Ala Ala Arg Ala Val Arg Ile Tyr Leu Arg Glu Val Arg Glu Gly
145                 150                 155                 160

Gln Ala Arg Ala Arg Gly Ile Pro Tyr Glu Lys Lys Lys Arg Lys Arg
                165                 170                 175

Pro Ser Val Thr Thr Ser Ala Val Gly Val Asn Val Ser Ala Val Ala
            180                 185                 190

Ala Thr Gln Ala Val Asp Tyr Gly Gly Gly Ser Gly Gly Thr Ala Gly
        195                 200                 205
```

```
Asn Leu Gly Thr Ala Thr Thr Thr Thr Ser Leu
    210                 215


<210> SEQ ID NO 138
<211> LENGTH: 1159
<212> TYPE: DNA
<213> ORGANISM: Gossypium hirsutum
<220> FEATURE:
<221> NAME/KEY: misc_feature
<223> OTHER INFORMATION: Ceres CLONE ID no. 1942084
<220> FEATURE:
<221> NAME/KEY: misc_feature
<223> OTHER INFORMATION: Encodes the peptide sequence at SEQ ID NO. 139

<400> SEQUENCE: 138

acgtcccaca tcatcgatat tcctgttctt gctacttggt tttttttct aacatcaatt     60

cattttcttt ccttctttaa ctcagaatca tatcttcttc tctatcacca ataaagagaa    120

tacaagcaaa tctttcctgt caccgggggg ggggggagcc tatcacttct ttcaatatga    180

accctaatac tactatttta cctaacctaa gagcttagga ttttgatagg tttagtgttc    240

ttttttgttt taaatcgatg gattctggtt ccggagccaa cccgaatagc atcaacgagg    300

gttcatcatc agctacagca ccggtgctga tggattcaca acaaggtgga gctggtgaat    360

tgtcttcttc tccagctcat ccaccgagtc gctacgagtc acaaaagcgt cgcgactgga    420

acactttctt gcagtacttg aagaaccaca agccccccact gacgctatct cgttgcagcg    480

gcgcacacgt aatcgagttc ttgaaatatc ttgaccagtt cggcaaaact aaggttcacg    540

taacggcttg tccttatttc ggacatgcaa acccgcccga tccttgttct tgtccactca    600

agcaagcgtg ggtagcctc gacgcgttga tcggacggct gagagctgct tatgaagaaa    660

acggtggacg tcgggaatca aaccctttttg ggacaagggc tgtgaggatt tatttgaggg    720

aagtgagagg agggcaggct aaagctagag ggattcctta tgagaaaaag aagcgaaaaa    780

ggcctactac tacggctgtg tcggcggctt ctggtactca accacctggt ggtgctgccg    840

gtgatgatag ttctggtgga actacggcta acgtgggtac tgtcaccgct gctgctacca    900

ctaatagctt atagttgttc tcttaattac tatttttatt ttttattttg tcttctaata    960

gctgttttat atgtgattat gatgagttat cacatgaact aagtttagtt agcaatcttg   1020

tttaatcact ttcgacattt ttccacttct acagtttctt catttcttgt catgcatgaa   1080

catgattact atatatataa acacatacat atatatgtat aagttgaaat aaaaacaata   1140

agacgagagt tattaatct                                                1159


<210> SEQ ID NO 139
<211> LENGTH: 218
<212> TYPE: PRT
<213> ORGANISM: Gossypium hirsutum
<220> FEATURE:
<221> NAME/KEY: misc_feature
<223> OTHER INFORMATION: Ceres CLONE ID no. 1942084
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (27)..(159)
<223> OTHER INFORMATION: Pfam Name: DUF640
      Pfam Description: Protein of unknown function (DUF640)

<400> SEQUENCE: 139

Met Asp Ser Gly Ser Gly Ala Asn Pro Asn Ser Ile Asn Glu Gly Ser
```

```
1               5                   10                  15

Ser Ser Ala Thr Ala Pro Val Leu Met Asp Ser Gln Gln Gly Gly Ala
            20                  25                  30

Gly Glu Leu Ser Ser Ser Pro Ala His Pro Pro Ser Arg Tyr Glu Ser
        35                  40                  45

Gln Lys Arg Arg Asp Trp Asn Thr Phe Leu Gln Tyr Leu Lys Asn His
    50                  55                  60

Lys Pro Pro Leu Thr Leu Ser Arg Cys Ser Gly Ala His Val Ile Glu
65                  70                  75                  80

Phe Leu Lys Tyr Leu Asp Gln Phe Gly Lys Thr Lys Val His Val Thr
                85                  90                  95

Ala Cys Pro Tyr Phe Gly His Ala Asn Pro Pro Asp Pro Cys Ser Cys
            100                 105                 110

Pro Leu Lys Gln Ala Trp Gly Ser Leu Asp Ala Leu Ile Gly Arg Leu
        115                 120                 125

Arg Ala Ala Tyr Glu Glu Asn Gly Gly Arg Arg Glu Ser Asn Pro Phe
    130                 135                 140

Gly Thr Arg Ala Val Arg Ile Tyr Leu Arg Glu Val Arg Gly Gly Gln
145                 150                 155                 160

Ala Lys Ala Arg Gly Ile Pro Tyr Glu Lys Lys Lys Arg Lys Arg Pro
                165                 170                 175

Thr Thr Thr Ala Val Ser Ala Ala Ser Gly Thr Gln Pro Pro Gly Gly
            180                 185                 190

Ala Ala Gly Asp Asp Ser Ser Gly Gly Thr Thr Ala Asn Val Gly Thr
        195                 200                 205

Val Thr Ala Ala Ala Thr Thr Asn Ser Leu
    210                 215
```

<210> SEQ ID NO 140
<211> LENGTH: 1533
<212> TYPE: DNA
<213> ORGANISM: Panicum virgatum
<220> FEATURE:
<221> NAME/KEY: misc_feature
<223> OTHER INFORMATION: Ceres CLONE ID no. 1988960
<220> FEATURE:
<221> NAME/KEY: misc_feature
<223> OTHER INFORMATION: Encodes the peptide sequence at SEQ ID NO. 141

<400> SEQUENCE: 140

```
acctctcccc aagctcgctc aactcagctg ctggcctcct ctcccgtccc tttccaccga     60

tcgagcttct tctaactgcc tgtccatgca tgtcgtcagc ttgtgttgtg tagcttctgt    120

ttccctggtg tctggtcgat cgatcgtgcg cgcacggatt gtctagtggt aggctcttgg    180

ccctgcgcct acagtacgcc cacacatgga tcaagggccc tgtaaaccct gttctgcagc    240

gacccaccgt gtcgatcatt aaccgggcgg cgacactctg gctgttctgg aatctggatc    300

aattcgcctt cgccttcttg gagtaggtgc agatctgggt tggccttcgt ggacaggcgg    360

cggcgaagga gctatggaga tggccggcgc ggcggacagc ccgggcctgg cggcggcgcg    420

gccgaaccgg tacgagtcgc agaagcgccg ggactggcag acgttcgggc agtacctgcg    480

caaccaccgg ccgccgctgg agctggcccg gtgcagcggc gcgcacgtgc tcgagttcct    540

ccgctacctg gaccagttcg gcaagaccaa ggtgcacgcg ccggggtgcc ccttcttcgg    600

ccacccgtcg ccgccggcgc cgtgcccgtg cccgctcaag caggcgtggg gcagcctcga    660

cgcgctcgtc ggccgcctcc gcgccgccta tgaggagcac ggcggccgcc ccgaggccaa    720
```

```
ccccttcggg gcgcgcgccg tccggctcta cctccgcgag gtccgcgaca cccaggccaa    780

ggcgcgcggc atcgcctacg agaagaagcg ccgcaagcgc cacccgccgg cacacaggca    840

ggccaagcag cagcaggacg ccggccagca gcagcagcag cactaccacc cccaccacca    900

ccaccaggcg tcgcccgccg cggccgcggt gaccgagagt aggcgcgtgc tggctgacat    960

ggccgaaccg ccggcgccgc acttcctgat cccgcacgcg cagttcctcc acggccactt   1020

cctggtgccg gtcaccgagc cgaccgaccc caccgcgggc atgggcggcg gcggcaccgg   1080

cgaggacttg gtgctggcaa tggcggccgc cgccgaggcg cacgccgccg cggccgggtt   1140

cttgatgccg ctgtccttct ttcactagct agcttgctgg gtccactctc cgctgcctct   1200

atagctccat gggcagggat gcaaggctag gtaattaggc gtaatcaagc atgcaggttt   1260

tgctaatggc gatcggcctg atctctgcgc gccgtttggt cgtccatccg gcttttggtg   1320

tttatgcgca gtcgtctcct ccgcgcgaca ttgccggcgg cgcttgcatc aaccgctgct   1380

gccttctggt tgtattttgg gtgcgtggtt ttgtggacgc agtgatagaa tggctggatt   1440

agacggctct gtgtgttttt ctccatgact cggatcttgt gggaatttca tgtactacag   1500

ctgatctcaa tcgacttaac atttttcctg gtt                                1533
```

```
<210> SEQ ID NO 141
<211> LENGTH: 264
<212> TYPE: PRT
<213> ORGANISM: Panicum virgatum
<220> FEATURE:
<221> NAME/KEY: misc_feature
<223> OTHER INFORMATION: Ceres CLONE ID no. 1988960
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (1)..(133)
<223> OTHER INFORMATION: Pfam Name: DUF640
      Pfam Description: Protein of unknown function (DUF640)

<400> SEQUENCE: 141

Met Glu Met Ala Gly Ala Ala Asp Ser Pro Gly Leu Ala Ala Ala Arg
1               5                   10                  15

Pro Asn Arg Tyr Glu Ser Gln Lys Arg Arg Asp Trp Gln Thr Phe Gly
            20                  25                  30

Gln Tyr Leu Arg Asn His Arg Pro Pro Leu Glu Leu Ala Arg Cys Ser
        35                  40                  45

Gly Ala His Val Leu Glu Phe Leu Arg Tyr Leu Asp Gln Phe Gly Lys
    50                  55                  60

Thr Lys Val His Ala Pro Gly Cys Pro Phe Phe Gly His Pro Ser Pro
65                  70                  75                  80

Pro Ala Pro Cys Pro Cys Pro Leu Lys Gln Ala Trp Gly Ser Leu Asp
                85                  90                  95

Ala Leu Val Gly Arg Leu Arg Ala Ala Tyr Glu Glu His Gly Gly Arg
            100                 105                 110

Pro Glu Ala Asn Pro Phe Gly Ala Arg Ala Val Arg Leu Tyr Leu Arg
        115                 120                 125

Glu Val Arg Asp Thr Gln Ala Lys Ala Arg Gly Ile Ala Tyr Glu Lys
    130                 135                 140

Lys Arg Arg Lys Arg His Pro Pro Ala His Arg Gln Ala Lys Gln Gln
145                 150                 155                 160

Gln Asp Ala Gly Gln Gln Gln Gln Gln His Tyr His Pro His His His
```

```
                165                 170                 175

His Gln Ala Ser Pro Ala Ala Ala Ala Val Thr Glu Ser Arg Arg Val
            180                 185                 190

Leu Ala Asp Met Ala Glu Pro Pro Ala Pro His Phe Leu Ile Pro His
        195                 200                 205

Ala Gln Phe Leu His Gly His Phe Leu Val Pro Val Thr Glu Pro Thr
    210                 215                 220

Asp Pro Thr Ala Gly Met Gly Gly Gly Gly Thr Gly Glu Asp Leu Val
225                 230                 235                 240

Leu Ala Met Ala Ala Ala Ala Glu Ala His Ala Ala Ala Ala Gly Phe
                245                 250                 255

Leu Met Pro Leu Ser Phe Phe His
            260


<210> SEQ ID NO 142
<211> LENGTH: 214
<212> TYPE: PRT
<213> ORGANISM: Medicago truncatula
<220> FEATURE:
<221> NAME/KEY: misc_feature
<223> OTHER INFORMATION: Public GI ID no. 92891522
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (47)..(179)
<223> OTHER INFORMATION: Pfam Name: DUF640
      Pfam Description: Protein of unknown function (DUF640)

<400> SEQUENCE: 142

Met Asn Ser Leu Gln Glu Phe Glu Ser Ser Thr Asn Asn Lys Asp Met
1               5                   10                  15

Met Asn Thr Asn Pro Met Ile Asn Ile Thr Asn Pro Ser Ser Ser Met
            20                  25                  30

Thr Met Thr Ile Pro Ser Ser Ser Thr Thr Ser Ala Ser Ser Ser Ser
        35                  40                  45

Thr Ala Thr Thr Ser Pro Pro Ser Thr Thr Ser Thr Thr Thr Pro Ser
    50                  55                  60

Arg Tyr Glu Asn Gln Lys Arg Arg Asp Trp Asn Thr Phe Gly Gln Tyr
65                  70                  75                  80

Leu Arg Asn His Arg Pro Pro Leu Ser Leu Ser Arg Cys Ser Gly Ala
                85                  90                  95

His Val Leu Glu Phe Leu Arg Tyr Leu Asp Gln Phe Gly Lys Thr Lys
            100                 105                 110

Val His Thr Leu Ile Cys Pro Phe Tyr Gly His Pro Asn Pro Pro Ala
        115                 120                 125

Ser Cys Pro Cys Pro Leu Arg Gln Ala Trp Gly Ser Leu Asp Ala Leu
    130                 135                 140

Ile Gly Arg Leu Arg Ala Ala Phe Glu Glu Asn Gly Gly Lys Pro Glu
145                 150                 155                 160

Ala Asn Pro Phe Gly Ala Arg Ala Val Arg Leu Tyr Leu Arg Glu Val
                165                 170                 175

Arg Asp Ser Gln Ala Lys Ala Arg Gly Ile Ser Tyr Glu Lys Lys Lys
            180                 185                 190

Arg Lys Arg Pro Pro Gln Pro Pro Pro Pro Pro Pro Ser Asn Asn Ala
        195                 200                 205
```

Thr Ile Thr Asp Leu His
210

<210> SEQ ID NO 143
<211> LENGTH: 828
<212> TYPE: DNA
<213> ORGANISM: Glycine max
<220> FEATURE:
<221> NAME/KEY: misc_feature
<223> OTHER INFORMATION: Ceres CLONE ID no. 1073674
<220> FEATURE:
<221> NAME/KEY: misc_feature
<223> OTHER INFORMATION: Encodes the peptide sequence at SEQ ID NO. 89

<400> SEQUENCE: 143

```
acactctttc tctcaatttc tctctctttt aaaacactaa tcactaaaat cttgattcac     60
tatatcgtca aaaccaacgc taaatcaatt aaactctctc aaagaaaaca agacaaagcc    120
ctacttttga tggattcagg gtcacaacga ccggggcctg ttagcgaagg cgatccgggt    180
ccgtccatcg taaccccctc ttcaccgcct gcgacgccta gcaggtacga gtcgcagaaa    240
cgacgtgact ggaccacgtt cttgcagtac ctcaagaacc acaagccgcc tctttccttg    300
tcacggtgta gcggagcaca tgccatcgag ttcctcaagt acttagatca gttcggtaag    360
accaaagtcc acgtggcggc atgtccttac tttggccatc agcaacctcc gtctccttgc    420
gcttgtcctc tcaagcaagc ctgggggtct ctcgatgccc tgatcggacg gttgagagca    480
gcctacgaag agaacggtgg acggcccgag tcgaacccgt tcgcggcacg tgcggttagg    540
atttacttga gggaagtcag agaaagtcaa gccaaggccc gtgggagacc ctacgagaaa    600
aagaaacgga aacggccaac aactgttacc accgtgagag ttgacgttgc ttcgtcgaga    660
caaagtgaag gagatggttg taacatcggt gatccgtcgt atgtggccga ggctgtacct    720
ccttaattaa gttattatta ttgtcatgat atattaaata cattatatat gtctggaact    780
cacatcacct tcttgagtta actattgaaa atatttttgt tctagttc                 828
```

<210> SEQ ID NO 144
<211> LENGTH: 799
<212> TYPE: DNA
<213> ORGANISM: Brassica napus
<220> FEATURE:
<221> NAME/KEY: misc_feature
<223> OTHER INFORMATION: Ceres CLONE ID no. 1118987
<220> FEATURE:
<221> NAME/KEY: misc_feature
<223> OTHER INFORMATION: Encodes the peptide sequence at SEQ ID NO. 90

<400> SEQUENCE: 144

```
aaattctcga ttcgcttata ttctcaaaac caacgctaaa taaaaacact ctcaaagaaa     60
aacaaaaaaa aaaccctagt tttgatggaa tcgactgatt cggggtcaca acaacatgga    120
ggtgacccag gtccgtcctc cgtaacgccc tcttcacctc cggcgacgcc gcctagcagg    180
tacgagtcgc aaaaacgacg tgactggaac acgttcttgc agtacctcaa gaaccacaag    240
ccgcctctcg cgttatcacg atgtagcgga gcgcacgtga tcgagttcct caagtaccta    300
gatcagttcg gtaagaccaa agtccacgtg gcgacctgcc cttacttcgg acatcagcag    360
cctccctctc cttgcgcttg tcctctcaag caagcctggg gatctctcga tgctctgatc    420
ggacggttga gagctgcgta cgaggagcac ggtgggaggc ctgattccaa ccctttcgcc    480
gcacgtgcgg tcaggattta cttgagagaa gtcagagaaa gtcaagccaa ggcacgtggg    540
attccatacg agaagaagaa acggaaacgg gcaccaactg tcactaccgc tagaattgac    600
```

```
gttgctccgt cgagacaaag tgaaggaggt ggtggttgta acgacagtga tccgtctgtc    660

gccgaagctg taccgcctta aattaaatta ttatatcata ttaattagtt ttcttgttat    720

attaagcatg gaactcacac ctttcgtact ataatgtatt ttatttttct atatgaacta    780

ttaagagttt tcttttgcc                                                 799
```

<210> SEQ ID NO 145
<211> LENGTH: 797
<212> TYPE: DNA
<213> ORGANISM: Parthenium argenta
<220> FEATURE:
<221> NAME/KEY: misc_feature
<223> OTHER INFORMATION: Ceres CLONE ID no. 1603237
<220> FEATURE:
<221> NAME/KEY: misc_feature
<223> OTHER INFORMATION: Encodes the peptide sequence at SEQ ID NO. 94

<400> SEQUENCE: 145

```
aacgaaataa accctaatca aacacccacc cactcaccca caaacatgtt aagcccaaca     60

tcctcttcat cttcaatagc ctcaaccgcc tcaaccgcca ccagtcgcct caaccgctac    120

gagagccaaa aacgccgtga ctggaacaca ttcggtcagt tcctccgtaa ccacgaccca    180

cccttaaccc tttccaactg caccagcaca cacgttatcg agttcctccg ttaccttgac    240

ccgtttggca aaactaaagt ccacacacat ctctgtccat ccttcggtca acccaaccct    300

cccacactct gcccgtgccc cctccgtcag gcctggggca gcctcgatgc cctcattggt    360

cgtctccggg cagcttttga agaaaacggt gggcagcccg agagtaaccc gtttggagct    420

agggctgtta ggttttattt acgtgaagtt aaggatgctc aagctaaagc tagagggatt    480

agttgtgaga agaagaggac gaagaaacgg ccaccgccac ccactccgga tatttgtttg    540

gatcgctgat cgcgggcgtg ggtgaccttt tgctatcgct gatcgcgggc gtgggtgacc    600

ttttgctaat gggtgtacct gggtggttgg gccgggttgt ttgacttaaa aaaaaaaaag    660

ttacccgagt taatggttaa tatcattgtc tggttaatta atgggtataa agctatgtaa    720

tttgaatatt gaactcgata ttctgtttct tggaaatggt tagccataat tttgaagatc    780

attattgtta ttatctt                                                   797
```

<210> SEQ ID NO 146
<211> LENGTH: 229
<212> TYPE: PRT
<213> ORGANISM: Glycine max
<220> FEATURE:
<221> NAME/KEY: misc_feature
<223> OTHER INFORMATION: Ceres SEED LINE ME24507
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (28)..(160)
<223> OTHER INFORMATION: Pfam Name: DUF640
      Pfam Description: Protein of unknown function (DUF640)

<400> SEQUENCE: 146

```
Met Ala Ser Ala Ser Gly Gly Ala Pro Pro Pro Gln Pro Thr Ser Thr
1               5                   10                  15

Glu Ala Ala Pro Ala Ser Gly Ser Ser Ala Pro Ala Ile Ser Ala Ala
            20                  25                  30
```

-continued

```
Pro Pro Gln Pro Gly Gly Ser Ser Pro Ala Pro Pro Ser Arg Tyr Glu
        35                  40                  45

Ser Gln Lys Arg Arg Asp Trp Asn Thr Phe Leu Gln Tyr Leu Gln Asn
    50                  55                  60

His Lys Pro Pro Leu Thr Leu Ala Arg Cys Ser Gly Ala His Val Ile
65                  70                  75                  80

Glu Phe Leu Lys Tyr Leu Asp Gln Phe Gly Lys Thr Lys Val His Ile
                85                  90                  95

Thr Gly Cys Pro Tyr Tyr Gly Tyr Pro Asn Pro Pro Ala Pro Cys Ala
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Asn Gly Gly Arg Pro Glu Ser Asn Pro
    130                 135                 140

Phe Gly Ala Arg Ala Val Arg Ile Tyr Leu Arg Glu Val Arg Glu Gly
145                 150                 155                 160

Gln Ala Lys Ala Arg Gly Ile Pro Tyr Glu Lys Lys Lys Arg Lys Arg
                165                 170                 175

Thr Thr Val Val Thr Val Ser Ser Gly Gly Gly Gly Ser Ser Gly Ala
            180                 185                 190

Val Ala Ser Pro Ser Gly Gly Gly Asp Thr Ala Ile Gly Gly Gly Ala
        195                 200                 205

Gly Ser Ser Ala Ser Leu Thr Ser Ser Ala Thr Ala Thr Ala Asn Asp
    210                 215                 220

Thr Thr Thr Thr Val
225
```

INCREASING LOW LIGHT TOLERANCE IN PLANTS

CROSS-REFERENCE TO RELATED APPLICATION

This application is a divisional of U.S. application Ser. No. 12/307,561, filed Nov. 23, 2009, now U.S. Pat. No. 8,344, 210, which is a National Stage application under 35 U.S.C. §371 of International Application No. PCT/US2007/072877, having an International Filing Date of Jul. 5, 2007, which claims the benefit of priority of U.S. Provisional Application Ser. No. 60/818,569, having a filing date of Jul. 5, 2006, all of which are incorporated herein in their entirety.

TECHNICAL FIELD

This document relates to methods and materials involved in tolerance of plants to low light conditions. For example, this document provides transgenic plants and seeds comprising nucleic acids encoding polypeptides that confer tolerance to conditions of low light irradiance.

BACKGROUND

Light is the source of energy that fuels plant growth through photosynthesis. Light is also a developmental signal that modulates morphogenesis, such as de-etiolation and the transition to reproductive development. Since plants cannot choose their surroundings, they are forced to adapt their growth to ambient light conditions and have evolved complex mechanisms for monitoring the quantity and quality of the surrounding light. For example, many kinds of plants respond to growth under dense canopies or at high densities by growing faster and taller (Cerdan and Chory (2003) *Nature,* 423: 881). Densely planted crops tend to place energy into stem and petiole elongation to lift the leaves into the sunlight rather than putting energy into storage or reproductive structures. The response to low light conditions negatively affects crop yields by reducing the amount of harvestable products such as seeds, fruits and tubers. In addition, tall spindly plants tend to be less wind resistant and lodge more easily, further reducing crop yield.

There is a continuing need for plants that can thrive under less than optimal environmental conditions. One strategy to improve a plant's ability to withstand suboptimal environmental conditions relies upon traditional plant breeding methods. Another approach involves genetic manipulation of plant characteristics through the introduction of exogenous nucleic acids conferring a desirable trait.

SUMMARY

This document provides methods and materials related to low light tolerance in plants, plant cells, and seeds. For example, this document provides transgenic plants having increased tolerance to conditions of low light irradiance, nucleic acids used to generate transgenic plants having increased tolerance to low light conditions, and methods for making transgenic plants having increased tolerance to low light conditions. Transgenic plants having increased tolerance to low light conditions can exhibit a reduction in one or more responses typically elicited by low light stress. For example, a low light-tolerant transgenic plant have a hypocotyl length, when exposed to low light conditions, e.g., an irradiance of 0.01 to 20 $\mu$mol/m$^2$/s of light, that is shorter than the typical hypocotyl length of corresponding wild-type plants grown under similar conditions. Increasing the tolerance of plants to low light conditions can produce healthier plants and a higher crop yield under conditions of low light irradiance, such as those occurring during high-density cultivation of plants.

In one aspect, a method of modulating the low light tolerance of a plant is provided. The method comprises introducing into a plant cell an exogenous nucleic acid comprising a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146, where a plant produced from the plant cell exhibits a phenotypic difference relative to a corresponding control plant under low light conditions. The nucleotide sequence can encode a polypeptide comprising an amino acid sequence corresponding to SEQ ID NO:88.

In another aspect, a method of modulating the low light tolerance of a plant is provided. The method comprises introducing into a plant cell an exogenous nucleic acid comprising a nucleotide sequence having 80 percent or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145, where a plant produced from the plant cell exhibits a phenotypic difference relative to a corresponding control plant under low light conditions. The nucleotide sequence can comprise the nucleotide sequence set forth in SEQ ID NO:87.

The low light conditions can comprise an irradiance of about 0.01 to about 20 $\mu$mol/m$^2$/s of light. The phenotypic difference can comprise a decreased hypocotyl length. The exogenous nucleic acid can be operably linked to a regulatory region. The regulatory region can be a tissue-preferential, broadly expressing, or inducible promoter. The plant can be a dicot. The plant can be a member of the genus *Brassica, Glycine, Gossypium, Helianthus, Lactuca*, or *Medicago*. The plant can be a monocot. The plant can be a member of the genus *Cocos, Elaeis, Oryza, Panicum*, or *Zea*. The method can further comprises the step of producing a plant from the plant cell. The introducing step can comprise introducing the nucleic acid into a plurality of plant cells. The method can further comprise the step of producing a plurality of plants from the plant cells. The method can further comprise the step of selecting one or more plants from the plurality of plants that have the phenotypic difference.

In another aspect, a method of producing a plant is provided. The method comprises growing a plant cell comprising an exogenous nucleic acid comprising a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146, where the plant exhibits a phenotypic difference relative to a corresponding control plant under low light conditions. The nucleotide sequence can encode a polypeptide comprising an amino acid sequence corresponding to SEQ ID NO:88.

In another aspect, a method of producing a plant is provided. The method comprises growing a plant cell comprising an exogenous nucleic acid comprising a nucleotide sequence having 80 percent or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs: 129-130, SEQ ID NO:132, SEQ ID NO:134, SEQ ID NO:136, SEQ ID NO:138, SEQ ID NO:140, and SEQ ID NOs:143-145, where the plant exhibits a phenotypic difference relative to a corresponding control plant under low light conditions. The nucleotide sequence can comprise the nucleotide sequence set forth in SEQ ID NO:87.

The low light conditions can comprise an irradiance of about 0.01 to about 20 $\mu mol/m^2/s$ of light. The phenotypic difference can comprise a decreased hypocotyl length. The exogenous nucleic acid can be operably linked to a regulatory region. The regulatory region can be a tissue-preferential, broadly expressing, or inducible promoter. The plant can be a dicotyledonous plant. The plant can be a member of the genus *Brassica, Glycine, Gossypium, Helianthus, Lactuca*, or *Medicago*. The plant can be a monocotyledonous plant. The plant can be a member of the genus *Cocos, Elaeis, Oryza, Panicum*, or *Zea*.

In another aspect, a plant comprising an exogenous nucleic acid is provided. The exogenous nucleic acid comprises a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146, where the plant exhibits a phenotypic difference relative to a corresponding control plant under low light conditions. The nucleotide sequence can encode a polypeptide comprising an amino acid sequence corresponding to SEQ ID NO:88.

In another aspect, a plant comprising an exogenous nucleic acid is provided. The exogenous nucleic acid comprises a nucleotide sequence having 80 percent or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145, where the plant exhibits a phenotypic difference relative to a corresponding control plant under low light conditions. The nucleotide sequence can comprise the nucleotide sequence set forth in SEQ ID NO:87.

The low light conditions can comprise an irradiance of about 0.01 to about 20 $\mu mol/m^2/s$ of light. The phenotypic difference can comprise a decreased hypocotyl length. The exogenous nucleic acid can be operably linked to a regulatory region. The regulatory region can be a tissue-preferential, broadly expressing, or inducible promoter. The plant can be a dicot. The plant can be a member of the genus *Brassica, Glycine, Gossypium, Helianthus, Lactuca*, or *Medicago*. The plant can be a monocot. The plant can be a member of the genus *Cocos, Elaeis, Oryza, Panicum*, or *Zea*.

Progeny of any of the plants described above also are provided. The progeny exhibits a phenotypic difference relative to a corresponding control plant under low light conditions. Seed, vegetative tissue, and fruit from any of the plants described above also are provided, as are food products and feed products comprising seed or vegetative tissue from any of the plants described above.

In another aspect, an isolated nucleic acid molecule is provided. The isolated nucleic acid molecule comprises a nucleotide sequence having 95% or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145.

In another aspect, an isolated nucleic acid is provided. The isolated nucleic acid molecule comprises a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of Clone 28780 (SEQ ID NO:88) with homologous and/or orthologous amino acid sequences Clone 1285138 (SEQ ID NO:100), Clone 1373087 (SEQ ID NO:104), Clone 1440417 (SEQ ID NO:106), Clone 1505805 (SEQ ID NO:108), Clone 828846 (SEQ ID NO:110), Clone 832857 (SEQ ID NO:112), Clone 847799 (SEQ ID NO:114), Clone 856813 (SEQ ID NO:116), Clone 870022 (SEQ ID NO:118), Clone 1025179 (SEQ ID NO:120), Clone 1084747 (SEQ ID NO:122), Clone 1464359 (SEQ ID NO:124), Clone 604111(a) (SEQ ID NO:126), Clone 964932 (SEQ ID NO:128), and Clone 604111(b) (SEQ ID NO:146).

FIG. 3 is a schematic diagram depicting the time course for measuring parameters of adult plants grown under normal light (NL) or low light (LL) conditions. NL and LL refer to conditions of irradiance with about 150 and 15 μmol/m$^2$/s of light, respectively.

DETAILED DESCRIPTION

Figure 2:
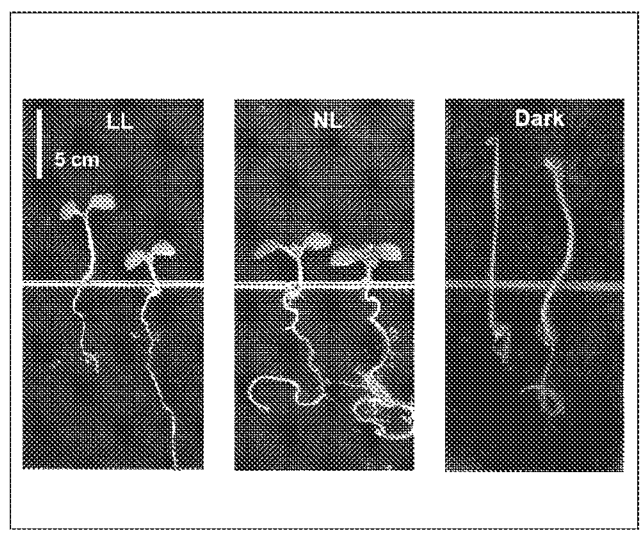
FIG. 2 is an image of $T_3$ seedlings from a single insertion event of transgenic line ME05917 (right) and corresponding non-transgenic segregants (left) that were grown in the dark or under conditions of irradiation with 10 or 100 μmol/m$^2$/s of white light (LL or NL, respectively).

The invention features methods and materials related to modulating the tolerance of plants to conditions of low light irradiation. The methods can include transforming a plant with a nucleic acid encoding a polypeptide, the expression of which results in increased tolerance to low light conditions. Plants produced using such methods can be grown to produce seeds that, in turn, can be used to grow plants having an increased tolerance to conditions of low light irradiance.

Low light conditions can include conditions under which a plant is irradiated with about 0.01 to 20 μmol/m$^2$/s of white light. Plants grown under low light conditions typically exhibit one or more phenotypic changes, or responses, such as an increase in extension growth. Low light tolerance refers to the ability of a plant to grow under low light irradiance levels while exhibiting a low light response that is less than the corresponding low light response exhibited by a control plant. For example, a plant that is tolerant to low light conditions can exhibit less hypocotyl elongation when exposed to low light conditions than a corresponding control plant grown under similar conditions.

Polypeptides

The term "polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

Polypeptides described herein include low light-tolerance polypeptides that, when expressed in a plant, can modulate the tolerance of the plant to conditions of low light irradiation. Modulation of the level of low light tolerance can be either an increase or a decrease in the level of low light tolerance relative to the corresponding level in a control plant.

A low light-tolerance polypeptide can contain a DUF640 domain, which is a conserved region found in a family of plant polypeptides including the resistance protein-like polypeptide. SEQ ID NO:88 sets forth the amino acid sequence of an *Arabidopsis* clone, identified herein as Ceres Clone 28780 (SEQ ID NO:87), that is predicted to encode a polypeptide containing a DUF640 domain. A low light-tolerance polypeptide can comprise the amino acid sequence set forth in SEQ ID NO:88. Alternatively, a low light-tolerance polypeptide can be a homolog, ortholog, or variant of the polypeptide having the amino acid sequence set forth in SEQ ID NO:88. For example, a low light-tolerance polypeptide can have an amino acid sequence with greater than 63% sequence identity, e.g., 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, to the amino acid sequence set forth in SEQ ID NO:88.

Amino acid sequences of homologs and/or orthologs of the polypeptide having the amino acid sequence set forth in SEQ ID NO:88 are provided in FIG. 1. For example, the alignment in FIG. 1 provides the amino acid sequences of Ceres Clone 28780 (SEQ ID NO:88), Clone 1285138 (SEQ ID NO:100), Clone 1373087 (SEQ ID NO:104), Clone 1440417 (SEQ ID NO:106), Clone 1505805 (SEQ ID NO:108), Clone 828846 (SEQ ID NO:110), Clone 832857 (SEQ ID NO:112), Clone 847799 (SEQ ID NO:114), Clone 856813 (SEQ ID NO:116), Clone 870022 (SEQ ID NO:118), Clone 1025179 (SEQ ID NO:120), Clone 1084747 (SEQ ID NO:122), Clone 1464359 (SEQ ID NO:124), Clone 604111(a) (SEQ ID NO:126), Clone 964932 (SEQ ID NO:128), and Clone 604111(b) (SEQ ID NO:146). Other homologs and/or orthologs include SEQ ID NOs:89-90, SEQ ID NOs:92-94, SEQ ID NO:131, SEQ ID NO:133, SEQ ID NO:135, SEQ ID NO:137, SEQ ID NO:139, and SEQ ID NOs:141-142. In some cases, a low light-tolerance polypeptide includes a polypeptide having at least 80% sequence identity, e.g., 80%, 85%, 90%, 95%, 97%, 98%, or 99% sequence identity, to an amino acid sequence corresponding to any one of SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, or SEQ ID NO:146.

A low light-tolerance polypeptide encoded by a recombinant nucleic acid can be a native low light-tolerance polypeptide, i.e., one or more additional copies of the coding sequence for a low light-tolerance polypeptide that is naturally present in the cell. Alternatively, a low light-tolerance polypeptide can be heterologous to the cell, e.g., a transgenic *Lycopersicon* plant can contain the coding sequence for a low light-tolerance polypeptide from a *Glycine* plant.

A low light-tolerance polypeptide can include additional amino acids that are not involved in modulation of low light tolerance, and thus can be longer than would otherwise be the case. For example, a low light-tolerance polypeptide can include an amino acid sequence that functions as a reporter. Such a low light-tolerance polypeptide can be a fusion protein in which a green fluorescent protein (GFP) polypeptide is fused to, e.g., SEQ ID NO:88, or in which a yellow fluorescent protein (YFP) polypeptide is fused to, e.g., SEQ ID NO:88. In some embodiments, a low light-tolerance polypeptide includes a purification tag, a chloroplast transit peptide, a mitochondrial transit peptide, or a leader sequence added to the amino or carboxy terminus.

Low light-tolerance polypeptide candidates suitable for use in the invention can be identified by analysis of nucleotide and polypeptide sequence alignments. For example, performing a query on a database of nucleotide or polypeptide sequences can identify homologs and/or orthologs of low light-tolerance polypeptides. Sequence analysis can involve BLAST, Reciprocal BLAST, or PSI-BLAST analysis of non-redundant databases using known low light-tolerance polypeptide amino acid sequences. Those polypeptides in the database that have greater than 40% sequence identity can be identified as candidates for further evaluation for suitability as a low light-tolerance polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains suspected of being present in low light-tolerance polypeptides, e.g., conserved functional domains.

The identification of conserved regions in a template or subject polypeptide can facilitate production of variants of wild type low light-tolerance polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam and genome.wustl.edu/Pfam. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Amino acid residues corresponding to Pfam domains included in low light-tolerance polypeptides provided herein are set forth in the sequence listing. For example, amino acid residues 13 to 145 of the amino acid sequence set forth in SEQ ID NO:88 correspond to a DUF640 domain, as indicated in fields <222> and <223> for SEQ ID NO:88 in the sequence listing.

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

Typically, polypeptides that exhibit at least about 40% amino acid sequence identity are useful to identify conserved regions. Conserved regions of related polypeptides can exhibit at least 45% amino acid sequence identity (e.g., at least 50%, at least 60%, at least 70%, at least 80%, or at least 90% amino acid sequence identity). In some embodiments, a conserved region of target and template polypeptides exhibit at least 92%, 94%, 96%, 98%, or 99% amino acid sequence identity. Amino acid sequence identity can be deduced from amino acid or nucleotide sequences. In certain cases, highly conserved domains have been identified within low light-tolerance polypeptides. These conserved regions can be useful in identifying functionally similar (orthologous) low light-tolerance polypeptides.

In some instances, suitable low light-tolerance polypeptides can be synthesized on the basis of consensus functional domains and/or conserved regions in polypeptides that are homologous low light-tolerance polypeptides. Domains are groups of substantially contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Representative homologs and/or orthologs of the low light-tolerance polypeptide set forth in SEQ ID NO:88 are shown in FIG. 1. FIG. 1 represents an alignment of the amino acid sequence of the low light-tolerance polypeptide set forth in SEQ ID NO:88 with the amino acid sequences of corresponding homologs and/or orthologs. The amino acid sequences of the low light-tolerance polypeptide set forth in SEQ ID NO:88 and its corresponding homologs and/or orthologs have been aligned to identify conserved amino acids, as shown in FIG. 1. A dash in an aligned sequence represents a gap, i.e., a lack of an amino acid at that position. Identical amino acids or conserved amino acid substitutions among aligned sequences are identified by boxes. Each conserved region contains a sequence of contiguous amino acid residues.

Useful polypeptides can be constructed based on the conserved regions in FIG. 1. Such a polypeptide includes the conserved regions arranged in the order depicted in the Figure from amino-terminal end to carboxy-terminal end, and has at least 80% sequence identity to an amino acid sequence corresponding to any one of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, or SEQ ID NO:146. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

Conserved regions can be identified by homologous polypeptide sequence analysis as described above. The suitability of polypeptides for use as low light-tolerance polypeptides can be evaluated by functional complementation studies.

Useful polypeptides can also be identified based on the polypeptides set forth in FIG. 1 using algorithms designated as Hidden Markov Models. A "Hidden Markov Model (HMM)" is a statistical model of a consensus sequence for a group of homologous and/or orthologous polypeptides. See, Durbin et al., *Biological Sequence Analysis: Probabilistic Models of Proteins and Nucleic Acids*, Cambridge University Press, Cambridge, UK (1998). An HMM is generated by the program HMMER 2.3.2 using the multiple sequence alignment of the group of homologous and/or orthologous sequences as input and the default program parameters. The multiple sequence alignment is generated by ProbCons (Do et al., *Genome Res.,* 15(2):330-40 (2005)) version 1.11 using a set of default parameters: -c, —consistency REPS of 2; -ir, —iterative-refinement REPS of 100; -pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. The HMMER 2.3.2 package was released Oct. 3, 2003 under a GNU general public license, and is available from various sources on the World Wide Web such as hmmer.janelia.org, hmmer wustl.edu, and fr.com/hmmer232/. Hmmbuild outputs the model as a text file.

The HMM for a group of homologous and/or orthologous polypeptides can be used to determine the likelihood that a subject polypeptide sequence is a better fit to that particular HMM than to a null HMM generated using a group of sequences that are not homologous and/or orthologous. The likelihood that a subject polypeptide sequence is a better fit to an HMM than to a null HMM is indicated by the HMM bit score, a number generated when the subject sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 400, and often is higher.

A low light-tolerance polypeptide can fit an HMM provided herein with an HMM bit score greater than 400 (e.g., greater than 401, 405, 410, 415, 420, 425, 430, 435, 440, 445, 450, 460, 470, 480, 490, or 500). In some cases, a low light-tolerance polypeptide can fit an HMM provided herein with an HMM bit score that is about 80%, 81%, 82%, 83%, 84%, 85%, 86%, 87%, 88%, 89%, 90%, 91%, 92%, 93%, 94%, 95%, 96%, 97%, 98%, or 99% of the HMM bit score of any homologous and/or orthologous polypeptide provided in Table 34, so long as the low-light tolerance polypeptide is not SEQ ID NO:102.

Nucleic Acids

The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An "isolated" nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al., *Nucleic Acids Res.,* 31(13):3497-500 (2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Recombinant constructs are also provided herein and can be used to transform plants or plant cells in order to modulate low light tolerance. A recombinant nucleic acid construct comprises a nucleic acid encoding a low light-tolerance polypeptide as described herein, operably linked to a regulatory region suitable for expressing the low light-tolerance polypeptide in the plant or cell. Thus, a nucleic acid can comprise a coding sequence that encodes any of the low light-tolerance polypeptides as set forth in SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, or SEQ ID NO:146. Examples of nucleic acids encoding low light-tolerance polypeptides are set forth in SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145. In some cases, a recombinant nucleic acid construct can include a nucleic acid comprising less than the full-length coding sequence of a low light-tolerance polypeptide. In some cases, a recombinant nucleic acid construct can include a nucleic acid comprising a coding sequence, a gene, or a fragment of a coding sequence or gene in an antisense orientation so that the antisense strand of RNA is transcribed.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given low light-tolerance polypeptide can be modified such that optimal expression in a particular plant species is obtained, using appropriate codon bias tables for that species.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Mountain View, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Regulatory Regions

The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano et al., *Plant Cell,* 1:855-866 (1989); Bustos et al., *Plant Cell,* 1:839-854 (1989); Green et al., *EMBO J.,* 7:4035-4044 (1988); Meier et al., *Plant Cell,* 3:309-316 (1991); and Zhang et al., *Plant Physiology,* 110: 1069-1079 (1996).

Examples of various classes of promoters are described below. Some of the promoters indicated below as well as additional promoters are described in more detail in U.S. patent application Ser. Nos. 60/505,689; 60/518,075; 60/544, 771; 60/558,869; 60/583,691; 60/619,181; 60/637,140; 60/757,544; 60/776,307; 10/957,569; 11/058,689; 11/172, 703; 11/208,308; 11/274,890; 60/583,609; 60/612,891; 11/097,589; 11/233,726; 11/408,791; 11/414,142; 10/950, 321; PCT/US05/011105; PCT/US05/034308; and PCT/US05/23639. Nucleotide sequences of promoters are set forth in SEQ ID NOs:1-86. It will be appreciated that a promoter may meet criteria for one classification based on its activity in one plant species, and yet meet criteria for a different classification based on its activity in another plant species.

Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO:75), YP0144 (SEQ ID NO:54), YP0190 (SEQ ID NO:58), p13879 (SEQ ID NO:74), YP0050 (SEQ ID NO:34), p32449 (SEQ ID NO:76), 21876 (SEQ ID NO:1), YP0158 (SEQ ID NO:56), YP0214 (SEQ ID NO:60), YP0380 (SEQ ID NO:69), PT0848 (SEQ ID NO:26), and PT0633 (SEQ ID NO:7) promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104: 997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535 (SEQ ID NO:3), PT0668 (SEQ ID NO:2), PT0886 (SEQ ID NO:29), YP0144 (SEQ ID NO:54), YP0380 (SEQ ID NO:69), and PT0585 (SEQ ID NO:4).

Vascular Tissue Promoters

Examples of promoters that have high or preferential activity in vascular bundles include YP0087 (SEQ ID NO:82), YP0093 (SEQ ID NO:83), YP0108 (SEQ ID NO:84), YP0022 (SEQ ID NO:80), and YP0080 (SEQ ID NO:81). Other vascular tissue-preferential promoters include the glycine-rich cell wall protein GRP 1.8 promoter (Keller and Baumgartner, *Plant Cell,* 3(10):1051-1061 (1991)), the Commelina yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380 (SEQ ID NO:69), PT0848 (SEQ ID NO:26), YP0381 (SEQ ID NO:70), YP0337 (SEQ ID NO:65), PT0633 (SEQ ID NO:7), YP0374 (SEQ ID NO:67), PT0710 (SEQ ID NO:18), YP0356 (SEQ ID NO:66), YP0385 (SEQ ID NO:72), YP0396 (SEQ ID NO:73), YP0388 (SEQ ID NO:85), YP0384 (SEQ ID NO:71), PT0688 (SEQ ID NO:15), YP0286 (SEQ ID NO:64), YP0377 (SEQ ID NO:68), PD1367 (SEQ ID NO:77), PD0901 (SEQ ID NO:79), and PD0898 (SEQ ID NO:78). Examples of nitrogen-inducible promoters include PT0863 (SEQ ID NO:27), PT0829 (SEQ ID NO:23), PT0665 (SEQ ID NO:10), and PT0886 (SEQ ID NO:29). Examples of shade-inducible promoters include PR0924 (SEQ ID NO:86), and PT0678 (SEQ ID NO:13).

Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other Promoters

Other classes of promoters include, but are not limited to, leaf-preferential, stem/shoot-preferential, callus-preferential, guard cell-preferential, such as PT0678 (SEQ ID NO:13), and senescence-preferential promoters. Promoters designated YP0086 (SEQ ID NO:35), YP0188 (SEQ ID NO:57), YP0263 (SEQ ID NO:61), PT0758 (SEQ ID NO:22), PT0743 (SEQ ID NO:21), PT0829 (SEQ ID NO:23), YP0119 (SEQ ID NO:48), and YP0096 (SEQ ID NO:38), as described in the above-referenced patent applications, may also be useful.

Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, more than one regulatory region can be operably linked to the sequence of a polynucleotide encoding a low light-tolerance polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Transgenic Plants and Plant Cells

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant. Progeny includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low light-tolerance polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

Plant Species

The polynucleotides and vectors described herein can be used to transform a number of monocotyledonous and dicotyledonous plants and plant cell systems, including dicots such as alfalfa, almond, amaranth, apple, apricot, avocado, beans (including kidney beans, lima beans, dry beans, green beans), brazil nut, broccoli, cabbage, canola, carrot, cashew, castor bean, cherry, chick peas, chicory, chocolate, clover, cocoa, coffee, cotton, cottonseed, crambe, eucalyptus, flax, foxglove, grape, grapefruit, hazelnut, hemp, *jatropha*, jojoba, lemon, lentils, lettuce, linseed, macadamia nut, mango, melon (e.g., watermelon, cantaloupe), mustard, neem, olive, orange, peach, peanut, pear, peas, pecan, pepper, pistachio, plum, poplar, poppy, potato, pumpkin, oilseed rape, quinoa, rapeseed (high erucic acid and canola), safflower, sesame, soaptree bark, soybean, spinach, strawberry, sugar beet, sunflower, sweet potatoes, tea, tomato, walnut, and yams, as well as monocots such as banana, barley, bluegrass, coconut, corn, date palm, fescue, field corn, garlic, millet, oat, oil palm, onion, palm kernel oil, pineapple, popcorn, rice, rye, ryegrass, *sorghum*, sudangrass, sugarcane, sweet corn, switchgrass, turf grasses, timothy, and wheat. Gymnosperms such as fir, pine, and spruce can also be suitable.

Thus, the methods and compositions described herein can be used with dicotyledonous plants belonging, for example, to the orders Apiales, Arecales, Aristolochiales, Asterales, Batales, Campanulales, Capparales, Caryophyllales, Casuarinales, Celastrales, Cornales, Cucurbitales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Linales, Magniolales, Malpighiales, Malvales, Myricales, Myrtales, Nymphaeales, Papaverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Solanales, Trochodendrales, Theales, Umbellales, Urticates, and Violales. The methods and compositions described herein also can be utilized with monocotyledonous plants such as those belonging to the orders Alismatales, Arales, Arecales, Asparagales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales, Zingiberales, and with plants belonging to Gymnospermae, e.g., Cycadales, Ephedrales, Ginkgoales, Gnetales, Taxales, and Pinales.

The methods and compositions can be used over a broad range of plant species, including species from the dicot genera *Abelmoschus, Acer, Acokanthera, Aconitum, Aesculus, Alangium, Alchornea, Alexa, Alseodaphne, Amaranthus, Ammodendron, Anabasis, Anacardium, Andrographis, Angophora, Anisodus, Apium, Apocynum, Arabidopsis, Arachis, Argemone, Artemisia, Asclepias, Atropa, Azadirachta, Beilschmiedia, Berberis, Bertholletia, Beta, Betula, Bixa, Bleekeria, Borago, Brassica, Calendula, Camellia, Camptotheca, Canarium, Cannabis, Capsicum, Carthamus, Carya, Catharanthus, Centella, Cephaelis, Chelidonium, Chenopodium, Chrysanthemum, Cicer, Cichorium, Cinchona, Cinnamomum, Cissampelos, Citrus, Citrullus, Cocculus, Cocos, Coffea, Cola, Coleus, Convolvulus, Coptis, Corylus, Corymbia, Crambe, Crotalaria, Croton, Cucumis, Cucurbita, Cuphea, Cytisus, Datura, Daucus, Dendromecon, Dianthus, Dichroa, Digitalis, Dioscorea, Duguetia, Erythroxylum, Eschscholzia, Eucalyptus, Euphorbia, Euphoria, Ficus, Fragaria, Galega, Gelsemium, Glaucium, Glycine, Glycyrrhiza, Gossypium, Helianthus, Heliotropium, Hemsleya, Hevea, Hydrastis, Hyoscyamus, Jatropha, Juglans, Lactuca, Landolphia, Lavandula, Lens, Linum, Litsea, Lobelia, Luffa, Lupinus, Lycopersicon, Macadamia, Mahonia, Majorana, Malus, Mangifera, Manihot, Meconopsis, Medicago, Menispermum, Mentha, Micropus, Nicotiana, Ocimum, Olea, Origanum, Papaver, Parthenium, Persea, Petunia, Phaseolus, Physostigma, Pilocarpus, Pistacia, Pisum, Poinsettia, Populus, Prunus, Psychotria, Pyrus, Quillaja, Rabdosia, Raphanus, Rauwolfia, Rhizocarya, Ricinus, Rosa, Rosmarinus, Rubus, Rubia, Salix, Salvia, Sanguinaria, Scopolia, Senecio, Sesamum, Simmondsia, Sinapis, Sinomenium, Solanum, Sophora, Spinacia, Stephania, Strophanthus, Strychnos, Tagetes, Tanacetum, Theobroma, Thymus, Trifolium, Trigonella, Vaccinium, Vicia, Vigna, Vinca*, and *Vitis*; and the monocot genera *Agrostis, Allium, Alstroemeria, Ananas, Andropogon, Areca, Arundo, Asparagus, Avena, Cocos, Colchicum, Convallaria, Curcuma, Cynodon, Elaeis, Eragrostis, Erianthus, Festuca, Festulolium, Galanthus, Hemerocallis, Hordeum, Lemna, Lolium, Miscanthus, Musa, Oryza, Panicum, Pennisetum, Phalaris, Phleum, Phoenix, Poa, Ruscus, Saccharum, Secale, Sorghum, Spartina, Triticosecale, Triticum, Uniola, Veratrum, Zea*, and *Zoysia*; and the gymnosperm genera *Abies, Cephalotaxus, Cunninghamia, Ephedra, Picea, Pinus, Pseudotsuga*, and *Taxus*.

In some embodiments, a plant can be a species selected from *Abelmoschus esculentus* (okra), *Abies* spp. (fir), *Acer* spp. (maple), *Allium cepa* (onion), *Alstroemeria* spp., *Ananas comosus* (pineapple), *Andrographis paniculata, Andropogon gerardii* (big bluestem), *Artemisia annua, Arundo donax* (giant reed), *Atropa belladonna, Avena sativa*, bamboo, bentgrass (*Agrostis* spp.), *Berberis* spp., *Beta vulgaris* (sugarbeet), *Bixa orellana, Brassica juncea, Brassica napus* (canola), *Brassica rapa, Brassica oleracea* (broccoli, cauliflower, brusselsprouts), *Calendula officinalis, Camellia sinensis* (tea), *Camptotheca acuminate, Cannabis sativa, Capsicum annum* (hot & sweet pepper), *Carthamus tinctorius* (safflower), *Catharanthus roseus, Cephalotaxus* spp., *Chrysanthemum parthenium, Cinchona officinalis, Citrullus lanatus* (watermelon), *Coffea arabica* (coffee), *Colchicum autumnale, Coleus forskohlii, Cucumis melo* (melon), *Cucumis sativus* (cucumber), *Cucurbita maxima* (squash), *Cucurbita moschata* (squash), *Cynodon dactylon* (bermudagrass), *Datura stomonium, Dianthus caryophyllus* (carnation), *Digitalis lanata, Digitalis purpurea, Dioscorea* spp., *Elaeis guineensis* (palm), *Ephedra sinica, Ephedra* spp., *Erianthus* spp., *Erythroxylum coca, Eucalyptus* spp. (eucalyptus), *Festuca arundinacea* (tall fescue), *Fragaria ananassa* (strawberry), *Galanthus wornorii, Glycine max* (soybean), *Gossypium hirsutum* (cotton), *Gossypium herbaceum, Helianthus annuus* (sunflower), *Hevea* spp. (rubber), *Hordeum vulgare, Hyoscyamus* spp., *Jatropha curcas* (*Jatropha*), *Lactuca sativa* (lettuce), *Linum usitatissimum* (flax), *Lupinus albus* (lupin), *Lycopersicon esculentum* (tomato), *Lycopodium serratum* (=*Huperzia serrata*), *Lycopodium* spp., *Manihot esculenta* (cassava), *Medicago sativa* (alfalfa), *Mentha piperita* (mint), *Mentha spicata* (mint), *Miscanthus* spp., *Miscanthus giganteus* (*miscanthus*), *Musa paradisiaca* (banana), *Nicotiana tabacum* (tobacco), *Oryza sativa* (rice), *Panicum* spp., *Panicum virgatum* (switchgrass), *Papaver somniferum* (opium poppy), *Papaver orientale, Parthenium argentatum* (guayule), *Pennisetum glaucum* (pearl millet), *Pennisetum purpureum* (elephant grass), *Petunia* spp. (*petunia*), *Phalaris arundinacea* (reed canarygrass), *Pinus* spp. (pine), *Poinsettia pulcherrima* (poinsettia), *Populus* spp., *Populus balsamifera* (poplar), *Populus tremuloides* (aspen), *Rauwolfia serpentina, Rauwolfia* spp., *Ricinus communis* (castor), *Rosa* spp. (rose), *Saccharum* spp. (energycane), *Salix* spp. (willow), *Sanguinaria canadensis, Scopolia* spp., *Secale cereale* (rye), *Solanum melongena* (eggplant), *Solanum tuberosum* (potato), *Sorghum* spp., *Sorghum almum, Sorghum bicolor* (*sorghum*), *Sorghum halapense, Sorghum vulgare, Spartina pectinata* (prairie cordgrass), *Spinacea oleracea* (spinach), *Tanacetum parthenium, Taxus baccata, Taxus brevifolia, Theobroma cacao* (cocoa), *Triticale* (wheat X rye), *Triticum aestivum* (wheat), *Uniola paniculata* (oats), *Veratrum californica, Vinca rosea, Vitis vinifera* (grape), and *Zea mays* (corn).

Transgenic Plant Phenotypes

A transformed cell, callus, tissue, or plant can be identified and isolated by selecting or screening the engineered plant material for particular traits or activities, e.g., expression of a selectable marker gene or modulation of low-light tolerance. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

A population of transgenic plants can be screened and/or selected for those members of the population that have a desired trait or phenotype conferred by expression of the transgene. For example, a population of progeny of a single transformation event can be screened for those plants having a desired level of expression of a low light tolerance polypeptide or nucleic acid. As an alternative, a population of plants comprising independent transformation events can be screened for those plants having increased tolerance to conditions of low light irradiation. Selection and/or screening can be carried out over one or more generations, which can be useful to identify those plants that have a desired trait, such as an increased tolerance to conditions of low light irradiation. Selection and/or screening can also be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is exhibited by the plant.

The phenotype of a transgenic plant can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

The phenotype of a transgenic plant and a corresponding control plant that either lacks the transgene or does not express the transgene can be evaluated under particular environmental conditions. For example, the phenotype of a transgenic plant and a corresponding control plant can be evaluated under conditions of low light irradiance. Low light conditions are conditions under which a plant is exposed to an irradiance of about 0.01 μmol/m$^2$/s of light to about 20 μmol/m$^2$/s of light at room temperature and about 70% relative humidity. For example, conditions under which a plant is exposed to 0.01, 1, 5, 10, 15, or 20 μmol/m$^2$/s of light are low light conditions. Sources of lighting and other equipment appropriate for controlling light conditions are known to those in art.

Low light conditions typically have light of a combination of wavelengths, such as white light. White light can be supplied, e.g., by 32 watt fluorescent bulbs (Sylvania, F032/841/ECO, Danvers, Mass.), providing a red:far-red ratio of 13:1. Red wavelengths typically range from a photon irradiance of about 630 to about 700 nm. Far-red wavelengths typically range from a photon irradiance of about 700 to about 750 nm.

In some embodiments, the phenotype of a transgenic plant is assayed under low light conditions in which there is continuous low light during the light period of a light/dark cycle. Continuous low light conditions can be, for example, 16 hours of irradiance with 0.01 to 20 μmol/m$^2$/s of light alternating with 8 hours of darkness. The phenotype of a transgenic plant is assayed once the plant has been exposed to continuous low light conditions during the light period of the light/dark cycle for seven days.

A transgenic plant comprising an exogenous nucleic acid encoding a low light-tolerance polypeptide can exhibit one or more of the following phenotypic differences relative to a corresponding control plant under low light conditions: decreased extension growth, e.g., decreased petiole length, decreased hypocotyl length, decreased internode spacing, and decreased leaf elongation in cereals; increased leaf development, e.g., increased leaf thickness and reduced leaf area growth; decreased apical dominance, e.g., increased branching and tillering; increased chloroplast development, e.g., increased chlorophyll synthesis and a change in the balance of the chlorophyll a:b ratio; alterations in flowering and seed/fruit production, e.g., an increased rate of flowering, an increase in seed set, and increased fruit development; and an increase in storage organ deposition.

Typically, a difference (e.g., an increase) in a morphological feature in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the dimensions of any individual morphological feature is statistically significant at $p<0.01$, $p<0.005$, or $p<0.001$. A statistically significant difference in, for example, a morphological feature in a transgenic plant compared to the corresponding morphological feature a control plant indicates that (1) expression of the recombinant nucleic acid present in the transgenic plant confers the alteration in the morphological feature and/or (2) the recombinant nucleic acid warrants further study as a candidate for altering the morphological feature in a plant.

One suitable phenotype to measure is hypocotyl length. When wild-type seedlings are grown under low light conditions, the hypocotyl length is typically significantly increased relative to the hypocotyl length found in wild-type seedlings grown under conditions of irradiance with about 100 μmol/m$^2$/s of white light.

Seedlings of a transgenic plant and seedlings of a corresponding control plant that either lacks the transgene or does not express the transgene can be grown under low light conditions and, at the appropriate time, hypocotyl lengths from seedlings of each group can be measured. Under low light conditions, a seedling in which the expression of a low light-tolerance polypeptide is increased can have a significantly shorter hypocotyl length than a seedling of a corresponding control plant. The hypocotyl length can be shorter by at least 10 percent, e.g., 10, 15, 20, 25, 30, 35, 40, 45, 50, 55, 60, 65, 70, 75, or more than 75 percent, as compared to the hypocotyl length of a corresponding control plant.

Transgenic plants provided herein have particular uses in agricultural industries. For example, transgenic plants expressing a low light-tolerance polypeptide provided herein can be superior to corresponding control plants in maintaining development and maturation under low light conditions. Such a trait can increase plant survival and seedling establishment at high plant densities, even in crops when plants are near mature growth stages. Transgenic plants expressing a low light-tolerance polypeptide can be more densely planted than those that are not tolerant to low light conditions. Expression of a low light-tolerant polypeptide in plants can provide increased yields compared to plants that are not low light tolerant and that are grown under similar conditions. In addition, expression of polypeptide conferring low light-tolerance in a plant, such as corn, can ensure reasonable seed set in the event that low light conditions prevail during critical stages of plant development, e.g., pollination.

The materials and methods described herein are useful for modifying biomass characteristics, such as characteristics of biomass renewable energy source plants. A biomass renewable energy source plant is a plant having or producing material (either raw or processed) that comprises stored solar energy that can be converted to fuel. In general terms, such plants comprise dedicated energy crops as well as agricultural and woody plants. Examples of biomass renewable energy source plants include: switchgrass, elephant grass, giant chinese silver grass, energycane, giant reed (also known as wild cane), tall fescue, bermuda grass, *sorghum*, napier grass (also known as uganda grass), *triticale*, rye, winter wheat, shrub poplar, shrub willow, big bluestem, reed canary grass, and corn.

Information that the polypeptides disclosed herein can modulate low light tolerance can be useful in breeding of plants. Based on the effect of disclosed polypeptides on low light tolerance, one can search for and identify polymorphisms linked to genetic loci for such polypeptides. Polymorphisms that can be identified include simple sequence repeats (SSRs), rapid amplification of polymorphic DNA (RAPDs), amplified fragment length polymorphisms (AFLPs) and restriction fragment length polymorphisms (RFLPs).

If a polymorphism is identified, its presence and frequency in populations is analyzed to determine if it is statistically significantly correlated to an alteration in low light tolerance. Those polymorphisms that are correlated with an alteration in low light tolerance can be incorporated into a marker assisted breeding program to facilitate the development of lines that have a desired alteration in low light tolerance. Typically, a polymorphism identified in such a manner is used with polymorphisms at other loci that are also correlated with a desired alteration in low light tolerance.

Articles of Manufacture

Seeds of transgenic plants described herein can be conditioned and bagged in packaging material by means known in the art to form an article of manufacture. Packaging material such as paper and cloth are well known in the art. A package of seed can have a label e.g., a tag or label secured to the packaging material, a label printed on the packaging material, or a label inserted within the package.

Plants, plant tissues, and/or seeds from plants grown from seeds having an exogenous nucleic acid encoding a low light-tolerance polypeptide can be used for making products including, without limitation, human and animal foods, textiles, oils, and/or ethanol.

The invention will be further described in the following examples, which do not limit the scope of the invention described in the claims.

EXAMPLES

Example 1

Transgenic Plants

The following symbols are used in the Examples: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

Ceres Clone 28780 (genomic locus At1g07090; SEQ ID NO:87) is a cDNA clone that was isolated from *Arabidopsis* and is predicted to encode a 196 amino acid polypeptide (SEQ ID NO:88) designated LSH6. Ceres Clone 28780 was cloned into a Ti plasmid vector, CRS 338, containing a phosphinothricin acetyltransferase gene, which confers transformed plants with Finale® resistance. The construct made using the CRS 338 vector contained Ceres Clone 28780 operably linked to a CaMV 35S promoter. Wild-type *Arabidopsis thaliana* ecotype Wassilewskija (Ws) plants were transformed with the construct containing Ceres Clone 28780. The transformation was performed essentially as described in Bechtold and Pelletier, *Methods Mol Biol.*, 82:259-66 (1998).

A transgenic *Arabidopsis* line containing Ceres Clone 28780 was designated ME05917. The presence of the vector containing Ceres Clone 28780 in the transgenic *Arabidopsis* line transformed with the vector was confirmed by Finale® resistance, polymerase chain reaction (PCR) amplification from green leaf tissue extract, and/or sequencing of PCR products.

The segregation of Finale® resistance for $T_2$ plants from events -01 and -08 of ME05917 was 3:1 (resistant:sensitive).

Example 2

Identification of Transgenic Plants Tolerant to Low Light Conditions

Wild-type and transgenic seeds were sterilized, plated on solid 0.5×MS medium containing 5 g/L sucrose, and stratified at 4° C. in the dark for three days. After stratification, plates containing the seeds were allowed to reach room temperature. The plates were then transferred to a Conviron walk-in growth chamber (Controlled Environments Inc., Pambina, N. Dak.) at 22° C. and 70% humidity with a 16:8 hour light:dark cycle. Lighting was supplied by 32 watt fluorescent bulbs (Sylvania, F032/841/ECO, Danvers, Mass.), providing a red:far-red ratio of 13:1. The plates were covered with three layers of shade cloth (New York wire, charcoal fiberglass screen, 857650; Home Depot, Atlanta, Ga.) such that the irradiance was about 10 μmol/m$^2$/s. The plates were rotated daily and monitored for changes in hypocotyl elongation. After 48 hours, the plates were scored for late germinators, which were eliminated from consideration as candidate plants having reduced hypocotyl elongation under low light conditions. Each seedling was transplanted to an 8×8 cm well of a flat containing a total of 18 wells (three wells by six wells) and measuring 24 cm by 48 cm in size.

Seedlings maintained under conditions of irradiance with about 10 μmol/$m^2$/s of light for seven days at 22° C. were analyzed for hypocotyl length. Transgenic seedlings having a shorter hypocotyl length than the hypocotyl length of corresponding wild-type seedlings were selected and analyzed using PCR and DNA sequencing to identify the transgenes. The transgenic *Arabidopsis* line ME05917, described in Example 1, was identified as having reduced hypocotyl elongation under the low light conditions as compared to wild-type control plants.

Example 3

Characterization of the Low Light Tolerance of Seedlings from ME05917 Events $T_2$ and $T_3$ seedlings from events -01 and -08 of ME05917 were grown under low light conditions and evaluated for hypocotyl length as described in Example 2. A Chi-square test was performed to compare transgenic seedlings and corresponding non-transgenic segregants having a short or a long hypocotyl. A hypocotyl having a length similar to the hypocotyl length typically exhibited by wild-type *Arabidopsis* seedlings grown under normal light conditions (e.g., about 100 μmol/$m^2$/s of white light) was considered a short hypocotyl, whereas a hypocotyl having a length similar to that typically exhibited by wild-type *Arabidopsis* seedlings grown under low light conditions (e.g., about 10 μmol/$m^2$/s of white light) was considered a long hypocotyl. Wild-type *Arabidopsis* seeds grown for seven days at 22° C. under conditions of irradiance with about 100 μmol/$m^2$/s of white light and a 16:8 hour light:dark cycle typically form hypocotyls that are about 1-3 mm in length. Under conditions of irradiance with about 10 μmol/$m^2$/s of white light, the hypocotyls typically are about 5-7 mm in length.

Seedlings from events -01 and -08 of ME05917 displayed a short hypocotyl under low light conditions in both the $T_2$ and $T_3$ generations, and the transgene was linked to the short hypocotyl phenotype with a confidence level of $p<0.05$ (Table 1).

TABLE 1

Chi-square comparison of the hypocotyl length of transgenic seedlings and non-transgenic segregants grown under low light irradiance (10 μmol/$m^2$/s) for seven days

| Plants | Short Hypocotyl | Long Hypocotyl | Chi-Square | p-value |
|---|---|---|---|---|
| $T_2$ seedlings from event -01 of ME05917 | 42 | 0 | 39.71 | 2.95E−10 |
| $T_2$ non-transgenic segregants of event -01 of ME05917 | 2 | 8 | | |
| $T_3$ seedlings from event -01 of ME05917 | 38 | 2 | 46.93 | 7.37E−12 |
| $T_3$ non-transgenic segregants of event -01 of ME05917 | 2 | 21 | | |
| $T_2$ seedlings from event -08 of ME05917 | 15 | 7 | 10.91 | 9.57E−04 |
| $T_2$ non-transgenic segregants of event -08 of ME05917 | 0 | 8 | | |
| $T_3$ seedlings from event -08 of ME05917 | 37 | 8 | 43.8 | 3.63E−11 |
| $T_3$ non-transgenic segregants of event -08 of ME05917 | 1 | 28 | | |

The expression level of genomic locus At1g07090 in two week old $T_3$ plants from single insertion events -01-09 and -08-28 of the transgenic line ME05917 was determined using RT-PCR and quantitative RT-PCR. The plants were grown under conditions of irradiance with about 100 μmol/$m^2$/s of white light. Aerial tissue was collected from five plants from each of events -01-09 and -08-28 of ME05917 and from five corresponding non-transgenic segregant plants. The tissues were flash frozen in liquid nitrogen, and total RNA was extracted from the tissues using a plant RNeasy kit (Qiagen, Valenica, Calif.). First strand cDNA was synthesized using 1000 ng of total RNA and Superscript II (Invitrogen, Carlsbad, Calif.). PCR was performed using one μL of the first strand cDNA reaction. The PCR conditions were as follows: 94° C. for five minutes; 25 cycles of 94° C. for 30 seconds, 58° C. for one minute, and 72° C. for 40 seconds; and 72° C. for seven minutes. Expression of tubulin was measured as an internal standard. The primers used to detect expression of tubulin were: TUB-F1, 5'-GTTGAGCCGTACAATGCAAC-3' (SEQ ID NO:95) and TUB-R1, 5'-CTGTTCGTCCACTTCCTTG-3' (SEQ ID NO:96). The primers used to detect expression of At1g07090 were: 05917-F, 5'-AGCAGGTATGAGTCACAGAAGCGA-3' (SEQ ID NO:97) and 05917-R, 5'-ACAGATGGAGCACCGACGTTACAA-3' (SEQ ID NO:98). Equal volumes of the PCR reactions were analyzed using 1% agarose gel electrophoresis. Quantitative PCR was performed using an iCycler system (BioRad, Hercules, Calif.) and standard protocols.

The expression level of At1g07090, as analyzed using RT-PCR, was elevated in $T_3$ plants from both events of ME05917 analyzed, -01-09 and -08-28, as compared to the expression level of At1g07090 in corresponding wild-type or non-transgenic segregant plants. Analysis of At1g07090 expression using quantitative PCR indicated that the expression level of At1g07090 was increased by 312-fold and 233-fold in ME05917 plants from events -01-09 and -08-28, respectively, compared to the expression level of At1g07090 in non-transgenic segregant plants of event -01-28 of ME05917. These results indicated that the expression level of At1g07090 in plants from event -01-09 was about 34% higher than the expression level in plants from event -08-28.

The low light tolerance, as measured by reduced hypocotyl elongation, of seedlings from ME05917 events was characterized further. $T_2$ seedlings from events -01 and -08 of ME05917, $T_3$ seedlings from single insertion events -01-09 and -08-28 of the homozygous ME05917 line, $T_3$ non-transgenic segregants of ME05917-01-28, and wild-type *Arabidopsis thaliana* ecotype Wassilewskija (Ws) seedlings were grown under conditions of irradiance with about 10 μmol/$m^2$/s of white light as described in Example 2. The hypocotyl lengths of about ten seedlings from each event were measured after seven days using digital calipers.

The average hypocotyl length of $T_2$ and $T_3$ seedlings from each event of ME05917 analyzed was significantly shorter than the average hypocotyl length of corresponding non-transgenic segregants or wild-type seedlings (Table 2).

TABLE 2

| Hypocotyl length of seedlings from ME05917 events grown under conditions of irradiance with about 10 μmol/m²/s of white light | | | | | | |
|---|---|---|---|---|---|---|
| | $T_2$ seedlings from event -01 | $T_2$ seedlings from event -08 | $T_3$ seedlings from event -01-09 | $T_3$ seedlings from event -08-28 | Non-transgenic segregants of event -01-28 | Wild-type seedlings |
| Average hypocotyl length (mm) ± standard deviation | 2.098 ± 0.451 | 2.503 ± 0.893 | 1.868 ± 0.169 | 2.071 ± 0.289 | 4.358 ± 0.443 | 4.931 ± 0.312 |
| p-value versus non-transgenic segregants | 4.54E−09 | 2.54E−03 | 2.00E−09 | 4.67E−10 | N/A | N/A |
| p-value versus wild-type seedlings | 2.66E−10 | 7.68E−04 | 5.43E−12 | 3.43E−13 | N/A | N/A |

$T_3$ seedlings from single insertion events -01-09 and -08-28 of the homozygous ME05917 line, $T_3$ non-transgenic segregants of ME05917-01-28, and wild-type *Arabidopsis thaliana* ecotype Wassilewskija (Ws) seedlings were also grown under conditions of irradiance with about 100 μmol/m²/s of white light as described in Example 2. The hypocotyl lengths of about ten seedlings from each event were measured after seven days using digital calipers.

The average hypocotyl length of $T_3$ seedlings from each event of ME05917 analyzed was significantly shorter than the average hypocotyl length of corresponding non-transgenic segregants or wild-type seedlings (Table 3).

TABLE 3

| Hypocotyl length of $T_3$ seedlings from ME05917 events grown under conditions of irradiance with about 100 μmol/m2/s of white light | | | | |
|---|---|---|---|---|
| | Event -01-09 | Event -08-28 | Non-transgenic segregants of event -01-28 | Wild-type seedlings |
| Average hypocotyl length (mm) ± standard deviation | 1.535 ± 0.232 | 1.754 ± 0.183 | 2.187 ± 0.356 | 2.077 ± 0.224 |
| p-value versus non-transgenic segregants | 1.95E−04 | 4.39E−03 | N/A | N/A |
| p-value versus wild-type seedlings | 4.70E−05 | 2.50E−03 | N/A | N/A |

$T_3$ seedlings from single insertion events -01-09 and -08-28 of the homozygous ME05917 line, $T_3$ non-transgenic segregants of ME05917-01-28, and wild-type *Arabidopsis thaliana* ecotype Wassilewskija (Ws) seedlings were also grown in the dark. The seeds were prepared as described in Example 2 and exposed to about 100 μmol/m²/s of white light for two hours to promote uniform germination prior to covering the plates with aluminum foil. The seeds were grown in the dark at 22° C. and 70% humidity for five days, after which the hypocotyl lengths of about ten seedlings from each event were measured using digital calipers.

The average hypocotyl length of $T_3$ seedlings from each event of ME05917 analyzed was significantly shorter than the average hypocotyl length of corresponding non-transgenic segregants or wild-type seedlings (Table 4).

TABLE 4

| Hypocotyl length of $T_3$ seedlings from ME05917 events grown in the dark | | | | |
|---|---|---|---|---|
| | Event -01-09 | Event -08-28 | Non-transgenic segregants of event -01-28 | Wild-type seedlings |
| Average hypocotyl length (mm) ± standard deviation | 9.496 ± 1.526 | 10.850 ± 0.887 | 13.008 ± 1.317 | 12.494 ± 1.420 |
| p-value versus non-transgenic segregants | 1.28E−05 | 3.32E−04 | N/A | N/A |
| p-value versus wild-type seedlings | 1.70E−04 | 7.18E−03 | N/A | N/A |

No cotyledon phenotypes were observed in transgenic seedlings as compared to non-transgenic segregating controls (FIG. 2). Interestingly, $T_3$ seedlings from event -01-09 of ME05917 had a shorter average hypocotyl length than $T_3$ seedlings from event -08-28 of ME05917 when grown in the dark or under conditions of irradiance with about 100 μmol/m²/s of white light ($p<0.05$). As presented above, the expression level of At1g07090 in plants from event -01-09 was higher than the expression level in plants from event -08-28. Taken together, these results suggest that reduction in hypocotyl elongation is proportional to the expression level of At1g07090 in ME05917 plants.

Example 4

Characterization of the Low Light Tolerance of Adult Plants from ME05917 Events Seeds from transgenic ME05917 plants and corresponding control plants were sown in a checkerboard pattern in no-hole utility flats. Wild-type *Arabidopsis thaliana* ecotype Wassilewskija (Ws) plants and non-transgenic segregating plants were used as control plants. The flats were covered with propagation domes and maintained at 4° C. in the dark for three days. The flats were then transferred to a Conviron walk-in growth chamber (Controlled Environments Inc.) with a 16:8 hour light:dark cycle, a relative humidity of 70%, a temperature of 22° C., and an irradiance of about 150 μmol/m²/s of light having a red to far-red ratio greater than one. The propagation domes were removed after four days. After three weeks, the flats were divided into two groups of plants. One group, referred to as the normal light treatment (NLT) group, remained under the same conditions, with a 16:8 hour light:dark cycle, a relative humidity of 70%, a temperature of 22° C., and an irradiance of about 150 μmol/m²/s of light having a red to far-red ratio greater than one, for the duration of the experiment. The other group, referred to as the low light stress treatment (LLT) group, was placed under three layers of shade screen to reduce the irradiance to about 15 μmol/m²/s without altering the spectral quality. After one week, the shade screens were removed, and the low light stress treatment group was once again grown under an irradiance of about 150 μmol/m²/s.

Measurements were taken at four different stages (FIG. 3). Stage one occurred after three weeks of growth under normal light conditions (irradiance of about 150 μmol/m²/s) and before transfer of the LLT group to low light conditions (irradiance of about 15 μmol/m²/s). Stage two occurred after three weeks of growth under normal light conditions and one week of growth under low light conditions for the LLT group, and before transfer of the LLT group back to normal light conditions. Stage three occurred one week after transfer of the LLT back to normal light conditions, when the plants were five weeks old. Stage four occurred after senescence, when the plants were eight weeks old. Photosynthetic efficiency was measured at stage two, and rosette areas were measured at stages one and two. Fresh weight was measured at stages one, two, and three. Dry weight and seed yield were determined at stage four. Six to nine replicate plant samples were measured at each stage for each treatment group, and the average values and standard deviations were calculated.

To measure photosynthetic efficiency, plants were first placed in the dark for at least 20 minutes. Rosettes were removed from the plants by cutting at the rosette-root junction. Detached rosettes were placed in the middle of the stage of a CF Imager (Technologica Ltd., Essex, UK). Chlorophyll fluorescence was measured with a pulse intensity of 4400 μmol/m²/s and a pulse length of 800 ms. The area of each rosette was also measured using the CF imager.

After measuring photosynthetic efficiency and rosette area, the rosette was removed from the CF imager and weighed along with the stem from which it was removed. The weight was recorded as the fresh weight measurement.

Seed and dry weight measurements were obtained when plants were eight weeks old. Plants were harvested individually and allowed to dry completely at 28° C. for three days. The seed was separated from the dried plant material using a sieve (300 μM mesh size) and weighed. The dried plant material was added to the seed and the combined weight was recorded as the dry weight.

Results $T_3$ plants from single insertion events -01-09 and -08-28 of the homozygous ME05917 line, $T_3$ non-transgenic segregants of ME05917-01-28, and wild-type *Arabidopsis thaliana* ecotype Wassilewskija (Ws) plants were grown under conditions of irradiance with about 150 μmol/m²/s of light and analyzed to determine the number of days that elapsed between seed sowing (after stratification) and primary bolt emergence of about one cm, or days to bolt. $T_3$ plants from event -01-09 were not observed to differ significantly in days to bolt from corresponding non-transgenic segregant or wild-type control plants (Table 5). $T_3$ plants from event -08-28 also were observed to not differ significantly from non-transgenic segregants in days to bolt, whereas the average number of days to bolt for plants from event -08-28 was significantly lower than the average number of days to bolt for wild-type plants (Table 5). On average, transgenic and control plants bolted about 15 to 17 days post-germination (Table 5).

TABLE 5

Days to bolt for $T_3$ plants from ME05917 events

| | Event -01-09 | Event -08-28 | Non-transgenic segregants of event -01-28 | Wild-type *Arabidopsis* Ws plants |
|---|---|---|---|---|
| Average days to bolt ± standard deviation | 17.267 ± 1.163 | 15.278 ± 1.274 | 16.529 ± 0.943 | 17.056 ± 0.791 |
| p-value versus non-transgenic segregants | 6.12E−02 | 5.40E−02 | N/A | N/A |
| p-value versus wild-type plants | 5.27E−01 | 1.49E−05 | N/A | N/A |

Rosette areas of $T_3$ plants from single insertion events -01-09 and -08-28 of the homozygous ME05917 line, $T_3$ non-transgenic segregants of ME05917-01-28, and wild-type *Arabidopsis thaliana* ecotype Wassilewskija (Ws) plants in the NLT or LLT group were analyzed at stage one (three weeks old) and stage two (four weeks old), as described above. The average rosette area of $T_3$ plants from events -01-09 and -08-28 of ME05917 was significantly smaller than the average rosette area of corresponding non-transgenic segregants and wild-type plants after three weeks of growth under conditions of irradiance with about 150 μmol/m²/s of light, in the absence of any low light treatment (Table 6). As presented in Table 6, the average rosette area of plants from events -01-09 and -08-28 was about 50% smaller than the average rosette area of non-transgenic segregants, and more than 60% smaller than the average rosette area of wild-type plants under conditions of irradiance with about 150 μmol/m²/s of light.

At stage two, the average rosette area of plants from events -01-09 and -08-28 of ME05917 was significantly smaller than the average rosette area of control plants, regardless of whether the plants were in the LLT or the NLT group. As presented in Table 6, the average rosette area of plants from events -01-09 and -08-28 in the LLT group was about 23% and 50% smaller, respectively, than the average rosette area of non-transgenic segregants in the LLT group. The average rosette area of plants from events -01-09 and -08-28 in the NLT group was about 37% and 35% smaller, respectively, than the average rosette area of non-transgenic segregants in the NLT group (Table 6).

Although the rosette areas of plants from events -01-09 and -08-28 of ME05917 were reduced (Table 6), the photosynthetic efficiency was similar to that of non-transgenic segregating and wild-type controls. As presented in Table 7, there were no significant differences in photosynthetic efficiency between plants from events -01-09 and -08-28 of ME05917 and non-transgenic segregrants or wild-type plants in the LLT or NLT group at stage two.

TABLE 6

Rosette area of $T_3$ plants from ME05917 events

| | Average rosette area ± standard deviation | p-value versus non-transgenic segregants | p-value versus wild-type plants |
|---|---|---|---|
| Event -01-09<br>3 weeks under 150 μmol/m²/s of light | 210.286 ± 25.736 | 1.34E−07 | 3.01E−07 |
| Event -01-09<br>3 weeks under 150 μmol/m²/s of light and<br>1 week under 15 μmol/m²/s of light | 508.171 ± 88.517 | 5.66E−03 | 4.63E−03 |
| Event -01-09<br>4 weeks under 150 μmol/m²/s of light | 455.942 ± 93.474 | 7.59E−04 | 1.42E−07 |
| Event -08-28<br>3 weeks under 150 μmol/m²/s of light | 208.410 ± 44.842 | 8.91E−08 | 3.32E−08 |
| Event -08-28<br>3 weeks under 150 μmol/m²/s of light and<br>1 week under 15 μmol/m²/s of light | 332.390 ± 75.840 | 7.57E−06 | 3.08E−06 |
| Event -08-28<br>4 weeks under 150 μmol/m²/s of light | 465.543 ± 100.938 | 1.55E−03 | 4.10E−07 |
| Non-transgenic segregants of event -01-28<br>3 weeks under 150 μmol/m²/s of light | 414.811 ± 49.785 | N/A | N/A |
| Non-transgenic segregants of event -01-28<br>3 weeks under 150 μmol/m²/s of light and<br>1 week under 15 μmol/m²/s of light | 663.623 ± 114.433 | N/A | N/A |
| Non-transgenic segregants of event -01-28<br>4 weeks under 150 μmol/m²/s of light | 721.074 ± 164.671 | N/A | N/A |
| Wild-type *Arabidopsis* Ws plants<br>3 weeks under 150 μmol/m²/s of light | 558.520 ± 67.430 | N/A | N/A |
| Wild-type *Arabidopsis* Ws plants<br>3 weeks under 150 μmol/m²/s of light and<br>1 week under 15 μmol/m²/s of light | 632.495 ± 63-954 | N/A | N/A |
| Wild-type *Arabidopsis* Ws plants<br>4 weeks under 150 μmol/m²/s of light | 1003.666 ± 122.442 | N/A | N/A |

TABLE 7

| Photosynthetic efficiency of four week old $T_3$ plants from ME05917 events | | | |
|---|---|---|---|
| | Average photosynthetic efficiency ± standard deviation | p-value versus non-transgenic segregants | p-value versus wild-type plants |
| Event -01-09 4 weeks under 150 μmol/m$^2$/s of light | 0.784 ± 0.011 | 6.70E−01 | 2.12E−01 |
| Event -01-09 3 weeks under 150 μmol/m$^2$/s of light and 1 week under 15 μmol/m$^2$/s of light | 0.769 ± 0.009 | 4.07E−01 | 6.95E−01 |
| Event -08-28 4 weeks under 150 μmol/m$^2$/s of light | 0.780 ± 0.011 | 2.12E−01 | 5.12E−02 |
| Event -08-28 3 weeks under 150 μmol/m$^2$/s of light and 1 week under 15 μmol/m$^2$/s of light | 0.768 ± 0.010 | 4.19E−01 | 8.32E−01 |
| Non-transgenic segregants of event -01-28 4 weeks under 150 μmol/m$^2$/s of light | 0.787 ± 0.010 | N/A | N/A |
| Non-transgenic segregants of event -01-28 3 weeks under 150 μmol/m$^2$/s of light and 1 week under 15 μmol/m$^2$/s of light | 0.772 ± 0.007 | N/A | N/A |
| Wild-type *Arabidopsis* Ws plants 4 weeks under 150 μmol/m$^2$/s of light | 0.790 ± 0.003 | N/A | N/A |
| Wild-type *Arabidopsis* Ws plants 3 weeks under 150 μmol/m$^2$/s of light and 1 week under 15 μmol/m$^2$/s of light | 0.767 ± 0.007 | N/A | N/A |

Biomass accumulation was assessed based on measurement of the fresh weight of aerial tissues from ME05917 plants and non-transgenic segregants, as described above. The fresh weights of $T_3$ plants from events -01-09 and -08-28 of ME05917 were significantly less than the fresh weights of non-transgenic segregating controls in the LLT group at stages one (3 weeks old), two (four weeks old), and three (five weeks old; Table 8). In the NLT group, the fresh weights of $T_3$ plants from events -01-09 and -08-28 were also significantly less than the fresh weights of non-transgenic segregating controls at stages one and two (Table 8). At stage three, plants from events -01-09 and -08-28 also had fresh weights that were less than the fresh weights of non-transgenic segregating controls, but the difference was less statistically significant (Table 8).

TABLE 8

| Fresh weights of three, four, and five week old $T_3$ plants from ME05917 events | | |
|---|---|---|
| | Average fresh weight ± standard deviation | p-value versus non-transgenic segregants |
| Event -01-09 3 weeks under 150 μmol/m$^2$/s of light | 0.155 ± 0.031 | 4.27E−06 |
| Event -08-28 3 weeks under 150 μmol/m$^2$/s of light | 0.127 ± 0.030 | 4.23E−07 |
| Non-transgenic segregants of event -01-28 3 weeks under 150 μmol/m$^2$/s of light | 0.283 ± 0.044 | N/A |
| Event -01-09 3 weeks under 150 μmol/m$^2$/s of light and 1 week under 15 μmol/m$^2$/s of light | 0.583 ± 0.090 | 4.92E−04 |
| Event -08-28 3 weeks under 150 μmol/m$^2$/s of light and 1 week under 15 μmol/m$^2$/s of light | 0.443 ± 0.149 | 1.33E−04 |

TABLE 8-continued

| Fresh weights of three, four, and five week old $T_3$ plants from ME05917 events | | |
|---|---|---|
| | Average fresh weight ± standard deviation | p-value versus non-transgenic segregants |
| Non-transgenic segregants of event -01-28 3 weeks under 150 μmol/m$^2$/s of light and 1 week under 15 μmol/m$^2$/s of light | 0.841 ± 0.144 | N/A |
| Event -01-09 3 weeks under 150 μmol/m$^2$/s of light, 1 week under 15 μmol/m$^2$/s of light and 1 week under 150 μmol/m$^2$/s of light | 1.786 ± 0.534 | 1.25E−03 |
| Event -08-28 3 weeks under 150 μmol/m$^2$/s of light, 1 week under 15 μmol/m$^2$/s of light and 1 week under 150 μmol/m$^2$/s of light | 1.199 ± 0.416 | 3.19E−05 |
| Non-transgenic segregants of event -01-28 3 weeks under 150 μmol/m$^2$/s of light, 1 week under 15 μmol/m$^2$/s of light and 1 week under 150 μmol/m$^2$/s of light | 2.686 ± 0.429 | N/A |
| Event -01-09 4 weeks under 150 μmol/m$^2$/s of light | 1.001 ± 0.177 | 1.56E−03 |
| Event -08-28 4 weeks under 150 μmol/m$^2$/s of light | 1.136 ± 0.213 | 1.91E−02 |
| Non-transgenic segregants of event -01-28 4 weeks under 150 μmol/m$^2$/s of light | 1.498 ± 0.324 | N/A |
| Event -01-09 5 weeks under 150 μmol/m$^2$/s of light | 2.002 ± 0.500 | 5.31E−02 |
| Event -08-28 5 weeks under 150 μmol/m$^2$/s of light | 2.005 ± 0.486 | 5.61E−02 |
| Non-transgenic segregants of event -01-28 5 weeks under 150 μmol/m$^2$/s of light | 3.050 ± 1.347 | N/A |

Although differences in biomass were observed between plants in the LLT and NLT group (Table 8), all of the plants appeared developmentally similar at all stages of growth through bolting, flowering, and senescence. All of the plants flowered prior to low light treatment (Table 5), but growth of reproductive tissue seemed to slow down during low light treatment and the stems appeared weak and spindly. Most of the biomass increases during this time appeared to be due to growth of the rosette. After one week of low light treatment, plants in the LLT group were returned to conditions of irradiance with 150 μmol/m$^2$/s of light for one week. During this period, the stems of $T_3$ plants from events -01-09 and -08-28 of ME05917 and non-transgenic segregating control plants increased in strength, and growth of reproductive tissues seemed to accelerate. After one week of irradiance with 150 μmol/m$^2$/s of light, at stage three, both transgenic ME05917 plants and control plants had segments on most stems where siliques failed to form. No visible differences were observed between transgenic ME05917 plants and non-transgenic segregating control plants in the ability to form siliques under low light stress. All plants continued to develop normally through the termination of flowering and senescence.

After senescence, plants were collected and average dry weight, seed weight, and harvest index (total seed weight divided by total dry weight) were calculated. At harvest, $T_3$ plants from events -01-09 and -08-28 of ME05917 in the LLT group had average dry weights that were 31% and 42% lower, respectively, than the average dry weight of non-transgenic segregating controls in the LLT group (Table 9).

TABLE 9

Dry weight of eight week old $T_3$ plants from ME05917 events after senescence

| | Average dry weight ± standard deviation | p-value versus non-transgenic segregants | p-value versus wild-type plants |
|---|---|---|---|
| Event -01-09 3 weeks under 150 μmol/m$^2$/s of light, 1 week under 15 μmol/m$^2$/s of light, and 4 weeks under 150 μmol/m$^2$/s of light | 0.480 ± 0.113 | 2.18E−02 | 2.79E−03 |
| Event -08-28 3 weeks under 150 μmol/m$^2$/s of light, 1 week under 15 μmol/m$^2$/s of light, and 4 weeks under 150 μmol/m$^2$/s of light | 0.407 ± 0.125 | 4.54E−03 | 2.68E−04 |
| Non-transgenic segregants of event -08-27 3 weeks under 150 μmol/m$^2$/s of light, 1 week under 15 μmol/m$^2$/s of light, and 4 weeks under 150 μmol/m$^2$/s of light | 0.695 ± 0.218 | N/A | N/A |
| Wild-type *Arabidopsis* Ws plants 3 weeks under 150 μmol/m$^2$/s of light, 1 week under 15 μmol/m$^2$/s of light, and 4 weeks under 150 μmol/m$^2$/s of light | 0.683 ± 0.166 | N/A | N/A |
| Event -01-09 8 weeks under 150 μmol/m$^2$/s of light | 0.535 ± 0.188 | 1.15E−05 | 5.80E−06 |
| Event -08-28 8 weeks under 150 μmol/m$^2$/s of light | 0.833 ± 0.161 | 3.27E−04 | 1.12E−02 |
| Non-transgenic segregants of event -08-27 8 weeks under 150 μmol/m$^2$/s of light | 1.463 ± 0.267 | N/A | N/A |
| Wild-type *Arabidopsis* Ws plants 8 weeks under 150 μmol/m$^2$/s of light | 1.082 ± 0.295 | N/A | N/A |

$T_3$ plants from events -01-09 and -08-28 of ME05917 in the NLT group had average dry weights that were 63% and 43% lower, respectively, than the average dry weight of non-transgenic segregating controls in the NLT group (Table 9).

The average seed weight of $T_3$ plants from events -01-09 and -08-28 of ME05917 in the LLT group was 25% and 37% lower, respectively, than the average seed weight of non-transgenic segregating controls in the LLT group (Table 10).

TABLE 10

Seed weight of eight week old $T_3$ plants from ME05917 events after senescence

| | Average seed weight ± standard deviation | p-value versus non-transgenic segregants | p-value versus wild-type plants |
|---|---|---|---|
| Event -01-09 3 weeks under 150 μmol/m$^2$/s of light, 1 week under 15 μmol/m$^2$/s of light, and 4 weeks under 150 μmol/m$^2$/s of light | 0.162 ± 0.045 | 3.58E−02 | 7.01E−04 |

TABLE 10-continued

Seed weight of eight week old $T_3$ plants from ME05917 events after senescence

| | Average seed weight ± standard deviation | p-value versus non-transgenic segregants | p-value versus wild-type plants |
|---|---|---|---|
| Event -08-28 3 weeks under 150 μmol/m$^2$/s of light, 1 week under 15 μmol/m$^2$/s of light, and 4 weeks under 150 μmol/m$^2$/s of light | 0.136 ± 0.043 | 2.98E−03 | 2.57E−05 |
| Non-transgenic segregants of event -08-27 3 weeks under 150 μmol/m$^2$/s of light, 1 week under 15 μmol/m$^2$/s of light, and 4 weeks under 150 μmol/m$^2$/s of light | 0.215 ± 0.052 | N/A | N/A |
| Wild-type *Arabidopsis* Ws plants 3 weeks under 150 μmol/m$^2$/s of light, 1 week under 15 μmol/m$^2$/s of light, and 4 weeks under 150 μmol/m$^2$/s of light | 0.245 ± 0.051 | N/A | N/A |
| Event -01-09 8 weeks under 150 μmol/m$^2$/s of light | 0.181 ± 0.044 | 3.00E−06 | 1.56E−07 |
| Event -08-28 8 weeks under 150 μmol/m$^2$/s of light | 0.265 ± 0.042 | 3.24E−05 | 1.84E−04 |
| Non-transgenic segregants of event -08-27 8 weeks under 150 μmol/m$^2$/s of light | 0.515 ± 0.077 | N/A | N/A |
| Wild-type *Arabidopsis* Ws plants 8 weeks under 150 μmol/m$^2$/s of light | 0.397 ± 0.110 | N/A | N/A |

The average seed weight of $T_3$ plants from events -01-09 and -08-28 of ME05917 in the NLT group was 65% and 49% lower, respectively, than the average seed weight of non-transgenic segregating controls in the NLT group (Table 10).

The average harvest index of $T_3$ plants from events -01-09 and -08-28 of ME05917 was not observed to differ significantly from the average harvest index of non-transgenic segregating controls in the LLT or NLT group (Table 11).

TABLE 11

Harvest index of eight week old $T_3$ plants from ME05917 events after senescence

| | Average harvest index ± standard deviation | p-value versus non-transgenic segregants | p-value versus wild-type plants |
|---|---|---|---|
| Event -01-09 3 weeks under 150 μmol/m$^2$/s of light, 1 week under 15 μmol/m$^2$/s of light, and 4 weeks under 150 μmol/m$^2$/s of light | 0.337 ± 0.035 | 2.40E−01 | 8.18E−02 |
| Event -08-28 3 weeks under 150 μmol/m$^2$/s of light, 1 week under 15 μmol/m$^2$/s of light, and 4 weeks under 150 μmol/m$^2$/s of light | 0.332 ± 0.031 | 3.25E−01 | 3.22E−02 |
| Non-transgenic segregants of event -08-27 3 weeks under 150 μmol/m$^2$/s of light, 1 week under 15 μmol/m$^2$/s of light, and 4 weeks under 150 μmol/m$^2$/s of light | 0.316 ± 0.038 | N/A | N/A |
| Wild-type *Arabidopsis* Ws plants 3 weeks under 150 μmol/m$^2$/s of light, 1 week under 15 μmol/m$^2$/s of light, and 4 weeks under 150 μmol/m$^2$/s of light | 0.364 ± 0.014 | N/A | N/A |
| Event -01-09 8 weeks under 150 μmol/m$^2$/s of light | 0.348 ± 0.034 | 6.86E−01 | 1.56E−01 |
| Event -08-28 8 weeks under 150 μmol/m$^2$/s of light | 0.324 ± 0.051 | 1.53E−01 | 4.84E−02 |
| Non-transgenic segregants of event -08-27 8 weeks under 150 μmol/m$^2$/s of light | 0.354 ± 0.020 | N/A | N/A |
| Wild-type *Arabidopsis* Ws plants 8 weeks under 150 μmol/m$^2$/s of light | 0.367 ± 0.014 | N/A | N/A |

Overall, $T_3$ plants from events -01-09 and -08-28 of ME05917 were observed to have a shorter plant height at harvest than non-transgenic segregating controls or wild type plants.

Example 5

Transgenic Plants

The following DNA clones were isolated from *Arabidopsis thaliana* plants. Each of the DNA clones encodes a polypeptide that is the same as or similar to members of a family designated as the light-dependent short hypocotyls (LSH) polypeptide family (Zhao et al., *Plant J.,* 37(5):694-706 (2004)). Ceres ANNOT ID no. 832857 (genomic locus At1g16910; SEQ ID NO:111) is a DNA clone that is predicted to encode a 164 amino acid polypeptide (SEQ ID NO:112) designated LSH8. Ceres ANNOT ID no. 1290753 (genomic locus At5g28490; SEQ ID NO:101) is a DNA clone that is predicted to encode a 190 amino acid polypeptide (SEQ ID NO:102) designated LSH1. Ceres ANNOT ID no. 856813 (genomic locus At5g58500; SEQ ID NO:115) is a DNA clone that is predicted to encode a 182 amino acid polypeptide (SEQ ID NO:116) designated LSH5. Ceres ANNOT ID no. 828846 (SEQ ID NO:109) is a DNA clone that is predicted to encode a 219 amino acid polypeptide (SEQ ID NO:110) designated LSH3. Ceres CLONE ID no. 1025179 (SEQ ID NO:119) is a DNA clone that is predicted to encode a 195 amino acid polypeptide (SEQ ID NO:120) designated LSH4. Ceres ANNOT ID no. 870022 (SEQ ID NO:117) is a DNA clone that is predicted to encode a 195 amino acid polypeptide (SEQ ID NO:118) designated LSH7. Ceres ANNOT ID no. 1285138 (SEQ ID NO:99) is a DNA clone that is predicted to encode a 188 amino acid polypeptide (SEQ ID NO:100) designated LSH9. Ceres ANNOT ID no. 847799 (SEQ ID NO:113) is a DNA clone that is predicted to encode a 191 amino acid polypeptide (SEQ ID NO:114) designated LSH9.

Ceres CLONE ID no. 604111(a) (SEQ ID NO:125) and Ceres CLONE ID no. 604111(b) (SEQ ID NO:129) are DNA clones that were isolated from a *Glycine max* plant. Ceres CLONE ID no. 604111(a) (SEQ ID NO:125) is predicted to encode a 229 amino acid polypeptide (SEQ ID NO:126) designated as an orthologous LSH6 polypeptide. Ceres CLONE ID no. 604111(b) (SEQ ID NO:129) is predicted to encode a 229 amino acid polypeptide (SEQ ID NO:146) designated as an orthologous LSH6 polypeptide.

Ceres CLONE ID no. 1464359 (SEQ ID NO:123) is a DNA clone that was isolated from a *Zea mays* plant. Ceres CLONE ID no. 1464359 (SEQ ID NO:123) is predicted to encode a 183 amino acid polypeptide (SEQ ID NO:124) designated as an orthologous LSH6 polypeptide.

The following DNA clones were isolated from *Brassica napus* plants. Ceres CLONE ID no. 964932 (SEQ ID NO:127) is a DNA clone that is predicted to encode a 199 amino acid polypeptide (SEQ ID NO:128) designated as an orthologous LSH6 polypeptide. Ceres CLONE ID no. 1084747 (SEQ ID NO:121) is a DNA clone that is predicted to encode a 198 amino acid polypeptide (SEQ ID NO:122) designated as an orthologous LSH6 polypeptide.

Ceres ANNOT ID no. 1373087 (SEQ ID NO:103) is a DNA clone that was isolated from an *Oryza sativa* plant. Ceres ANNOT ID no. 1373087 (SEQ ID NO:103) is predicted to encode a 212 amino acid polypeptide (SEQ ID NO:104) designated as an orthologous LSH6 polypeptide.

The following DNA clones were isolated from *Populus balsamifera* subsp. *Trichocarpa* plants. Ceres ANNOT ID no. 1440417 (SEQ ID NO:105) is a DNA clone that is predicted to encode a 228 amino acid polypeptide (SEQ ID NO:106) designated as an orthologous LSH6 polypeptide. Ceres ANNOT ID no. 1505805 (SEQ ID NO:107) is a DNA clone that is predicted to encode a 240 amino acid polypeptide (SEQ ID NO:108) designated as an orthologous LSH6 polypeptide.

Each of Ceres ANNOT ID no. 832857, Ceres ANNOT ID no. 1290753, Ceres ANNOT ID no. 856813, Ceres ANNOT ID no. 828846, Ceres ANNOT ID no. 870022, Ceres ANNOT ID no. 1285138, Ceres ANNOT ID no. 847799, Ceres CLONE ID no. 604111(a), Ceres CLONE ID no. 1464359, Ceres CLONE ID no. 964932, Ceres CLONE ID no. 1084747, Ceres ANNOT ID no. 1373087, Ceres ANNOT ID no. 1440417, and Ceres ANNOT ID no. 1505805 was cloned into a Ti plasmid vector, CRS 338, containing a phosphinothricin acetyltransferase gene, which confers transformed plants with Finale® resistance. The constructs made using the CRS 338 vector contained Ceres ANNOT ID no. 832857, Ceres ANNOT ID no. 1290753, Ceres ANNOT ID no. 856813, Ceres ANNOT ID no. 828846, Ceres ANNOT ID no. 870022, Ceres ANNOT ID no. 1285138, Ceres ANNOT ID no. 847799, Ceres CLONE ID no. 604111(a), Ceres CLONE ID no. 1464359, Ceres CLONE ID no. 964932, Ceres CLONE ID no. 1084747, Ceres ANNOT ID no. 1373087, Ceres ANNOT ID no. 1440417, or Ceres ANNOT ID no. 1505805, each operably linked to a CaMV 35S promoter. Constructs also were made using CRS 338 that contained Ceres CLONE ID no. 1025179, Ceres CLONE ID no. 604111 (a), or Ceres CLONE ID no. 604111(b), each operably linked to a p326 promoter. Wild-type *Arabidopsis thaliana* ecotype Wassilewskija (Ws) plants were transformed separately with each construct containing Ceres ANNOT ID no. 832857, Ceres ANNOT ID no. 1290753, Ceres ANNOT ID no. 856813, Ceres ANNOT ID no. 828846, Ceres CLONE ID no. 1025179, Ceres ANNOT ID no. 870022, Ceres ANNOT ID no. 1285138, Ceres ANNOT ID no. 847799, Ceres CLONE ID no. 604111(a), Ceres CLONE ID no. 604111(b), Ceres CLONE ID no. 1464359, Ceres CLONE ID no. 964932, Ceres CLONE ID no. 1084747, Ceres ANNOT ID no. 1373087, Ceres ANNOT ID no. 1440417, or Ceres ANNOT ID no. 1505805. The transformations were performed essentially as described in Bechtold and Pelletier, *Methods Mol Biol.,* 82:259-66 (1998). The following information about each transgenic *Arabidopsis* line is presented in Table 12: DNA clone, sequence identifier of the nucleotide sequence of the DNA clone, sequence identifier of the amino acid sequence of the polypeptide encoded by the DNA clone, the promoter operably linked to the DNA clone, and the designation of the transgenic line.

TABLE 12

Transgenic *Arabidopsis* lines

| DNA clone | DNA SEQ ID NO: | Amino acid SEQ ID NO: | Promoter | Transgenic line designation |
|---|---|---|---|---|
| Ceres ANNOT ID no. 832857 | 111 | 112 | CaMV 35S | ME23423 |
| Ceres ANNOT ID no. 856813 | 115 | 116 | CaMV 35S | ME23517 |
| Ceres ANNOT ID no. 1290753 | 101 | 102 | CaMV 35S | ME23453<br>ME16623 |
| Ceres ANNOT ID no. 828846 | 109 | 110 | CaMV 35S | ME25288 |

TABLE 12-continued

| Transgenic *Arabidopsis* lines | | | | |
|---|---|---|---|---|
| DNA clone | DNA SEQ ID NO: | Amino acid SEQ ID NO: | Promoter | Transgenic line designation |
| Ceres CLONE ID no. 1025179 | 119 | 120 | p326 | ME24513 ME24480 ME24762 |
| Ceres ANNOT ID no. 870022 | 117 | 118 | CaMV 35S | ME16579 |
| Ceres ANNOT ID no. 1285138 | 99 | 100 | CaMV 35S | ME16572 |
| Ceres ANNOT ID no. 847799 | 113 | 114 | CaMV 35S | ME23459 |
| Ceres CLONE ID no. 604111(a) | 125 | 126 | CaMV 35S | ME25680 ME24978 |
| Ceres CLONE ID no. 604111(a) | 125 | 126 | p326 | ME24758 |
| Ceres CLONE ID no. 604111(b) | 129 | 146 | p326 | ME24507 |
| Ceres CLONE ID no. 1464359 | 123 | 124 | CaMV 35S | ME25661 |
| Ceres CLONE ID no. 964932 | 127 | 128 | CaMV 35S | ME25647 |
| Ceres CLONE ID no. 1084747 | 121 | 122 | CaMV 35S | ME25665 |
| Ceres ANNOT ID no. 1373087 | 103 | 104 | CaMV 35S | ME25698 |
| Ceres ANNOT ID no. 1440417 | 105 | 106 | CaMV 35S | ME25953 |
| Ceres ANNOT ID no. 1505805 | 107 | 108 | CaMV 35S | ME25957 |

The presence of the vector containing Ceres ANNOT ID no. 832857, Ceres ANNOT ID no. 1290753, Ceres ANNOT ID no. 856813, Ceres CLONE ID no. 1025179, Ceres ANNOT ID no. 870022, Ceres ANNOT ID no. 1285138, Ceres ANNOT ID no. 847799, Ceres CLONE ID no. 1464359, Ceres CLONE ID no. 964932, or Ceres CLONE ID no. 1084747 in each transgenic *Arabidopsis* line transformed with the vector was confirmed by Finale® resistance, polymerase chain reaction (PCR) amplification from green leaf tissue extract, and/or sequencing of PCR products. The presence of the vector containing Ceres ANNOT ID no. 828846, Ceres ANNOT ID no. 1373087, Ceres ANNOT ID no. 1440417, or Ceres ANNOT ID no. 1505805 in each transgenic *Arabidopsis* line transformed with the vector was confirmed by Finale® resistance, polymerase chain reaction (PCR) amplification from green leaf tissue extract, and/or partial sequencing of PCR products. The presence of the vector containing Ceres CLONE ID no. 604111(a) in transgenic *Arabidopsis* lines ME25680 and ME24978 was confirmed by Finale® resistance, polymerase chain reaction (PCR) amplification from green leaf tissue extract, and/or sequencing of PCR products. The presence of the vector containing Ceres CLONE ID no. 604111(a) in transgenic *Arabidopsis* line ME24758 was confirmed by Finale® resistance, polymerase chain reaction (PCR) amplification from green leaf tissue extract, and/or partial sequencing of PCR products. The presence of the vector containing Ceres CLONE ID no. 604111(b) in transgenic *Arabidopsis* line ME24507 was confirmed by Finale® resistance, polymerase chain reaction (PCR) amplification from green leaf tissue extract, and/or sequencing of PCR products.

The segregation of Finale® resistance for $T_2$ plants from events -02, -03, and -04 of ME23423 was 3:1 (resistant: sensitive), and the segregation for $T_2$ plants from event -01 of ME23423 was 15:1. The segregation of Finale® resistance for $T_2$ plants from events -01, -02, and -03 of ME23517 was 15:1, 3:1, and 2:1, respectively. The segregation of Finale® resistance for $T_2$ plants from events -02, -04, and -05 of ME23453 was 3:1.

Wild-type seeds and seeds from transgenic lines ME23423, ME23517, ME25288, ME16579, ME16572, ME23459, ME25661, ME25647, ME25665, ME25698, ME25953, ME25957, ME16623, ME23453, ME24513, ME24480, ME24762, ME25680, ME24978, ME24758, and ME24507 were plated as described in Example 2. Seedlings maintained under conditions of irradiance with about 10 μmol/m²/s of light for seven days at 22° C. were analyzed for hypocotyl length. The transgenic *Arabidopsis* lines ME23423, ME23517, ME25288, ME16579, ME16572, ME23459, ME25661, ME25647, ME25665, ME25698, ME25953, ME25957, ME16623, ME23453, ME24513, ME24480, ME24762, ME25680, ME24978, ME24758, and ME24507 were identified as having reduced hypocotyl elongation under the low light conditions as compared to wild-type control plants.

Example 6

Characterization of the Low Light Tolerance of Seedlings from ME23423 Events $T_2$ and $T_3$ seedlings from events -01, -02, -03, -04, and -08, and $T_2$ seedlings from events -07 and -09, of ME23423 containing Ceres ANNOT ID no. 832857 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, -04, and -08 of ME23423 displayed a short hypocotyl under low light conditions in both the $T_2$ and $T_3$ generations, and seedlings from events -07 and -09 displayed a short hypocotyl under low light conditions in the $T_2$ generation. The transgene was linked to the short hypocotyl phenotype with a confidence level of $p \leq 0.05$ (Table 13).

TABLE 13

Chi-square comparison of the hypocotyl length of ME23423 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 29 | 6 | 12.93 | 3.24E−04 |
| $T_2$ non-transgenic segregants of event -01 | 0 | 4 | | |
| $T_3$ seedlings from event -01-99 | 42 | 2 | 34.72 | 3.80E−09 |
| $T_3$ non-transgenic segregants of event -01-99 | 1 | 8 | | |
| $T_2$ seedlings from event -02 | 19 | 10 | 9.17 | 2.46E−03 |
| $T_2$ non-transgenic segregants of event -02 | 1 | 9 | | |
| $T_3$ seedlings from event -02-99 | 59 | 4 | 38.63 | 5.13E−10 |
| $T_3$ non-transgenic segregants of event -02-99 | 1 | 8 | | |
| $T_2$ seedlings from event -03 | 20 | 13 | 3.94 | 4.70E−02 |
| $T_2$ non-transgenic segregants of event -03 | 1 | 5 | | |
| $T_3$ seedlings from event -03-99 | 38 | 3 | 23.44 | 1.29E−06 |
| $T_3$ non-transgenic segregants of event -03-99 | 5 | 11 | | |

TABLE 13-continued

Chi-square comparison of the hypocotyl length of ME23423 transgenic seedlings and non-transgenic segregants grown under low light irradiance (10 μmol/$m^2$/s) for seven days

| Plants | Short Hypocotyl | Long Hypocotyl | Chi-Square | p-value |
|---|---|---|---|---|
| $T_2$ seedlings from event -04 | 26 | 2 | 25.28 | 4.96E−07 |
| $T_2$ non-transgenic segregants of event -04 | 0 | 7 | | |
| $T_3$ seedlings from event -04-99 | 55 | 5 | 38.36 | 5.89E−10 |
| $T_3$ non-transgenic segregants of event -04-99 | 0 | 8 | | |
| $T_2$ seedlings from event -07 | 56 | 4 | 10.96 | 9.29E−04 |
| $T_2$ non-transgenic segregants of event -07 | 12 | 7 | | |
| $T_2$ seedlings from event -08 | 65 | 7 | 26.8 | 2.26E−07 |
| $T_2$ non-transgenic segregants of event -08 | 1 | 6 | | |
| $T_3$ seedlings from event -08-99 | 43 | 9 | 4.32 | 3.77E−02 |
| $T_3$ non-transgenic segregants of event -08-99 | 1 | 2 | | |
| $T_2$ seedlings from event -09 | 52 | 6 | 38.26 | 6.18E−10 |
| $T_2$ non-transgenic segregants of event -09 | 3 | 16 | | |

The physical appearances of $T_1$ ME23423 plants were similar to those of corresponding control plants. There were no observable or statistically significant differences between $T_2$ ME23423 and control plants in germination, onset of flowering, rosette area, fertility, and general morphology/architecture.

Example 7

Characterization of the Low Light Tolerance of Seedlings from ME23517 Events $T_2$ and $T_3$ seedlings from events -01, -02, and -03 of ME23517 containing Ceres ANNOT ID no. 856813 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, and -03 of ME23517 displayed a short hypocotyl under low light conditions in both the $T_2$ and $T_3$ generations, and the transgene was linked to the short hypocotyl phenotype with a confidence level of p≤0.05 (Table 14).

TABLE 14

Chi-square comparison of the hypocotyl length of ME23517 transgenic seedlings and non-transgenic segregants grown under low light irradiance (10 μmol/$m^2$/s) for seven days

| Plants | Short Hypocotyl | Long Hypocotyl | Chi-Square | p-value |
|---|---|---|---|---|
| $T_2$ seedlings from event -01 | 77 | 0 | 79 | 6.21E−19 |
| $T_2$ non-transgenic segregants of event -01 | 0 | 2 | | |
| $T_3$ seedlings from event -01-99 | 13 | 1 | 12.57 | 3.92E−04 |
| $T_3$ non-transgenic segregants of event -01-99 | 3 | 9 | | |
| $T_2$ seedlings from event -02 | 57 | 2 | 64.23 | 1.11E−15 |
| $T_2$ non-transgenic segregants of event -02 | 1 | 19 | | |
| $T_3$ seedlings from event -02-99 | 14 | 1 | 12.8 | 3.74E−04 |
| $T_3$ non-transgenic segregants of event -02-99 | 2 | 7 | | |
| $T_2$ seedlings from event -03 | 42 | 2 | 53.36 | 2.78E−13 |
| $T_2$ non-transgenic segregants of event -03 | 4 | 28 | | |
| $T_3$ seedlings from event -03-99 | 16 | 3 | 18.84 | 1.42E−05 |
| $T_3$ non-transgenic segregants of event -03-99 | 2 | 15 | | |

The physical appearances of $T_1$ ME23517 plants were similar to those of corresponding control plants. There were no observable or statistically significant differences between $T_2$ ME23517 and control plants in germination, onset of flowering, rosette area, fertility, and general morphology/architecture.

Example 8

Characterization of the Low Light Tolerance of Seedlings from ME23453 and ME16623 Events $T_2$ and $T_3$ seedlings from events -02, -04, and -05, and $T_3$ seedlings from event -03, of ME23453 containing Ceres ANNOT ID no. 1290753 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -02, -04, and -05 of ME23453 displayed a short hypocotyl under low light conditions in both the $T_2$ and $T_3$ generations, and seedlings from event -03 displayed a short hypocotyl under low light conditions in the $T_3$ generation. The transgene was linked to the short hypocotyl phenotype with a confidence level of p≤0.05 (Table 15).

TABLE 15

Chi-square comparison of the hypocotyl length of ME23453 transgenic seedlings and non-transgenic segregants grown under low light irradiance (10 μmol/$m^2$/s) for seven days

| Plants | Short Hypocotyl | Long Hypocotyl | Chi-Square | p-value |
|---|---|---|---|---|
| $T_2$ seedlings from event -02 | 52 | 0 | 62.49 | 2.68E−15 |
| $T_2$ non-transgenic segregants of event -02 | 4 | 23 | | |
| $T_3$ seedlings from event -02-99 | 33 | 0 | 27.79 | 1.35E−07 |
| $T_3$ non-transgenic segregants of event -02-99 | 5 | 10 | | |
| $T_3$ seedlings from event -03-99 | 27 | 1 | 19.28 | 1.13E−05 |
| $T_3$ non-transgenic segregants of event -03-99 | 1 | 4 | | |
| $T_2$ seedlings from event -04 | 63 | 0 | 68.42 | 1.32E−16 |
| $T_2$ non-transgenic segregants of event -04 | 2 | 15 | | |

TABLE 15-continued

Chi-square comparison of the hypocotyl length of ME23453 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_3$ seedlings from event -04-99 | 30 | 0 | 43 | 5.47E−11 |
| $T_3$ non-transgenic segregants of event -04-99 | 0 | 13 | | |
| $T_2$ seedlings from event -05 | 50 | 2 | 54.45 | 1.59E−13 |
| $T_2$ non-transgenic segregants of event -05 | 3 | 21 | | |
| $T_3$ seedlings from event -05-99 | 13 | 0 | 9.45 | 2.11E−03 |
| $T_3$ non-transgenic segregants of event -05-99 | 5 | 6 | | |

$T_1$ ME23453 plants exhibited a late flowering phenotype as compared to corresponding control plants. There were no observable or statistically significant differences between $T_2$ ME23453 and control plants in germination, onset of flowering, rosette area, fertility, and general morphology/architecture.

$T_2$ and $T_3$ seedlings from events -03 and -04, and $T_2$ seedlings from event -02, of ME16623 containing Ceres ANNOT ID no. 1290753 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -03 and -04 of ME16623 displayed a short hypocotyl under low light conditions in both the $T_2$ and $T_3$ generations, and seedlings from event -02 displayed a short hypocotyl under low light conditions in the $T_2$ generation. The transgene was linked to the short hypocotyl phenotype with a confidence level of $p \leq 0.05$ (Table 16).

TABLE 16

Chi-square comparison of the hypocotyl length of ME16623 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -02 | 56 | 3 | 53.68 | 2.63E−13 |
| $T_2$ non-transgenic segregants of event -02 | 2 | 17 | | |
| $T_2$ seedlings from event -03 | 48 | 4 | 24.62 | 7.00E−07 |
| $T_2$ non-transgenic segregants of event -03 | 4 | 9 | | |
| $T_3$ seedlings from event -03-99 | 39 | 6 | 9.53 | 2.02E−03 |
| $T_3$ non-transgenic segregants of event -03-99 | 9 | 9 | | |
| $T_2$ seedlings from event -04 | 56 | 3 | 61.32 | 4.86E−15 |
| $T_2$ non-transgenic segregants of event -04 | 0 | 17 | | |
| $T_3$ seedlings from event -04-99 | 13 | 3 | 7.72 | 5.47E−03 |
| $T_3$ non-transgenic segregants of event -04-99 | 0 | 3 | | |

Example 9

Characterization of the Low Light Tolerance of Seedlings from ME25288 Events $T_2$ and $T_3$ seedlings from event -02 of ME25288 containing Ceres ANNOT ID no. 828846 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -02 of ME25288 displayed a short hypocotyl under low light conditions in both the $T_2$ and $T_3$ generations, and the transgene was linked to the short hypocotyl phenotype with a confidence level of $p \leq 0.05$ (Table 17).

TABLE 17

Chi-square comparison of the hypocotyl length of ME25288 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -02 | 35 | 5 | 10.11 | 1.48E−03 |
| $T_2$ non-transgenic segregants of event -02 | 3 | 5 | | |
| $T_3$ seedlings from event -02-99 | 39 | 6 | 24.73 | 6.58E−07 |
| $T_3$ non-transgenic segregants of event -02-99 | 2 | 11 | | |

Example 10

Characterization of the Low Light Tolerance of Seedlings from ME24513, ME24480, and ME24762 Events $T_2$ and $T_3$ seedlings from events -01, -02, -03, and -08 of ME24513 containing Ceres CLONE ID no. 1025179 operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, and -08 of ME24513 displayed a short hypocotyl under low light conditions in both the $T_2$ and $T_3$ generations, and the transgene was linked to the short hypocotyl phenotype with a confidence level of $p \leq 0.05$ (Table 18).

TABLE 18

Chi-square comparison of the hypocotyl length of ME24513 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 53 | 2 | 59.52 | 1.21E−14 |
| $T_2$ non-transgenic segregants of event -01 | 0 | 15 | | |
| $T_3$ seedlings from event -01-99 | 17 | 0 | 19 | 1.31E−05 |
| $T_3$ non-transgenic segregants of event -01-99 | 0 | 2 | | |

TABLE 18-continued

Chi-square comparison of the hypocotyl length of ME24513 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -02 | 43 | 17 | 14.13 | 1.70E−04 |
| $T_2$ non-transgenic segregants of event -02 | 4 | 14 | | |
| $T_3$ seedlings from event -02-99 | 50 | 0 | 34.64 | 3.97E−09 |
| $T_3$ non-transgenic segregants of event -02-99 | 1 | 2 | | |
| $T_2$ seedlings from event -03 | 55 | 2 | 33.69 | 6.46E−09 |
| $T_2$ non-transgenic segregants of event -03 | 8 | 13 | | |
| $T_3$ seedlings from event -03-99 | 15 | 0 | 18 | 2.21E−05 |
| $T_3$ non-transgenic segregants of event -03-99 | 0 | 3 | | |
| $T_2$ seedlings from event -08 | 50 | 14 | 21.07 | 4.44E−06 |
| $T_2$ non-transgenic segregants of event -08 | 2 | 12 | | |
| $T_3$ seedlings from event -08-99 | 34 | 4 | 8.1 | 4.43E−03 |
| $T_3$ non-transgenic segregants of event -08-99 | 5 | 5 | | |

$T_2$ and $T_3$ seedlings from events -02, -04, and -05, and $T_2$ seedlings from events -01 and -07, of ME24480 containing Ceres CLONE ID no. 1025179 operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -02, -04, and -05 of ME24480 displayed a short hypocotyl under low light conditions in both the $T_2$ and $T_3$ generations, and seedlings from events -01 and -07 displayed a short hypocotyl under low light conditions in the $T_2$ generation. The transgene was linked to the short hypocotyl phenotype with a confidence level of $p \leq 0.05$ (Table 19).

TABLE 19

Chi-square comparison of the hypocotyl length of ME24480 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 39 | 2 | 23.46 | 1.28E−06 |
| $T_2$ non-transgenic segregants of event -01 | 3 | 7 | | |
| $T_2$ seedlings from event -02 | 36 | 1 | 5.26 | 2.19E−02 |
| $T_2$ non-transgenic segregants of event -02 | 6 | 2 | | |
| $T_3$ seedlings from event -02-99 | 16 | 0 | 19 | 1.31E−05 |
| $T_3$ non-transgenic segregants of event -02-99 | 0 | 3 | | |
| $T_2$ seedlings from event -04 | 24 | 3 | 11.19 | 8.21E−04 |
| $T_2$ non-transgenic segregants of event -04 | 5 | 8 | | |
| $T_3$ seedlings from event -04-99 | 23 | 0 | 24.22 | 8.61E−07 |
| $T_3$ non-transgenic segregants of event -04-99 | 8 | 17 | | |
| $T_2$ seedlings from event -05 | 38 | 0 | 23.62 | 1.17E−06 |
| $T_2$ non-transgenic segregants of event -05 | 4 | 5 | | |

TABLE 19-continued

Chi-square comparison of the hypocotyl length of ME24480 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_3$ seedlings from event -05-99 | 26 | 0 | 18.72 | 1.51E−05 |
| $T_3$ non-transgenic segregants of event -05-99 | 4 | 6 | | |
| $T_2$ seedlings from event -07 | 41 | 0 | 15.58 | 7.89E−05 |
| $T_2$ non-transgenic segregants of event -07 | 16 | 8 | | |

$T_2$ and $T_3$ seedlings from events -01, -02, -03, -04, -05, and -06 of ME24762 containing Ceres CLONE ID no. 1025179 operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, -04, -05, and -06 of ME24762 displayed a short hypocotyl under low light conditions in both the $T_2$ and $T_3$ generations, and the transgene was linked to the short hypocotyl phenotype with a confidence level of $p \leq 0.05$ (Table 20).

TABLE 20

Chi-square comparison of the hypocotyl length of ME24762 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 53 | 2 | 46.93 | 7.34E−12 |
| $T_2$ non-transgenic segregants of event -01 | 1 | 10 | | |
| $T_3$ seedlings from event -01-99 | 41 | 0 | 38.81 | 4.67E−10 |
| $T_3$ non-transgenic segregants of event -01-99 | 8 | 18 | | |
| $T_2$ seedlings from event -02 | 44 | 0 | 57.25 | 3.83E−14 |
| $T_2$ non-transgenic segregants of event -02 | 1 | 17 | | |
| $T_3$ seedlings from event -02-99 | 31 | 1 | 40.57 | 1.90E−10 |
| $T_3$ non-transgenic segregants of event -02-99 | 1 | 16 | | |
| $T_2$ seedlings from event -03 | 39 | 1 | 43 | 5.48E−11 |
| $T_2$ non-transgenic segregants of event -03 | 0 | 9 | | |
| $T_3$ seedlings from event -03-99 | 45 | 0 | 45.37 | 1.63E−11 |
| $T_3$ non-transgenic segregants of event -03-99 | 1 | 7 | | |
| $T_2$ seedlings from event -04 | 46 | 5 | 8.63 | 3.30E−03 |
| $T_2$ non-transgenic segregants of event -04 | 10 | 7 | | |
| $T_3$ seedlings from event -04-99 | 45 | 7 | 14.28 | 1.58E−04 |
| $T_3$ non-transgenic segregants of event -04-99 | 0 | 3 | | |
| $T_2$ seedlings from event -05 | 42 | 0 | 54.41 | 1.63E−13 |
| $T_2$ non-transgenic segregants of event -05 | 2 | 19 | | |
| $T_3$ seedlings from event -05-99 | 51 | 2 | 47.24 | 6.27E−12 |
| $T_3$ non-transgenic segregants of event -05-99 | 1 | 11 | | |

TABLE 20-continued

Chi-square comparison of the hypocotyl length of ME24762 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -06 | 23 | 0 | 9.55 | 2.00E−03 |
| $T_2$ non-transgenic segregants of event -06 | 11 | 6 | | |
| $T_3$ seedlings from event -06-99 | 37 | 1 | 13.38 | 2.54E−04 |
| $T_3$ non-transgenic segregants of event -06-99 | 5 | 4 | | |

Example 11

Characterization of the Low Light Tolerance of Seedlings from ME16579 Events $T_2$ and $T_3$ seedlings from event -07, $T_3$ seedlings from event -02, and $T_3$ and $T_4$ seedlings from event -05 of ME16579 containing Ceres ANNOT ID no. 870022 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -07 of ME16579 displayed a short hypocotyl under low light conditions in both the $T_2$ and $T_3$ generations, seedlings from event -02 displayed a short hypocotyl under low light conditions in the $T_3$ generation, and seedlings from event -05 displayed a short hypocotyl under low light conditions in the $T_3$ and $T_4$ generations. The transgene was linked to the short hypocotyl phenotype with a confidence level of $p \leq 0.05$ (Table 21).

TABLE 21

Chi-square comparison of the hypocotyl length of ME16579 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_3$ seedlings from event -02-99 | 6 | 11 | 3.85 | 4.97E−02 |
| $T_3$ non-transgenic segregants of event -02-99 | 39 | 24 | | |
| $T_3$ seedlings from event -05-99 | 42 | 0 | 57 | 4.36E−14 |
| $T_3$ non-transgenic segregants of event -05-99 | 0 | 15 | | |
| $T_4$ seedlings from event -05-99-99 | 60 | 1 | 58.52 | 2.01E−14 |
| $T_4$ non-transgenic segregants of event -05-99-99 | 0 | 7 | | |
| $T_2$ seedlings from event -07 | 26 | 1 | 24.58 | 7.14E−07 |
| $T_2$ non-transgenic segregants of event -07 | 1 | 7 | | |
| $T_3$ seedlings from event -07-99 | 59 | 0 | 73.8 | 8.65E−18 |
| $T_3$ non-transgenic segregants of event -07-99 | 1 | 19 | | |

Example 12

Characterization of the Low Light Tolerance of Seedlings from ME16572 Events $T_2$ and $T_3$ seedlings from events -01, -04, and -05, and $T_2$ seedlings from events -02 and -03, of ME16572 containing Ceres ANNOT ID no. 1285138 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -04, and -05 of ME16572 displayed a short hypocotyl under low light conditions in both the $T_2$ and $T_3$ generations, and seedlings from events -02 and -03 displayed a short hypocotyl under low light conditions in the $T_2$ generation. The transgene was linked to the short hypocotyl phenotype with a confidence level of $p \leq 0.05$ (Table 22).

TABLE 22

Chi-square comparison of the hypocotyl length of ME16572 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 46 | 9 | 6.23 | 1.25E−02 |
| $T_2$ non-transgenic segregants of event -01 | 3 | 4 | | |
| $T_3$ seedlings from event -01-99 | 27 | 3 | 6.98 | 8.27E−03 |
| $T_3$ non-transgenic segregants of event -01-99 | 0 | 1 | | |
| $T_2$ seedlings from event -02 | 21 | 0 | 45.8 | 1.31E−11 |
| $T_2$ non-transgenic segregants of event -02 | 7 | 43 | | |
| $T_2$ seedlings from event -03 | 57 | 5 | 37.53 | 9.02E−10 |
| $T_2$ non-transgenic segregants of event -03 | 2 | 11 | | |
| $T_2$ seedlings from event -04 | 37 | 3 | 16.49 | 4.90E−05 |
| $T_2$ non-transgenic segregants of event -04 | 8 | 10 | | |
| $T_3$ seedlings from event -04-99 | 20 | 2 | 6.97 | 8.29E−03 |
| $T_3$ non-transgenic segregants of event -04-99 | 0 | 1 | | |
| $T_2$ seedlings from event -05 | 64 | 0 | 24.58 | 7.11E−07 |
| $T_2$ non-transgenic segregants of event -05 | 7 | 4 | | |
| $T_3$ seedlings from event -05-99 | 39 | 3 | 6.49 | 1.08E−02 |
| $T_3$ non-transgenic segregants of event -05-99 | 7 | 4 | | |

Example 13

Characterization of the Low Light Tolerance of Seedlings from ME23459 Events $T_2$ and $T_3$ seedlings from events -02, -05, and -08, and $T_2$ seedlings from event -04, of ME23459 containing Ceres ANNOT ID no. 847799 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -02, -05, and -08 of ME23459 displayed a short hypocotyl under low light conditions in both the $T_2$ and $T_3$ generations, and seedlings from event -04 displayed a short hypocotyl under low light conditions in the $T_2$ generation. The transgene was linked to the short hypocotyl phenotype with a confidence level of $p \leq 0.05$ (Table 23).

TABLE 23

Chi-square comparison of the hypocotyl length of ME23459 transgenic seedlings and non-transgenic segregants grown under low light irradiance (10 μmol/$m^2$/s) for seven days

| Plants | Short Hypocotyl | Long Hypocotyl | Chi-Square | p-value |
|---|---|---|---|---|
| $T_2$ seedlings from event -02 | 52 | 3 | 32.79 | 1.03E−08 |
| $T_2$ non-transgenic segregants of event -02 | 7 | 14 | | |
| $T_3$ seedlings from event - 02-99 | 53 | 1 | 64.66 | 8.89E−16 |
| $T_3$ non-transgenic segregants of event -02-99 | 0 | 16 | | |
| $T_2$ seedlings from event -04 | 62 | 3 | 18.73 | 1.50E−05 |
| $T_2$ non-transgenic segregants of event -04 | 5 | 5 | | |
| $T_2$ seedlings from event -05 | 64 | 0 | 52.44 | 4.44E−13 |
| $T_2$ non-transgenic segregants of event -05 | 4 | 10 | | |
| $T_3$ seedlings from event - 05-99 | 44 | 1 | 36.81 | 1.30E−09 |
| $T_3$ non-transgenic segregants of event -05-99 | 7 | 16 | | |
| $T_2$ seedlings from event -08 | 63 | 0 | 74.12 | 7.36E−18 |
| $T_2$ non-transgenic segregants of event -08 | 1 | 16 | | |
| $T_3$ seedlings from event - 08-99 | 54 | 1 | 54.61 | 1.47E−13 |
| $T_3$ non-transgenic segregants of event -08-99 | 2 | 14 | | |

Example 14

Characterization of the Low Light Tolerance of Seedlings from ME25680, ME24978, ME24758, and ME24507 Events $T_2$ and $T_3$ seedlings from events -01, -04, -06, -07, -08, -09, and -10 of ME25680 containing Ceres CLONE ID no. 604111(a) operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -04, -06, -07, -08, -09, and -10 of ME25680 displayed a short hypocotyl under low light conditions in both the $T_2$ and $T_3$ generations, and the transgene was linked to the short hypocotyl phenotype with a confidence level of $p \leq 0.05$ (Table 24).

TABLE 24

Chi-square comparison of the hypocotyl length of ME25680 transgenic seedlings and non-transgenic segregants grown under low light irradiance (10 μmol/$m^2$/s) for seven days

| Plants | Short Hypocotyl | Long Hypocotyl | Chi-Square | p-value |
|---|---|---|---|---|
| $T_2$ seedlings from event -01 | 54 | 1 | 34.65 | 3.95E−09 |
| $T_2$ non-transgenic segregants of event -01 | 9 | 13 | | |
| $T_3$ seedlings from event - 01-99 | 58 | 7 | 20.43 | 6.20E−06 |
| $T_3$ non-transgenic segregants of event -01-99 | 5 | 9 | | |
| $T_2$ seedlings from event -04 | 43 | 14 | 22.24 | 2.40E−06 |
| $T_2$ non-transgenic segregants of event -04 | 1 | 13 | | |
| $T_3$ seedlings from event - 04-99 | 46 | 5 | 7.61 | 5.81E−03 |
| $T_3$ non-transgenic segregants of event -04-99 | 9 | 6 | | |
| $T_2$ seedlings from event -06 | 60 | 2 | 29.96 | 4.41E−08 |
| $T_2$ non-transgenic segregants of event -06 | 8 | 10 | | |
| $T_3$ seedlings from event - 06-99 | 62 | 7 | 34.14 | 5.12E−09 |
| $T_3$ non-transgenic segregants of event -06-99 | 0 | 7 | | |
| $T_2$ seedlings from event -07 | 49 | 7 | 30.22 | 3.86E−08 |
| $T_2$ non-transgenic segregants of event -07 | 4 | 15 | | |
| $T_3$ seedlings from event - 07-99 | 57 | 4 | 17.17 | 3.42E−05 |
| $T_3$ non-transgenic segregants of event -07-99 | 7 | 7 | | |
| $T_2$ seedlings from event -08 | 57 | 5 | 20.05 | 7.54E−06 |
| $T_2$ non-transgenic segregants of event -08 | 7 | 9 | | |
| $T_3$ seedlings from event - 08-99 | 13 | 1 | 14.7 | 1.26E−04 |
| $T_3$ non-transgenic segregants of event -08-99 | 0 | 5 | | |
| $T_2$ seedlings from event -09 | 50 | 8 | 41.69 | 1.07E−10 |
| $T_2$ non-transgenic of event -09 | 2 | 20 | | |
| $T_3$ seedlings from event - 09-99 | 57 | 0 | 46.98 | 7.16E−12 |
| $T_3$ non-transgenic segregants of event -09-99 | 3 | 8 | | |
| $T_2$ seedlings from event -10 | 49 | 20 | 11.46 | 7.11E−04 |
| $T_2$ non-transgenic segregants of event -10 | 2 | 9 | | |
| $T_3$ seedlings from event - 10-99 | 49 | 12 | 14.71 | 1.25E−04 |
| $T_3$ non-transgenic segregants of event -10-99 | 4 | 10 | | |

$T_2$ and $T_3$ seedlings from event -01, and $T_3$ seedlings from events -02 and -03, of ME24978 containing Ceres CLONE ID no. 604111(a) operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -01 of ME24978 displayed a short hypocotyl under low light conditions in both the $T_2$ and $T_3$ generations, and seedlings from events -02 and -03 displayed a short hypocotyl under low light conditions in the $T_3$ generation. The transgene was linked to the short hypocotyl phenotype with a confidence level of $p \leq 0.05$ (Table 25).

TABLE 25

Chi-square comparison of the hypocotyl length of ME24978 transgenic seedlings and non-transgenic segregants grown under low light irradiance (10 μmol/m$^2$/s) for seven days

| Plants | Short Hypocotyl | Long Hypocotyl | Chi-Square | p-value |
|---|---|---|---|---|
| $T_2$ seedlings from event -01 | 47 | 1 | 44.01 | 3.27E−11 |
| $T_2$ non-transgenic segregants of event -01 | 3 | 13 | | |
| $T_3$ seedlings from event -01-99 | 51 | 5 | 30.81 | 2.85E−08 |
| $T_3$ non-transgenic segregants of event -01-99 | 3 | 11 | | |
| $T_3$ seedlings from event -02-99 | 50 | 11 | 15.34 | 8.97E−05 |
| $T_3$ non-transgenic segregants of event -02-99 | 1 | 6 | | |
| $T_3$ seedlings from event -03-99 | 54 | 2 | 15.53 | 8.12E−05 |
| $T_3$ non-transgenic segregants of event -03-99 | 7 | 5 | | |

$T_2$ and $T_3$ seedlings from event -03, and $T_2$ seedlings from event -01, of ME24758 containing Ceres CLONE ID no. 604111(a) operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -03 of ME24758 displayed a short hypocotyl under low light conditions in both the $T_2$ and $T_3$ generations, and seedlings from event -01 displayed a short hypocotyl under low light conditions in the $T_2$ generation. The transgene was linked to the short hypocotyl phenotype with a confidence level of p≤0.05 (Table 26).

TABLE 26

Chi-square comparison of the hypocotyl length of ME24758 transgenic seedlings and non-transgenic segregants grown under low light irradiance (10 μmol/m$^2$/s) for seven days

| Plants | Short Hypocotyl | Long Hypocotyl | Chi-Square | p-value |
|---|---|---|---|---|
| $T_2$ seedlings from event -01 | 55 | 4 | 15.04 | 1.06E−04 |
| $T_2$ non-transgenic segregants of event -01 | 8 | 7 | | |
| $T_2$ seedlings from event -03 | 54 | 2 | 39.72 | 2.93E−10 |
| $T_2$ non-transgenic segregants of event -03 | 5 | 13 | | |
| $T_3$ seedlings from event -03-99 | 13 | 1 | 20.26 | 6.76E−06 |
| $T_3$ non-transgenic segregants of event -03-99 | 0 | 10 | | |

$T_2$ and $T_3$ seedlings from events -01, -03, -05, and -09, $T_2$ seedlings from event -02, and $T_3$ seedlings from event -10 of ME24507 containing Ceres CLONE ID no. 604111(b) operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -03, -05, and -09 of ME24507 displayed a short hypocotyl under low light conditions in both the $T_2$ and $T_3$ generations, seedlings from event -02 displayed a short hypocotyl under low light conditions in the $T_2$ generation, and seedlings from event -10 displayed a short hypocotyl under low light conditions in the $T_3$ generation. The transgene was linked to the short hypocotyl phenotype with a confidence level of p≤0.05 (Table 27).

TABLE 27

Chi-square comparison of the hypocotyl length of ME24507 transgenic seedlings and non-transgenic segregants grown under low light irradiance (10 μmol/m$^2$/s) for seven days

| Plants | Short Hypocotyl | Long Hypocotyl | Chi-Square | p-value |
|---|---|---|---|---|
| $T_2$ seedlings from event -01 | 21 | 4 | 8.73 | 3.13E−03 |
| $T_2$ non-transgenic segregants of event -01 | 1 | 4 | | |
| $T_3$ seedlings from event -01-99 | 28 | 0 | 22.65 | 1.95E−06 |
| $T_3$ non-transgenic segregants of event -01-99 | 6 | 10 | | |
| $T_2$ seedlings from event -02 | 42 | 8 | 4.67 | 3.08E−02 |
| $T_2$ non-transgenic segregants of event -02 | 12 | 8 | | |
| $T_2$ seedlings from event -03 | 46 | 13 | 38.52 | 5.41E−10 |
| $T_2$ non-transgenic segregants of event -03 | 0 | 21 | | |
| $T_3$ seedlings from event -03-99 | 35 | 2 | 13.19 | 2.81E−04 |
| $T_3$ non-transgenic segregants of event -03-99 | 6 | 6 | | |
| $T_2$ seedlings from event -05 | 42 | 11 | 30.39 | 3.54E−08 |
| $T_2$ non-transgenic segregants of event -05 | 4 | 23 | | |
| $T_3$ seedlings from event -05-99 | 42 | 4 | 28.69 | 8.51E−08 |
| $T_3$ non-transgenic segregants of event -05-99 | 8 | 18 | | |
| $T_2$ seedlings from event -09 | 70 | 6 | 24.25 | 8.44E−07 |
| $T_2$ non-transgenic segregants of event -09 | 0 | 3 | | |
| $T_3$ seedlings from event -09-99 | 47 | 2 | 39.57 | 3.71E−10 |
| $T_3$ non-transgenic segregants of event -09-99 | 0 | 6 | | |
| $T_3$ seedlings from event -10-99 | 54 | 6 | 8.28 | 4.02E−03 |
| $T_3$ non-transgenic segregants of event -10-99 | 1 | 2 | | |

Example 15

Characterization of the Low Light Tolerance of Seedlings from ME25661 Events $T_2$ and $T_3$ seedlings from events -01, -02, -03, -04, -05, and -09 of ME25661 containing Ceres CLONE ID no. 1464359 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, -04, -05, and -09 of ME25661 displayed a short hypocotyl under low light conditions in both the $T_2$ and $T_3$ generations, and the transgene was linked to the short hypocotyl phenotype with a confidence level of p≤0.05 (Table 28).

TABLE 28

Chi-square comparison of the hypocotyl length of ME25661 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 61 | 0 | 52.73 | 3.82E−13 |
| $T_2$ non-transgenic segregants of event -01 | 5 | 13 | | |
| $T_3$ seedlings from event -01-99 | 37 | 0 | 29.82 | 4.75E−08 |
| $T_3$ non-transgenic segregants of event -01-99 | 2 | 5 | | |
| $T_2$ seedlings from event -02 | 61 | 1 | 58.23 | 2.34E−14 |
| $T_2$ non-transgenic segregants of event -02 | 3 | 15 | | |
| $T_3$ seedlings from event -02-99 | 55 | 0 | 40.66 | 1.81E−10 |
| $T_3$ non-transgenic segregants of event -02-99 | 5 | 9 | | |
| $T_2$ seedlings from event -03 | 61 | 2 | 37.24 | 1.04E−09 |
| $T_2$ non-transgenic segregants of event -03 | 6 | 11 | | |
| $T_3$ seedlings from event -03-99 | 48 | 9 | 17.56 | 2.78E−05 |
| $T_3$ non-transgenic segregants of event -03-99 | 6 | 12 | | |
| $T_2$ seedlings from event -04 | 57 | 0 | 79 | 6.21E−19 |
| $T_2$ non-transgenic segregants of event -04 | 0 | 22 | | |
| $T_3$ seedlings from event -04-99 | 53 | 3 | 35.12 | 3.10E−09 |
| $T_3$ non-transgenic segregants of event -04-99 | 7 | 15 | | |
| $T_2$ seedlings from event -05 | 53 | 3 | 58.9 | 1.66E−14 |
| $T_2$ non-transgenic segregants of event -05 | 1 | 20 | | |
| $T_3$ seedlings from event -05-99 | 61 | 1 | 66.22 | 4.04E−16 |
| $T_3$ non-transgenic segregants of event -05-99 | 1 | 15 | | |
| $T_2$ seedlings from event -09 | 53 | 1 | 71.35 | 2.99E−17 |
| $T_2$ non-transgenic segregants of event -09 | 0 | 22 | | |
| $T_3$ seedlings from event -09-99 | 65 | 0 | 72.25 | 1.90E−17 |
| $T_3$ non-transgenic segregants of event -09-99 | 1 | 13 | | |

Example 16

Characterization of the Low Light Tolerance of Seedlings from ME25647 Events $T_2$ and $T_3$ seedlings from events -01, -03, -04, -05, -06, -08, -09, and -10 of ME25647 containing Ceres CLONE ID no. 964932 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -03, -04, -05, -06, -08, -09, and -10 of ME25647 displayed a short hypocotyl under low light conditions in both the $T_2$ and $T_3$ generations, and the transgene was linked to the short hypocotyl phenotype with a confidence level of $p \leq 0.05$ (Table 29).

TABLE 29

Chi-square comparison of the hypocotyl length of ME25647 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 39 | 1 | 68.19 | 1.49E−16 |
| $T_2$ non-transgenic segregants of event -01 | 1 | 35 | | |
| $T_3$ seedlings from event -01-99 | 19 | 0 | 22.19 | 2.47E−06 |
| $T_3$ non-transgenic segregants of event -01-99 | 10 | 21 | | |
| $T_2$ seedlings from event -03 | 45 | 17 | 16.89 | 3.97E−05 |
| $T_2$ non-transgenic segregants of event -03 | 3 | 14 | | |
| $T_3$ seedlings from event -03-99 | 39 | 12 | 29.83 | 4.71E−08 |
| $T_3$ non-transgenic segregants of event -03-99 | 1 | 19 | | |
| $T_2$ seedlings from event -04 | 62 | 0 | 60.45 | 7.55E−15 |
| $T_2$ non-transgenic segregants of event -04 | 3 | 13 | | |
| $T_3$ seedlings from event -04-99 | 38 | 0 | 40.71 | 1.77E−10 |
| $T_3$ non-transgenic segregants of event -04-99 | 1 | 8 | | |
| $T_2$ seedlings from event -05 | 55 | 1 | 68.85 | 1.06E−16 |
| $T_2$ non-transgenic segregants of event -05 | 0 | 18 | | |
| $T_3$ seedlings from event -05-99 | 48 | 0 | 42.35 | 7.62E−11 |
| $T_3$ non-transgenic segregants of event -05-99 | 3 | 9 | | |
| $T_2$ seedlings from event -06 | 55 | 2 | 46.05 | 1.15E−11 |
| $T_2$ non-transgenic segregants of event -06 | 2 | 11 | | |
| $T_3$ seedlings from event -06-99 | 51 | 7 | 19.89 | 8.22E−06 |
| $T_3$ non-transgenic segregants of event -06-99 | 5 | 10 | | |
| $T_2$ seedlings from event -08 | 54 | 0 | 73 | 1.30E−17 |
| $T_2$ non-transgenic segregants of event -08 | 0 | 19 | | |
| $T_3$ seedlings from event -08-99 | 68 | 1 | 37.19 | 1.07E−09 |
| $T_3$ non-transgenic segregants of event -08-99 | 3 | 5 | | |
| $T_2$ seedlings from event -09 | 51 | 6 | 53 | 3.34E−13 |
| $T_2$ non-transgenic segregants of event -09 | 0 | 20 | | |
| $T_3$ seedlings from event -09-99 | 44 | 5 | 38.67 | 5.03E−10 |
| $T_3$ non-transgenic segregants of event -09-99 | 0 | 12 | | |
| $T_2$ seedlings from event -10 | 62 | 8 | 21.85 | 2.95E−06 |
| $T_2$ non-transgenic segregants of event-10 | 0 | 4 | | |
| $T_3$ seedlings from event -10-99 | 61 | 6 | 36.28 | 1.71E−09 |
| $T_3$ non-transgenic segregants of event -10-99 | 0 | 7 | | |

Example 17

Characterization of the Low Light Tolerance of Seedlings from ME25665 Events $T_2$ and $T_3$ seedlings from events -03, -06, and -08, and $T_2$ seedlings from event -04, of ME25665 containing Ceres CLONE ID no. 1084747 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -03, -06, and -08 of ME25665 displayed a short hypocotyl under low light conditions in both the $T_2$ and $T_3$ generations, and seedlings from event -04 displayed a short hypocotyl under low light conditions in the $T_2$ generation. The transgene was linked to the short hypocotyl phenotype with a confidence level of p≤0.05 (Table 30).

TABLE 30

Chi-square comparison of the hypocotyl length of ME25665 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -03 | 58 | 18 | 11.1 | 8.63E−04 |
| $T_2$ non-transgenic segregants of event -03 | 0 | 4 | | |
| $T_3$ seedlings from event -03-99 | 57 | 4 | 11.59 | 6.64E−04 |
| $T_3$ non-transgenic segregants of event -03-99 | 0 | 1 | | |
| $T_2$ seedlings from event -04 | 20 | 11 | 8.43 | 3.70E−03 |
| $T_2$ non-transgenic segregants of event -04 | 0 | 6 | | |
| $T_2$ seedlings from event -06 | 46 | 11 | 39.42 | 3.41E−10 |
| $T_2$ non-transgenic segregants of event -06 | 1 | 22 | | |
| $T_3$ seedlings from event -06-99 | 46 | 7 | 24.91 | 6.00E−07 |
| $T_3$ non-transgenic segregants of event -06-99 | 2 | 10 | | |
| $T_2$ seedlings from event -08 | 53 | 11 | 34.2 | 4.97E−09 |
| $T_2$ non-transgenic segregants of event -08 | 1 | 15 | | |
| $T_3$ seedlings from event -08-99 | 67 | 3 | 48.5 | 3.31E−12 |
| $T_3$ non-transgenic segregants of event -08-99 | 0 | 6 | | |

Example 18

Characterization of the Low Light Tolerance of Seedlings from ME25698 Events $T_2$ seedlings from events -01, -02, -04, -05, and -07 of ME25698 containing Ceres ANNOT ID no. 1373087 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -04, -05, and -07 of ME25698 displayed a short hypocotyl under low light conditions in the $T_2$ generation, and the transgene was linked to the short hypocotyl phenotype with a confidence level of p≤0.05 (Table 31).

TABLE 31

Chi-square comparison of the hypocotyl length of ME25698 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 47 | 15 | 11.25 | 7.94E−04 |
| $T_2$ non-transgenic segregants of event -01 | 6 | 12 | | |
| $T_2$ seedlings from event -02 | 38 | 23 | 16.92 | 3.89E−05 |
| $T_2$ non-transgenic segregants of event -02 | 1 | 16 | | |
| $T_2$ seedlings from event -04 | 42 | 13 | 30.2 | 3.90E−08 |
| $T_2$ non-transgenic segregants of event -04 | 2 | 21 | | |
| $T_2$ seedlings from event -05 | 51 | 11 | 24.08 | 9.24E−07 |
| $T_2$ non-transgenic segregants of event -05 | 3 | 13 | | |
| $T_2$ seedlings from event -07 | 43 | 6 | 11.88 | 5.66E−04 |
| $T_2$ non-transgenic segregants of event -07 | 11 | 11 | | |

Example 19

Characterization of the Low Light Tolerance of Seedlings from ME25953 Events $T_2$ seedlings from events -01 and -02 of ME25953 containing Ceres ANNOT ID no. 1440417 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01 and -02 of ME25953 displayed a short hypocotyl under low light conditions in the $T_2$ generation, and the transgene was linked to the short hypocotyl phenotype with a confidence level of p≤0.05 (Table 32).

TABLE 32

Chi-square comparison of the hypocotyl length of ME25953 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 77 | 0 | 78 | 1.03E−18 |
| $T_2$ non-transgenic segregants of event -01 | 0 | 1 | | |
| $T_2$ seedlings from event -02 | 46 | 4 | 57.48 | 3.42E−14 |
| $T_2$ non-transgenic segregants of event -02 | 1 | 26 | | |

Example 20

Characterization of the Low Light Tolerance of Seedlings from ME25957 Events $T_2$ seedlings from events -01 and -06 of ME25957 containing Ceres ANNOT ID no. 1505805 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01 and -06 of ME25957 displayed a short hypocotyl under low light conditions in the $T_2$ generation, and the transgene was linked to the short hypocotyl phenotype with a confidence level of p≤0.05 (Table 33).

TABLE 33

Chi-square comparison of the hypocotyl length of ME25957 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 48 | 4 | 56.6 | 5.33E−14 |
| $T_2$ non-transgenic segregants of event -01 | 0 | 21 | | |
| $T_2$ seedlings from event -06 | 46 | 0 | 16.59 | 4.64E−05 |
| $T_2$ non-transgenic segregants of event -06 | 17 | 8 | | |

Example 21

Determination of Functional Homolog and/or Ortholog Sequences

A subject sequence was considered a functional homolog or ortholog of a query sequence if the subject and query sequences encoded proteins having a similar function and/or activity. A process known as Reciprocal BLAST (Rivera et al., *Proc. Natl. Acad. Sci. USA,* 95:6239-6244 (1998)) was used to identify potential functional homolog and/or ortholog sequences from databases consisting of all available public and proprietary peptide sequences, including NR from NCBI and peptide translations from Ceres clones.

Before starting a Reciprocal BLAST process, a specific query polypeptide was searched against all peptides from its source species using BLAST in order to identify polypeptides having BLAST sequence identity of 80% or greater to the query polypeptide and an alignment length of 85% or greater along the shorter sequence in the alignment. The query polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog and/or ortholog sequence with a specific query polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a query polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original query polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog or ortholog.

Functional homologs and/or orthologs were identified by manual inspection of potential functional homolog and/or ortholog sequences. Representative functional homologs and/or orthologs for SEQ ID NO:88 are shown in FIG. 1.

Example 22

Generation of Hidden Markov Models

Hidden Markov Models (HMMs) were generated by the program HMMER 2.3.2 using groups of sequences as input that are homologous and/or orthologous to SEQ ID NO:88. To generate each HMM, the default HMMER 2.3.2 program parameters configured for glocal alignments were used. An HMM was generated using the sequences aligned in FIG. 1 as input. When fitted to the HMM, the sequences had the HMM bit scores listed in Table 34. Other homologous and/or orthologous sequences also were fitted to the HMM, and these sequences are listed in Table 34 along with their corresponding HMM bit scores.

TABLE 34

HMM bit scores of polypeptides that are homologous and/or orthologous to Ceres Clone 28780 (SEQ ID NO: 88)

| Designation | Species | SEQ ID NO: | HMM bit score |
|---|---|---|---|
| Ceres CLONE ID no. 28780 | *Arabidopsis thaliana* | 88 | 428.7 |
| Ceres Clone 1073674 | *Glycine max* | 89 | 419 |
| Ceres Clone 1118987 | *Brassica napus* | 90 | 418.4 |
| Ceres ANNOT 1461298 | *Populus balsamifera* subsp. *trichocarpa* | 92 | 435 |
| Public GI 34907938 | *Oryza sativa* subsp. *japonica* | 93 | 419.6 |
| Ceres Clone 1603237 | *Parthenium argentatum* | 94 | 345.8 |
| Ceres ANNOT ID no. 1285138 | *Arabidopsis thaliana* | 100 | 391.8 |
| Ceres ANNOT ID no. 1373087 | *Oryza sativa* | 104 | 419.6 |
| Ceres ANNOT ID no. 1440417 | *Populus balsamifera* subsp. *trichocarpa* | 106 | 431.3 |
| Ceres ANNOT ID no. 1505805 | *Populus balsamifera* subsp. *trichocarpa* | 108 | 414.8 |
| Ceres ANNOT ID no. 828846 | *Arabidopsis thaliana* | 110 | 422.5 |
| Ceres ANNOT ID no. 832857 | *Arabidopsis thaliana* | 112 | 372.2 |
| Ceres ANNOT ID no. 847799 | *Arabidopsis thaliana* | 114 | 391.8 |
| Ceres ANNOT ID no. 856813 | *Arabidopsis thaliana* | 116 | 414.2 |
| Ceres ANNOT ID no. 870022 | *Arabidopsis thaliana* | 118 | 390.3 |
| Ceres CLONE ID no. 1025179 | *Arabidopsis thaliana* | 120 | 421.5 |
| Ceres CLONE ID no. 1084747 | *Brassica napus* | 122 | 418.2 |
| Ceres CLONE ID no. 1464359 | *Zea mays* | 124 | 408.4 |
| Ceres CLONE ID no. 604111(a) | *Glycine max* | 126 | 429.7 |
| Ceres CLONE ID no. 964932 | *Brassica napus* | 128 | 427 |

TABLE 34-continued

HMM bit scores of polypeptides that are homologous and/or orthologous to Ceres Clone 28780 (SEQ ID NO: 88)

| Designation | Species | SEQ ID NO: | HMM bit score |
|---|---|---|---|
| Ceres CLONE ID no. 1855399 | *Gossypium hirsutum* | 131 | 424 |
| Ceres CLONE ID no. 1858527 | *Panicum virgatum* | 133 | 380.7 |
| Ceres CLONE ID no. 1896482 | Unknown | 135 | 416.3 |
| Ceres CLONE ID no. 1934537 | *Gossypium hirsutum* | 137 | 424.2 |
| Ceres CLONE ID no. 1942084 | *Gossypium hirsutum* | 139 | 416.4 |
| Ceres CLONE ID no. 1988960 | *Panicum virgatum* | 141 | 380.9 |
| Public GI ID no. 92891522 | *Medicago truncatula* | 142 | 418.1 |
| Ceres CLONE ID no. 604111(b) | *Glycine max* | 146 | 429.9 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of modulating the low light tolerance of a plant, said method comprising introducing into a plant cell an exogenous nucleic acid comprising a nucleotide sequence encoding a polypeptide having 95% or greater sequence identity to SEQ ID NO: 112, wherein a plant produced from said plant cell exhibits a phenotypic difference relative to a corresponding control plant under low light conditions, wherein said phenotypic difference is a shortened hypocotyl.

2. A method of producing a plant, said method comprising growing a plant cell comprising an exogenous nucleic acid comprising a nucleotide sequence encoding a polypeptide having 95% or greater sequence identity to SEQ ID NO: 112, wherein said plant exhibits a phenotypic difference relative to a corresponding control plant under low light conditions, wherein said phenotypic difference is a shortened hypocotyl.

3. A plant comprising an exogenous nucleic acid, said exogenous nucleic acid comprising a nucleotide sequence encoding a polypeptide having 95% or greater sequence identity to SEQ ID NO: 112, wherein said plant exhibits a phenotypic difference relative to a corresponding control plant under low light conditions, wherein said phenotypic difference is a shortened hypocotyl.

4. A plant comprising an exogenous nucleic acid, said exogenous nucleic acid comprising a nucleotide sequence having 97% or greater sequence identity to SEQ ID NO: 111, wherein said plant exhibits a phenotypic difference relative to a corresponding control plant under low light conditions, wherein said phenotypic difference is a shortened hypocotyl.

5. The plant of claim 3, wherein said low light conditions comprise an irradiance of about 0.01 to about 20 $\mu$mol/m$^2$/s of light.

6. The plant of claim 3, wherein said exogenous nucleic acid is operably linked to a regulatory region.

7. The plant of claim 3, wherein said regulatory region is a tissue-preferential, broadly expressing, or inducible promoter.

8. The plant of claim 3, wherein said plant is a dicot.

9. The plant of claim 8, wherein said plant is a member of the genus *Brassica, Glycine, Gossypium, Helianthus, Lactuca*, or *Medicago*.

10. The plant of claim 3, wherein said plant is a monocot.

11. The plant of claim 10, wherein said plant is a member of the genus *Cocos, Elaeis, Oryza, Panicum*, or *Zea*.

12. Progeny of the plant of claim 3, wherein said progeny comprises said exogenous nucleic acid, and wherein said progeny exhibits a phenotypic difference relative to a corresponding control plant under low light conditions.

13. Seed from the plant according to claim 3, said seed comprising said exogenous nucleic acid.

14. Vegetative tissue from the plant according to claim 3, said vegetative tissue comprising said exogenous nucleic acid.

15. Fruit from the plant according to claim 3, said fruit comprising said exogenous nucleic acid.

16. A food product comprising seed or vegetative tissue from the plant according to claim 3, said food product comprising said exogenous nucleic acid.

17. A feed product comprising seed or vegetative tissue from the plant according to claim 3, said feed product comprising said exogenous nucleic acid.

* * * * *